US012807605B2

(12) United States Patent
Dorich et al.

(10) Patent No.: US 12,807,605 B2
(45) Date of Patent: Nov. 24, 2026

(54) PYRIDO-[3,4-D]PYRIDAZINE AMINE DERIVATIVES USEFUL AS NLRP3 INHIBITORS

(71) Applicant: Ventus Therapeutics U.S., Inc., Waltham, MA (US)

(72) Inventors: Stéphane Dorich, Pointe-Claire (CA); Stéphane Ciblat, Montreal (CA)

(73) Assignee: Ventus Therapeutics U.S., Inc., Waltham, MA (US)

( * ) Notice: Subject to any disclaimer, the term of this patent is extended or adjusted under 35 U.S.C. 154(b) by 220 days.

(21) Appl. No.: 18/799,636

(22) Filed: Aug. 9, 2024

(65) Prior Publication Data

US 2024/0409540 A1 Dec. 12, 2024

Related U.S. Application Data

(63) Continuation of application No. 18/785,350, filed on Jul. 26, 2024, now Pat. No. 12,398,136, which is a continuation of application No. 18/763,277, filed on Jul. 3, 2024, now Pat. No. 12,312,351, which is a continuation of application No. 18/190,920, filed on Mar. 27, 2023, now Pat. No. 12,331,048, which is a continuation of application No. PCT/US2023/064967, filed on Mar. 24, 2023.

(60) Provisional application No. 63/443,874, filed on Feb. 7, 2023, provisional application No. 63/420,930, filed on Oct. 31, 2022.

(51) Int. Cl.
*C07D 471/04* (2006.01)

(52) U.S. Cl.
CPC .................................. *C07D 471/04* (2013.01)

(58) Field of Classification Search
CPC .................................................... C07D 471/04
USPC ....................................................... 514/234.2
See application file for complete search history.

(56) References Cited

U.S. PATENT DOCUMENTS

| | | | |
|---|---|---|---|
| 3,753,988 | A | 8/1973 | Rodway et al. |
| 4,522,811 | A | 6/1985 | Eppstein et al. |
| 5,089,494 | A | 2/1992 | Iwase et al. |
| 5,324,727 | A | 6/1994 | Iwase et al. |
| 5,565,472 | A | 10/1996 | Hamanaka |
| 5,621,027 | A | 4/1997 | Roschger et al. |
| 5,763,263 | A | 6/1998 | Dehlinger |
| 5,849,741 | A | 12/1998 | Watanabe et al. |
| 6,114,530 | A | 9/2000 | Yuan et al. |
| 6,218,392 | B1 | 4/2001 | Watanabe et al. |
| 6,288,064 | B1 | 9/2001 | Watanabe et al. |
| 6,316,438 | B1 | 11/2001 | Yu et al. |
| 6,353,103 | B1 | 3/2002 | Yuan et al. |
| 6,486,158 | B1 | 11/2002 | Wang et al. |
| 6,858,624 | B2 | 2/2005 | Hagen et al. |
| 7,087,621 | B2 | 8/2006 | Sang et al. |
| 7,560,551 | B2 | 7/2009 | Cee et al. |
| 7,666,898 | B2 | 2/2010 | Chang et al. |
| 7,790,882 | B2 | 9/2010 | Carreira |
| 8,067,608 | B2 | 11/2011 | Beachy et al. |
| 8,106,066 | B2 | 1/2012 | Schumacher et al. |
| 8,318,793 | B2 | 11/2012 | Turner et al. |
| 8,329,698 | B2 | 12/2012 | Cravo et al. |
| 8,338,591 | B2 | 12/2012 | Yoon et al. |
| 8,445,473 | B2 | 5/2013 | Wang et al. |
| 8,575,183 | B2 | 11/2013 | Cushing et al. |
| 8,642,660 | B2 | 2/2014 | Goldfarb |
| 8,658,801 | B2 | 2/2014 | Loiseleur et al. |
| 8,674,097 | B2 | 3/2014 | Cravo et al. |
| 8,791,113 | B2 | 7/2014 | Dorsch et al. |
| 8,846,673 | B2 | 9/2014 | Duan et al. |
| 8,895,587 | B2 | 11/2014 | Cassayre et al. |

(Continued)

FOREIGN PATENT DOCUMENTS

| | | | |
|---|---|---|---|
| CL | 2023003154 | A1 | 4/2024 |
| CL | 2024001524 | A1 | 11/2024 |

(Continued)

OTHER PUBLICATIONS

Dal Piaz et al. “Isoxazolo [3, 4-d] pyridazinones and analogues as Leishmania mexicana PDE inhibitors” II Farmaco (2002); 57(2):89-96.

(Continued)

*Primary Examiner* — Niloofar Rahmani

(74) *Attorney, Agent, or Firm* — Fenwick & West LLP; Heidi A. Eriacher; Christine McCain

(57) ABSTRACT

The present disclosure relates to inhibitors of NLRP3 of Formula (I):

(I)

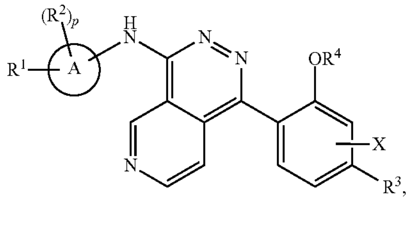

or a pharmaceutically acceptable salt, solvate, clathrate, hydrate, stereoisomer, tautomer, isotopically labeled compound, or prodrug thereof, wherein Ring A is a 5- to 8-membered monocyclic heterocycloalkyl comprising at least one O ring atom, p is 0 or 1, and $R^1$, $R^2$, $R^3$, $R^4$, and X are as defined herein, useful in the treatment of diseases and disorders inhibited by said protein.

18 Claims, No Drawings

(56) References Cited

U.S. PATENT DOCUMENTS

| | | | | |
|---|---|---|---|---|
| 8,912,202 | B2 | 12/2014 | Staehle et al. | |
| 8,932,557 | B2 | 1/2015 | Chen et al. | |
| 8,940,724 | B2 | 1/2015 | Cushing et al. | |
| 8,980,929 | B2 | 3/2015 | Hicks et al. | |
| 8,981,087 | B2 | 3/2015 | Shuttleworth et al. | |
| 9,023,490 | B2 | 5/2015 | Che | |
| 9,198,907 | B2 | 12/2015 | Lahser et al. | |
| 9,266,855 | B2 | 2/2016 | Turner et al. | |
| 9,309,231 | B2 | 4/2016 | Zhang et al. | |
| 9,458,168 | B2 | 10/2016 | Trzupek et al. | |
| 9,481,672 | B2 | 11/2016 | Fürstner et al. | |
| 9,593,108 | B2 | 3/2017 | Maccoss et al. | |
| 9,598,417 | B2 | 3/2017 | Haßfeld et al. | |
| 9,617,279 | B1 | 4/2017 | Zhang | |
| 9,675,073 | B2 | 6/2017 | Rawal et al. | |
| 9,765,039 | B2 | 9/2017 | Fairfax et al. | |
| 9,879,022 | B2 | 1/2018 | Trzupek et al. | |
| 9,949,977 | B2 | 4/2018 | Fürstner et al. | |
| 9,949,978 | B2 | 4/2018 | Fürstner et al. | |
| 10,167,294 | B2 | 1/2019 | Mohan et al. | |
| 10,287,284 | B2 | 5/2019 | Mjalli et al. | |
| 10,300,062 | B2 | 5/2019 | Fürstner et al. | |
| 10,519,146 | B2 | 12/2019 | Lanman et al. | |
| 10,717,734 | B2 | 7/2020 | Findlay et al. | |
| 10,736,897 | B2 | 8/2020 | Li et al. | |
| 10,793,577 | B2 | 10/2020 | Mohan et al. | |
| 10,857,123 | B2 | 12/2020 | Hacini-Rachinel | |
| 10,874,672 | B2 | 12/2020 | Babu et al. | |
| 11,254,553 | B2 | 2/2022 | Magerl et al. | |
| 11,254,653 | B2 | 2/2022 | Farady et al. | |
| 11,319,319 | B1 * | 5/2022 | Dorich ................. | C07D 471/04 |
| 11,618,751 | B1 | 4/2023 | Dorich et al. | |
| 11,851,422 | B2 | 12/2023 | Vandyck et al. | |
| 12,168,657 | B2 | 12/2024 | Dorich et al. | |
| 12,195,460 | B2 | 1/2025 | Dorich | |
| 12,281,112 | B2 | 4/2025 | Dorich et al. | |
| 2003/0124053 | A1 | 7/2003 | Barrett et al. | |
| 2004/0242886 | A1 | 12/2004 | Gupta et al. | |
| 2006/0156485 | A1 | 7/2006 | Lim | |
| 2006/0276505 | A1 | 12/2006 | Nelson et al. | |
| 2007/0179123 | A1 | 8/2007 | Chiang et al. | |
| 2009/0082358 | A1 | 3/2009 | Nishimura et al. | |
| 2009/0105266 | A1 | 4/2009 | Glatthar et al. | |
| 2009/0124624 | A1 | 5/2009 | Augereau et al. | |
| 2009/0239896 | A1 | 9/2009 | Chang et al. | |
| 2009/0318476 | A1 | 12/2009 | Ramtohul | |
| 2011/0124661 | A1 | 5/2011 | Brnardic et al. | |
| 2011/0150833 | A1 | 6/2011 | Feng et al. | |
| 2011/0152246 | A1 | 6/2011 | Buckman et al. | |
| 2011/0160187 | A1 | 6/2011 | Yoon et al. | |
| 2011/0178117 | A1 | 7/2011 | Converso et al. | |
| 2011/0218211 | A1 | 9/2011 | Bergeron et al. | |
| 2012/0030841 | A1 | 2/2012 | Koerber et al. | |
| 2013/0079342 | A1 | 3/2013 | Dransfield et al. | |
| 2013/0165440 | A1 | 6/2013 | Anand et al. | |
| 2014/0107151 | A1 | 4/2014 | Goldstein et al. | |
| 2014/0194480 | A1 | 7/2014 | Hoppe et al. | |
| 2016/0194320 | A1 | 7/2016 | Turner et al. | |
| 2016/0237059 | A1 | 8/2016 | Straub et al. | |
| 2018/0093956 | A1 | 4/2018 | Dai et al. | |
| 2018/0215731 | A1 | 8/2018 | Crew et al. | |
| 2020/0055865 | A1 | 2/2020 | Kim et al. | |
| 2020/0061063 | A1 | 2/2020 | Fürstner et al. | |
| 2020/0075870 | A1 | 3/2020 | Boudreault et al. | |
| 2020/0123133 | A1 | 4/2020 | No et al. | |
| 2020/0207720 | A1 | 7/2020 | Tanzer et al. | |
| 2020/0266360 | A1 | 8/2020 | Jeon et al. | |
| 2020/0361898 | A1 | 11/2020 | Farady et al. | |
| 2021/0009577 | A1 | 1/2021 | Lanman et al. | |
| 2021/0130359 | A1 | 5/2021 | Cooper et al. | |
| 2021/0221808 | A1 | 7/2021 | Chen et al. | |
| 2022/0340567 | A1 | 10/2022 | Dorich et al. | |
| 2023/0159526 | A1 | 5/2023 | Dorich et al. | |
| 2023/0212152 | A1 | 7/2023 | Arnold et al. | |
| 2023/0303559 | A1 | 9/2023 | Dorich et al. | |
| 2024/0158396 | A1 | 5/2024 | Dorich et al. | |
| 2024/0174661 | A1 | 5/2024 | Dorich et al. | |
| 2024/0174668 | A1 | 5/2024 | Dorich et al. | |
| 2024/0199606 | A1 | 6/2024 | Dorich et al. | |
| 2024/0239808 | A1 | 7/2024 | Berry et al. | |
| 2024/0360127 | A1 | 10/2024 | Dorich et al. | |
| 2024/0360128 | A1 | 10/2024 | Dorich et al. | |
| 2024/0360129 | A1 | 10/2024 | Dorich et al. | |
| 2024/0360130 | A1 | 10/2024 | Dorich et al. | |
| 2024/0368160 | A1 | 11/2024 | Dorich et al. | |
| 2024/0383896 | A1 | 11/2024 | Dorich et al. | |

FOREIGN PATENT DOCUMENTS

| | | | |
|---|---|---|---|
| CL | 2024002874 | A1 | 12/2024 |
| CL | 2024002824 | A1 | 2/2025 |
| CL | 2025001262 | A1 | 8/2025 |
| CL | 2025001163 | A1 | 10/2025 |
| CN | 1984904 | A | 6/2007 |
| CN | 103992311 | A | 8/2014 |
| CN | 108697709 | A | 10/2018 |
| CN | 110563722 | A | 12/2019 |
| CN | 111093773 | A | 5/2020 |
| CN | 202011562172-X | | 12/2020 |
| CN | 2021100906872 | | 1/2021 |
| CN | 2021105927697 | | 5/2021 |
| CN | 2021106294390 | | 6/2021 |
| CN | 2021107915923 | | 7/2021 |
| CN | 2021108434969 | | 7/2021 |
| CN | 202110940018-X | | 8/2021 |
| CN | 2021101726650 | | 8/2021 |
| CN | 2021109400137 | | 8/2021 |
| CN | 202210015181-X | | 1/2022 |
| CN | 2022100156993 | | 1/2022 |
| CN | 115417856 | A | 12/2022 |
| CN | 116726020 | A | 9/2023 |
| CN | 116789674 | A | 9/2023 |
| CN | 116969920 | A | 10/2023 |
| CN | 118056822 | A | 5/2024 |
| EP | 0449203 | B1 | 12/1994 |
| EP | 0683212 | A1 | 11/1995 |
| EP | 0623112 | B1 | 12/1998 |
| EP | 0722936 | B1 | 5/2004 |
| EP | 1451202 | B1 | 8/2008 |
| EP | 1984354 | B1 | 8/2009 |
| EP | 2285786 | B1 | 10/2013 |
| EP | 2411379 | B1 | 12/2014 |
| EP | 1984353 | B1 | 12/2015 |
| EP | 2445886 | B1 | 3/2016 |
| EP | 2847190 | B1 | 4/2016 |
| EP | 2571876 | B1 | 9/2016 |
| EP | 2742029 | B1 | 10/2016 |
| EP | 2621914 | B1 | 12/2016 |
| EP | 2459543 | B1 | 8/2017 |
| EP | 3045456 | B1 | 10/2017 |
| EP | 2880030 | B1 | 1/2018 |
| EP | 2709983 | B1 | 4/2018 |
| EP | 3126330 | B1 | 2/2019 |
| EP | 3066100 | B1 | 4/2019 |
| EP | 3536685 | A1 | 9/2019 |
| EP | 3553049 | A1 | 10/2019 |
| EP | 2585461 | B1 | 2/2020 |
| EP | 3604298 | A1 | 2/2020 |
| EP | 3613751 | A1 | 2/2020 |
| EP | 2852572 | B1 | 4/2020 |
| EP | 3237419 | B1 | 2/2021 |
| GB | 1303061 | A | 1/1973 |
| GB | 2063249 | A | 6/1981 |
| HK | 20098858 | | 4/2024 |
| JP | H03284669 | A | 12/1991 |
| JP | H06135938 | A | 5/1994 |
| JP | 2009120486 | A | 6/2009 |
| WO | WO-8911279 | A1 | 11/1989 |
| WO | WO-9315058 | A1 | 8/1993 |
| WO | WO-9605176 | A1 | 2/1996 |
| WO | WO-9807430 | A1 | 2/1998 |
| WO | WO-0056719 | A1 | 9/2000 |
| WO | WO-03045967 | A1 | 6/2003 |
| WO | WO-2004099158 | A1 | 11/2004 |

(56) References Cited

FOREIGN PATENT DOCUMENTS

| | | | |
|---|---|---|---|
| WO | WO-2005016000 | A1 | 2/2005 |
| WO | WO-2005033288 | A2 | 4/2005 |
| WO | WO-2006004589 | A2 | 1/2006 |
| WO | WO-2006090273 | A2 | 8/2006 |
| WO | WO-2006110516 | A1 | 10/2006 |
| WO | WO-2007038367 | A1 | 4/2007 |
| WO | WO-2007056184 | A2 | 5/2007 |
| WO | WO-2007056281 | A2 | 5/2007 |
| WO | WO-2007056580 | A2 | 5/2007 |
| WO | WO-2007087276 | A1 | 8/2007 |
| WO | WO-2007093402 | A1 | 8/2007 |
| WO | WO-2008017161 | A1 | 2/2008 |
| WO | WO-2008128968 | A1 | 10/2008 |
| WO | WO-2008137084 | A2 | 11/2008 |
| WO | WO-2009035568 | A1 | 3/2009 |
| WO | WO-2009038812 | A1 | 3/2009 |
| WO | WO-2009079008 | A1 | 6/2009 |
| WO | WO-2009086303 | A2 | 7/2009 |
| WO | WO-2009126947 | A2 | 10/2009 |
| WO | WO-2009140163 | A1 | 11/2009 |
| WO | WO-2009152909 | A1 | 12/2009 |
| WO | WO-2009157386 | A1 | 12/2009 |
| WO | WO-2010021934 | A2 | 2/2010 |
| WO | WO-2010036544 | A1 | 4/2010 |
| WO | WO-2010101949 | A1 | 9/2010 |
| WO | WO-2010109005 | A1 | 9/2010 |
| WO | WO-2010112545 | A1 | 10/2010 |
| WO | WO-2010117935 | A1 | 10/2010 |
| WO | WO-2010117936 | A1 | 10/2010 |
| WO | WO-2010151791 | A1 | 12/2010 |
| WO | WO-2011012883 | A1 | 2/2011 |
| WO | WO-2011019780 | A1 | 2/2011 |
| WO | WO-2011075607 | A1 | 6/2011 |
| WO | WO-2011123751 | A2 | 10/2011 |
| WO | WO-2011146358 | A1 | 11/2011 |
| WO | WO-2012000595 | A1 | 1/2012 |
| WO | WO-2012003264 | A1 | 1/2012 |
| WO | WO-2012037132 | A1 | 3/2012 |
| WO | WO-2012041814 | A1 | 4/2012 |
| WO | WO-2012156400 | A1 | 11/2012 |
| WO | WO-2012158810 | A1 | 11/2012 |
| WO | WO-2013020622 | A1 | 2/2013 |
| WO | WO-2013026939 | A1 | 2/2013 |
| WO | WO-2013078254 | A1 | 5/2013 |
| WO | WO-2013167495 | A1 | 11/2013 |
| WO | WO-2013176698 | A1 | 11/2013 |
| WO | WO-2014019344 | A1 | 2/2014 |
| WO | WO-2014079935 | A1 | 5/2014 |
| WO | WO-2014079941 | A1 | 5/2014 |
| WO | WO-2014080291 | A2 | 5/2014 |
| WO | WO-2014086737 | A1 | 6/2014 |
| WO | WO-2014131315 | A1 | 9/2014 |
| WO | WO-2015001348 | A1 | 1/2015 |
| WO | WO-2015036560 | A1 | 3/2015 |
| WO | WO-2015067549 | A1 | 5/2015 |
| WO | WO-2015150995 | A1 | 10/2015 |
| WO | WO-2016086200 | A9 | 6/2016 |
| WO | WO-2016103037 | A1 | 6/2016 |
| WO | WO-2016131098 | A1 | 8/2016 |
| WO | WO-2017100726 | A1 | 6/2017 |
| WO | WO-2017136871 | A1 | 8/2017 |
| WO | WO-2017140778 | A1 | 8/2017 |
| WO | WO-2017144341 | A1 | 8/2017 |
| WO | WO-2017184604 | A1 | 10/2017 |
| WO | WO-2017184623 | A1 | 10/2017 |
| WO | WO-2017184624 | A1 | 10/2017 |
| WO | WO-2018015445 | A1 | 1/2018 |
| WO | WO-2018031680 | A1 | 2/2018 |
| WO | WO-2018080216 | A1 | 5/2018 |
| WO | WO-2018138050 | A1 | 8/2018 |
| WO | WO-2018144649 | A1 | 8/2018 |
| WO | WO-2018172925 | A1 | 9/2018 |
| WO | WO-2018174678 | A1 | 9/2018 |
| WO | WO-2018217651 | A1 | 11/2018 |
| WO | WO-2018218071 | A1 | 11/2018 |
| WO | WO-2018221433 | A1 | 12/2018 |
| WO | WO-2019017741 | A1 | 1/2019 |
| WO | WO-2019038215 | A1 | 2/2019 |
| WO | WO-2019223548 | A1 | 11/2019 |
| WO | WO-2020021015 | A1 | 1/2020 |
| WO | WO-2020163248 | A1 | 8/2020 |
| WO | WO-2020234715 | A1 | 11/2020 |
| WO | WO2021188450 | A1 | 9/2021 |
| WO | WO-2021193897 | A1 | 9/2021 |
| WO | WO-2021239885 | A1 | 12/2021 |
| WO | WO-2022135567 | A1 | 6/2022 |
| WO | WO-2022166890 | A1 | 8/2022 |
| WO | WO-2022216971 | A1 | 10/2022 |
| WO | WO-2022229315 | A1 | 11/2022 |
| WO | WO-2022230912 | A1 | 11/2022 |
| WO | WO-2022238347 | A1 | 11/2022 |
| WO | WO-2022253326 | A1 | 12/2022 |
| WO | WO-2022253936 | A1 | 12/2022 |
| WO | WO-2023003002 | A1 | 1/2023 |
| WO | WO-2023275366 | A1 | 1/2023 |
| WO | WO-2023278438 | A1 | 1/2023 |
| WO | WO-2023026222 | A1 | 3/2023 |
| WO | WO-2023028534 | A1 | 3/2023 |
| WO | WO-2023028536 | A1 | 3/2023 |
| WO | WO-2023066377 | A1 | 4/2023 |
| WO | WO-2023066825 | A1 | 4/2023 |
| WO | WO-2023088856 | A1 | 5/2023 |
| WO | WO-2023088987 | A1 | 5/2023 |
| WO | WO-2023129987 | A1 | 7/2023 |
| WO | WO-2023131277 | A1 | 7/2023 |
| WO | WO-2023178099 | A1 | 9/2023 |
| WO | WO2023183901 | A1 | 9/2023 |
| WO | WO-2023183943 | A1 | 9/2023 |
| WO | WO-2023186020 | A1 | 10/2023 |
| WO | WO-2023194964 | A1 | 10/2023 |
| WO | WO-2023220408 | A1 | 11/2023 |
| WO | WO-2023232917 | A1 | 12/2023 |
| WO | WO-2024006559 | A1 | 1/2024 |
| WO | WO-2024012551 | A1 | 1/2024 |
| WO | WO-2024013395 | A1 | 1/2024 |
| WO | WO-2024017924 | A1 | 1/2024 |
| WO | WO-2024023266 | A1 | 2/2024 |
| WO | WO-2024028782 | A1 | 2/2024 |
| WO | WO-2024033845 | A1 | 2/2024 |
| WO | WO-2024041460 | A1 | 2/2024 |
| WO | WO-2024064245 | A1 | 4/2024 |
| WO | WO-2024090469 | A1 | 5/2024 |
| WO | WO-2024094150 | A1 | 5/2024 |
| WO | WO-2024094185 | A1 | 5/2024 |
| WO | WO-2024097598 | A1 | 5/2024 |
| WO | WO-2024097629 | A1 | 5/2024 |
| WO | WO-2024099992 | A1 | 5/2024 |
| WO | WO-2024099993 | A1 | 5/2024 |
| WO | WO-2024099996 | A1 | 5/2024 |
| WO | WO-2024109922 | A1 | 5/2024 |
| WO | WO-2024121086 | A1 | 6/2024 |
| WO | WO-2024121184 | A1 | 6/2024 |
| WO | WO-2024137319 | A1 | 6/2024 |
| WO | WO-2024138045 | A1 | 6/2024 |
| WO | WO-2024140704 | A1 | 7/2024 |
| WO | WO-2024140824 | A1 | 7/2024 |
| WO | WO-2024141535 | A1 | 7/2024 |
| WO | WO-2024145623 | A1 | 7/2024 |
| WO | WO-2024148029 | A2 | 7/2024 |
| WO | WO-2024160690 | A1 | 8/2024 |
| WO | WO-2024160691 | A1 | 8/2024 |
| WO | WO-2024160692 | A1 | 8/2024 |
| WO | WO-2024160693 | A1 | 8/2024 |
| WO | WO-2024160694 | A1 | 8/2024 |
| WO | WO 2025/059481 | A1 | 3/2025 |

OTHER PUBLICATIONS

Database Registry No. 154865-64-2, "Pyrido[2,3-d]pyridazin-8-amine, N-(1-methylethyl)-5-phenyl-(CA Index Name)", STN Entry Date May 6, 1994, 1 printed page.

(56) References Cited

OTHER PUBLICATIONS

Deng, Xq et al. "Pharmacophore modelling and virtual screening for identification of new Aurora-A kinase inhibitors" Chemical Biology & Drug Design (2008); 71(6):533-539.
Donnell et al. "Identification of pyridazino [4, 5-b] indolizines as selective PDE4B inhibitors" Bioorganic & Medicinal Chemistry Letters (2010); 20(7):2163-2167.
Dorich, Stephane, et al. "Discovery of novel NLRP3 inhibitors enabled by a highthroughput screen" Bioorganic & Medicinal Chemistry Letters (2025); 122: 130184, 7 pages.
Ibrahim et al. "Palladium-catalyzed synthesis of substituted pyrido [2, 3-d] pyridazines at positions 5 and 8" Synthesis (2012); 44(20):3216-3224.
International Search Report and Written Opinion for International Application No. PCT/US2022/023893, mailed Oct. 28, 2022, 18 pages.
International Search Report and Written Opinion for International Application No. PCT/US2023/064967, dated Jul. 3, 2023, 9 pages.
U.S. Appl. No. 18/891,602, filed Sep. 20, 2024, by Dorich et al.
U.S. Appl. No. 18/936,409, filed Nov. 4, 2024, by Dorich et al.
U.S. Appl. No. 19/084,304, filed Mar. 19, 2025, by Dorich et al.
Alikhan et al., Hidradenitis suppurativa: a comprehensive review. J Am Acad Dermatol. Apr. 2009;60(4):539-561; quiz 562-563. doi: 10.1016/j.jaad.2008.11.911.
Allen et al. The NLRP3 inflammasome functions as a negative regulator of tumorigenesis during colitis-associated cancer. J Exp Med. May 10, 2010;207(5):1045-56. doi: 10.1084/jem.20100050. Epub Apr. 12, 2010.
Alsenz et al. "High throughput solubility measurement in drug discovery and development" Adv Drug Deliv. Rev. (2007); 59(7):546-567.
Amsler et al. The inflammasome as a target of modulation by DNA viruses. Future Virol. Apr. 1, 2013;8(4):357-370. doi: 10.2217/fvl.13.22.
Artlett et al. The inflammasome activating caspase 1 mediates fibrosis and myofibroblast differentiation in systemic sclerosis. Arthritis Rheum. Nov. 2011;63(11):3563-74. doi: 10.1002/art.30568.
Baldwin et al. Inhibiting the Inflammasome: A Chemical Perspective. J Med Chem. Mar. 10, 2016;59(5):1691-710. doi: 10.1021/acs.jmedchem.5b01091.
Basiorka et al. The NLRP3 inflammasome functions as a driver of the myelodysplastic syndrome phenotype. Blood. Dec. 22, 2016;128(25):2960-2975. doi: 10.1182/blood-2016-07-730556. Epub Oct. 13, 2016.
Behalo, M.S. et al. (Nov. 2017) Synthesis of Novel Phthalazine Derivatives as Potential Anticancer and Antioxidant Agents Based on 1-Chloro-4-(4-phenoxyphenyl)phthalazine. J Heterocyclic Chem. 54(6):3591-3599, DOI: 10.1002/jhet.2985.
Bertoni et al. "A novel knock-in mouse model of cryopyrin-associated periodic syndromes with development of amyloidosis: therapeutic efficacy of proton pump inhibitors" J. Allergy Clin. Immunol. (2020); 145:368-378e13.
Braddock et al. Targeting IL-1 in inflammatory disease: new opportunities for therapeutic intervention. Nat Rev Drug Discov. Apr. 2004;3(4):330-9. doi: 10.1038/nrd1342.
Byrne et al. "Empaglifozin blunts worsening cardiac dysfunction associated with reduced NLRP3 (nucleotide-binding domain-like receptor protein 3) inflammasome activation in heart failure" Circ. Heart Fail. (2020); 13(1):e006277, 19 pages.
Chakraborty et al. "NLRP3 inflammasome in traumatic brain injury: Its implication in the disease pathophysiology and potential as a therapeutic target" Life Sciences (2023); 314(121352):1-8.
Chen, P. et al. "Stem cells from human exfoliated deciduous teeth alleviate liver cirrhosis via inhibition of Gasdermin D-executed hepatocyte pyroptosis" Front. Immunol. (2022); 13(860225):1-12.
Chen, Y. et al. "The NLRP3 inflammasome: contributions to inflammation-related diseases" Cellular & Molecular Biology Letters (2023); 28:51, 27 pages.
Cheng, J. et al. "Microglial autophagy defect causes Parkinson disease-like symptoms by accelerating inflammasome activation in mice" Autophagy (2020); 16(12):2193-2205.
Cheung A.K., et al., "Discovery of Small Molecule Splicing Modulators of Survival Motor Neuron-2 (SMN2) for the Treatment of Spinal Muscular Atrophy (SMA)," Journal of Medicinal Chemistry, 2018, vol. 61, pp. 11021-11036.
Cho et al. "Autophagy in microglia degrades extracellular beta-amyloid fibrils and regulates the NLRP3 inflammasome" Autophagy (2014); 10:1761-1775.
Coll, R. C. et al. "A small-molecule inhibitor of the NLRP3 inflammasome for the treatment of inflammatory diseases" Nature Medicine, 21(3):248-255; including "Online Methods", 2 pages (2015).
Colotta et al. "Synthesis and structure-activity relationships of 1-aminophthalazinium salts as GABAA receptor antagonists" European Journal of Medicinal Chemistry (1994); 29(2):95-105.
Cook et al., The NLRP3 inflammasome, a target for therapy in diverse disease states. Eur J Immunol. Mar. 2010;40(3):631-634. doi: 10.1002/eji.200940162.
Co-pending U.S. Appl. No. 17/528,928, inventors Stephane; Dorich et al., filed on Nov. 17, 2021.
Co-pending U.S. Appl. No. 17/679,898, inventors Dorich; Stéphane et al., filed on Feb. 24, 2022.
Co-pending U.S. Appl. No. 17/704,983, inventors Dorich; Stéphane et al., filed on Mar. 25, 2022.
Co-pending U.S. Appl. No. 17/974,342, inventors Dorich; Stéphane et al., filed on Oct. 26, 2022.
Co-pending U.S. Appl. No. 17/984,018, inventors Dorich; Stéphane et al., filed on Nov. 9, 2022.
Co-pending U.S. Appl. No. 18/190,920, inventors Dorich; Stephane et al., filed on Mar. 27, 2023.
Co-pending U.S. Appl. No. 18/480,164, inventors Stéphane; Dorich et al., filed on Oct. 3, 2023.
Co-pending U.S. Appl. No. 18/480,925, inventors Stéphane; Dorich et al., filed on Oct. 4, 2023.
Co-pending U.S. Appl. No. 18/534,906, inventors Dorich; Stephane et al., filed on Dec. 11, 2023.
Co-pending U.S. Appl. No. 18/763,210, inventors Dorich: Stephane et al., filed on Jul. 3, 2024.
Co-pending U.S. Appl. No. 18/763,243, inventors Dorich; Stephane et al., filed on Jul. 3, 2024.
Co-pending U.S. Appl. No. 18/763,258, inventors Dorich; Stephane et al., filed on Jul. 3, 2024.
Co-pending U.S. Appl. No. 18/763,277, inventors Dorich; Stephane et al., filed on Jul. 3, 2024.
Co-pending U.S. Appl. No. 18/763,302, inventors Dorich; Stephane et al., filed on Jul. 3, 2024.
Co-pending U.S. Appl. No. 18/785,350, inventors Dorich; Stephane et al., filed on Jul. 26, 2024.
Corcoran et al. "Pharmacological inhibition of the nod-like receptor family pyrin domain containing 3 inflammasome with MCC950" Pharmacological Reviews (2021); 73(3):968-1000.
Database Registry No. RN 1018067-04-3, "3-Pyridazinamine, 6-(4-chlorophenyl)-N-[(tetrahydro-2-furanyl)methyl]-" (CA Index Name). STN, Chemical Abstracts Service; entered Apr. 29, 2008; 1 printed page.
Database Registry No. RN 1018166-04-5, "3-Pyridazinamine, 6-(4-bromophenyl)-N-[(tetrahydro-2-furanyl)methyl]-" (CA Index Name). STN, Chemical Abstracts Service; entered Apr. 29, 2008; 1 printed page.
Database Registry No. RN 1027552-60-8, "Pyrido[3,4-d]pyridazin-4-amine, 7-(3-methyl-2-pyridinyl)-1-[4-(trifluoromethyl)phenyl]-" (CA Index Name). STN, Chemical Abstracts Service; entered Jun. 12, 2008; 1 printed page.
Database Registry No. RN 2060799-65-5, "Pyrido[2,3-d]pyridazin-8-a:mine, 5-(5-bromo-2-thienyl)-N-(1-methylethyl)-" (CA Index Name). STN, Chemical Abstracts Service; entered Jan. 29, 2017; 1 printed page.
Database Registry No. RN 2062164-56-9, "Pyrido[2,3-d]pyridazin-8-amine, N-(I-methylethyl)-5-[5-(5-methyl-2-pyridinyl)-2-thienyl]-)" (Ca Index Name). Stn, Chemical Abstracts Service; entered Jan. 31, 2017; 1 printed page.

(56) References Cited

OTHER PUBLICATIONS

Database Registry No. RN 2062164-57-0, Pyrido[2,3-d]pyridazin-8-amine, N-(I-methylethyl)-5-[5-(5-methyl-2-pyridinyl)-2-thienyl]-, hydrochloride (1:1) (CA Index Name). STN, Chemical Abstracts Service; entered Jan. 31, 2017; 1 printed page.
Database Registry No. RN1002033-19-3, "1-Phthalazinamine, 4-(4-methylphenyl)-N-[2-(4-morpholinyl)ethyl]-" (CA Index Name). STN, Chemical Abstracts Service; entered Feb. 7, 2008; 1 printed page.
Database Registry No. RN1078602-84-2, "1-Phthalazinamine, N-[2-(4-morpholinyl)ethyl]-4-phenyl-, ethanedioate (1:1)" (CA Index Name). STN, Chemical Abstracts Service; entered Dec. 2, 2008; 1 printed page.
Database Registry No. RN1090015-30-7, "1-Phthalazinamine, 4-(4-fluorophenyl)-N-[2-methyl-2-(4-morpholinyl)propyl]-" (CA Index Name). STN, Chemical Abstracts Service; entered Dec. 25, 2008; 1 printed page.
Database Registry No. RN1090983-56-4, "1-Phthalazinamine, 4-(4-fluorophenyl)-N-[2-(4-methoxyphenyl)-2-(4-morpholinyl)ethyl]-" (CA Index Name). STN, Chemical Abstracts Service; entered Dec. 28, 2008; 1 printed page.
Database Registry No. RN1135019-11-2, "1-Phthalazinamine, 4-(3,4-dimethylphenyl)-N-[2-(4-morpholinyl)ethyl]-, ethanedioate (1:2)" (CA Index Name). STN, Chemical Abstracts Service; entered Apr. 15, 2009; 1 printed page.
Database Registry No. RN1181498-12-3, "Benzamide, 4-[4-(cyclopentylamino)-1-phthalazinyl]-" (CA Index Name). STN, Chemical Abstracts Service; entered Sep. 9, 2009; 1 printed page.
Database Registry No. RN1217112-04-3, "1-Phthalazinamine, 4-(4-methylphenyl)-N-[2-(4-morpholinyl)ethyl]-, ethanedioate (1:2)" (CA Index Name). STN, Chemical Abstracts Service; entered Apr. 6, 2010; 1 printed page.
Database Registry No. RN1267866-53-4, "1-Phthalazinamine, 4-(4-fluorophenyl)-N-3-pyrrolidinyl-" (CA Index Name). STN, Chemical Abstracts Service; entered Mar. 10, 2011; 1 printed page.
Database Registry No. RN1310214-26-6, "1-Phthalazinamine, 4-(4-methylphenyl)-N-3-pyrrolidinyl-" (CA Index Name). STN, Chemical Abstracts Service; entered Jun. 23, 2011; 1 printed page.
Database Registry No. RN1340893-35-7, "1-Phthalazinamine, 4-[3-(4-fluorophenyl)-1,2,4-oxadiazol-5-yl]-N-[2-(4-morpholinyl)ethyl]-" (CA Index Name). STN, Chemical Abstracts Service; entered Nov. 4, 2011; 1 printed page.
Database Registry No. RN1340906-77-5, "1-Phthalazinamine, 4-(3-cyclopropyl-1,2,4-oxadiazol-5-yl)-N-[2-(4-morpholinyl)ethyl]-" (CA Index Name). STN, Chemical Abstracts Service; entered Nov. 4, 2011; 1 printed page.
Database Registry No. RN1340993-30-7, "1-Phthalazinamine, N-[2-(4-morpholinyl)ethyl]-4-(3-phenyl-1,2,4-oxadiazol-5-yl)-" (CA Index Name). STN, Chemical Abstracts Service; entered Nov. 4, 2011; 1 printed page.
Database Registry No. RN1351271-90-3, "3-Pyridazinamine, N-(I-methylethyl)-6-(1,2,3,4-tetrahydro-5-isoquinolinyl)-" (CA Index Name). STN, Chemical Abstracts Service; entered Dec. 19, 2011; 1 printed page.
Database Registry No. RN1482843-77-5, "1-Naphthalenol, 2-[6-(propylamino)-3-pyridazinyl]-" (CA Index Name). STN, Chemical Abstracts Service; entered Nov. 28, 2013; 1 printed page.
Database Registry No. RN1485079-65-9, "1-Naphthalenol, 2-[6-(ethylamino)-3-pyridazinyl]-" (CA Index Name). STN, Chemical Abstracts Service; entered Dec. 2, 2013; 1 printed page.
Database Registry No. RN1488322-94-6, "1-Phthalazinamine, 4-(2-methoxyphenyl)-N-methyl-" (CA Index Name). STN, Chemical Abstracts Service; entered Dec. 5, 2013; 1 printed page.
Database Registry No. RN1494117-54-2, "1-Phthalazinamine, 4-(2-methoxy-5-methylphenyl)-Nmethyl-" (CA Index Name). STN, Chemical Abstracts Service; entered Dec. 13, 2013; 1 printed page.
Database Registry No. RN1496330-00-7, "1-Phthalazinamine, 4-(5-fluoro-2-methoxyphenyl)-Nmethyl-" (CA Index Name). STN, Chemical Abstracts Service; entered Dec. 16, 2013; 1 printed page.
Database Registry No. RN1562335-33-4, "2,7-Naphthalenediol, 3-[6-[(2,2,6,6-tetramethyl-4-piperidinyl)oxy]-3-pyridazinyl]-" (CA Index Name). STN, Chemical Abstracts Service; entered Mar. 4, 2014; 1 printed page.
Database Registry No. RN1562335-37-8, "2,7-Naphthalenediol, 3-[6-[(2,2,6,6-tetramethyl-4-piperidinyl)amino]-3-pyridazinyl]-" (CA Index Name). STN, Chemical Abstracts Service; entered Mar. 4, 2014; 1 printed page.
Database Registry No. RN1647113-18-5, "6-Isoquinolinol, 7-[6-[(2,2,6,6-tetramethyl-4-piperidinyl)oxy]-3-pyridazinyl]-" (CA Index Name). STN, Chemical Abstracts Service; entered Feb. 13, 2015; 1 printed page.
Database Registry No. RN1647113-19-6, "Isoquinoline, 6-methoxy-7-[6-[(2,2,6,6- tetramethyl-4- piperidinyl)oxy]-3-pyridazinyl]-" (CA Index Name). STN, Chemical Abstracts Service; entered Feb. 13, 2015; 1 printed page.
Database Registry No. RN1647116-09-3, "6-Isoquinolinol, 3-propyl-7-[6-[(2,2,6,6-tetramethyl-4-piperidinyl)oxy]-3-pyridazinyl]-" (CA Index Name). STN, Chemical Abstracts Service; entered Feb. 13, 2015; 1 printed page.
Database Registry No. RN1647116-10-6, "6-Isoquinolinol, 3-(I-methylethyl)-7-[6-[(2,2,6,6-tetramethyl-4-piperidinyl)oxy]-3-pyridazinyl]-" (CA Index Name). STN, Chemical Abstracts Service; entered Feb. 13, 2015; 1 printed page.
Database Registry No. RN174542-71-3, "Phthalazine, 1-(4-methoxyphenyl)-4-(4-methylphenoxy)-" (CA Index Name). STN, Chemical Abstracts Service; entered Mar. 26, 1996; 1 printed page.
Database Registry No. RN1892513-27-7, "Acetonitrile, 2-[[6-(5,6,7,8-tetrahydro-2-naphthalenyl)-3-pyridazinyl]amino]-" (CA Index Name). STN, Chemical Abstracts Service; entered Apr. 18, 2016; 1 printed page.
Database Registry No. RN1893453-26-3, "3-Pyridazinamine, N-(I-methylethyl)-6-(2-naphthalenyl)-" (CA Index Name). STN, Chemical Abstracts Service; entered Apr. 20, 2016; 1 printed page.
Database Registry No. RN2198981-59-6, "Cyclopentanecarboxylic acid, 3-hydroxy-4-[[4-(4-methoxyphenyl)-1-phthalazinyl]amino]-" (CA Index Name). STN,Chemical Abstracts Service; entered Mar. 26, 2018; 1 printed page.
Database Registry No. RN2332630-59-6, Index Name Not yet Assigned. STN, Chemical Abstracts Service; entered Jun. 13, 2019; 1 printed page.
Database Registry No. RN2344192-58-9, "3-Pyridazinamine, N-pentyl-6-(5,6,7,8-tetrahydro-2-naphthalenyl)-" (CA Index Name). STN, Chemical Abstracts Service; entered Jun. 24, 2019; 1 printed page.
Database Registry No. RN296248-99-2, "4-Piperidinol, 1-[3-ethyl-9-[[2-(4-morpholinyl)ethyl]amino]-3Hpyrazolo[4',3':5,6]pyrido[3,4-d]pyridazin-6-yl]-" (CA Index Name). STN, Chemical Abstracts Service; entered Oct. 17, 2000; 1 printed page.
Database Registry No. RN30181-95-4, "1-Phthalazinamine, N-[2-(4-morpholinyl)ethyl]-4-phenyl-" (CA Index Name). STN, Chemical Abstracts Service; entered Nov. 16, 1984; 1 printed page.
Database Registry No. RN312591-18-7, "1-Phthalazinamine, 4-(4-chlorophenyl)-N-[2-(4-morpholinyl)ethyl]-" (CA Index Name). STN, Chemical Abstracts Service; entered Jan. 3, 2001; 1 printed page.
Database Registry No. RN361998-09-6, "1-Phthalazinamine, N-(3,4-dichlorophenyl)-4-(4-methoxyphenyl)-" (CA Index Name). STN, Chemical Abstracts Service; entered Oct. 14, 2001; 1 printed page.
Database Registry No. RN447430-57-1, "1-Phthalazinamine, N-cyclohexyl-4-(3,4-dimethylphenyl)-" (CA Index Name). STN, Chemical Abstracts Service; entered Sep. 6, 2002; 1 printed page.
Database Registry No. RN447430-58-2, "1-Phthalazinamine, N-cyclohexyl-4-(4-methylphenyl)-" (CA Index Name). STN, Chemical Abstracts Service; entered Sep. 6, 2002; 1 printed page.
Database Registry No. RN447430-60-6, "1-Phthalazinamine, N-cyclohexyl-4-(2,4-dimethylphenyl)-" (CA Index Name). STN, Chemical Abstracts Service; entered Sep. 6, 2002; 1 printed page.
Database Registry No. RN447430-62-8, "1-Phthalazinamine, N-cyclohexyl-4-(2,5-dimethylphenyl)-" (CA Index Name). STN, Chemical Abstracts Service; entered Sep. 6, 2002; 1 printed page.
Database Registry No. RN447430-63-9, "1-Phthalazinamine, N-cyclohexyl-4-(4-fluorophenyl)-" (CA Index Name). STN, Chemical Abstracts Service; entered Sep. 6, 2002; 1 printed page.

(56) References Cited

OTHER PUBLICATIONS

Database Registry No. RN447430-65-1, "1-Phthalazinamine, 4-(4-chlorophenyl)-N-cyclohexyl-" (CA Index Name). STN, Chemical Abstracts Service; entered Sep. 6, 2002; 1 printed page.
Database Registry No. RN447431-24-5, "1-Phthalazinamine, N,4-bis(4-fluorophenyl)-" (CA Index Name). STN, Chemical Abstracts Service; entered Sep. 6, 2002; 1 printed page.
Database Registry No. RN487025-40-1, "Benzamide, 4-[[4-(4-hydroxyphenyl)-1-phthalazinyl]amino]-"(CA Index Name). STN, Chemical Abstracts Service; entered Feb. 7, 2003; 1 printed page.
Database Registry No. RN496027-82-8, "1-Propanone, 1-[4-[[4-(3,4-dimethylphenyl)-1-phthalazinyl]oxy]phenyl]-" (CA Index Name). STN, Chemical Abstracts Service; entered Feb. 28, 2003; 1 printed page.
Database Registry No. RN694474-51-6 "Phthalazine, 1-(cyclohexyloxy)-4-(4-methylphenyl)-" (CA Index Name). STN, Chemical Abstracts Service; entered Jun. 17, 2004; 1 printed page.
Database Registry No. RN742121-05-7, "Ethanone, 1-[4-[[4-(4-methylphenyl)-1-phthalazinyl]oxy]phenyl]-" (CA Index Name). STN, Chemical Abstracts Service; entered Sep. 10, 2004; 1 printed page.
Database Registry No. RN78351-72-1, "1-Phthalazinamine, N-(4-fluorophenyl)-4-phenyl-" (CA Index Name). STN, Chemical Abstracts Service; entered Nov. 16, 1984; 1 printed page.
Database Registry No. RN78352-14-4, "1-Phthalazinamine, 4-(4-chlorophenyl)-N-[3-(trifluoromethyl)phenyl]-" (CA Index Name). STN, Chemical Abstracts Service; entered Nov. 16, 1984; 1 printed page.
Database Registry No. RN792956-18-4, "1-Phthalazinamine, 4-(4-fluorophenyl)-N-[2-(4-morpholinyl)ethyl]-" (CA Index Name). STN, Chemical Abstracts Service; entered Dec. 6, 2004; 1 printed page.
Database Registry No. RN852664-73-4, "1-Phthalazinamine, N-cycloheptyl-4-(4-methylphenyl)-" (CA Index Name). STN, Chemical Abstracts Service; entered Jun. 22, 2005; 1 printed page.
Database Registry No. RN852915-63-0, "1-Phthalazinamine, N-[2-methyl-2-(4-morpholinyl)propyl]-4-phenyl-" (CA Index Name). STN, Chemical Abstracts Service; entered Jun. 24, 2005; 1 printed page.
Database Registry No. RN930002-29-2, "1-Phthalazinamine, 4-(3,4-dimethylphenyl)-N-[2-(4-morpholinyl)ethyl]-" (CA Index Name). STN, Chemical Abstracts Service; entered Apr. 13, 2007; 1 printed page.
Database Registry No. RN934264-83-2, "1-Phthalazinamine, 7-methoxy-4-(4-methoxyphenyl)-N-4-piperidinyl-" (CA Index Name). STN, Chemical Abstracts Service; entered May 4, 2007; 1 printed page.
De Nardo et al. New insights into mechanisms controlling the NLRP3 inflammasome and its role in lung disease. Am J Pathol. Jan. 2014;184(1):42-54. doi: 10.1016/j.ajpath.2013.09.007. Epub Oct. 30, 2013.
Dempsey et al. Inhibiting the NLRP3 inflammasome with MCC950 promotes non-phlogistic clearance of amyloid-B and cognitive function in APP/PS1 mice. Brain Behav Immun. Mar. 2017;61:306-316. doi: 10.1016/j.bbi.2016.12.014. Epub Dec. 18, 2016.
Dolunay et al. Inhibition of NLRP3 Inflammasome Prevents LPS-Induced Inflammatory Hyperalgesia in Mice: Contribution of NF-κB, Caspase-1/11, ASC, NOX, and NOS Isoforms. Inflammation. Apr. 2017;40(2):366-386. doi: 10.1007/s10753-016-0483-3.
Doyle et al. NLRP3 has a protective role in age-related macular degeneration through the induction of IL-18 by drusen components. Nat Med. May 2012;18(5):791-8. doi: 10.1038/nm.2717.
Duewell et al. "NLRP3 inflammasomes are required for atherogenesis and activated by cholesterol crystals" Nature (2010); 464(7293):1357-1361.Erratum in: Nature. Jul. 29, 2010;466(7306):652.
Epsztajn et al. "Application of organolithium and related reagents in synthesis, Part XII. Synthesis of phenyl-and pyridylpyridopyridazinones and their derivatives". Monatshefte für Chemie/Chemical Monthly (May 21, 1993) 124(5): 549-558.
Fan et al. "Systemic activation of NLRP3 inflammasome and plasma alpha-synuclein levels are correlated with motor severity and progression in Parkinson's disease" J. Neuroinflamm. (2020); 17(1):11, 10 pages.
Fang et al. Increased expression of NLRP3 inflammasome components and interleukin-18 in patients with bullous pemphigoid. J Dermatol Sci. Aug. 2016;83(2):116-23. doi: 10.1016/j.jdermsci.2016.04.009. Epub Apr. 29, 2016.
Feng et al., The role of NLRP3 inflammasome in 5-fluorouracil resistance of oral squamous cell carcinoma. J Exp Clin Cancer Res. Jun. 21, 2017;36(1):81, 14 pages. doi: 10.1186/s13046-017-0553-x.
Ferreira et al. "NLRP3 Inflammasome and Mineralocorticoid Receptors Are Associated with Vascular Dysfunction in Type 2 Diabetes Mellitus" Cells (2019); 8(1595):1-8.
Gaidt et al. "The NLRP3 inflammasome renders cell death pro-inflammatory" Journal of Molecular Biology (2018); 430(2):133-141.
Gaul et al. "Hepatocyte pyroptosis and release of inflammasome particles induce stellate cell activation and liver fibrosis" J. Hepatol. (2021); 74(1):156-167.
Granata et al., NLRP3 inflammasome activation in dialyzed chronic kidney disease patients. PLoS One. Mar. 23, 2015;10(3):e0122272. doi: 10.1371/journal.pone.0122272, 16 pages.
Gu, P. et al. "Mitochondrial uncoupling protein 1 antagonizes atherosclerosis by blocking NLRP3 inflammasome-dependent interleukin-1beta production" Sci. Adv. (2021); 7(50):eabl4024, 14 pages.
Gugliandolo et al. NLRP3 Inflammasome Activation in a Transgenic Amyotrophic Lateral Sclerosis Model. Inflammation. Feb. 2018;41(1):93-103. doi: 10.1007/s10753-017-0667-5.
Haneklaus et al. "NLRP3 at the interface of metabolism and inflammation" Immunol. Rev. (2015); 265:53-62.
Henao-Meija et al. Inflammasome-mediated dysbiosis regulates progression of NAFLD and obesity. Nature. Feb. 1, 2012;482(7384):179-85. doi: 10.1038/nature10809.
Heneka et al. "NLRP3 is activated in Alzheimer's disease and contributes to pathology in APP/PS1 mice" Nature (2013); 493:674-678.
Hu et al. ATM is down-regulated by N-Myc-regulated microRNA-421. Proc Natl Acad Sci U S A. Jan. 26, 2010;107(4):1506-11. doi: 10.1073/pnas.0907763107. Epub Jan. 4, 2010.
Huang et al., NLRP3 inflammasome activation promotes inflammation-induced carcinogenesis in head and neck squamous cell carcinoma. J Exp Clin Cancer Res. Sep. 2, 2017; 36(1):116, doi: 10.1186/s13046-017-0589-y, 13 pages.
Iannitti et al., IL-1 receptor antagonist ameliorates inflammasome-dependent inflammation in murine and human cystic fibrosis. Nat Commun. Mar. 14, 2016; 7:10791. doi: 10.1038/ncomms10791, 16 pages.
Inoue et al. The role of interferon-β in the treatment of multiple sclerosis and experimental autoimmune encephalomyelitis—in the perspective of inflammasomes. Immunology. May 2013;139(1):11-8. doi: 10.1111/imm.12081.
Ising et al. "NLRP3 inflammasome activation drives tau pathology" Nature (2019); 575(7784):669-673.
Ismael et al., MCC950, the Selective Inhibitor of Nucleotide Oligomerization Domain-Like Receptor Protein-3 Inflammasome, Protects Mice against Traumatic Brain Injury. J Neurotrauma. Jun. 1, 2018;35(11):1294-1303. doi: 10.1089/neu.2017.5344.
Jager et al., D38 Flying: Reaching New Heights in Sarcoidosis: Key Role of Nlrp3 Inflammasome Activation in Granuloma Generation of Sarcoidosis. American Journal of Respiratory and Critical Care Medicine 191 (2015): 1 page.
Jia et al. Activation of NLRP3 inflammasome in peripheral nerve contributes to paclitaxel-induced neuropathic pain. Mol Pain. Jan.-Dec. 2017;13:1744806917719804. doi: 10.1177/1744806917719804, 11 pages.
Jimenez et al. "MicroRNA 223 3p negatively regulates the NLRP3 inflammasome in acute and chronic liver injury" Mol. Ther. (2020); 28(2):653-663.
Johnsen, M. et al. (Dec. 2003) New antithrombotic 1-Phthalazinamines with Serotonin Antagonistic Properties. Arch. Pharm Pharm Med Chem, 336(12):591-597, DOI: 10.1002/ARDP.200300775.
Kaizerman et al. Addressing PXR liabilities of phthalazine-based hedgehog/smoothened antagonists using novel pyridopyridazines. Bioorg Med Chem Lett. Aug. 1, 2010;20(15):4607-10. doi: 10.1016/j.bmcl.2010.06.006. Epub Jun. 8, 2010.

(56) References Cited

OTHER PUBLICATIONS

Kassab E.A., "Synthesis and Behaviour of 4-[4'-chloro-3'-methyl phenyl]-1 [2H]—phthalazinone Towards Certain Electrophiles and Nucleophiles," Egyptian Journal of Chemistry, 2005, vol. 48(2), pp. 183-199.
Kim et al. "Auranofin prevents liver fibrosis by system Xc-mediated inhibition of NLRP3 inflammasome" Commun. Biol. (2021); 4(1):824, 15 pages.
Kim et al. Role for NLRP3 Inflammasome-mediated, IL-1β-Dependent Responses in Severe, Steroid-Resistant Asthma. Am J Respir Crit Care Med. Aug. 1, 2017;196(3):283-297. doi: 10.1164/rccm.201609-1830OC.
Lazaridis et al. Activation of NLRP3 Inflammasome in Inflammatory Bowel Disease: Differences Between Crohn's Disease and Ulcerative Colitis. Dig Dis Sci. Sep. 2017;62(9):2348-2356. doi: 10.1007/s10620-017-4609-8. Epub May 18, 2017.
Lee, E. et al. "MPTP-driven NLRP3 inflammasome activation in microglia plays a central role in dopaminergic neurodegeneration" Cell Death Differ. (2019); 26(2):213-228.
Lee, H.M. et al. "Upregulated NLRP3 inflammasome activation in patients with type 2 diabetes" Diabetes (2013); 62:194-204.
Legrand-Poels et al. "Free fatty acids as modulators of the NLRP3 inflammasome in obesity/type 2 diabetes" Biochem. Pharm. (2014); 92:131-141.
Li et al. (2016) Dysregulation of the NLRP3 inflammasome complex and related cytokines in patients with multiple myeloma, Hematology, 21:3, 144-151, DOI: 10.1179/1607845415Y.0000000029.
Li et al. Aging-related gene signature regulated by Nlrp3 predicts glioma progression. Am J Cancer Res. 2015;5(1):442-9.
Li, H., et al. "Therapeutic potential of MCC950, a specific inhibitor of NLRP3 inflammasome" Eur J Pharmacol. (2022); 928(175091):1-9.
Li, N., et al., "Recent Progress and Prospects of Small Molecules for NLRP3 Inflammasome Inhibition," Journal of Medicinal Chemistry (2023) Article ASAP, DOI: 10.1021/acs.jmedchem.3c01370, pp. 1-27.
Liao et al. "Retinal pigment epithelium cell death is associated with NLRP3 inflammasome activation by All-trans Retinal" Investigative Opthalmology & Visual Science (2019); 60:3034-3045.
Liu, X. et al. "Channelling inflammation: gasdermins in physiology and disease" Nature Reviews Drug Discovery (2021); 20(5):384-405.
Loukovaara et al. NLRP3 inflammasome activation is associated with proliferative diabetic retinopathy. Acta Ophthalmol. Dec. 2017;95(8):803-808. doi: 10.1111/aos.13427. Epub Mar. 8, 2017.
Lu et al. Hyperactivation of the NLRP3 Inflammasome in Myeloid Cells Leads to Severe Organ Damage in Experimental Lupus. J Immunol. Feb. 1, 2017;198(3):1119-1129; DOI: https://doi.org/10.4049/jimmunol.1600659 .
Ma, X. et al. "NLRP3 inflammasome activation in liver cirrhotic patients" Biochem. Biophys. Res. Commun. (2018); 505(1):40-44.
Ma, X. et al. "Prussian blue nanozyme as a pyroptosis inhibitor alleviates neurodegeneration" Adv. Mater. (2022); 34(15):e2106723, 12 pages.
Masters, Specific inflammasomes in complex diseases. Clin Immunol. Jun. 2013;147(3):223-228. doi: 10.1016/j.clim.2012.12.006.
Menu et al. The NLRP3 inflammasome in health and disease: the good, the bad and the ugly. Clin Exp Immunol. Oct. 2011;166(1):1-15. doi: 10.1111/j.1365-2249.2011.04440.x. Epub Jul. 15, 2011.
Moossavi et al. "Role of the NLRP3 inflammasome in cancer" Mol. Cancer (2018); 17(1):158, 13 pages.
Mridha et al. "NLRP3 inflammasome blockade reduces liver inflammation and fibrosis in experimental NASH in mice" J. Hepatol. (2017); 66(5):1037-1046.
Neudecker et al., Myeloid-derived miR-223 regulates intestinal inflammation via repression of the NLRP3 inflammasome. J Exp Med. Jun. 5, 2017;214(6):1737-1752. doi: 10.1084/jem.20160462.
Nguyen, L.T., et al. "Role of NLRP3 Inflammasome in Parkinson's Disease and Therapeutic Considerations" J Parkinson's Dis. (2022); 12(7):2117-2133.
Niebuhr et al., Impaired NLRP3 inflammasome expression and function in atopic dermatitis due to Th2 milieu. Allergy. Aug. 2014;69(8):1058-1067. doi: 10.1111/all.12428.
Omenetti et al. "Increased NLRP3-dependent interleukin 1beta secretion in patients with familial Mediterranean fever: correlation with MEFV genotype" Ann Rheum Dis. (2014); 73(2):462-469.
Ozaki et al. "Targeting the NLRP3 inflammasome in chronic inflammatory diseases: current perspectives" Journal Inflammation Research (2015); 8:15-27.
Paldino et al. "Pyroptotic cell death in the R6/2 mouse model of Huntington's disease: new insight on the inflammasome" Cell Death Discov. (2020); 6:69, 12 pages.
Perregaux et al.; Identification and characterization of a novel class of interleukin-1 post-translational processing inhibitors. J Pharmacol Exp Ther. Oct. 2001;299(1):187-197.
Peukert, S., et al., "A method for estimating the risk of drug-induced phototoxicity and its application to smoothened inhibitors†," Med. Chem. Commun., (2011); 2:973-976.
Pike et al. "Dopamine signaling modulates microglial NLRP3 inflammasome activation: implications for Parkinson's disease" Journal of Neuroinflammation (2022); 19(50):1-16.
Primiano et al., Efficacy and Pharmacology of the NLRP3 Inflammasome Inhibitor CP-456,773 (CRID3) in Murine Models of Dermal and Pulmonary Inflammation. J Immunol. Sep. 15, 2016;197(6):2421-2433. doi: 10.4049/jimmunol.1600035.
PubChem CID 42507259 "2-methoxy-1-(1,3,4,5-tetrahydro-2H-pyrido[4,3-b]indol-2-yl)ethanone" Entered May 30, 2009, Modified Jan. 15, 2023, 7 pages.
Puyang et al., Retinal Ganglion Cell Loss is Delayed Following Optic Nerve Crush in NLRP3 Knockout Mice. Sci Rep. Feb. 19, 2016;6:20998. doi: 10.1038/srep20998, 8 pages.
Qin et al., Propionibacterium acnes induces IL-1β secretion via the NLRP3 inflammasome in human monocytes. J Invest Dermatol. Feb. 2014;134(2):381-388. doi: 10.1038/jid.2013.309.
Qin, Y et al. "Impaired autophagy in microglia aggravates dopaminergic neuro-degeneration by regulating NLRP3 inflammasome activation in experimental models of Parkinson's disease" Brain Behav. Immun. (2021); 91:324-338.
Ridker et al., Cantos Trial Group. Antiinflammatory Therapy with Canakinumab for Atherosclerotic Disease. N Engl J Med. Sep. 21, 2017;377(12):1119-1131. doi: 10.1056/NEJMoa1707914.
Ridker et al., Cantos Trial Group. Effect of interleukin-1β inhibition with canakinumab on incident lung cancer in patients with atherosclerosis: exploratory results from a randomised, double-blind, placebo-controlled trial. Lancet. Oct. 21, 2017;390(10105):1833-1842. doi: 10.1016/S0140-6736(17)32247-X.
Sako "Product class 18: pyridopyridazines". Science of Synthesis (2004) 16: 1109-1153.
Sandanger et al. "The NLRP3 inflammasome is up-regulated in cardiac fibroblasts and mediates myocardial ischaemia-reperfusion injury" Cardiovasc. Res. (2013); 99:164-174.
Sano et al., Tet2-Mediated Clonal Hematopoiesis Accelerates Heart Failure Through a Mechanism Involving the IL-1β/NLRP3 Inflammasome. J Am Coll Cardiol. Feb. 27, 2018;71(8):875-886. doi: 10.1016/j.jacc.2017.12.037.
Sayed, M.A. et al. (1991) Synthesis and reactions of 4-aryl-1(2H) phthalazinones. Chinese Journal of Chemistry, 9(1):45-53, DOI: 10.1002/cjoc.19910090107.
Schroder et al., The inflammasomes. Cell. Mar. 19, 2010;140(6):821-832. doi: 10.1016/j.cell.2010.01.040.
Schroder et al., The NLRP3 inflammasome: a sensor for metabolic danger? Science. Jan. 15, 2010;327(5963):296-300. doi: 10.1126/science.1184003.
Scott et al., A randomised trial evaluating anakinra in early active rheumatoid arthritis. Clin Exp Rheumatol. Jan.-Feb. 2016;34(1):88-93.
Sefik et al. "Inflammasome activation in infected macrophages drives COVID-19 pathology" Nature (2022); 606(7914):585-593.
Sharif et al. "Structural mechanism for NEK7-licensed activation of NLRP3 inflammasome" Nature (2019); 570(7761):338-343.

(56) References Cited

OTHER PUBLICATIONS

Shen, C. et al. "Molecular mechanism for NLRP6 inflammasome assembly and activation" Proceedings of the National Academy of Sciences (2019); 116(6):2052-2057.
Siew et al. "Galectin-3 is required for the microglia-mediated brain inflammation in a model of Huntington's disease" Nat. Commun. (2019); 10(1):3473, 18 pages.
Stackowicz et al. "Neutrophil-specific gain-of-function mutations in Nlrp3 promote development of cryopyrin-associated periodic syndrome" J. Exp. Med. (2021); 2018(10):e20201466, 11 pages.
Stienstra et al. "Inflammasome is a central player in the induction of obesity and insulin resistance" Proc. Natl. Acad. Sci. (2011); 108:15324-15329.
Stienstra et al. "The inflammasome-mediated caspase-1 activation controls adipocyte differentiation and insulin sensitivity" Cell Metab. (2010); 12:593-605.
Strowig et al., Inflammasomes in health and disease. Nature. Jan. 18, 2012;481(7381):278-286. doi: 10.1038/nature10759.
Su et al. "Recent progress on the discovery of NLRP3 inhibitors and their therapeutic potential", Current Medicinal Chemistry, (2021); 28(3):569-582.
Tarallo et al., DICER1 loss and Alu RNA induce age-related macular degeneration via the NLRP3 inflammasome and MyD88. Cell. May 11, 2012;149(4):847-859. doi: 10.1016/j.cell.2012.03.036.
Terrone et al. "Inflammation and reactive oxygen species in status epilepticus: Biomarkers and implications for therapy" Epilepsy & Behavior (2019); 101(106275):1-9.
Van Hout et al., The selective NLRP3-inflammasome inhibitor MCC950 reduces infarct size and preserves cardiac function in a pig model of myocardial infarction. Eur Heart J. Mar. 14, 2017;38(11):828-836. doi: 10.1093/eurheartj/ehw247.
Walsh et al., Inflammasomes in the CNS. Nat Rev Neurosci. Feb. 2014;15(2):84-97. doi: 10.1038/nrn3638.
Wang, C. et al. "NLRP3 inflammasome activation triggers gasdermin D-independent inflammation" Science Immunology (2021); 6(64):eabj3859, 1-12.
Wang et al., Activation of NLRP3 inflammasome enhances the proliferation and migration of A549 lung cancer cells. Oncol Rep. Apr. 2016;35(4):2053-2064. doi: 10.3892/or.2016.4569.
Wang, Y. et al. "Thioredoxin-1 attenuates atherosclerosis development through inhibiting NLRP3 inflammasome" Endocrine (2020); 70(1):65-70.
Wen et al., A role for the NLRP3 inflammasome in metabolic diseases—did Warburg miss inflammation? Nat Immunol. Mar. 19, 2012;13(4):352-357. doi: 10.1038/ni.2228.
Wu et al., NLRP3 (Nucleotide Oligomerization Domain-Like Receptor Family, Pyrin Domain Containing 3)-Caspase-1 Inflammasome Degrades Contractile Proteins: Implications for Aortic Biomechanical Dysfunction and Aneurysm and Dissection Formation. Arterioscler Thromb Vasc Biol. Apr. 2017;37(4):694-706. doi: 10.1161/ATVBAHA.116.307648.
Wu, X. et al. "Nicotine promotes atherosclerosis via ROS-NLRP3-mediated endothelial cell pyroptosis" Cell Death Dis. (2018); 9(2):171, 12 pages.
Xiao, L. et al. "Cryo-EM structures of the active NLRP3 inflammasome disc" Nature (2023); 613(7944):595-600.
Yan, Y. et al. "Dopamine controls systemic inflammation through inhibition of NLRP3 inflammasome" Cell (2015); 160:62-73.
Yang X. et al. "Pannexin 1 channels contribute to IL-1β expression via NLRP3/caspase-1 inflammasome in Aspergillus Fumigatus Keratitis" Current Eye Research (2019); 44:716-725.
Yao, C. et al. "Enhanced cardiomyocyte NLRP3 inflammasome signaling promotes atrial fibrillation" Circulation (2018); 138:2227-2242.
Yin, Z. et al. "Transcriptome analysis of human adipocytes implicates the NOD-like receptor pathway in obesity-induced adipose inflammation" Mol. Cell. Endocrinol. (2014); 394:80-87.
Zahid et al. "Pharmacological Inhibitors of the NLRP3 Inflammasome" Front Immunol. (2019); 10:2538, 10 pages.
Zeng, C. et al. "NLRP3 inflammasome-mediated pyroptosis contributes to the pathogenesis of non-ischemic dilated cardiomyopathy" Redox Biol. (2020); 34:101523, 13 pages.
Zhang et al., Increased Expression of NLRP3 Inflammasome in Wall of Ruptured and Unruptured Human Cerebral Aneurysms: Preliminary Results. J Stroke Cerebrovasc Dis. May 2015;24(5):972-979. doi: 10.1016/j.jstrokecerebrovasdis.2014.12.019.
Zheng, F. et al. "NLRP3 inflammasomes show high expression in aorta of patients with atherosclerosis" Heart Lung and Circulation (2013); 22:746-750.
Zhu, Z. et al. "Alpinetin exerts anti-inflammatory anti-oxidative and anti-angio-genic effects through activating the Nrf2 pathway and inhibiting NLRP3 pathway in carbon tetrachloride-induced liver fibrosis" Int. Immunopharmacology (2021); 96(107660):1-11.

* cited by examiner

PYRIDO-[3,4-D]PYRIDAZINE AMINE DERIVATIVES USEFUL AS NLRP3 INHIBITORS

RELATED APPLICATIONS

This application is a continuation of U.S. patent application Ser. No. 18/785,350, filed Jul. 26, 2024, which is a continuation of U.S. patent application Ser. No. 18/763,277, filed Jul. 3, 2024, which is a continuation of U.S. patent application Ser. No. 18/190,920, filed Mar. 27, 2023, which is a continuation of International PCT Application No. PCT/US2023/064967, filed Mar. 24, 2023, which claims priority to U.S. Provisional Application 63/420,930, filed Oct. 31, 2022, and U.S. Provisional Application No. 63/443,874, filed Feb. 7, 2023, the entire contents of each of which are incorporated herein by reference.

FIELD OF DISCLOSURE

The present disclosure is directed to inhibitors of NLR family pyrin domain containing 3 (NLRP3) proteins. The inhibitors described herein are useful in the treatment of diseases and disorders associated with the modulation of NLRP3 proteins. In particular, the invention is concerned with compounds and pharmaceutical compositions inhibiting NLRP3, methods of treating diseases and disorders associated with NLRP3 using said compounds and pharmaceutical compositions, and methods of synthesizing said compounds and compositions.

BACKGROUND

Innate immune responses are mediated by different types of receptors termed pattern-recognition receptors (PRRs). PRRs recognize the presence of pathogen-associated molecular patterns (PAMPs) and damage-associated molecular patterns (DAMPs). Once engaged these receptors trigger the activation of downstream inflammatory pathways that will help resolve injury. However, in many instances this activation can be uncontrolled and leads to disease.

The inflammasomes represent a class of PRRs that are crucial components of the innate immune response. Activation of the inflammasomes trigger a cascade of events that releases IL-10, IL-18, and promotes an inflammatory form of cell death called pyroptosis induced by the activation of Gasdermin. Pyroptosis is a unique form of inflammatory cell death that leads to the release of not only cytokines but also other intracellular components that promote a broader immune response both of the innate and acquired immune system. Thus, inflammasome activation is a major regulatory of the inflammatory cascade.

NLRP3 is the most characterized inflammasome and has been shown to be critical in innate immunity and inflammatory responses. While several other NLR complexes, such as NLRC4, are activated under very specific circumstances, NLRP3 can be activated by numerous stimuli and should be seen as a sensor of intracellular homeostatic imbalance. Therefore, its precise functioning is essential. In addition to playing a role in host immune defense, dysregulation of NLRP3 has been linked to the pathogenesis of many inflammatory disorders. These include genetic diseases such as cryopyrin-associated periodic syndromes (CAPS) which is caused by gain-of-function mutations in the NLRP3 gene, as well as many prevalent neurologic and systemic diseases. Importantly, NLRP3 hyperactivation has been demonstrated pre-clinically to play a critical role in a plethora of inflammatory and degenerative diseases including, NASH, atherosclerosis and other cardiovascular diseases, Alzheimer's disease, Parkinson's disease, diabetes, gout, and numerous other autoinflammatory diseases. Thus, there is an unmet need in the field to develop small molecules for modulating NLRP3 activity to treat various diseases and disorders.

SUMMARY

In one aspect, the present disclosure provides, inter alia, a compound of Formula (I):

(I)

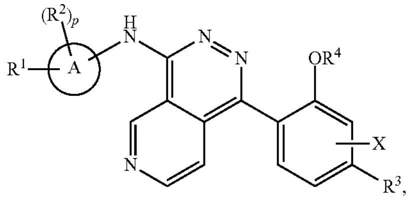

or a pharmaceutically acceptable salt, solvate, clathrate, hydrate, stereoisomer, tautomer, isotopically labeled compound, or prodrug thereof, wherein:

A is a 5- to 8-membered monocyclic heterocycloalkyl, wherein the heterocycloalkyl comprises at least one O ring atom;

$R^1$ is halogen, $C_1$-$C_6$ alkyl, or $C_1$-$C_6$ alkoxy;

$R^2$ is halogen or $C_1$-$C_6$ alkyl;

or $R^1$ and $R^2$, together with the atoms to which they are attached, form a 3- or 4-membered carbocyclic ring;

$R^3$ is —OH, halogen, $C_1$-$C_6$ alkyl, or $C_1$-$C_6$ alkoxy;

X is H, —OH, halogen, —$NH_2$, —$NH(C_1$-$C_6$ alkyl), —$N(C_1$-$C_6$ alkyl$)_2$, or $C_1$-$C_6$ alkyl; and $R^4$ is H, $C_1$-$C_6$ alkyl, or —$C(O)(C_1$-$C_6$ alkyl); and p is 0 or 1, wherein each instance of alkyl, alk-, or carbocyclic is independently substituted with 0, 1, 2, or 3 halogen atoms, and when $R^3$ is Cl, then

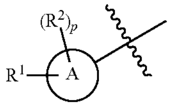

is not

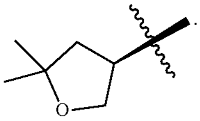
.

In some embodiments, the compound of Formula (I) is not

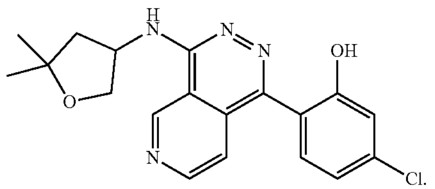 [SMILES: CC1(C)CC(Nc2nnc(-c3ccc(Cl)cc3O)c3ccncc23)CO1]

In some embodiments, the compound has a Kpu,u of >0.3.

In another aspect, the present disclosure provides, inter alia, suitable compounds selected from Tables 1 or 2, and pharmaceutically acceptable salts, solvates, clathrates, hydrates, stereoisomers, or tautomers thereof.

In another aspect, the present disclosure provides, inter alia, suitable compounds selected from:

(R)-5-chloro-2-(4-((4,4-dimethyltetrahydrofuran-3-yl) amino)pyrido[3,4-d]pyridazin-1-yl)phenol;

5-(difluoromethyl)-2-(4-((2-(methoxy-d3)-2-methylpropyl) amino)pyrido[3,4-d]pyridazin-1-yl)phenol;

(R)-5-chloro-2-(4-((3,3-dimethyltetrahydro-2H-pyran-4-yl) amino)pyrido[3,4-d]pyridazin-1-yl)phenol;

(S)-5-chloro-2-(4-((2,2-dimethyltetrahydro-2H-pyran-4-yl) amino)pyrido[3,4-d]pyridazin-1-yl)phenol;

(R)-2-(4-((5,5-dimethyltetrahydrofuran-3-yl)amino)pyrido [3,4-d]pyridazin-1-yl)-5-methylphenol; and (S)-2-(4-(((4-methylmorpholin-2-yl)methyl)amino)pyrido [3,4-d]pyridazin-1-yl)-5-(trifluoromethyl)phenol and pharmaceutically acceptable salts, solvates, clathrates, hydrates, stereoisomers, or tautomers thereof.

Another aspect of the disclosure relates to pharmaceutical compositions comprising (R)-5-chloro-2-(4-((4,4-dimethyltetrahydrofuran-3-yl)amino)pyrido[3,4-d]pyridazin-1-yl) phenol or a pharmaceutically acceptable salt thereof, and a pharmaceutically acceptable diluent or carrier.

Another aspect of the disclosure relates to pharmaceutical compositions comprising 5-(difluoromethyl)-2-(4-((2-(methoxy-d3)-2-methylpropyl)amino)pyrido[3,4-d] pyridazin-1-yl)phenol or a pharmaceutically acceptable salt thereof, and a pharmaceutically acceptable diluent or carrier.

Another aspect of the disclosure relates to pharmaceutical compositions comprising (R)-5-chloro-2-(4-((3,3-dimethyltetrahydro-2H-pyran-4-yl)amino)pyrido[3,4-d]pyridazin-1-yl)phenol or a pharmaceutically acceptable salt thereof, and a pharmaceutically acceptable diluent or carrier.

Another aspect of the disclosure relates to pharmaceutical compositions (S)-5-chloro-2-(4-((2,2-dimethyltetrahydro-2H-pyran-4-yl)amino)pyrido[3,4-d]pyridazin-1-yl)phenol or a pharmaceutically acceptable salt thereof, and a pharmaceutically acceptable diluent or carrier.

Another aspect of the disclosure relates to pharmaceutical compositions comprising (R)-2-(4-((5,5-dimethyltetrahydrofuran-3-yl)amino)pyrido[3,4-d]pyridazin-1-yl)-5-methylphenol or a pharmaceutically acceptable salt thereof, and a pharmaceutically acceptable diluent or carrier.

Another aspect of the disclosure relates to pharmaceutical compositions comprising (S)-2-(4-(((4-methylmorpholin-2-yl)methyl)amino)pyrido[3,4-d]pyridazin-1-yl)-5-(trifluoromethyl)phenol or a pharmaceutically acceptable salt thereof, and a pharmaceutically acceptable diluent or carrier.

In some aspects, the present disclosure provides compounds obtainable by, or obtained by, a method for preparing a compound as described herein (e.g., a method comprising one or more steps described in Schemes 1 and 2).

In some aspects, the present disclosure provides pharmaceutical compositions comprising a compound of the present disclosure, or a pharmaceutically acceptable salt thereof, and a pharmaceutically acceptable diluent or carrier.

In some aspects, the present disclosure provides an intermediate as described herein, being suitable for use in a method for preparing a compound as described herein (e.g., the intermediate is selected from the intermediates described in Examples 1-11).

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a compound of the present disclosure or a pharmaceutically acceptable salt thereof for use in treating or preventing a disease or disorder disclosed herein.

In some aspects, the present disclosure provides a compound of the present disclosure or a pharmaceutically acceptable salt thereof for use in treating a disease or disorder disclosed herein.

In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides use of a compound of the present disclosure or a pharmaceutically acceptable salt thereof in the manufacture of a medicament for treating a disease or disorder disclosed herein.

In some aspects, the present disclosure provides a method of treating or preventing an NLRP3-related disease or disorder selected from Parkinson's disease, Alzheimer's disease, multiple sclerosis, refractory epilepsy, stroke, ALS, headache/pain, and traumatic brain injury. The method comprises administering to the subject at least one therapeutically effective amount of the compound disclosed herein.

In some embodiments, the disease or disorder is inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease in a subject that has been determined to carry a germline or somatic non-silent mutation in NLRP3.

In some embodiments, the disease or disorder of the central nervous system is Parkinson's disease, Alzheimer's disease, traumatic brain injury, spinal cord injury, amyotrophic lateral sclerosis, or multiple sclerosis.

In some embodiments, the kidney disease is an acute kidney disease, a chronic kidney disease, or a rare kidney disease.

In some embodiments, the skin disease is psoriasis, hidradenitis suppurativa (HS), or atopic dermatitis.

In some embodiments, the rheumatic disease is dermatomyositis, Still's disease, or juvenile idiopathic arthritis.

In some embodiments, the NLRP3-related disease in a subject that has been determined to carry a germline or somatic non-silent mutation in NLRP3 is cryopyrin-associated autoinflammatory syndrome.

In some embodiments, the cryopyrin-associated autoinflammatory syndrome is familial cold autoinflammatory syndrome, Muckle-Wells syndrome, or neonatal onset multisystem inflammatory disease.

In some aspects, the present disclosure provides a method of preparing a compound of the present disclosure.

In some aspects, the present disclosure provides a method of preparing a compound, comprising one or more steps described herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

The present disclosure relates to phthalazine derivatives, pharmaceutically acceptable salts, solvates, clathrates, hydrates, stereoisomers (e.g., single stereoisomers, mixtures of stereoisomers, or racemic mixtures of stereoisomers), tautomers, prodrugs, and isotopically labeled compounds thereof, which may inhibit NLRP3 activity and are accordingly useful in methods of treatment of the human or animal body. Certain compounds of this invention demonstrate surprising and unexpected superiority with regard to brain penetration. The present disclosure also relates to processes for the preparation of these compounds, to pharmaceutical compositions comprising them and to their use in the treatment of disorders in which NLRP3 is implicated, such as inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease in a subject that has been determined to carry a germline or somatic non-silent mutation in NLRP3.

Definitions

Unless otherwise stated, the following terms used in the specification and claims have the following meanings set out below.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, I-propyl, n-butyl, s-butyl, t-butyl, n-pentyl, i-pentyl, or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

An alkyl group may be an "optionally substituted alkyl", which refers to an unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted carbocyclic or heterocycloalkyl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "cyano" refers to a nitrile radical (e.g., —CN).

As used herein, the term "cycloalkyl" or "carbocyclic" or "carbocyclyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl.

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more ring heteroatoms (such as O, N, S, P, or Se), e.g., 1 or 1-2 or 1-3 or 1-4 or 1-5 or 1-6 ring heteroatoms, or e.g., 1, 2, 3, 4, 5, or 6 ring heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, 5,6-dihydro-4H-cyclopenta[b]thiophenyl, and the like. In the case of multicyclic heterocycloalkyl, only one of the rings in the heterocycloalkyl needs to be non-aromatic (e.g., 4,5,6,7-tetrahydrobenzo[c]isoxazolyl).

As used herein, the term "optionally substituted heterocycloalkyl" refers to unsubstituted heterocycloalkyl having designated substituents replacing one or more hydrogen atoms on one or more carbon or heteroatom. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "hydroxy" or "hydroxyl" includes groups with an —OH or —O—.

As used herein, the term "halo" or "halogen" refers to fluoro, chloro, bromo and iodo.

The term "haloalkyl" or "haloalkoxyl" refers to an alkyl or alk-moiety of the alkoxyl substituted with one or more halogen atoms.

As used herein, the term "alkoxy" or "alkoxyl" includes substituted and unsubstituted alkyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

Unless otherwise specifically defined, the term "aryl" refers to cyclic, aromatic hydrocarbon groups that have 1 to 3 aromatic rings, including monocyclic or bicyclic groups such as phenyl, biphenyl, or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)$(OH)_2$, —OC(O)($C_1$-$C_6$) alkyl, —C(O)($C_1$-$C_6$) alkyl, —OC(O)O($C_1$-$C_6$) alkyl, —$NH_2$, NH(($C_1$-$C_6$) alkyl), N(($C_1$-$C_6$) alkyl)$_2$, —S(O)$_2$—($C_1$-$C_6$) alkyl, —S(O)NH($C_1$-$C_6$) alkyl, and —S(O)N(($C_1$-$C_6$) alkyl)$_2$.

The substituents can themselves be optionally substituted. Furthermore, when containing two or more fused rings, the aryl groups herein defined may have a saturated or partially unsaturated ring fused with a fully unsaturated aromatic ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, 10,11-dihydro-5H-dibenzo[a,d][7]annulenyl, and the like.

Unless otherwise specifically defined, "heteroaryl" means a monovalent monocyclic or polycyclic aromatic radical of 5 to 24 ring atoms, containing one or more ring heteroatoms selected from N, O, S, P, Se, or B, the remaining ring atoms being C. Heteroaryl as herein defined also means a bicyclic heteroaromatic group wherein the heteroatom is selected from N, O, S, P, Se, or B. Heteroaryl as herein defined also means a tricyclic heteroaromatic group containing one or more ring heteroatoms selected from N, O, S, P, Se, or B. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolinyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4] thiazinyl, benzoxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore, when containing two or more fused rings, the heteroaryl groups defined herein may have one or more saturated or partially unsaturated ring fused with a fully unsaturated aromatic ring, e.g., a 5-membered heteroaromatic ring containing 1 to 3 heteroatoms selected from N, O, S, P, Se, or B, or a 6-membered heteroaromatic ring containing 1 to 3 nitrogens, wherein the saturated or partially unsaturated ring includes 0 to 4 heteroatoms selected from N, O, S, P, Se, or B, and is optionally substituted with one or more oxo. In heteroaryl ring systems containing more than two fused rings, a saturated or partially unsaturated ring may further be fused with a saturated or partially unsaturated ring described herein. Exemplary ring systems of these heteroaryl groups include, for example, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuranyl, benzofuranonyl, indolinyl, oxindolyl, indolyl, 1,6-dihydro-7H-pyrazolo[3,4-c]pyridin-7-onyl, 7,8-dihydro-6H-pyrido[3,2-b]pyrrolizinyl, 8H-pyrido[3,2-b]pyrrolizinyl, 1,5,6,7-tetrahydrocyclopenta[b]pyrazolo[4,3-e]pyridinyl, 7,8-dihydro-6H-pyrido[3,2-b]pyrrolizine, pyrazolo[1,5-a]pyrimidin-7(4H)-only, 3,4-dihydropyrazino[1,2-a]indol-1(2H)-onyl, 7-oxabicyclo[2.2.1]heptanyl, or benzo[c][1,2]oxaborol-1(3H)-olyl.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

It is to be understood that the present disclosure provides methods for the synthesis of the compounds of any of the Formulae described herein. The present disclosure also provides detailed methods for the synthesis of various disclosed compounds of the present disclosure according to the following schemes as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, 5th edition, John Wiley & Sons: New York, 2001; Greene, T. W., Wuts, P. G. M., Protective Groups in Organic Synthesis, 3rd edition, John Wiley & Sons: New York, 1999; R. Larock, Comprehensive Organic Transformations, VCH Publishers (1989); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), incorporated by reference herein, are useful and recognized reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognise that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., Protective Groups in Organic Synthesis, 3rd edition, John Wiley & Sons: New York, 1999.

It is to be understood that, unless otherwise stated, any description of a method of treatment or prevention includes use of the compounds to provide such treatment or prevention as is described herein. It is to be further understood, unless otherwise stated, any description of a method of treatment or prevention includes use of the compounds to prepare a medicament to treat or prevent such condition. The treatment or prevention includes treatment or prevention of human or non-human animals including rodents and other disease models.

It is to be understood that, unless otherwise stated, any description of a method of treatment includes use of the compounds to provide such treatment as is described herein. It is to be further understood, unless otherwise stated, any description of a method of treatment includes use of the compounds to prepare a medicament to treat such condition. The treatment includes treatment of human or non-human animals including rodents and other disease models. As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. In one embodiment, the mammal is a human. A subject in need thereof can be one who has been previously diagnosed or identified as having a disease or disorder disclosed herein. A subject in need thereof can also be one who is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that does not respond or has not yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model. It is to be appreciated that references to "treating" or "treatment" include the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., Current Protocols in Molecular Biology, John Wiley and Sons, Inc. (2005); Sambrook et al., Molecular Cloning, A Laboratory Manual (3rd edition), Cold Spring Harbor Press, Cold Spring Harbor, New York (2000); Coligan et al., Current Protocols in Immunology, John Wiley & Sons, N.Y.; Enna et al., Current Protocols in Pharmacology, John Wiley & Sons, N.Y.; Fingl et al., The Pharmacological Basis of Therapeutics (1975), Remington's Pharmaceutical Sciences, Mack Publishing Co., Easton, PA, 18th edition (1990). These texts can also be referred to in making or using an aspect of the disclosure.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., ingestion), inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., a disease or disorder disclosed herein) and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

It is to be understood that, for any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are desired. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease or disorder disclosed herein and also preferably causing complete regression of the disease or disorder. Dosages can range from about 0.01 mg/kg per day to about 5000 mg/kg per day. An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

In some embodiments, the pharmaceutically acceptable salt is a sodium salt, a potassium salt, a calcium salt, a magnesium salt, a diethylamine salt, a choline salt, a meglumine salt, a benzathine salt, a tromethamine salt, an ammonia salt, an arginine salt, or a lysine salt.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognise the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition. An ordinarily skilled physician or veterinarian can readily determine and prescribe the effective amount of the drug required to counter or arrest the progress of the condition.

Techniques for formulation and administration of the disclosed compounds of the disclosure can be found in Remington: the Science and Practice of Pharmacy, 19th edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

As use herein, the phrase "compound of the disclosure" refers to those compounds which are disclosed herein, both generically and specifically.

Compounds of the Present Disclosure

In one aspect, the present disclosure provides, inter alia, a compound of Formula (I):

(I)

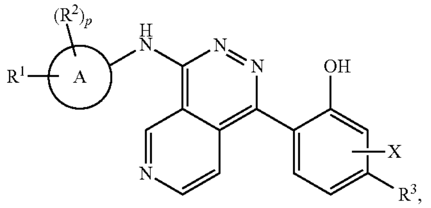

or a pharmaceutically acceptable salt, solvate, clathrate, hydrate, stereoisomer, tautomer, isotopically labeled compound, or prodrug thereof, wherein:

- A is a 5- to 8-membered monocyclic heterocycloalkyl, wherein the heterocycloalkyl comprises at least one O ring atom;
- $R^1$ is halogen, $C_1$-$C_6$ alkyl, or $C_1$-$C_6$ alkoxy;
- $R^2$ is halogen or $C_1$-$C_6$ alkyl;
- or $R^1$ and $R^2$, together with the atoms to which they are attached, form a 3- or 4-membered carbocyclic ring;
- $R^3$ is —OH, halogen, $C_1$-$C_6$ alkyl, or $C_1$-$C_6$ alkoxy;
- X is H, —OH, halogen, —$NH_2$, —$NH(C_1$-$C_6$ alkyl), —$N(C_1$-$C_6$ alkyl$)_2$, or $C_1$-$C_6$ alkyl; and
- $R^4$ is H, $C_1$-$C_6$ alkyl, or —$C(O)(C_1$-$C_6$ alkyl); and
- p is 0 or 1, wherein each instance of alkyl, alk-, or carbocyclic is independently substituted with 0, 1, 2, or 3 halogen atoms; and when $R^3$ is Cl, then

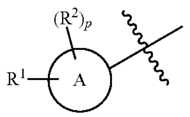

is not

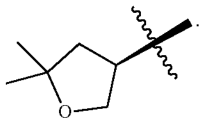

In some embodiments, the compound of Formula (I) is not

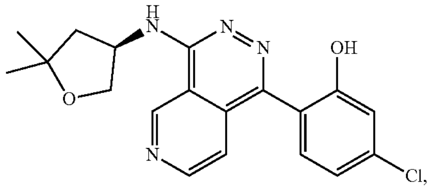 [SMILES: CC1(C)C[C@@H](Nc2nnc(-c3ccc(Cl)cc3O)c3ccncc23)CO1]

or a pharmaceutically acceptable salt, solvate, clathrate, hydrate, stereoisomer, tautomer, isotopically labeled compound, or prodrug thereof.

In some embodiments, the compound is of Formula (I) wherein p is 1; $R^1$ is $C_1$-$C_6$ alkyl or $C_1$-$C_6$ alkoxy; and $R^2$ is $C_1$-$C_6$ alkyl.

In some embodiments, A is a 5- to 8-membered monocyclic heterocycloalkyl, wherein the heterocycloalkyl comprises of at least one O ring atom. In some embodiments, A is a 5- to 8-membered monocyclic heterocycloalkyl, wherein the heterocycloalkyl comprises one O ring atom.

In some embodiments, A is a 5-membered monocyclic heterocycloalkyl, wherein the heterocycloalkyl comprises of at least one O ring atom. In some embodiments, A is a 5-membered monocyclic heterocycloalkyl, wherein the heterocycloalkyl comprises one O ring atom.

In some embodiments, A is a 6-membered monocyclic heterocycloalkyl, wherein the heterocycloalkyl comprises of at least one O ring atom. In some embodiments, A is a 6-membered monocyclic heterocycloalkyl, wherein the heterocycloalkyl comprises one O ring atom.

In some embodiments, A is a 7-membered monocyclic heterocycloalkyl, wherein the heterocycloalkyl comprises of at least one O ring atom. In some embodiments, A is a 7-membered monocyclic heterocycloalkyl, wherein the heterocycloalkyl comprises one O ring atom.

In some embodiments, A is a 8-membered monocyclic heterocycloalkyl, wherein the heterocycloalkyl comprises of at least one O ring atom. In some embodiments, A is a 8-membered monocyclic heterocycloalkyl, wherein the heterocycloalkyl comprises one O ring atom.

In some embodiments, p is 0 or 1.

In some embodiments, p is 0. In some embodiments, p is 1.

In some embodiments, $R^1$ is halogen, $C_1$-$C_6$ alkyl, or $C_1$-$C_6$ alkoxy, wherein the alkyl or alkoxy is independently substituted with 0, 1, 2, or 3 halogen atoms.

In some embodiments, $R^1$ is halogen, $C_1$-$C_6$ alkyl, or $C_1$-$C_6$ alkoxy, wherein the alkyl or alkoxy is substituted with 1, 2, or 3 halogen atoms.

In some embodiments, $R^1$ is halogen, $C_1$-$C_6$ alkyl, or $C_1$-$C_6$ alkoxy.

In some embodiments, $R^1$ is halogen.

In some embodiments, $R^1$ is F, Cl, Br, or I.

In some embodiments, $R^1$ is F. In some embodiments, $R^1$ is Cl. In some embodiments, $R^1$ is Br. In some embodiments, $R^1$ is I.

In some embodiments, $R^1$ is $C_1$-$C_6$ alkyl substituted with 0, 1, 2, or 3 halogen.

In some embodiments, $R^1$ is $C_1$-$C_6$ alkyl substituted with 1, 2, or 3 halogen.

In some embodiments, $R^1$ is $C_1$-$C_6$ alkyl.

In some embodiments, $R^1$ is methyl substituted with 0, 1, 2, or 3 halogen. In some embodiments, $R^1$ is ethyl substituted with 0, 1, 2, or 3 halogen. In some embodiments, $R^1$ is propyl substituted with 0, 1, 2, or 3 halogen. In some embodiments, $R^1$ is butyl substituted with 0, 1, 2, or 3 halogen. In some embodiments, $R^1$ is pentyl substituted with 0, 1, 2, or 3 halogen. In some embodiments, $R^1$ is hexyl substituted with 0, 1, 2, or 3 halogen. In some embodiments, each $R^1$ is isopropyl substituted with 0, 1, 2, or 3 halogen. In some embodiments, $R^1$ is isobutyl substituted with 0, 1, 2, or 3 halogen. In some embodiments, $R^1$ is isopentyl substituted with 0, 1, 2, or 3 halogen. In some embodiments, $R^1$ is isohexyl substituted with 0, 1, 2, or 3 halogen. In some embodiments, $R^1$ is secbutyl substituted with 0, 1, 2, or 3 halogen. In some embodiments, $R^1$ is secpentyl substituted with 0, 1, 2, or 3 halogen. In some embodiments, $R^1$ is sechexyl substituted with 0, 1, 2, or 3 halogen. In some embodiments, $R^1$ is tertbutyl substituted with 0, 1, 2, or 3 halogen.

In some embodiments, $R^1$ is methyl substituted with 1, 2, or 3 halogen. In some embodiments, $R^1$ is ethyl substituted with 1, 2, or 3 halogen. In some embodiments, $R^1$ is propyl substituted with 1, 2, or 3 halogen. In some embodiments, $R^1$ is butyl substituted with 1, 2, or 3 halogen. In some embodiments, $R^1$ is pentyl substituted with 1, 2, or 3 halogen. In some embodiments, $R^1$ is hexyl substituted with 1, 2, or 3 halogen. In some embodiments, each $R^1$ is isopropyl substituted with 1, 2, or 3 halogen. In some embodiments, $R^1$ is isobutyl substituted with 1, 2, or 3 halogen. In some embodiments, $R^1$ is isopentyl substituted with 1, 2, or 3 halogen. In some embodiments, $R^1$ is isohexyl substituted with 1, 2, or 3 halogen. In some embodiments, $R^1$ is secbutyl substituted with 1, 2, or 3 halogen. In some embodiments, $R^1$ is secpentyl substituted with 1, 2, or 3 halogen. In some embodiments, $R^1$ is sechexyl substituted with 1, 2, or 3 halogen. In some embodiments, $R^1$ is tertbutyl substituted with 1, 2, or 3 halogen.

In some embodiments, $R^1$ is methyl. In some embodiments, $R^1$ is ethyl. In some embodiments, $R^1$ is propyl. In some embodiments, $R^1$ is butyl. In some embodiments, $R^1$ is pentyl. In some embodiments, $R^1$ is hexyl. In some embodiments, each $R^1$ is isopropyl. In some embodiments, $R^1$ is isobutyl. In some embodiments, $R^1$ is isopentyl. In some embodiments, $R^1$ is isohexyl. In some embodiments, $R^1$ is secbutyl. In some embodiments, $R^1$ is secpentyl. In some embodiments, $R^1$ is sechexyl. In some embodiments, $R^1$ is tertbutyl.

In some embodiments, $R^1$ is $C_1$-$C_6$ alkoxy substituted with 0, 1, 2, or 3 halogen.

In some embodiments, $R^1$ is $C_1$-$C_6$ alkoxy substituted with 1, 2, or 3 halogen.

In some embodiments, $R^1$ is $C_1$-$C_6$ alkoxy.

In some embodiments, $R^1$ is $C_1$ alkoxy substituted with 0, 1, 2, or 3 halogen. In some embodiments, $R^1$ is $C_2$ alkoxy substituted with 0, 1, 2, or 3 halogen. In some embodiments, $R^1$ is $C_3$ alkoxy substituted with 0, 1, 2, or 3 halogen. In some embodiments, $R^1$ is $C_4$ alkoxy substituted with 0, 1, 2, or 3 halogen. In some embodiments, $R^1$ is $C_5$ alkoxy substituted with 0, 1, 2, or 3 halogen. In some embodiments, $R^1$ is $C_6$ alkoxy substituted with 0, 1, 2, or 3 halogen.

In some embodiments, $R^1$ is $C_1$ alkoxy substituted with 1, 2, or 3 halogen. In some embodiments, $R^1$ is $C_2$ alkoxy substituted with 1, 2, or 3 halogen. In some embodiments, $R^1$ is $C_3$ alkoxy substituted with 1, 2, or 3 halogen. In some embodiments, $R^1$ is $C_4$ alkoxy substituted with 1, 2, or 3 halogen. In some embodiments, $R^1$ is $C_5$ alkoxy substituted with 1, 2, or 3 halogen. In some embodiments, $R^1$ is $C_6$ alkoxy substituted with 1, 2, or 3 halogen.

In some embodiments, $R^1$ is $C_1$ alkoxy. In some embodiments, $R^1$ is $C_2$ alkoxy. In some embodiments, $R^1$ is $C_3$ alkoxy. In some embodiments, $R^1$ is $C_4$ alkoxy. In some embodiments, $R^1$ is $C_5$ alkoxy. In some embodiments, $R^1$ is $C_6$ alkoxy.

In some embodiments, $R^2$ is halogen or $C_1$-$C_6$ alkyl substituted with 0, 1, 2, or 3 halogen.

In some embodiments, $R^2$ is halogen or $C_1$-$C_6$ alkyl substituted with 1, 2, or 3 halogen.

In some embodiments, $R^2$ is halogen or $C_1$-$C_6$ alkyl.

In some embodiments, $R^2$ is halogen.

In some embodiments, $R^2$ is F, Cl, Br, or I.

In some embodiments, $R^2$ is F. In some embodiments, $R^2$ is Cl. In some embodiments, $R^2$ is Br. In some embodiments, $R^2$ is I.

In some embodiments, $R^2$ is $C_1$-$C_6$ alkyl substituted with 0, 1, 2, or 3 halogen.

In some embodiments, $R^2$ is $C_1$-$C_6$ alkyl substituted with 1, 2, or 3 halogen.

In some embodiments, $R^2$ is $C_1$-$C_6$ alkyl.

In some embodiments, $R^2$ is methyl substituted with 0, 1, 2, or 3 halogen. In some embodiments, $R^2$ is ethyl substituted with 0, 1, 2, or 3 halogen. In some embodiments, $R^2$ is propyl substituted with 0, 1, 2, or 3 halogen. In some embodiments, $R^2$ is butyl substituted with 0, 1, 2, or 3 halogen. In some embodiments, $R^2$ is pentyl substituted with 0, 1, 2, or 3 halogen. In some embodiments, $R^2$ is hexyl substituted with 0, 1, 2, or 3 halogen. In some embodiments, $R^2$ is isopropyl substituted with 0, 1, 2, or 3 halogen. In some embodiments, $R^2$ is isobutyl substituted with 0, 1, 2, or 3 halogen. In some embodiments, $R^2$ is isopentyl substituted with 0, 1, 2, or 3 halogen. In some embodiments, $R^2$ is isohexyl substituted with 0, 1, 2, or 3 halogen. In some embodiments, $R^2$ is secbutyl substituted with 0, 1, 2, or 3 halogen. In some embodiments, $R^2$ is secpentyl substituted with 0, 1, 2, or 3 halogen. In some embodiments, $R^2$ is sechexyl substituted with 0, 1, 2, or 3 halogen. In some embodiments, $R^2$ is tertbutyl substituted with 0, 1, 2, or 3 halogen.

In some embodiments, $R^2$ is methyl substituted with 1, 2, or 3 halogen. In some embodiments, $R^2$ is ethyl substituted with 1, 2, or 3 halogen. In some embodiments, $R^2$ is propyl substituted with 1, 2, or 3 halogen. In some embodiments, $R^2$ is butyl substituted with 1, 2, or 3 halogen. In some embodiments, $R^2$ is pentyl substituted with 1, 2, or 3 halogen. In some embodiments, $R^2$ is hexyl substituted with 1, 2, or 3 halogen. In some embodiments, $R^2$ is isopropyl substituted with 1, 2, or 3 halogen. In some embodiments, $R^2$ is isobutyl substituted with 1, 2, or 3 halogen. In some embodiments, $R^2$ is isopentyl substituted with 1, 2, or 3 halogen. In some embodiments, $R^2$ is isohexyl substituted with 1, 2, or 3 halogen. In some embodiments, $R^2$ is secbutyl substituted with 1, 2, or 3 halogen. In some embodiments, $R^2$ is secpentyl substituted with 1, 2, or 3 halogen. In some embodiments, $R^2$ is sechexyl substituted with 1, 2, or 3 halogen. In some embodiments, $R^2$ is tertbutyl substituted with 1, 2, or 3 halogen.

In some embodiments, $R^2$ is methyl. In some embodiments, $R^2$ is ethyl. In some embodiments, $R^2$ is propyl. In some embodiments, $R^2$ is butyl. In some embodiments, $R^2$ is pentyl. In some embodiments, $R^2$ is hexyl. In some embodiments, $R^2$ is isopropyl. In some embodiments, $R^2$ is isobutyl. In some embodiments, $R^2$ is isopentyl. In some embodiments, $R^2$ is isohexyl. In some embodiments, $R^2$ is secbutyl. In some embodiments, $R^2$ is secpentyl. In some embodiments, $R^2$ is sechexyl. In some embodiments, $R^2$ is tertbutyl.

In some embodiments, $R^1$ and $R^2$, together with the atoms to which they are attached, form a 3- or 4-membered carbocyclic ring substituted with 0, 1, 2, or 3 halogen atoms.

In some embodiments, $R^1$ and $R^2$, together with the atoms to which they are attached, form a 3- or 4-membered carbocyclic ring substituted with 1, 2, or 3 halogen atoms.

In some embodiments, $R^1$ and $R^2$, together with the atoms to which they are attached, form a 3- or 4-membered carbocyclic ring.

In some embodiments, $R^1$ and $R^2$, together with the atoms to which they are attached, form a 3-membered carbocyclic ring substituted with 0, 1, 2, or 3 halogen atoms.

In some embodiments, $R^1$ and $R^2$, together with the atoms to which they are attached, form a 3-membered carbocyclic ring substituted with 1, 2, or 3 halogen atoms.

In some embodiments, $R^1$ and $R^2$, together with the atoms to which they are attached, form a 3-membered carbocyclic ring.

In some embodiments, $R^1$ and $R^2$, together with the atoms to which they are attached, form a 4-membered carbocyclic ring substituted with 0, 1, 2, or 3 halogen atoms.

In some embodiments, $R^1$ and $R^2$, together with the atoms to which they are attached, form a 4-membered carbocyclic ring substituted with 1, 2, or 3 halogen atoms.

In some embodiments, $R^1$ and $R^2$, together with the atoms to which they are attached, form a 4-membered carbocyclic ring.

In some embodiments, p is 1 and each of $R^1$ and $R^2$ is independently $C_1$-$C_6$ alkyl or $C_1$-$C_6$ haloalkyl. In some embodiments, p is 1 and each of $R^1$ and $R^2$ is independently $C_1$-$C_6$ alkyl or $C_1$-$C_6$ haloalkyl, wherein $R^1$ and $R^2$ are attached to the same carbon atom on Ring A.

In some embodiments, p is 1 and each of $R^1$ and $R^2$ is methyl. In some embodiments, p is 1 and each of $R^1$ and $R^2$ is methyl, wherein $R^1$ and $R^2$ are attached to the same carbon atom on Ring A.

In some embodiments, $R^3$ is —OH, halogen, $C_1$-$C_6$ alkyl, or $C_1$-$C_6$ alkoxy, wherein the alkyl or alkoxy is independently substituted with 0, 1, 2, or 3 halogen.

In some embodiments, $R^3$ is —OH, halogen, $C_1$-$C_6$ alkyl, or $C_1$-$C_6$ alkoxy, wherein the alkyl or alkoxy is substituted with 1, 2, or 3 halogen.

In some embodiments, $R^3$ is —OH, halogen, $C_1$-$C_6$ alkyl, or $C_1$-$C_6$ alkoxy.

In some embodiments, $R^3$ is —OH.

In some embodiments, $R^3$ is halogen.

In some embodiments, $R^3$ is Br. In some embodiments, $R^3$ is Cl. In some embodiments, $R^3$ is F. In some embodiments, $R^3$ is I.

In some embodiments, $R^3$ is not halogen.

In some embodiments, $R^3$ is $C_1$-$C_6$ alkyl or $C_1$-$C_6$ alkoxy.

In some embodiments, $R^3$ is $C_1$-$C_6$ alkyl substituted with 0, 1, 2, or 3 halogen.

In some embodiments, $R^3$ is $C_1$-$C_6$ alkyl substituted with 1, 2, or 3 halogen.

In some embodiments, $R^3$ is $C_1$-$C_6$ alkyl.

In some embodiments, $R^3$ is methyl substituted with 0, 1, 2, or 3 halogen. In some embodiments, $R^3$ is ethyl substituted with 0, 1, 2, or 3 halogen. In some embodiments, $R^3$ is propyl substituted with 0, 1, 2, or 3 halogen. In some embodiments, $R^3$ is butyl substituted with 0, 1, 2, or 3 halogen. In some embodiments, $R^3$ is pentyl substituted with 0, 1, 2, or 3 halogen. In some embodiments, $R^3$ is hexyl substituted with 0, 1, 2, or 3 halogen. In some embodiments, $R^3$ is isopropyl substituted with 0, 1, 2, or 3 halogen. In some embodiments, $R^3$ is isobutyl substituted with 0, 1, 2, or 3 halogen. In some embodiments, $R^2$ independently is isopentyl substituted with 0, 1, 2, or 3 halogen. In some embodiments, $R^3$ is isohexyl substituted with 0, 1, 2, or 3 halogen. In some embodiments, $R^3$ is secbutyl substituted with 0, 1, 2, or 3 halogen. In some embodiments, $R^3$ is secpentyl substituted with 0, 1, 2, or 3 halogen. In some embodiments, $R^3$ is sechexyl substituted with 0, 1, 2, or 3 halogen. In some embodiments, $R^3$ is tertbutyl substituted with 0, 1, 2, or 3 halogen.

In some embodiments, $R^3$ is methyl substituted with 1, 2, or 3 halogen. In some embodiments, $R^3$ is ethyl substituted with 1, 2, or 3 halogen. In some embodiments, $R^3$ is propyl substituted with 1, 2, or 3 halogen. In some embodiments, $R^3$ is butyl substituted with 1, 2, or 3 halogen. In some embodiments, $R^3$ is pentyl substituted with 1, 2, or 3 halogen. In some embodiments, $R^3$ is hexyl substituted with 1, 2, or 3 halogen. In some embodiments, $R^3$ is isopropyl substituted with 1, 2, or 3 halogen. In some embodiments, $R^3$ is isobutyl substituted with 1, 2, or 3 halogen. In some embodiments, $R^2$ independently is isopentyl substituted with 1, 2, or 3 halogen. In some embodiments, $R^3$ is isohexyl substituted with 1, 2, or 3 halogen. In some embodiments, $R^3$ is secbutyl substituted with 1, 2, or 3 halogen. In some embodiments, $R^3$ is secpentyl substituted with 1, 2, or 3 halogen. In some embodiments, $R^3$ is sechexyl substituted with 1, 2, or 3 halogen. In some embodiments, $R^3$ is tertbutyl substituted with 1, 2, or 3 halogen.

In some embodiments, $R^3$ is methyl. In some embodiments, $R^3$ is ethyl. In some embodiments, $R^3$ is propyl. In some embodiments, $R^3$ is butyl. In some embodiments, $R^3$ is pentyl. In some embodiments, $R^3$ is hexyl. In some embodiments, $R^3$ is isopropyl. In some embodiments, $R^3$ is isobutyl. In some embodiments, $R^2$ independently is isopentyl. In some embodiments, $R^3$ is isohexyl. In some embodiments, $R^3$ is secbutyl. In some embodiments, $R^3$ is secpentyl. In some embodiments, $R^3$ is sechexyl. In some embodiments, $R^3$ is tertbutyl.

In some embodiments, $R^3$ is $C_1$-$C_6$ alkoxy substituted with 0, 1, 2, or 3 halogen.

In some embodiments, $R^3$ is $C_1$-$C_6$ alkoxy substituted with 1, 2, or 3 halogen.

In some embodiments, $R^3$ is $C_1$-$C_6$ alkoxy.

In some embodiments, $R^3$ is methoxy substituted with 0, 1, 2, or 3 halogen. In some embodiments, $R^3$ is ethoxy substituted with 0, 1, 2, or 3 halogen. In some embodiments, $R^3$ is propoxy substituted with 0, 1, 2, or 3 halogen. In some embodiments, $R^3$ is butoxy substituted with 0, 1, 2, or 3 halogen. In some embodiments, $R^3$ is pentoxy substituted with 0, 1, 2, or 3 halogen. In some embodiments, $R^3$ is hexoxy substituted with 0, 1, 2, or 3 halogen.

In some embodiments, $R^3$ is methoxy substituted with 1, 2, or 3 halogen. In some embodiments, $R^3$ is ethoxy substituted with 1, 2, or 3 halogen. In some embodiments, $R^3$ is propoxy substituted with 1, 2, or 3 halogen. In some embodiments, $R^3$ is butoxy substituted with 1, 2, or 3 halogen. In some embodiments, $R^3$ is pentoxy substituted with 1, 2, or 3 halogen. In some embodiments, $R^3$ is hexoxy substituted with 1, 2, or 3 halogen.

In some embodiments, $R^3$ is methoxy. In some embodiments, $R^3$ is ethoxy. In some embodiments, $R^3$ is propoxy. In some embodiments, $R^3$ is butoxy. In some embodiments, $R^3$ is pentoxy. In some embodiments, $R^3$ is hexoxy.

In some embodiments, $R^3$ is Cl, methyl, —$CF_3$, —$CHF_2$, or —$OCHF_2$.

In some embodiments, $R^3$ is —$CF_3$, —$CHF_2$, or —$OCHF_2$.

In some embodiments, $R^3$ is $—CF_3$. In some embodiments, $R^3$ is $—CHF_2$. In some embodiments, $R^3$ is $—OCHF_2$.

In some embodiments, X is H, —OH, halogen, $—NH_2$, $—NH(C_1-C_6$ alkyl), $—N(C_1-C_6$ alkyl$)_2$, or $C_1-C_6$ alkyl.

In some embodiments, X is —OH, halogen, $—NH_2$, $—NH(C_1-C_6$ alkyl), $—N(C_1-C_6$ alkyl$)_2$, or $C_1-C_6$ alkyl.

In some embodiments, X is H.

In some embodiments, X is halogen.

In some embodiments, X is Br, Cl, F, or I.

In some embodiments, X is Br. In some embodiments, X is Cl. In some embodiments, X is F.

In some embodiments, X is I.

In some embodiments, X is —OH.

In some embodiments, X is $—NH_2$. In some embodiments, X is $—NH(C_1-C_6$ alkyl).

In some embodiments, X is $—NH(C_1$ alkyl). In some embodiments, X is $—NH(C_2$ alkyl). In some embodiments, X is $—NH(C_3$ alkyl). In some embodiments, X is $—NH(C_4$ alkyl). In some embodiments, X is $—NH(C_5$ alkyl). In some embodiments, X is $—NH(C_6$ alkyl).

In some embodiments, X is $—N(C_1-C_6$ alkyl$)_2$.

In some embodiments, X is $—N(C_1$ alkyl$)_2$. In some embodiments, X is $—N(C_2$ alkyl$)_2$. In some embodiments, X is $—N(C_3$ alkyl$)_2$. In some embodiments, X is $—N(C_4$ alkyl$)_2$. In some embodiments, X is $—N(C_5$ alkyl$)_2$. In some embodiments, X is $—N(C_6$ alkyl$)_2$.

In some embodiments, X is $C_1-C_6$ alkyl.

In some embodiments, X is methyl. In some embodiments, X is ethyl. In some embodiments, X is propyl. In some embodiments, X is butyl. In some embodiments, X is pentyl. In some embodiments, X is hexyl. In some embodiments, each X is isopropyl. In some embodiments, X is isobutyl. In some embodiments, X is isopentyl. In some embodiments, X is isohexyl. In some embodiments, X is secbutyl. In some embodiments, X is secpentyl. In some embodiments, X is sechexyl. In some embodiments, X is tertbutyl.

In some embodiments, X is H or F.

In some embodiments, $R^4$ is H, $C_1-C_6$ alkyl, $C_2-C_6$ alkenyl, $C_2-C_6$ alkynyl, or $—C(O)(C_1-C_6$ alkyl).

In some embodiments, $R^4$ is $C_1-C_6$ alkyl, $C_2-C_6$ alkenyl, $C_2-C_6$ alkynyl, or $—C(O)(C_1-C_6$ alkyl).

In some embodiments, $R^4$ is H.

In some embodiments, $R^4$ is $C_1-C_6$ alkyl.

In some embodiments, $R^4$ is methyl. In some embodiments, $R^4$ is ethyl. In some embodiments, $R^4$ is propyl. In some embodiments, $R^4$ is butyl. In some embodiments, $R^4$ is pentyl. In some embodiments, $R^4$ is hexyl. In some embodiments, each $R^4$ is isopropyl. In some embodiments, $R^4$ is isobutyl. In some embodiments, $R^4$ is isopentyl. In some embodiments, $R^4$ is isohexyl. In some embodiments, $R^4$ is secbutyl. In some embodiments, $R^4$ is secpentyl. In some embodiments, $R^4$ is sechexyl. In some embodiments, $R^4$ is tertbutyl.

In some embodiments, $R^4$ is $—C(O)(C_1-C_6$ alkyl).

In some embodiments, $R^4$ is $—C(O)(C_1$ alkyl). In some embodiments, $R^4$ is $—C(O)(C_2$ alkyl). In some embodiments, $R^4$ is $—C(O)(C_3$ alkyl). In some embodiments, $R^4$ is $—C(O)(C_4$ alkyl). In some embodiments, $R^4$ is $—C(O)(C_5$ alkyl). In some embodiments, $R^4$ is $—C(O)(C_6$ alkyl).

In some embodiments, each instance of alkyl, alk-, or carbocyclic is independently substituted with 0, 1, 2, or 3 halogen atoms.

In some embodiments, each instance of alkyl is substituted with 0, 1, 2, or 3 halogen atoms.

In some embodiments, each instance of alk- is substituted with 0, 1, 2, or 3 halogen atoms.

In some embodiments, each instance of carbocyclic is substituted with 0, 1, 2, or 3 halogen atoms.

In certain embodiments, the phenyl ring system of formula (a):

(a)

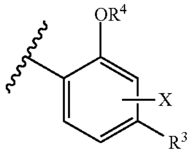

is of formula:

(a-1)

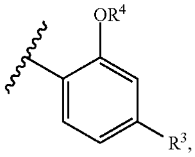

(a-2)

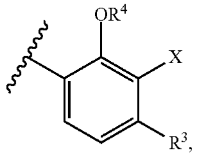

or (a-3)

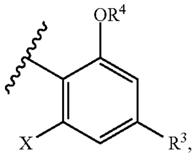

wherein X is halogen or $C_1-C_6$ alkyl, e.g., —F, —Cl, or $—CH_3$. In certain embodiments, $R^4$ is hydrogen. In certain embodiments, $R^3$ is halogen, $C_1-C_6$ alkyl, or $C_1-C_6$ alkoxy, e.g., —Cl, $—CHF_2$, $—CF_3$, $—CH_3$, or $—OCHF_2$.

In certain embodiments, the amine ring system of formula (b):

(b)

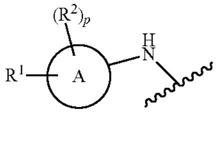

is of the formula:

(b-1)

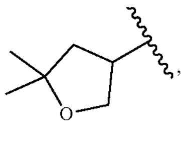

,

-continued (b-2)

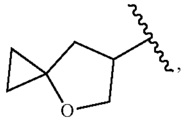

(b-3)

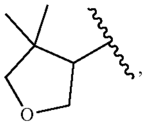

or (b-4)

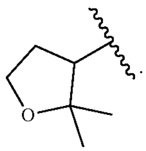

In certain embodiments, the amine ring system of formula:

(b)

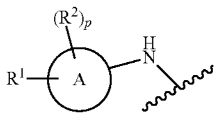

is of the formula:

(b-5)

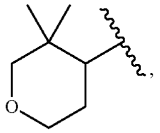

(b-6)

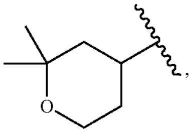

(b-7)

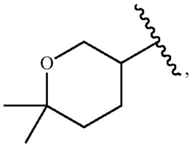

(b-8)

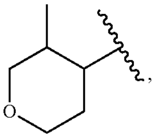

or (b-9)

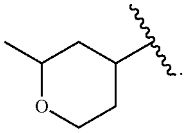

In some embodiments, the compound of Formula (I) is of Formula (I-a) or (I-b):

(I-a)

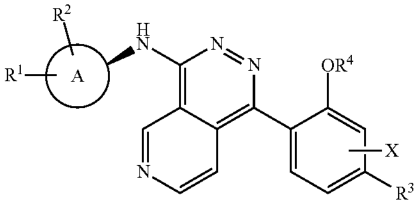

or (I-b)

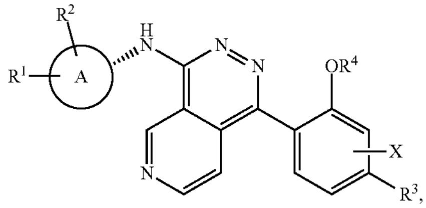

or a pharmaceutically acceptable salt, solvate, clathrate, hydrate, stereoisomer, tautomer, isotopically labeled compound, or prodrug thereof. In certain embodiments, the phenyl ring system of formula (a) is of formula (a-1), (a-2), or (a-3), wherein X is hydrogen, halogen or $C_1$-$C_6$ alkyl, e.g., —H, —F, —Cl, or —$CH_3$. In certain embodiments, $R^4$ is hydrogen. In certain embodiments, $R^3$ is halogen, $C_1$-$C_6$ alkyl, or $C_1$-$C_6$ alkoxy, e.g., —Cl, —$CHF_2$, —$CF_3$, —$CH_3$, or —$OCHF_2$. In certain embodiments, $R^3$ is $C_1$-$C_6$ alkyl or $C_1$-$C_6$ alkoxy, e.g., —$CHF_2$, —$CF_3$, —$CH_3$, or —$OCHF_2$. In certain embodiments, $R^3$ is $C_1$-$C_6$ alkyl, e.g., —$CHF_2$, —$CF_3$, or —$CH_3$. In certain embodiments, the amine ring system of formula (b) is of formula (b-1). In certain embodiments, $R^1$ is —$CH_3$ and $R^2$ is —$CH_3$.

In some embodiments, the compound of Formula (I) is of Formula (II-a), (II-b), or (II-c):

(II-a)

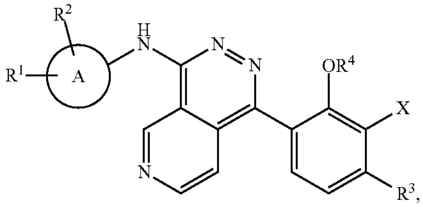

(II-b)

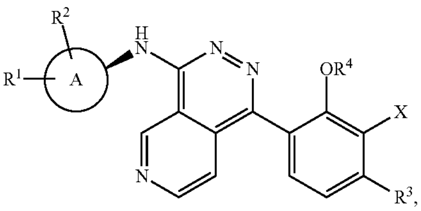

or (II-c)

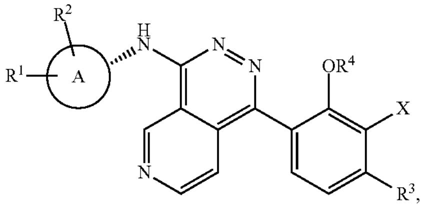

or a pharmaceutically acceptable salt, solvate, clathrate, hydrate, stereoisomer, tautomer, isotopically labeled compound, or prodrug thereof. In certain embodiments, X is halogen or $C_1$-$C_6$ alkyl, e.g., —F, —Cl, or —$CH_3$. In certain embodiments, $R^4$ is hydrogen. In certain embodiments, $R^3$ is halogen, $C_1$-$C_6$ alkyl, or $C_1$-$C_6$ alkoxy, e.g., —Cl, —$CHF_2$, —$CF_3$, —$CH_3$, or —$OCHF_2$. In certain embodiments, $R^3$ is $C_1$-$C_6$ alkyl or $C_1$-$C_6$ alkoxy, e.g., —$CHF_2$, —$CF_3$, —$CH_3$, or —$OCHF_2$. In certain embodiments, $R^3$ is $C_1$-$C_6$ alkyl, e.g., —$CHF_2$, —$CF_3$, or —$CH_3$. In certain embodiments, the amine ring system of formula (b) is of formula (b-1). In certain embodiments, $R^1$ is —$CH_3$ and $R^2$ is —$CH_3$.

In some embodiments, the compound of Formula (I) is of Formula (II-d), (II-e), or (II-f):

(II-d)

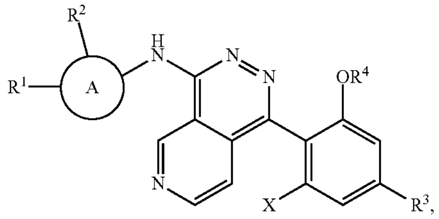

(II-e)

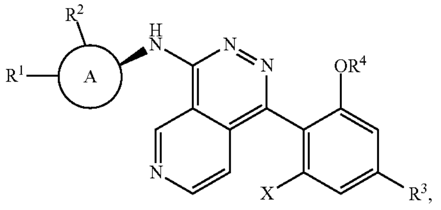

or (II-f)

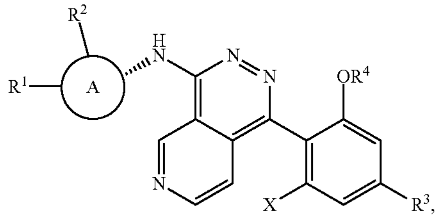

or a pharmaceutically acceptable salt, solvate, clathrate, hydrate, stereoisomer, tautomer, isotopically labeled compound, or prodrug thereof. In certain embodiments, X is halogen or $C_1$-$C_6$ alkyl, e.g., —F, —Cl, or —$CH_3$. In certain embodiments, $R^4$ is hydrogen. In certain embodiments, $R^3$ is halogen, $C_1$-$C_6$ alkyl, or $C_1$-$C_6$ alkoxy, e.g., —Cl, —$CHF_2$, —$CF_3$, —$CH_3$, or —$OCHF_2$. In certain embodiments, $R^3$ is $C_1$-$C_6$ alkyl or $C_1$-$C_6$ alkoxy, e.g., —$CHF_2$, —$CF_3$, —$CH_3$, or —$OCHF_2$. In certain embodiments, $R^3$ is $C_1$-$C_6$ alkyl, e.g., —$CHF_2$, —$CF_3$, or —$CH_3$. In certain embodiments, the amine ring system of formula (b) is of formula (b-1). In certain embodiments, $R^1$ is —$CH_3$ and $R^2$ is —$CH_3$.

In some embodiments, the compound of Formula (I) is of Formula (III-a), (III-b), or (III-c):

(III-a)

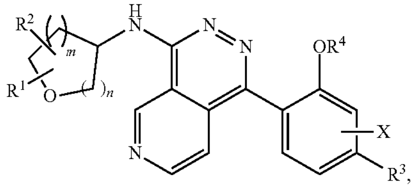

(III-b)

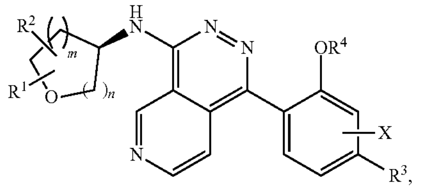

or (III-c)

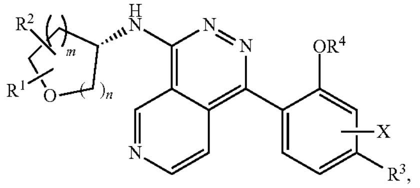

or a pharmaceutically acceptable salt, solvate, clathrate, hydrate, stereoisomer, tautomer, isotopically labeled compound, or prodrug thereof, wherein m is an integer from 0 to 2 and n is an integer from 1 to 2.

In some embodiments of Formula (III-a), (III-b), or (III-c), m is 0, 1, or 2.

In some embodiments of Formula (III-a), (III-b), or (III-c), m is 1 or 2.

In some embodiments of Formula (III-a), (III-b), or (III-c), m is 0. In some embodiments, m is 1. In some embodiments, m is 2.

In some embodiments of Formula (III-a), (III-b), or (III-c), n is 0, 1, or 2.

In some embodiments of Formula (III-a), (III-b), or (III-c), n is 1 or 2.

In some embodiments of Formula (III-a), (III-b), or (III-c), n is 0. In some embodiments, n is 1. In some embodiments, n is 2.

In some embodiments of Formula (III-a), (III-b), or (III-c), when one of m and n is 0, the other of m and n is 1 or 2.

In some embodiments of Formula (III-a), (III-b), or (III-c), when one of m and n is 0, the other of m and n is 1.

In some embodiments of Formula (III-a), (III-b), or (III-c), when one of m and n is 0, the other of m and n is 2.

In certain embodiments of Formula (III-a), (III-b), or (III-c), the phenyl ring system of formula (a) is of formula (a-1), (a-2), or (a-3), wherein X is hydrogen, halogen or $C_1$-$C_6$ alkyl, e.g., —H, —F, —Cl, or —$CH_3$. In certain embodiments, $R^4$ is hydrogen. In certain embodiments, $R^3$ is halogen, $C_1$-$C_6$ alkyl, or $C_1$-$C_6$ alkoxy, e.g., —Cl, —$CHF_2$, —$CF_3$, —$CH_3$, or —$OCHF_2$. In certain embodiments, $R^3$ is $C_1$-$C_6$ alkyl or $C_1$-$C_6$ alkoxy, e.g., —$CHF_2$, —$CF_3$, —$CH_3$, or —$OCHF_2$. In certain embodiments, $R^3$ is $C_1$-$C_6$ alkyl, e.g., —$CHF_2$, —$CF_3$, or —$CH_3$. In certain embodiments, $R^1$ is —$CH_3$ and $R^2$ is —$CH_3$.

In some embodiments, the compound of Formula (I) is of Formula (III-d), (III-e), or (III-f):

(III-d)

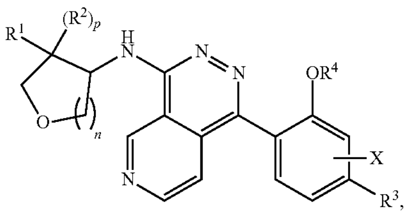

(III-e)

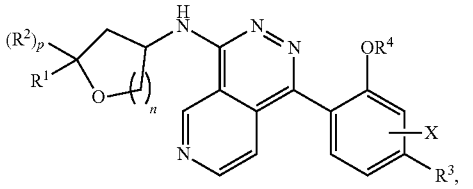

or (III-f)

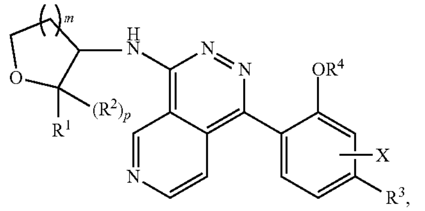

or a pharmaceutically acceptable salt, solvate, clathrate, hydrate, stereoisomer, tautomer, isotopically labeled compound, or prodrug thereof, wherein m is an integer from 0 to 2 and n is an integer from 1 to 2.

In certain embodiments of Formula (III-d), (III-e), or (III-f), the phenyl ring system of formula (a) is of formula (a-1), (a-2), or (a-3), wherein X is hydrogen, halogen or $C_1$-$C_6$ alkyl, e.g., —H, —F, —Cl, or —$CH_3$. In certain embodiments, $R^4$ is hydrogen. In certain embodiments, $R^3$ is halogen, $C_1$-$C_6$ alkyl, or $C_1$-$C_6$ alkoxy, e.g., —Cl, —$CHF_2$, —$CF_3$, —$CH_3$, or —$OCHF_2$. In certain embodiments, $R^3$ is $C_1$-$C_6$ alkyl or $C_1$-$C_6$ alkoxy, e.g., —$CHF_2$, —$CF_3$, —$CH_3$, or —$OCHF_2$. In certain embodiments, $R^3$ is $C_1$-$C_6$ alkyl, e.g., —$CHF_2$, —$CF_3$, or —$CH_3$. In certain embodiments, $R^1$ is —$CH_3$ and $R^2$ is —$CH_3$ (when p=1). In certain embodiments, $R^1$ is —$CH_3$ and $R^2$ is absent (when p=0).

In some embodiments, the compound of Formula (I) is of Formula (IV-a), (IV-b), or (IV-c):

(IV-a)

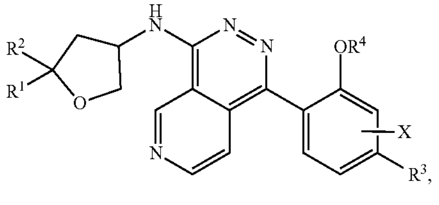

-continued (IV-b)

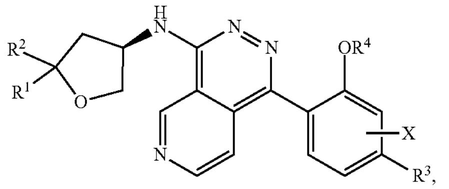

or (IV-c)

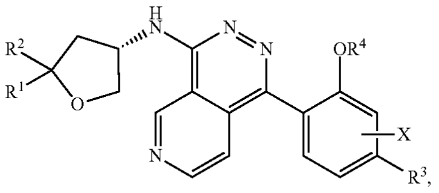

or a pharmaceutically acceptable salt, solvate, clathrate, hydrate, stereoisomer, tautomer, isotopically labeled compound, or prodrug thereof. In certain embodiments, the phenyl ring system of formula (a) is of formula (a-1), (a-2), or (a-3), wherein X is hydrogen, halogen or $C_1$-$C_6$ alkyl, e.g., —H, —F, —Cl, or —$CH_3$. In certain embodiments, $R^4$ is hydrogen. In certain embodiments, $R^3$ is halogen, $C_1$-$C_6$ alkyl, or $C_1$-$C_6$ alkoxy, e.g., —Cl, —$CHF_2$, —$CF_3$, —$CH_3$, or —$OCHF_2$. In certain embodiments, $R^3$ is $C_1$-$C_6$ alkyl or $C_1$-$C_6$ alkoxy, e.g., —$CHF_2$, —$CF_3$, —$CH_3$, or —$OCHF_2$. In certain embodiments, $R^3$ is $C_1$-$C_6$ alkyl, e.g., —$CHF_2$, —$CF_3$, or —$CH_3$. In certain embodiments, $R^1$ is —$CH_3$ and $R^2$ is —$CH_3$.

In some embodiments, the compound of Formula (I) is of Formula (IV-a1), (IV-b1), or (IV-c1):

(IV-a1)

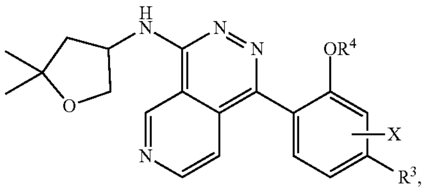

(IV-b1)

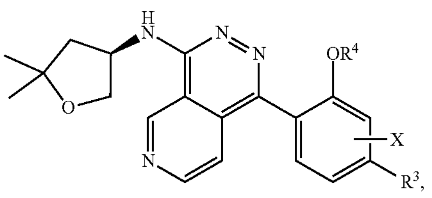

or (IV-c1)

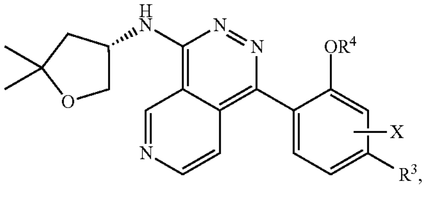

or a pharmaceutically acceptable salt, solvate, clathrate, hydrate, stereoisomer, tautomer, isotopically labeled compound, or prodrug thereof. In certain embodiments, the phenyl ring system of formula (a) is of formula (a-1), (a-2), or (a-3), wherein X is hydrogen, halogen or $C_1$-$C_6$ alkyl, e.g., —H, —F, —Cl, or —$CH_3$. In certain embodiments, $R^4$ is hydrogen. In certain embodiments, $R^3$ is halogen, $C_1$-$C_6$ alkyl, or $C_1$-$C_6$ alkoxy, e.g., —Cl, —$CHF_2$, —$CF_3$, —$CH_3$, or —$OCHF_2$. In certain embodiments, $R^3$ is $C_1$-$C_6$ alkyl or $C_1$-$C_6$ alkoxy, e.g., —$CHF_2$, —$CF_3$, —$CH_3$, or —$OCHF_2$. In certain embodiments, $R^3$ is $C_1$-$C_6$ alkyl, e.g., —$CHF_2$, —$CF_3$, or —$CH_3$.

In some embodiments, the compound of Formula (I) is of Formula (V-a), (V-b), or (V-c):

(V-a)

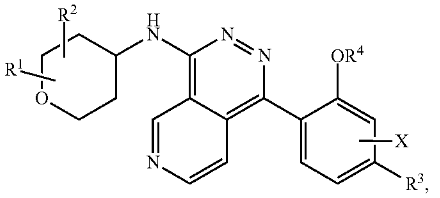

(V-b)

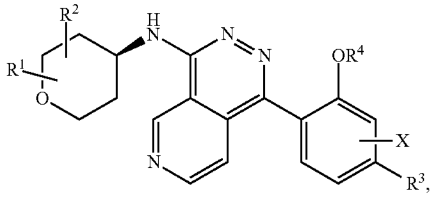

or (V-c)

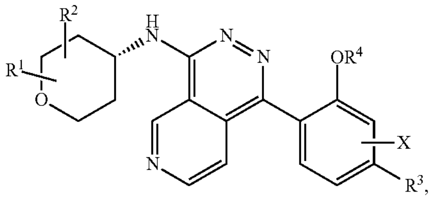

or a pharmaceutically acceptable salt, solvate, clathrate, hydrate, stereoisomer, tautomer, isotopically labeled compound, or prodrug thereof.

In some embodiments, the compound of Formula (I) is of Formula (V-a'), (V-b'), or (V-c'):

(V-a')

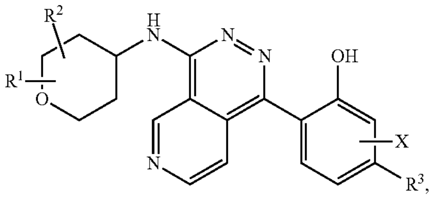

(V-b')

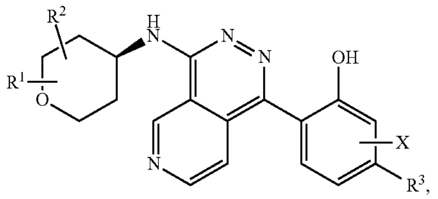

or

-continued (V-c')

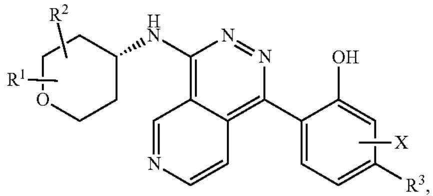

or a pharmaceutically acceptable salt, solvate, clathrate, hydrate, stereoisomer, tautomer, isotopically labeled compound, or prodrug thereof.

In certain embodiments, the phenyl ring system of formula (a) is of formula (a-1), (a-2), or (a-3), wherein X is hydrogen, halogen or $C_1$-$C_6$ alkyl, e.g., —H, —F, —Cl, or —$CH_3$. In certain embodiments, $R^3$ is halogen, $C_1$-$C_6$ alkyl, or $C_1$-$C_6$ alkoxy, e.g., —Cl, —$CHF_2$, —$CF_3$, —$CH_3$, or —$OCHF_2$. In certain embodiments, $R^3$ is $C_1$-$C_6$ alkyl or $C_1$-$C_6$ alkoxy, e.g., —$CHF_2$, —$CF_3$, —$CH_3$, or —$OCHF_2$. In certain embodiments, $R^3$ is $C_1$-$C_6$ alkyl, e.g., —$CHF_2$, —$CF_3$, or —$CH_3$. In certain embodiments, $R^1$ is —$CH_3$ and $R^2$ is —$CH_3$.

In some embodiments, the compound of Formula (I) is of Formula (VI-a), (VI-b), (VI-c), (VI-d), (VI-e), (VI-f), (VI-g), or (VI-h):

(VI-a)

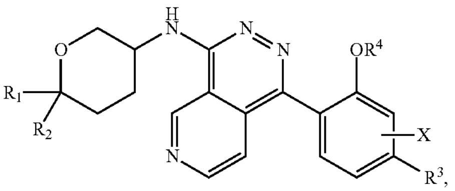

(VI-b)

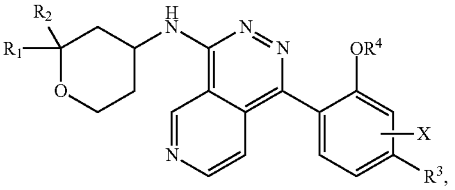

(VI-c)

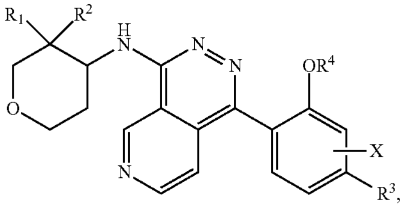

(VI-d)

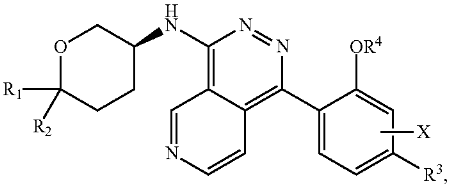

-continued (VI-e)

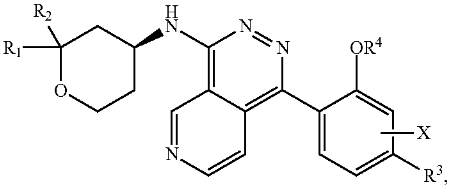

(VI-f)

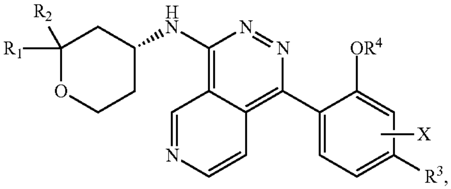

(VI-g)

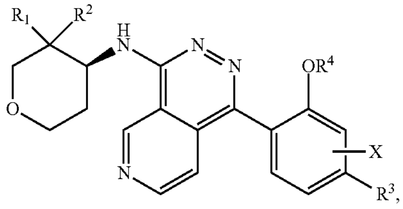

or (VI-h)

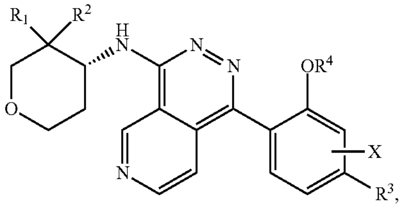

or a pharmaceutically acceptable salt, solvate, clathrate, hydrate, stereoisomer, tautomer, isotopically labeled compound, or prodrug thereof. In certain embodiments, the phenyl ring system of formula (a) is of formula (a-1), (a-2), or (a-3), wherein X is hydrogen, halogen or $C_1$-$C_6$ alkyl, e.g., —H, —F, —Cl, or —$CH_3$. In certain embodiments, $R^4$ is hydrogen. In certain embodiments, $R^3$ is halogen, $C_1$-$C_6$ alkyl, or $C_1$-$C_6$ alkoxy, e.g., —Cl, —$CHF_2$, —$CF_3$, —$CH_3$, or —$OCHF_2$. In certain embodiments, $R^3$ is $C_1$-$C_6$ alkyl or $C_1$-$C_6$ alkoxy, e.g., —$CHF_2$, —$CF_3$, —$CH_3$, or —$OCHF_2$. In certain embodiments, $R^3$ is $C_1$-$C_6$ alkyl, e.g., —$CHF_2$, —$CF_3$, or —$CH_3$. In certain embodiments, $R^1$ is —$CH_3$ and $R^2$ is —$CH_3$.

In some embodiments, the compound of Formula (I) is of Formula (VI-a1), (VI-b1), (VI-c1), (VI-d1), (VI-e1), (VI-f1), (VI-g1), or (VI-h1):

(VI-a1)

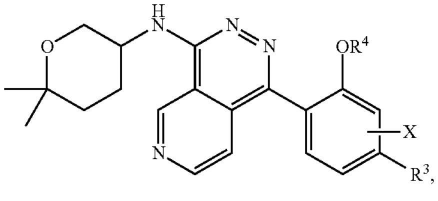

-continued (VI-b1)

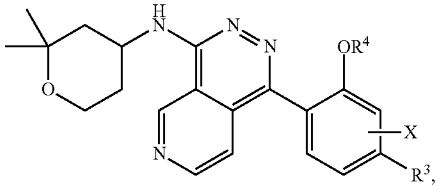

(VI-c1)

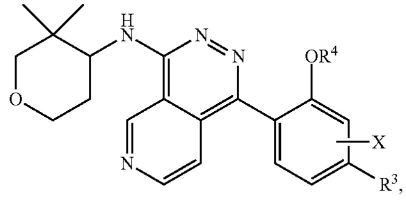

(VI-d1)

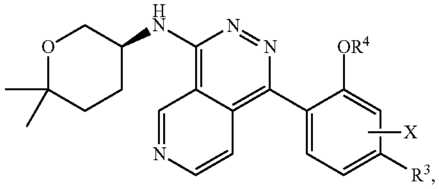

(VI-e1)

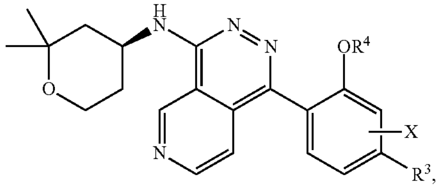

(VI-f1)

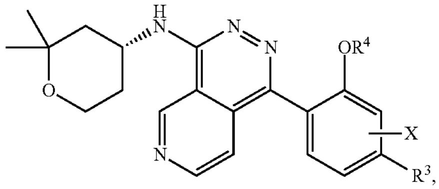

(VI-g1)

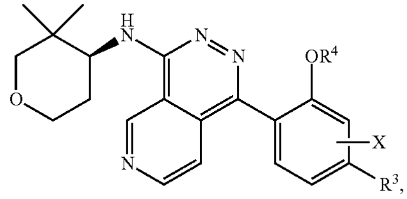

or (VI-h1)

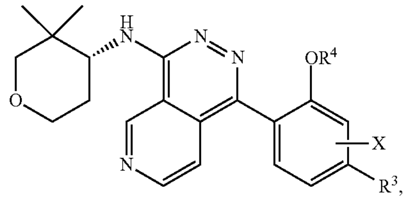

or a pharmaceutically acceptable salt, solvate, clathrate, hydrate, stereoisomer, tautomer, isotopically labeled compound, or prodrug thereof. In certain embodiments, the phenyl ring system of formula (a) is of formula (a-1), (a-2), or (a-3), wherein X is hydrogen, halogen or $C_1$-$C_6$ alkyl, e.g., —H, —F, —Cl, or —$CH_3$. In certain embodiments, $R^4$ is hydrogen. In certain embodiments, $R^3$ is halogen, $C_1$-$C_6$ alkyl, or $C_1$-$C_6$ alkoxy, e.g., —Cl, —$CHF_2$, —$CF_3$, —$CH_3$, or —$OCHF_2$. In certain embodiments, $R^3$ is $C_1$-$C_6$ alkyl or $C_1$-$C_6$ alkoxy, e.g., —$CHF_2$, —$CF_3$, —$CH_3$, or —$OCHF_2$. In certain embodiments, $R^3$ is $C_1$-$C_6$ alkyl, e.g., —$CHF_2$, —$CF_3$, or —$CH_3$.

In some embodiments, the compound is selected from a compound described in Table 1, or a pharmaceutically acceptable salt, solvate, clathrate, hydrate, stereoisomer, tautomer, isotopically labeled compound, or prodrug thereof.

In some embodiments, the compound is selected from a compound described in Table 1, or a pharmaceutically acceptable salt thereof.

In some embodiments, the compound is selected from a compound described in Table 1, or a solvate thereof.

In some embodiments, the compound is selected from a compound described in Table 1, or a clathrate thereof.

In some embodiments, the compound is selected from a compound described in Table 1, or a hydrate thereof.

In some embodiments, the compound is selected from a compound described in Table 1, or a stereoisomer thereof.

In some embodiments, the compound is selected from a compound described in Table 1, or a tautomer thereof.

In some embodiments, the compound is selected from a compound described in Table 1, or an isotopically labeled compound thereof.

In some embodiments, the compound is selected from a compound described in Table 1, or a prodrug thereof.

In some embodiments, the compound is selected from a compound described in Table 1. Stereochemistry which has been arbitrarily assigned is signified with an Asterix (*).

TABLE 1

| Cmpd. No. | Compound Name/Structure |
|---|---|
| 1* | 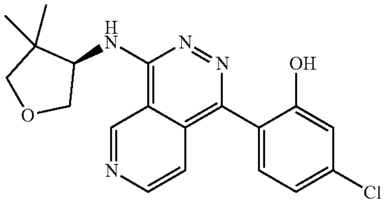 [SMILES: CC1(C)COC[C@@H]1Nc1nnc(-c2ccc(Cl)cc2O)c2ccncc12] (R)-5-chloro-2-(4-((4,4-dimethyltetrahydrofuran-3-yl)amino)pyrido[3,4-dipyridazin-1-yl)phenol |
| 1A | 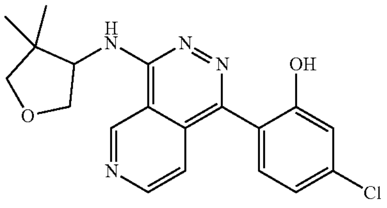 5-chloro-2-(4-((4,4-dimethyltetrahydrofuran-3-yl)amino)pyrido[3,4-d]pyridazin-1-yl)phenol |
| 1B* | 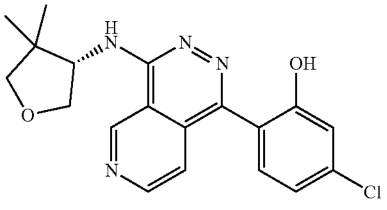 (S)-5-chloro-2-(4-(4,4-dimethyltetrahydrofuran-3-yl)amino)pyrido[3,4-d]pyridazin-1-yl)phenol |

TABLE 1-continued

| Cmpd. No. | Compound Name/Structure |
|---|---|
| 2 | 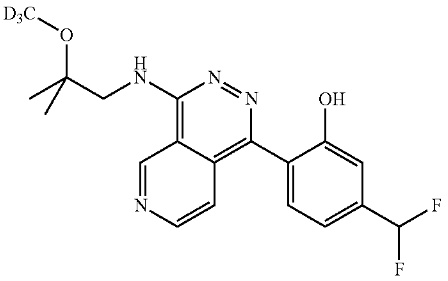 [SMILES: [2H]C([2H])([2H])OC(C)(C)CNc1nnc(-c2ccc(C(F)F)cc2O)c2ccncc12] 5-(difluoromethyl)-2-(4-((2-(methoxy-d3)-2-methylpropyl)amino)pyrido[3,4-d]pyridazin-1-yl)phenol |
| 3B* | 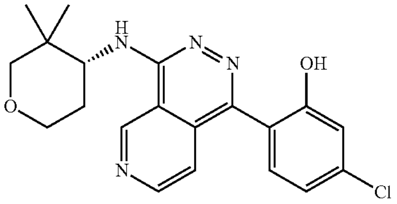 (R)-5-chloro-2-(4-((3,3-dimethyltetrahydro-2H-pyran-4-yl)amino)pyrido[3,4-d]pyridazin-1-yl)phenol |
| 3A | 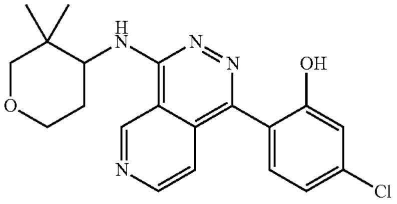 5-chloro-2-(4-((3,3-dimethyltetrahydro-2H-pyran-4-yl)amino)pyrido[3,4-d]pyridazin-1-yl)phenol |
| 3* | 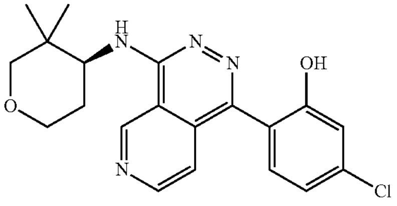 [SMILES: CC1(C)COCC[C@@H]1Nc1nnc(-c2ccc(Cl)cc2O)c2ccncc12] (S)-5-chloro-2-(4-((3,3-dimethyltetrahydro-2H-pyran-4-yl)amino)pyrido[3,4-d]pyridazin-1-yl)phenol |
| 4* | 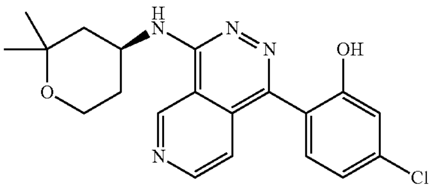 [SMILES: CC1(C)C[C@@H](Nc2nnc(-c3ccc(Cl)cc3O)c3ccncc23)CCO1] (S)-5-chloro-2-(4-((2,2-dimethyltetrahydro-2H-pyran-4-yl)amino)pyrido[3,4-d]pyridazin-1-yl)phenol |

TABLE 1-continued

| Cmpd. No. | Compound Name/Structure |
|---|---|
| 4A | 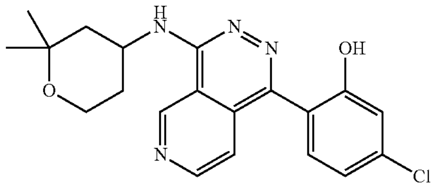 [SMILES: CC1(C)CC(Nc2nnc(-c3ccc(Cl)cc3O)c3ccncc23)CCO1] 5-chloro-2-(4-((2,2-dimethyltetrahydro-2H-pyran-4-yl)amino)pyrido[3,4-d]pyridazin-1-yl)phenol |
| 4B* | 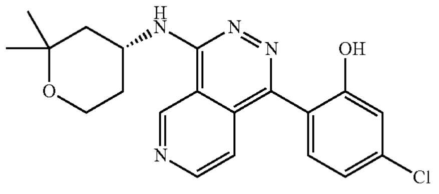 [SMILES: CC1(C)C[C@H](Nc2nnc(-c3ccc(Cl)cc3O)c3ccncc23)CCO1] (R)-5-chloro-2-(4-((2,2-dimethyltetrahydro-2H-pyran-4-yl)amino)pyrido[3,4-d]pyridazin-1-yl)phenol |
| 5A | 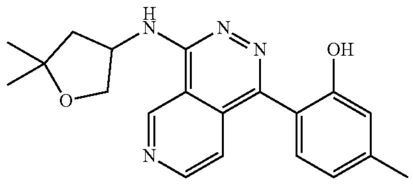 2-(4-((5,5-dimethyltetrahydrofuran-3-yl)amino)-pyrido[3,4-d]pyridazin-1-yl)-5-methylphenol |
| 5 | 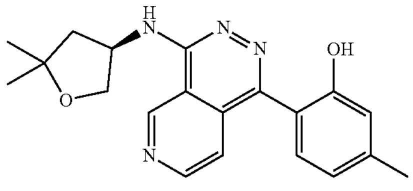 (R)-2-(4-((5,5-dimethyltetrahydrofuran-3-yl)amino)-pyrido[3,4-dipyridazin-1-yl)-5-methylphenol |
| 5B | 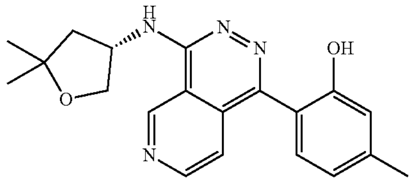 (S)-2-(4-((5,5-dimethyltetrahydrofuran-3-yl)amino)-pyrido[3,4-d]pyridazin-1-yl)-5-methylphenol |
| 6A | 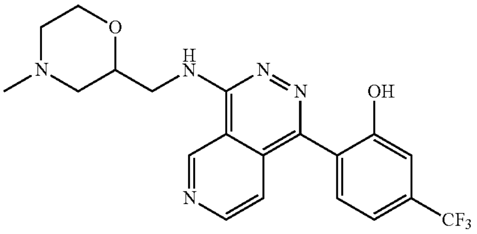 [SMILES: CN1CCOC(CNc2nnc(-c3ccc(C(F)(F)F)cc3O)c3ccncc23)C1] 2-(4-(((4-methylmorpholin-2-yl)methyl)amino)pyrido-[3,4-d]pyridazin-1-yl)-5-(trifluoromethyl)phenol |

TABLE 1-continued

| Cmpd. No. | Compound Name/Structure |
|---|---|
| 6* | 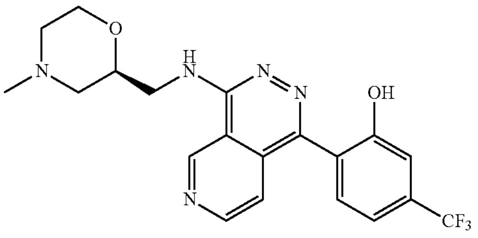 [SMILES: CN1CCO[C@@H](CNc2nnc(-c3ccc(C(F)(F)F)cc3O)c3ccncc23)C1] (S)-2-(4-(((4-methylmorpholin-2-yl)methyl)amino)pyrido-[3,4-d]pyridazin-1-yl)-5-(trifluoromethyl)phenol |
| 6B* | 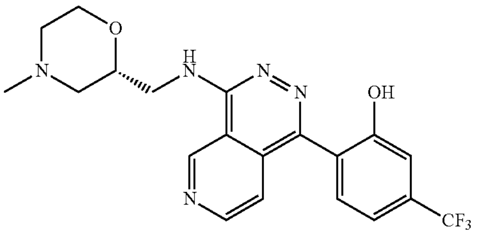 (R)-2-(4-(((4-methylmorpholin-2-yl)methyl)amino)pyrido-[3,4-dipyridazin-1-yl)-5-(trifluoromethyl)phenol |
| 9A | 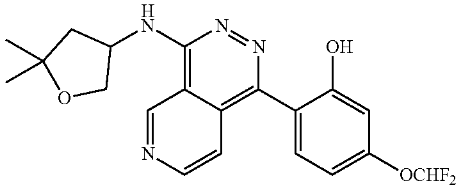 [SMILES: CC1(C)CC(Nc2nnc(-c3ccc(OC(F)F)cc3O)c3ccncc23)CO1] 5-(difluoromethoxy)-2-(4-((5,5-dimethyltetrahydrofuran-3-yl)amino)pyrido[3,4-d]pyridazin-1-yl)phenol |
| 9B* | 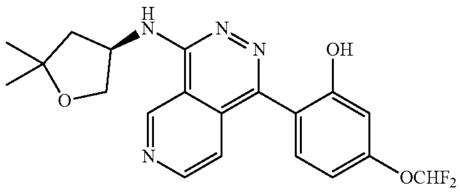 [SMILES: CC1(C)C[C@@H](Nc2nnc(-c3ccc(OC(F)F)cc3O)c3ccncc23)CO1] (R)-5-(difluoromethoxy)-2-(4-((5,5-dimethyltetrahydro-furan-3-yl)amino)pyrido[3,4-d]pyridazin-1-yl)phenol |
| 9* | 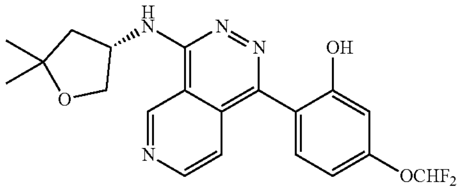 [SMILES: CC1(C)C[C@H](Nc2nnc(-c3ccc(OC(F)F)cc3O)c3ccncc23)CO1] (S)-5-(difluoromethoxy)-2-(4-((5,5-dimethyltetrahydro-furan-3-yl)amino)pyrido[3,4-d]pyridazin-1-yl)phenol |
| 10A | 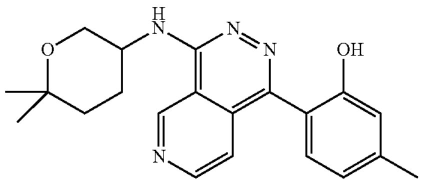 |

TABLE 1-continued

| Cmpd. No. | Compound Name/Structure |
| --- | --- |
| | 2-(4-((6,6-dimethyltetrahydro-2H-pyran-3-yl)amino)-pyrido[3,4-d]pyridazin-1-yl)-5-methylphenol |
| 10* | 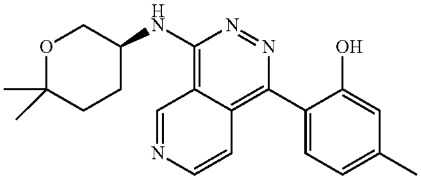<br>(S)-2-(4-((6,6-dimethyltetrahydro-2H-pyran-3-yl)amino)pyrido[3,4-d]pyridazin-1-yl)-5-methylphenol |
| 10B* | 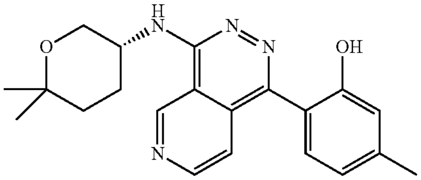<br>(R)-2-(4-((6,6-dimethyltetrahydro-2H-pyran-3-yl)-amino)pyrido[3,4-d]pyridazin-1-yl)-5-methylphenol |
| 11A | 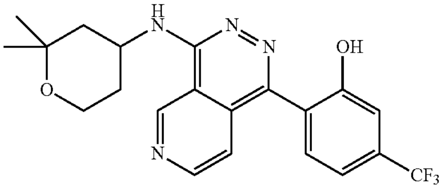<br>2-(4-((2,2-dimethyltetrahydro-2H-pyran-4-yl)amino)-pyrido[3,4-d]pyridazin-1-yl)-5-(trifluoromethyl)phenol |
| 11* | 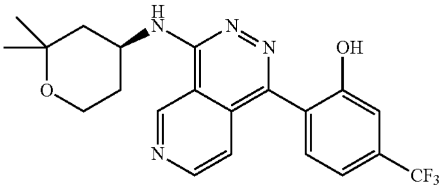 [SMILES: CC1(C)C[C@@H](Nc2nnc(-c3ccc(C(F)(F)F)cc3O)c3ccncc23)CCO1]<br>(S)-2-(4-((2,2-dimethyltetrahydro-2H-pyran-4-yl)-amino)pyrido[3,4-dipyridazin-1-yl)-5-(trifluoromethyl)phenol |
| 11B* | 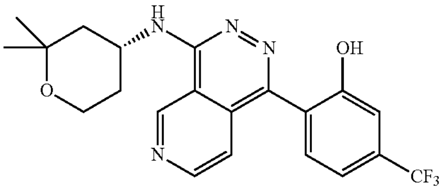 [SMILES: CC1(C)C[C@H](Nc2nnc(-c3ccc(C(F)(F)F)cc3O)c3ccncc23)CCO1]<br>(R)-2-(4-((2,2-dimethyltetrahydro-2H-pyran-4-yl)-amino)pyrido[3,4-dipyridazin-1-yl)-5-(trifluoromethyl)phenol |

TABLE 1-continued

| Cmpd. No. | Compound Name/Structure |
| --- | --- |
| 12A | 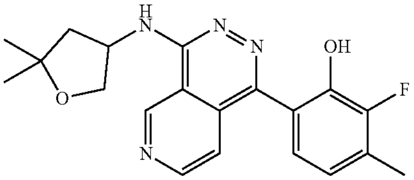 [SMILES: Cc1ccc(-c2nnc(NC3COC(C)(C)C3)c3cnccc23)c(O)c1F]<br>6-(4-((5,5-dimethyltetrahydrofuran-3-yl)amino)-pyrido[3,4-d]pyridazin-1-yl)-2-fluoro-3-methylphenol |
| 12* | 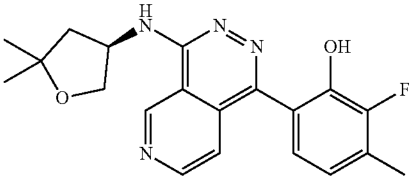 [SMILES: Cc1ccc(-c2nnc(N[C@H]3COC(C)(C)C3)c3cnccc23)c(O)c1F]<br>(R)-6-(4-((5,5-dimethyltetrahydrofuran-3-yl)-amino)pyrido[3,4-d]pyridazin-1-yl)-2-fluoro-3-methylphenol |
| 12B* | 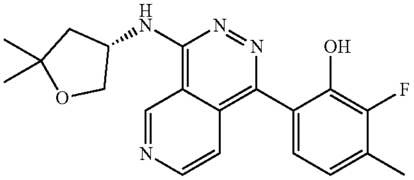 [SMILES: Cc1ccc(-c2nnc(N[C@@H]3COC(C)(C)C3)c3cnccc23)c(O)c1F]<br>(S)-6-(4-((5,5-dimethyltetrahydrofuran-3-yl)-amino)pyrido[3,4-d]pyridazin-1-yl)-2-fluoro-3-methylphenol |
| 13A | 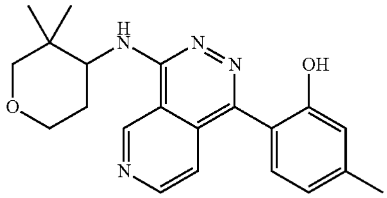 [SMILES: Cc1ccc(-c2nnc(NC3CCOCC3(C)C)c3cnccc23)c(O)c1]<br>2-(4-((3,3-dimethyltetrahydro-2H-pyran-4-yl)-amino)pyrido[3,4-d]pyridazin-1-yl)-5-methylphenol |
| 13B* | 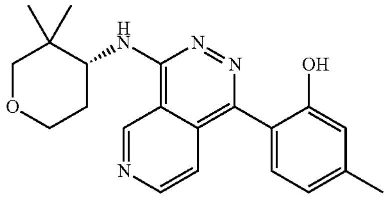 [SMILES: Cc1ccc(-c2nnc(N[C@@H]3CCOCC3(C)C)c3cnccc23)c(O)c1]<br>(R)-2-(4-((3,3-dimethyltetrahydro-2H-pyran-4-yl)amino)pyrido[3,4-d]pyridazin-1-yl)-5-methylphenol |
| 13* | 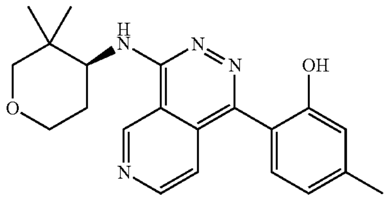 [SMILES: Cc1ccc(-c2nnc(N[C@H]3CCOCC3(C)C)c3cnccc23)c(O)c1] |

TABLE 1-continued

| Cmpd. No. | Compound Name/Structure |
|---|---|
| | (S)-2-(4-((3,3-dimethyltetrahydro-2H-pyran-4-yl)amino)pyrido[3,4-d]pyridazin-1-yl)-5-methylphenol |
| 14A | 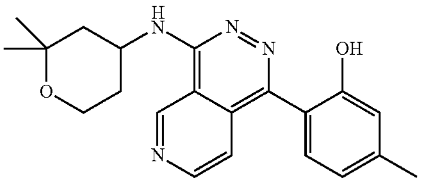 |
| | 2-(4-((2,2-dimethyltetrahydro-2H-pyran-4-yl)-amino)pyrido[3,4-d]pyridazin-1-yl)-5-methylphenol |
| 14B* | 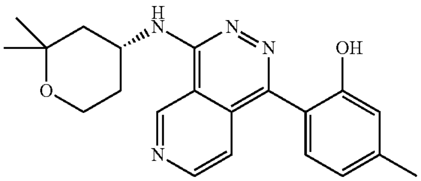 |
| | (R)-2-(4-((2,2-dimethyltetrahydro-2H-pyran-4-yl)-amino)pyrido[3,4-d]pyridazin-1-yl)-5-methylphenol |
| 14* | 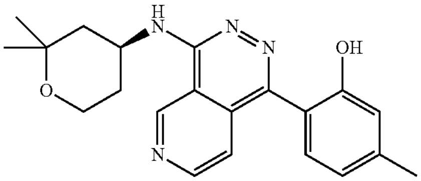 |
| | (S)-2-(4-((2,2-dimethyltetrahydro-2H-pyran-4-yl)amino)pyrido[3,4-d]pyridazin-1-yl)-5-methylphenol |
| 15A | 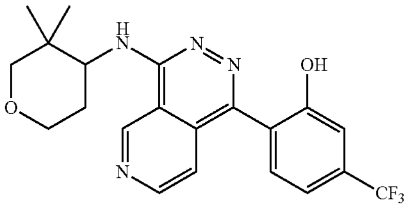 |
| | 2-(4-((3,3-dimethyltetrahydro-2H-pyran-4-yl)-amino)pyrido[3,4-d]pyridazin-1-yl)-5-(trifluoro-methyl)phenol |
| 15* | 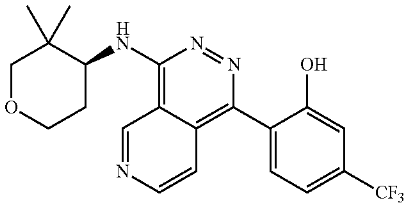 |
| | (S)-2-(4-((3,3-dimethyltetrahydro-2H-pyran-4-yl)-amino)pyrido[3,4-d]pyridazin-1-yl)-5-(trifluoro methyl)phenol |

TABLE 1-continued

| Cmpd. No. | Compound Name/Structure |
|---|---|
| 15B* | 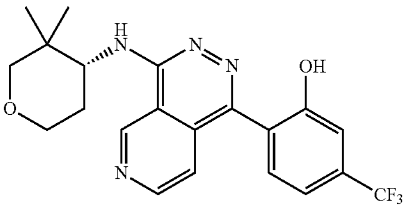 |
| | (R)-2-(4-((3,3-dimethyltetrahydro-2H-pyran-4-yl)-amino)pyrido[3,4-dipyridazin-1-yl)-5-(trifluoro-methyl)phenol |
| 16A | 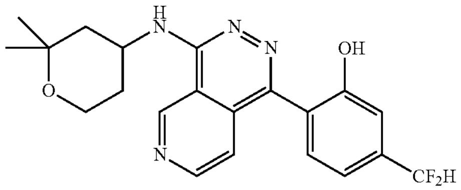 [SMILES: CC1(C)CC(Nc2nnc(-c3ccc(C(F)F)cc3O)c3ccncc23)CCO1] |
| | 5-(difluoromethyl)-2-(4-((2,2-dimethyltetrahydro-2H-pyran-4-yl)amino)pyrido[3,4-d]pyridazin-1-yl)phenol |
| 16B* | 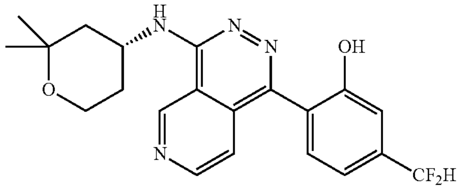 [SMILES: CC1(C)C[C@H](Nc2nnc(-c3ccc(C(F)F)cc3O)c3ccncc23)CCO1] |
| | (R)-5-(difluoromethyl)-2-(4-((2,2-dimethyltetrahydro-2H-pyran-4-yl)amino)pyrido[3,4-d]pyridazin-1-yl)phenol |
| 16* | 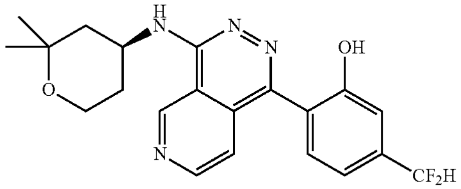 [SMILES: CC1(C)C[C@@H](Nc2nnc(-c3ccc(C(F)F)cc3O)c3ccncc23)CCO1] |
| | (S)-5-(difluoromethyl)-2-(4-((2,2-dimethyltetrahydro-2H-pyran-4-yl)amino)pyrido(3,4-d\|pyridazin-1-yl)phenol |
| 17A | 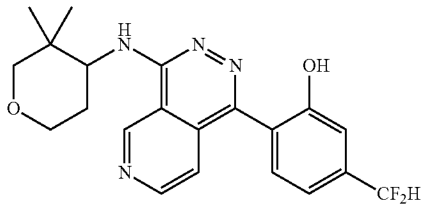 |
| | 5-(difluoromethyl)-2-(4-((3,3-dimethyltetrahydro-2H-pyran-4-yl)amino)pyrido[3,4-d]pyridazin-1-yl)phenol |

TABLE 1-continued

| Cmpd. No. | Compound Name/Structure |
|---|---|
| 17* | 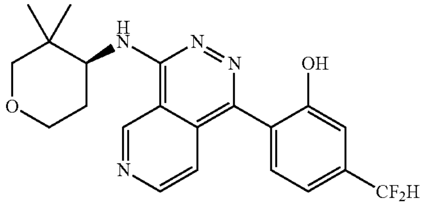<br>(S)-5-(difluoromethyl)-2-(4-((3,3-dimethyltetrahydro-2H-pyran-4-yl)amino)pyrido(3,4-d]pyridazin-1-yl)phenol |
| 17B* | 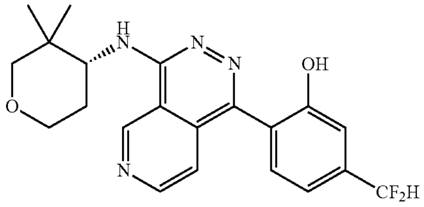<br>(R)-5-(difluoromethyl)-2-(4-((3,3-dimethyltetrahydro-2H-pyran-4-yl)amino)pyrido[3,4-d]pyridazin-1-yl)phenol |
| 18B | 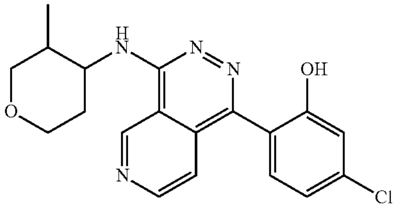 [SMILES: CC1COCCC1Nc1nnc(-c2ccc(Cl)cc2O)c2ccncc12]<br>5-chloro-2-(4-((3-methyltetrahydro-2H-pyran-4-yl)amino)pyrido[3,4-d]pyridazin-1-yl)phenol |
| 18A* | 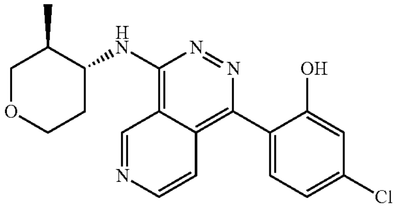 [SMILES: C[C@@H]1COCC[C@H]1Nc1nnc(-c2ccc(Cl)cc2O)c2ccncc12]<br>5-chloro-2-(4-(((3S,4R)-3-methyltetrahydro-2H-pyran-4-yl)amino)pyrido[3,4-d]pyridazin-1-yl)phenol |
| 18* | 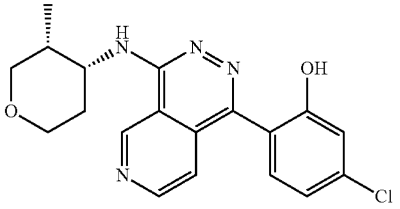 [SMILES: C[C@H]1COCC[C@H]1Nc1nnc(-c2ccc(Cl)cc2O)c2ccncc12]<br>5-chloro-2-(4-(((3R,4R)-3-methyltetrahydro-2H-pyran-4-yl)amino)pyrido[3,4-d]pyridazin-1-yl)phenol |

TABLE 1-continued

| Cmpd. No. | Compound Name/Structure |
|---|---|
| 18C* | 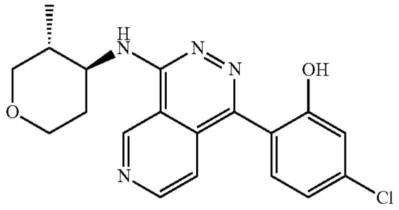 [SMILES: C[C@H]1COCC[C@@H]1Nc1nnc(-c2ccc(Cl)cc2O)c2ccncc12]<br>5-chloro-2-(4-(((3R,4S)-3-methyltetrahydro-2H-pyran-4-yl)amino)pyrido[3,4-d]pyridazin-1-yl)phenol |
| 18D* | 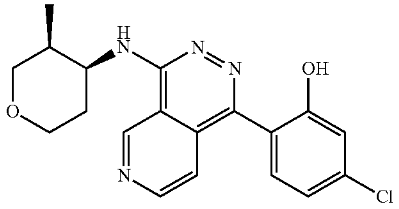 [SMILES: C[C@@H]1COCC[C@@H]1Nc1nnc(-c2ccc(Cl)cc2O)c2ccncc12]<br>5-chloro-2-(4-(((3S,4S)-3-methyltetrahydro-2H-pyran-4-yl)amino)pyrido[3,4-d]pyridazin-1-yl)phenol |
| 19A | 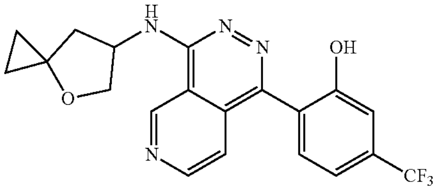 [SMILES: Oc1cc(C(F)(F)F)ccc1-c1nnc(NC2COC3(CC3)C2)c2cnccc12]<br>2-(4-((4-oxaspiro[2.4]heptan-6-yl)amino)pyrido[3,4-d]pyridazin-1-yl)-5-(trifluoromethyl)phenol |
| 19B* | 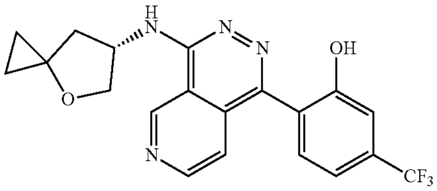 [SMILES: Oc1cc(C(F)(F)F)ccc1-c1nnc(N[C@@H]2COC3(CC3)C2)c2cnccc12]<br>(S)-2-(4-((4-oxaspiro[2.4]heptan-6-yl)amino)pyrido[3,4-d]pyridazin-1-yl)-5-(trifluoromethyl)phenol |
| 19* | 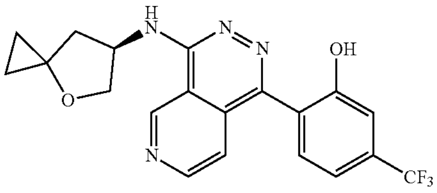 [SMILES: Oc1cc(C(F)(F)F)ccc1-c1nnc(N[C@H]2COC3(CC3)C2)c2cnccc12]<br>(R)-2-(4-((4-oxaspiro[2.4 ]heptan-6-y)amino)pyrido[3,4-d|pyridazin-1-yl)-5-(trifluoromethyl)phenol |
| 20A | 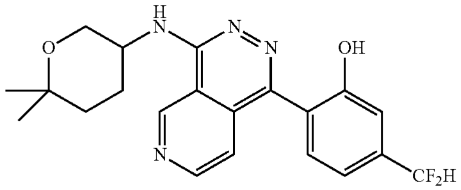 |

TABLE 1-continued

| Cmpd. No. | Compound Name/Structure |
|---|---|
| | 5-(difluoromethyl)-2-(4-((6,6-dimethyltetrahydro-2H-pyran-3-yl)amino)pyrido[3,4-d]pyridazin-1-yl)phenol |
| 20B* | 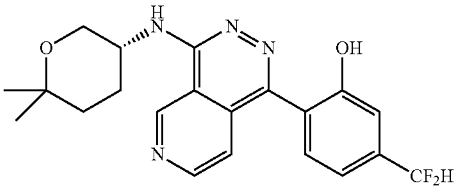 [SMILES: CC1(C)CC[C@@H](Nc2nnc(-c3ccc(C(F)F)cc3O)c3ccncc23)CO1] |
| | (R)-5-(difluoromethyl)-2-(4-((6,6-dimethyltetrahydro-2H-pyran-3-yl)amino)pyrido[3,4-d]pyridazin-1-yl)phenol |
| 20* | 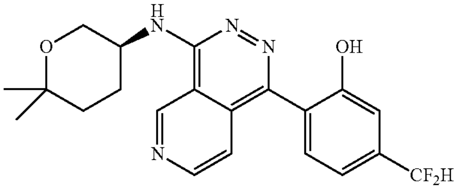 [SMILES: CC1(C)CC[C@H](Nc2nnc(-c3ccc(C(F)F)cc3O)c3ccncc23)CO1] |
| | (S)-5-(difluoromethyl)-2-(4-((6,6-dimethyltetrahydro-2H-pyran-3-yl)amino)pyrido[3,4-d]pyridazin-1-yl)phenol |
| 21A | 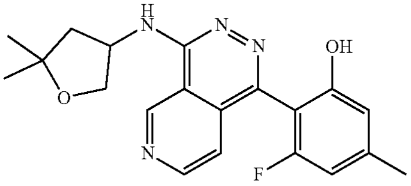 |
| | 2-(4-((5,5-dimethyltetrahydrofuran-3-yl)amino)-pyrido[3,4-d]pyridazin-1-yl)-3-fluoro-5-methylphenol |
| 21* | 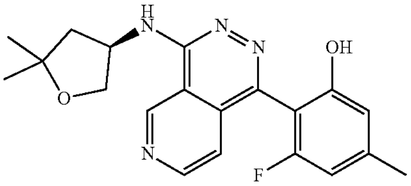 |
| | 2-(4-(((R)-5,5-dimethyltetrahydrofuran-3-yl)-amino)pyrido[3,4-d]pyridazin-1-yl)-3-fluoro-5-methylphenol |
| 21B* | 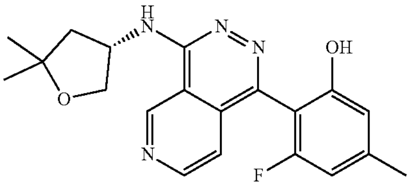 |
| | 2-(4-(((S)-5,5-dimethyltetrahydrofuran-3-yl)-amino)pyrido[3,4-dipyridazin-1-yl)-3-fluoro-5-methylphenol |

TABLE 1-continued

| Cmpd. No. | Compound Name/Structure |
|---|---|
| 22A | 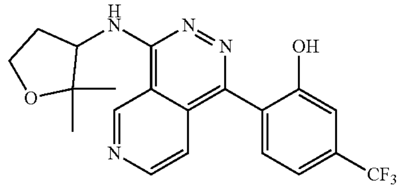 [SMILES: CC1(C)OCCC1Nc1nnc(-c2ccc(C(F)(F)F)cc2O)c2ccncc12] |
| | 2-(4-((2,2-dimethyltetrahydrofuran-3-yl)-amino)pyrido[3,4-d]pyridazin-1-yl)-5-(trifluoromethyl)phenol |
| 22B* | 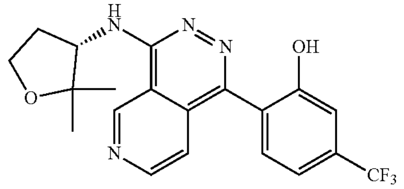 |
| | (S)-2-(4-((2,2-dimethyltetrahydrofuran-3-yl)-amino)pyrido[3,4-d]pyridazin-1-yl)-5-(trifluoromethyl)phenol |
| 22* | 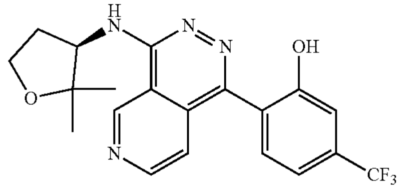 [SMILES: CC1(C)OCC[C@H]1Nc1nnc(-c2ccc(C(F)(F)F)cc2O)c2ccncc12] |
| | (R)-2-(4-((2,2-dimethyltetrahydrofuran-3-yl)-amino)pyrido[3,4-dipyridazin-1-yl)-5-(trifluoromethyl)phenol |
| 23A | 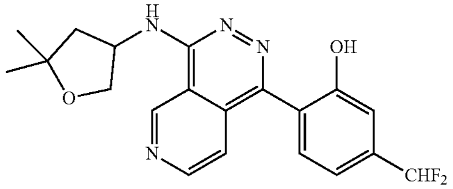 |
| | 5-(difluoromethyl)-2-(4-((5,5-dimethyltetrahydro-furan-3-yl)amino)pyrido[3,4-d]pyridazin-1-yl)phenol |
| 23* | 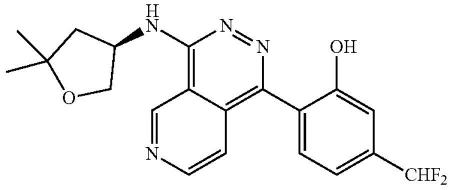 |
| | (R)-5-(difluoromethyl)-2-(4-((5,5-dimethyltetra-hydrofuran-3-yl)amino)pyrido[3,4-d]pyridazin-1-yl)phenol |
| 23B* | 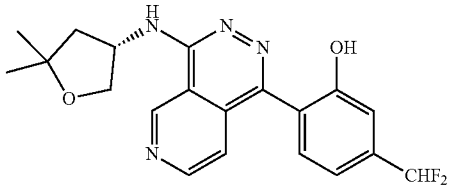 [SMILES: CC1(C)C[C@H](Nc2nnc(-c3ccc(C(F)F)cc3O)c3ccncc23)CO1] |

TABLE 1-continued

| Cmpd. No. | Compound Name/Structure |
|---|---|
| | (S)-5-(difluoromethyl)-2-(4-((5,5-dimethyltetrahydro-furan-3-yl)amino)pyrido[3,4-d]pyridazin-1-yl)phenol |

In some embodiments, the compound is a pharmaceutically acceptable salt of a compound described in Table 1.

In some embodiments, the compound is a prodrug of a compound described in Table 1.

In some embodiments, the compound is an isotopic derivative of any one of the compounds described in Table 1, or a prodrug or pharmaceutically acceptable salt thereof.

In some embodiments, the compound is an isotopic derivative of any one of the compounds described in Table 1, or a pharmaceutically acceptable salt thereof.

In some embodiments, the compound is an isotopic derivative of a prodrug of any one of the compounds described in Table 1, or a pharmaceutically acceptable salt thereof.

In some embodiments, the compound is an isotopic derivative of any one of the compounds described in Table 1.

In some embodiments, the compound is selected from a compound described in Table 2, or a pharmaceutically acceptable salt, solvate, clathrate, hydrate, stereoisomer, tautomer, isotopically labeled compound, or prodrug thereof.

In some embodiments, the compound is selected from a compound described in Table 2, or a pharmaceutically acceptable salt thereof.

In some embodiments, the compound is selected from a compound described in Table 2, or a solvate thereof.

In some embodiments, the compound is selected from a compound described in Table 2, or a clathrate thereof.

In some embodiments, the compound is selected from a compound described in Table 2, or a hydrate thereof.

In some embodiments, the compound is selected from a compound described in Table 2, or a stereoisomer thereof.

In some embodiments, the compound is selected from a compound described in Table 2, or a tautomer thereof.

In some embodiments, the compound is selected from a compound described in Table 2, or an isotopically labeled compound thereof.

In some embodiments, the compound is selected from a compound described in Table 2, or a prodrug thereof.

In some embodiments, the compound is selected from a compound described in Table 2. Stereochemistry which has been arbitrarily assigned is signified with an Asterix (*).

TABLE 2

| Cmpd. No. | Compound Name/Structure |
|---|---|
| 24* | 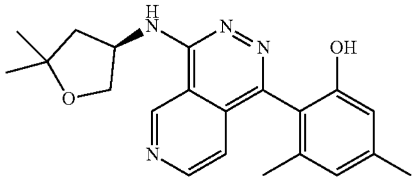 2-(4-(((R)-5,5-dimethyltetrahydrofuran-3-yl)amino)pyrido[3,4-d]pyridazin-1-yl)-3,5-dimethylphenol |

TABLE 2-continued

| Cmpd. No. | Compound Name/Structure |
|---|---|
| 24B* | 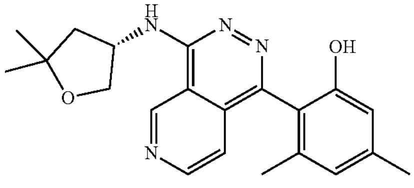 2-(4-(((S)-5,5-dimethyltetrahydrofuran-3-yl)amino)pyrido[3,4-d]pyridazin-1-yl)-3,5-dimethylphenol |
| 25A* | 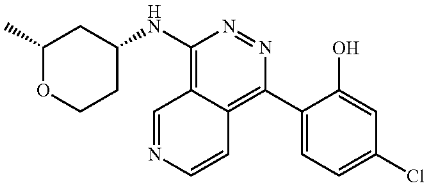 [SMILES: C[C@@H]1C[C@H](Nc2nnc(-c3ccc(Cl)cc3O)c3ccncc23)CCO1] 5-chloro-2-(4-(((2R,4R)-2-methyltetrahydro-2H-pyran-4-yl)amino)pyrido[3,4-d]pyridazin-1-yl)phenol |
| 25B* | 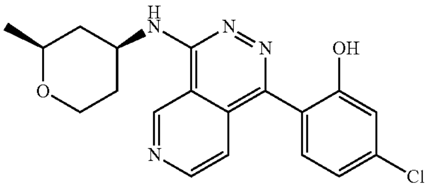 [SMILES: C[C@H]1C[C@@H](Nc2nnc(-c3ccc(Cl)cc3O)c3ccncc23)CCO1] 5-chloro-2-(4-(((2S,4S)-2-methyltetrahydro-2H-pyran-4-yl)amino)pyrido[3,4-d]pyridazin-1-yl)phenol |
| 25C* | 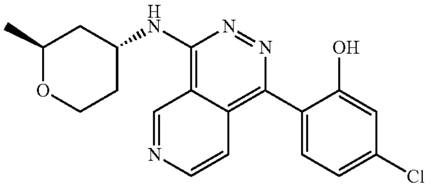 [SMILES: C[C@H]1C[C@H](Nc2nnc(-c3ccc(Cl)cc3O)c3ccncc23)CCO1] 5-chloro-2-(4-(((2S,4R)-2-methyltetrahydro-2H-pyran-4-yl)amino)pyrido[3,4-d]pyridazin-1-yl)phenol |
| 25D* | 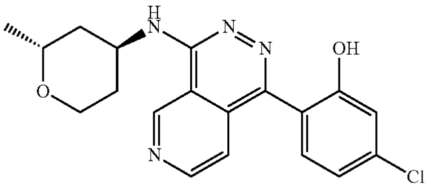 [SMILES: C[C@@H]1C[C@@H](Nc2nnc(-c3ccc(Cl)cc3O)c3ccncc23)CCO1] 5-chloro-2-(4-(((2R,4S)-2-methyltetrahydro-2H-pyran-4-yl)amino)pyrido[3,4-d]pyridazin-1-yl)phenol |
| 26* | 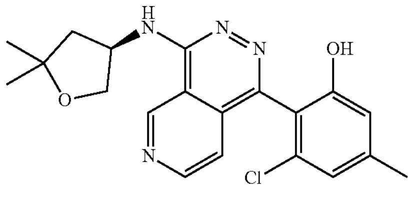 3-chloro-2-(4-(((R)-5,5-dimethyltetrahydrofuran-3-yl)amino)pyrido[3,4-d]pyridazin-1-yl)-5-methylphenol |

TABLE 2-continued

| Cmpd. No. | Compound Name/Structure |
|---|---|
| 26B* | 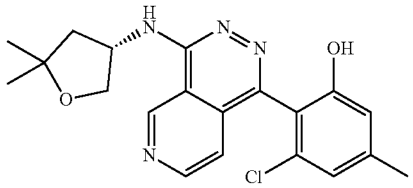 3-chloro-2-(4-(((S)-5,5-dimethyltetrahydrofuran-3-yl)amino) pyrido[3,4-d]pyridazin-1-yl)-5-methylphenol |

In some embodiments, the compound is a pharmaceutically acceptable salt of a compound described in Table 2.

In some embodiments, the compound is a prodrug of a compound described in Table 2.

In some embodiments, the compound is an isotopic derivative of any one of the compounds described in Table 2, or a prodrug or pharmaceutically acceptable salt thereof.

In some embodiments, the compound is an isotopic derivative of any one of the compounds described in Table 2, or a pharmaceutically acceptable salt thereof.

In some embodiments, the compound is an isotopic derivative of a prodrug of any one of the compounds described in Table 2, or a pharmaceutically acceptable salt thereof.

In some embodiments, the compound is an isotopic derivative of any one of the compounds described in Table 2.

In some aspects, the present disclosure provides a compound being an isotopic derivative (e.g., isotopically labeled compound) of any one of the compounds of the Formulae disclosed herein.

In another aspect, the present disclosure provides, inter alia, compounds selected from (R)-5-chloro-2-(4-((4,4-dimethyltetrahydrofuran-3-yl)amino)pyrido[3,4-d]pyridazin-1-yl)phenol;

5-(difluoromethyl)-2-(4-((2-(methoxy-d3)-2-methylpropyl)amino)pyrido[3,4-d]pyridazin-1-yl)phenol;

(R)-5-chloro-2-(4-((3,3-dimethyltetrahydro-2H-pyran-4-yl)amino)pyrido[3,4-d]pyridazin-1-yl)phenol;

(S)-5-chloro-2-(4-((2,2-dimethyltetrahydro-2H-pyran-4-yl)amino)pyrido[3,4-d]pyridazin-1-yl)phenol;

(R)-2-(4-((5,5-dimethyltetrahydrofuran-3-yl)amino)pyrido[3,4-d]pyridazin-1-yl)-5-methylphenol; and (S)-2-(4-(((4-methylmorpholin-2-yl)methyl)amino)pyrido[3,4-d]pyridazin-1-yl)-5-(trifluoromethyl)phenol.

In some embodiments, the compound is (R)-5-chloro-2-(4-((4,4-dimethyltetrahydrofuran-3-yl)amino)pyrido[3,4-d]pyridazin-1-yl)phenol.

In some embodiments, the compound is 5-(difluoromethyl)-2-(4-((2-(methoxy-d3)-2-methylpropyl)amino)pyrido[3,4-d]pyridazin-1-yl)phenol.

In some embodiments, the compound is (R)-5-chloro-2-(4-((3,3-dimethyltetrahydro-2H-pyran-4-yl)amino)pyrido[3,4-d]pyridazin-1-yl)phenol.

In some embodiments, the compound is (S)-5-chloro-2-(4-((2,2-dimethyltetrahydro-2H-pyran-4-yl)amino)pyrido[3,4-d]pyridazin-1-yl)phenol.

In some embodiments, the compound is (R)-2-(4-((5,5-dimethyltetrahydrofuran-3-yl)amino)pyrido[3,4-d]pyridazin-1-yl)-5-methylphenol.

In some embodiments, the compound is (S)-2-(4-(((4-methylmorpholin-2-yl)methyl)amino)pyrido[3,4-d]pyridazin-1-yl)-5-(trifluoromethyl)phenol.

In some embodiments, the compound is a pharmaceutically acceptable salt of any one of the compounds described herein.

In some aspects, the present disclosure provides a compound being an isotopic derivative (also referred to herein as an isotopically labeled compound) of any one of the compounds of the Formulae disclosed herein.

In some embodiments, the compound is an isotopic derivative of any one of the compounds described herein and prodrugs and pharmaceutically acceptable salts thereof.

In some embodiments, the compound is an isotopic derivative of any one of the compounds described herein and pharmaceutically acceptable salts thereof.

In some embodiments, the compound is an isotopic derivative of any one of prodrugs of the compounds described herein and pharmaceutically acceptable salts thereof.

In some embodiments, the compound is an isotopic derivative of any one of the compounds described herein.

It is understood that the isotopic derivative can be prepared using any of a variety of art-recognized techniques. For example, the isotopic derivative can generally be prepared by carrying out the procedures disclosed in the Schemes and/or in the Examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

The term "isotopic derivative", as used herein, refers to a derivative of a compound in which one or more atoms are isotopically enriched or labeled. For example, an isotopic derivative of a compound disclosed herein is isotopically enriched with regard to, or labeled with, one or more isotopes as compared to the corresponding disclosed compound. In some embodiments, the isotopic derivative is enriched with regard to, or labeled with, one or more atoms selected from $^{2}$H, $^{13}$C, $^{14}$C, $^{15}$N, $^{18}$O, $^{29}$Si, $^{31}$P, and $^{34}$S. In some embodiments, the isotopic derivative is a deuterium labeled compound (i.e., being enriched with $^{2}$H with regard to one or more atoms thereof). In some embodiments, the compound is a $^{18}$F labeled compound. In some embodiments, the compound is a $^{123}$I labeled compound, a $^{124}$I labeled compound, a $^{125}$I labeled compound, a $^{129}$I labeled compound, a $^{131}$I labeled compound, a $^{135}$I labeled compound, or any combination thereof. In some embodiments, the compound is a $^{33}$S labeled compound, a $^{34}$S labeled compound, a $^{35}$S labeled compound, a $^{36}$S labeled compound, or any combination thereof.

It is understood that the $^{18}$F, $^{123}$I, $^{124}$I, $^{125}$I, $^{129}$I, $^{131}$I, $^{135}$I, $^{32}$S, $^{34}$S, $^{35}$S, and/or $^{36}$S labeled compound, can be prepared using any of a variety of art-recognized techniques. For example, the deuterium labeled compound can generally be prepared by carrying out the procedures disclosed in the Schemes and/or in the Examples described herein, by substituting a $^{18}$F, $^{123}$I, $^{124}$I, $^{125}$I, $^{129}$I, $^{131}$I, $^{135}$I, $^{32}$S, $^{34}$S, $^{35}$S, and/or $^{36}$S labeled reagent for a non-isotope labeled reagent.

A compound of the invention or a pharmaceutically acceptable salt or solvate thereof that contains one or more of the aforementioned $^{18}$F, $^{123}$I, $^{124}$I, $^{125}$I, $^{129}$I, $^{131}$I, $^{135}$I, $^{32}$S, $^{34}$S, $^{35}$S, and $^{36}$S atom(s) is within the scope of the invention. Further, substitution with isotope (e.g., $^{18}$F, $^{123}$I, $^{124}$I, $^{125}$I, $^{129}$I, $^{131}$I, $^{135}$I, $^{32}$S, $^{34}$S, $^{35}$S, and/or $^{36}$S) may afford certain therapeutic advantages resulting from greater metabolic stability, e.g., increased in vivo half-life or reduced dosage requirements.

For the avoidance of doubt it is to be understood that, where in this specification a group is qualified by "described herein", the said group encompasses the first occurring and broadest definition as well as each and all of the particular definitions for that group.

A suitable pharmaceutically acceptable salt of a compound of the disclosure is, for example, an acid-addition salt of a compound of the disclosure which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, diethylamine, trimethylamine, piperidine, morpholine or tris-(2-hydroxyethyl)amine.

It will be understood that the compounds of any one of the Formulae disclosed herein and any pharmaceutically acceptable salts thereof, comprise stereoisomers, mixtures of stereoisomers, polymorphs of all isomeric forms of said compounds.

In some embodiments, the compound of Formula (I) is not:

1A

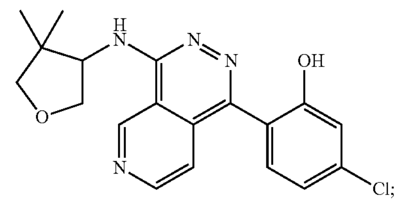

5-chloro-2-(4-((4,4-dimethyletrahydrofuran-3-yl) amino)pyrido[3,4-d]pyridazin-1-yl)phenol;

3A

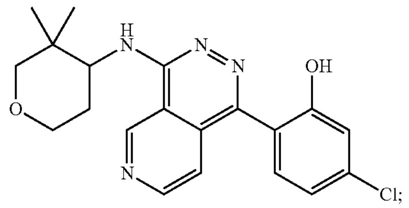

5-chloro-2-(4-((3,3-dimethyletrahydro-2H-pyran-4-yl)amino)pyrido[3,4-d]pyridazin-1-yl)phenol

4A

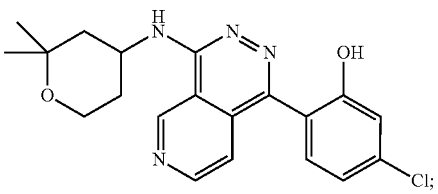

or 5-chloro-2-(4-((2,2-dimethyletrahydro-2H-pyran-4-yl)amino)pyrido[3,4-d]pyridazin-1-yl)phenol -continued

5A

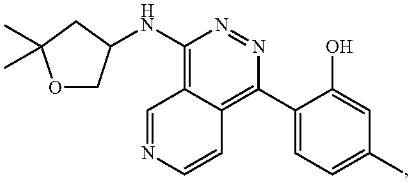

2-(4-((5,5-dimethyletrahydrofuran-3-yl) amino)pyrido[3,4-d]pyridazin-1-yl)-5-methylphenol or a pharmaceutically acceptable salt, solvate, clathrate, hydrate, stereoisomer, tautomer, isotopically labeled compound, or prodrug thereof.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral center" refers to a carbon atom bonded to four nonidentical substituents.

As used herein, the term "chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J. Chem. Educ. 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerizations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers." Isomers that differ in the arrangement of their atoms in space are termed "stereoisomers" Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this disclosure may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the disclosure may have geometric isomeric centers (E- and Z-isomers). It is to be understood that the present disclosure encompasses all optical, diastereoisomers and geometric isomers and mixtures thereof that possess inflammasome inhibitory activity.

It is to be understood that the compounds of any Formula described herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted compound disclosed herein. Suitable cations include sodium ion, potassium ion, magnesium ion, calcium ion, and an ammonium cation such as tetramethylammonium ion or diethylamine ion. The substituted compounds disclosed herein also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as H2O.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure and are substituted with various groups as described herein.

It is also to be understood that certain compounds of any one of the Formulae disclosed herein may exist in solvated as well as unsolvated forms such as, for example, hydrated forms. A suitable pharmaceutically acceptable solvate is, for example, a hydrate such as hemi-hydrate, a mono-hydrate, a di-hydrate or a tri-hydrate. It is to be understood that the disclosure encompasses all such solvated forms that possess inflammasome inhibitory activity.

It is also to be understood that certain compounds of any one of the Formulae disclosed herein may exhibit polymorphism, and that the disclosure encompasses all such forms, or mixtures thereof, which possess inflammasome inhibitory activity. It is generally known that crystalline materials may be analyzed using conventional techniques such as X-Ray Powder Diffraction analysis, Differential Scanning Calorimetry, Thermal Gravimetric Analysis, Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

Compounds of any one of the Formulae disclosed herein may exist in a number of different tautomeric forms and references to include all such forms. For the avoidance of doubt, where a compound can exist in one of several tautomeric forms, and only one is specifically described or shown, all others are nevertheless embraced by Formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

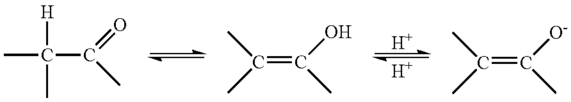

keto enol enolate

The compounds of any one of the Formulae disclosed herein may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include derivatives containing in vivo cleavable alkyl or acyl substituents at the ester or amide group in any one of the Formulae disclosed herein.

Accordingly, the present disclosure includes those compounds of any one of the Formulae disclosed herein as defined hereinbefore when made available by organic synthesis and when made available within the human or animal body by way of cleavage of a prodrug thereof. Accordingly, the present disclosure includes those compounds of any one of the Formulae disclosed herein that are produced by organic synthetic means and also such compounds that are produced in the human or animal body by way of metabolism of a precursor compound, that is a compound of any one of the Formulae disclosed herein may be a synthetically-produced compound or a metabolically-produced compound.

A suitable pharmaceutically acceptable prodrug of a compound of any one of the Formulae disclosed herein is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Pro-drugs, edited by H. Bundgaard, (Elsevier, 1985); c) A Textbook of Drug Design and Development, edited by Krogsgaard-Larsen and H. Bundgaard, Chapter 5 "Design and Application of Pro-drugs," by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pharm. Bull., 32, 692 (1984); g) T. Higuchi and V. Stella, "Pro-Drugs as Novel Delivery Systems," A.C.S. Symposium Series, Volume 14; and h) E. Roche (editor), "Bioreversible Carriers in Drug Design," Pergamon Press, 1987.

A suitable pharmaceutically acceptable prodrug of a compound of any one of the Formulae disclosed herein that possesses a hydroxy group is, for example, an in vivo cleavable ester or ether thereof. An in vivo cleavable ester or ether of a compound of any one of the Formulae disclosed herein containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_1$-$C_{10}$ alkanoyl groups such as acetyl, benzoyl, phenylacetyl and substituted benzoyl and phenylacetyl groups, $C_1$-$C_{10}$ alkoxycarbonyl groups such as ethoxycarbonyl, N,N—($C_1$-$C_6$ alkyl)$_2$ carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of any one of the Formulae disclosed herein that possesses a carboxy group is, for example, an in vivo cleavable amide thereof, for example an amide formed with an amine such as ammonia, a $C_{1-4}$ alkylamine such as methylamine, a ($C_1$-$C_4$ alkyl)$_2$-amine such as dimethylamine, N-ethyl-N-methylamine or diethylamine, a $C_1$-$C_4$ alkoxy-$C_2$-$C_4$ alkylamine such as 2-methoxyethylamine, a phenyl-$C_1$-$C_4$ alkylamine such as benzylamine and amino acids such as glycine or an ester thereof.

A suitable pharmaceutically acceptable prodrug of a compound of any one of the Formulae disclosed herein that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl.

The in vivo effects of a compound of any one of the Formulae disclosed herein may be exerted in part by one or more metabolites that are formed within the human or animal body after administration of a compound of any one of the Formulae disclosed herein. As stated hereinbefore, the in vivo effects of a compound of any one of the Formulae disclosed herein may also be exerted by way of metabolism of a precursor compound (a prodrug).

A suitable general route for the preparation of a compound of the application is using Protocol A and can be described in Scheme 1 herein.

Scheme 1

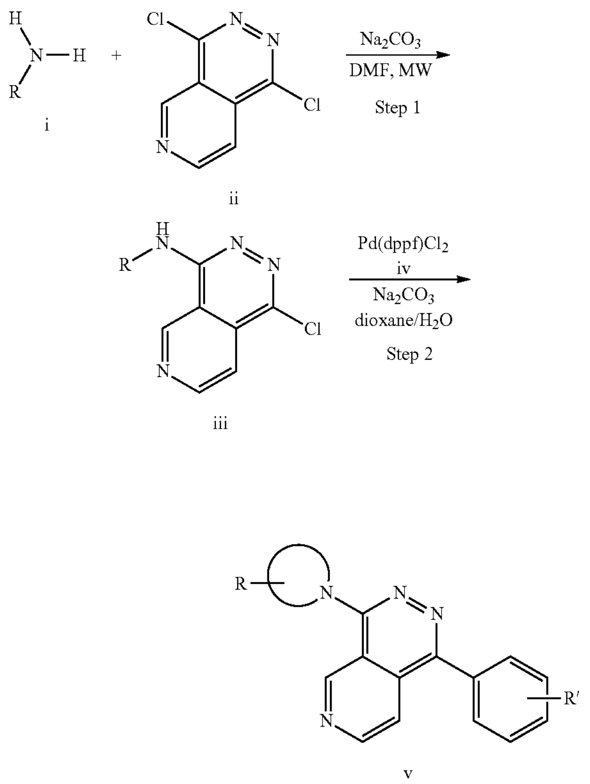

Examples presented herein, unless otherwise stated, are synthesized according to the general procedure presented in Scheme 1.

Step one involves an $S_NAr$ reaction between an amine (i) and an aryl dichloride (ii), to provide the target chloroaryl intermediate (iii). Step two involves cross-coupling between intermediate (iii) and the desired boronic acids or boronates (iv), optionally followed by deprotection of an alkyl ether (e.g., a methyl ether) on the phenyl ring, to generate the desired compound (v). Amine (i), aryl dichloride (ii), and boronic acid or boronate (iv) are either commercially available or known in the chemical literature, unless otherwise indicated.

Another suitable general route for the preparation of a compound of the instant disclosure is using Protocol B in Scheme 2 herein.

Scheme 2

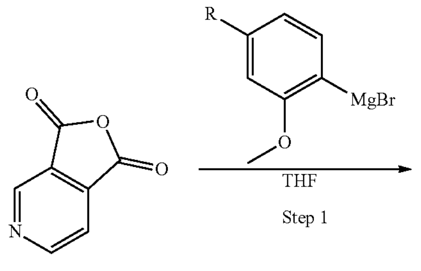

vii

-continued

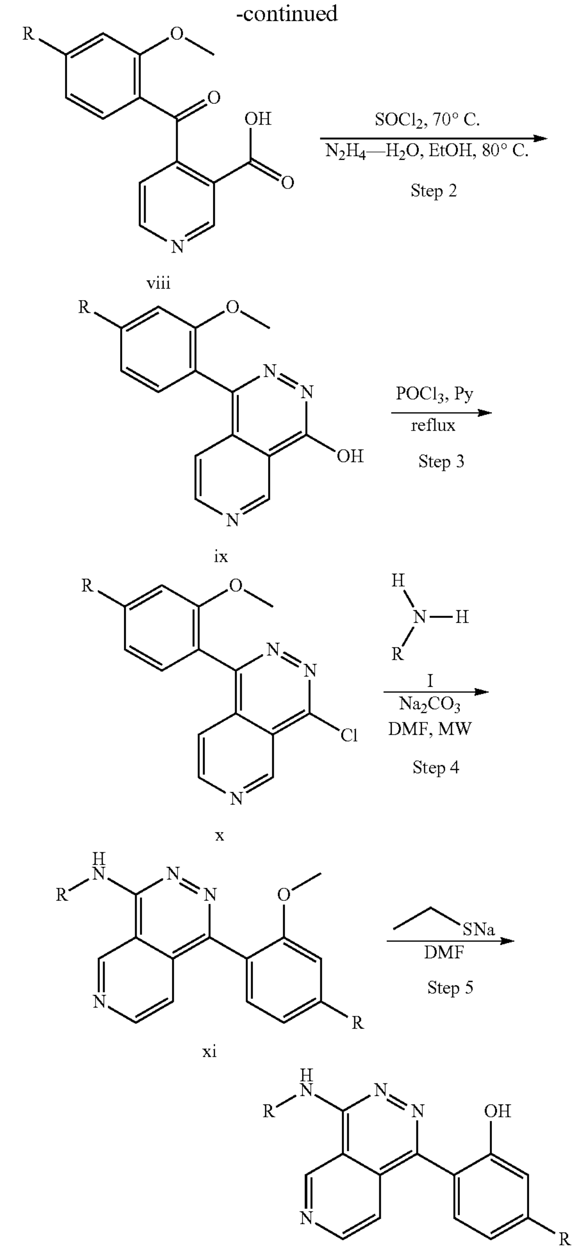

xii

Step One involves opening commercially available 3,4-pyridinedicarboxylic acid anhydride (vii) with a Grignard reagent to obtain carboxylic acid (viii). Step two features chlorination, then condensation with hydrazine to furnish pyridazinol (ix). Step three then involves another chlorination to furnish key intermediate (x), which in turn may be engaged in step four as a an SNAr reaction with an amine (i) to form azaphthalazines (xi). Step five then features a methyl ether deprotection then provides analogs (xii).

Biological Assays

Compounds designed, selected and/or optimized by methods described above and herein, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

Various in vitro or in vivo biological assays are may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, binding assays, cellular assays (cell lines, primary cells and whole blood), in vitro cell viability assays, as well as assays for determining NLRP3 potency, unbound clearance, solubility, permeability, metabolic stability (e.g., in hepatocytes), and CYP inhibition and time-dependent inhibition (TDI) assays (e.g., for de-risking potential adverse in vivo drug-drug interactions).

In some embodiments, the biological assay is described in the Examples, Assay Methods section. In some embodiments, the Assay Methods section refers to Example 12.

For example, in some embodiments, the compounds of the instant disclosure may be tested for their human-NLRP3 inhibition activity using known procedures, such as the methodology reported in Coll et al. *Nat Med.* (2015) 21(3): 248-255. See also the Examples, Assay Methods section. In some embodiments, the compounds of the instant disclosure may be tested for their human NLRP3 potency using known procedures. See, e.g., the human whole blood NLRP3 assay described in the Assay Method section of the Examples. In some embodiments, the compounds of the instant disclosure may further be tested for brain penetrance. See, e.g., the kp and kpu,u NLRP3 assay described in the Assay Method section of the Examples.

In other embodiments, the compounds of the instant disclosure may be tested for unbound clearance (Clu) following known procedures, such as described in Miller et al., *J. Med. Chem.* (2020) 63:12156-12170. For example, unbound clearance (Clu) may be calculated by dividing total clearance ('CL' in mL/min/kg) as measured in blood or plasma by the unbound fraction in plasma (fu).

In yet other embodiments, the permeability of compounds of the instant disclosure may be determined following known procedures, such as described in Wang et al. *J Mass Spectrom.* (2000) 35:71-76. For example, permeability across cell membranes may be measured using either Caco-2 or MDCK-MDR1 cell lines in Transwell plates, after measuring the compound in both apical and basolateral chambers, and reported as an apparent permeability Papp A-B in $10^{-6}$ cm/s.

In additional embodiments, the solubility of compounds of the instant disclosure may be determined following known procedures, such as described in Alsenz and Kansy, *Advanced Drug Delivery Reviews* (2007) 59:546-567, and Wang et al. *J Mass Spectrom.* (2000) 35:71-76. For example, the kinetic solubility in physiologically relevant media, such as phosphate buffered solution (PBS, pH 7.4) or simulated gastric fluid (SGF), may be measured using serial dilution and two hour incubation period, followed by filtration, and reported in M by LC-MS/MS. Thermodynamic solubility in physiologically relevant media may be measured by LC-MS/MS, after a twenty-four hour incubation, followed by filtration, and reported in mg/mL. Optimized solubility may be beneficial for manufacturing and further processing of the compound. Furthermore, optimized solubility allows for a more efficient in vitro analysis of the compound, including data collection around the compound's safety, drug-drug interactions, potency, selectivity, metabolism, and permeability.

Pharmaceutical Compositions

In some aspects, the present disclosure provides a pharmaceutical composition comprising a compound of the present disclosure as an active ingredient. In some embodiments, the present disclosure provides a pharmaceutical composition comprising at least one compound of each of the formulae described in Table 1, or a pharmaceutically acceptable salt, solvate, clathrate, hydrate, stereoisomer, tautomer, isotopically labeled compound, or prodrug thereof, and one or more pharmaceutically acceptable carriers or excipients. In some embodiments, the present disclosure provides a pharmaceutical composition comprising at least one compound of each of the formulae described in Table 2, or a pharmaceutically acceptable salt, solvate, clathrate, hydrate, stereoisomer, tautomer, isotopically labeled compound, or prodrug thereof, and one or more pharmaceutically acceptable carriers or excipients. In some embodiments, the present disclosure provides a pharmaceutical composition comprising at least one compound of each of the formulae described herein, or a pharmaceutically acceptable salt, solvate, clathrate, hydrate, stereoisomer, tautomer, isotopically labeled compound, or prodrug thereof, and one or more pharmaceutically acceptable carriers or excipients. In some embodiments, the pharmaceutical composition comprises one or more carrier, filler, vehicle, excipient, solubility enhancing agent, chelating agent, or a combination thereof. In some embodiments, the present disclosure provides a pharmaceutical composition comprising at least one compound described in Table 1. In some embodiments, the present disclosure provides a pharmaceutical composition comprising at least one compound described in Table 2. In some embodiments, the present disclosure provides a pharmaceutical composition comprising at least one compound described herein.

In some embodiments of the disclosure, the pharmaceutical composition comprises a compound described in Table 1 and a pharmaceutically acceptable carrier.

In some embodiments of the disclosure, the pharmaceutical composition comprises a compound described in Table 2 and a pharmaceutically acceptable carrier.

In some embodiments of the instant disclosure, the pharmaceutical composition comprises a compound of Formula I as described herein and a pharmaceutically acceptable carrier.

In one embodiment of the instant disclosure the pharmaceutical composition comprises (R)-5-chloro-2-(4-((4,4-dimethyltetrahydrofuran-3-yl)amino)pyrido[3,4-d]pyridazin-1-yl)phenol as described herein and a pharmaceutically acceptable carrier.

In another embodiment of the disclosure, the pharmaceutical composition comprises 5-(difluoromethyl)-2-(4-((2-(methoxy-d3)-2-methylpropyl)amino)pyrido[3,4-d]pyridazin-1-yl)phenol as described herein and a pharmaceutically acceptable carrier.

In another embodiment of the disclosure, the pharmaceutical composition comprises (R)-5-chloro-2-(4-((3,3-dimethyltetrahydro-2H-pyran-4-yl)amino)pyrido[3,4-d]

pyridazin-1-yl)phenol as described herein and a pharmaceutically acceptable carrier.

In another embodiment of the disclosure, the pharmaceutical composition comprises (S)-5-chloro-2-(4-((2,2-dimethyltetrahydro-2H-pyran-4-yl)amino)pyrido[3,4-d]pyridazin-1-yl)phenol described herein and a pharmaceutically acceptable carrier.

In one embodiment of the instant disclosure the pharmaceutical composition comprises (R)-2-(4-((5,5-dimethyltetrahydrofuran-3-yl)amino)pyrido[3,4-d]pyridazin-1-yl)-5-methylphenol as described herein and a pharmaceutically acceptable carrier.

In one embodiment of the instant disclosure the pharmaceutical composition comprises (S)-2-(4-(((4-methylmorpholin-2-yl)methyl)amino)pyrido[3,4-d]pyridazin-1-yl)-5-(trifluoromethyl)phenol as described herein and a pharmaceutically acceptable carrier.

The compounds of present disclosure can be formulated for oral administration in forms such as tablets, capsules (each of which includes sustained release or timed release formulations), pills, powders, granules, elixirs, tinctures, suspensions, syrups and emulsions. The compounds of present disclosure on can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulfated β-cyclodextrin (S-β-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilize the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ε-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

According to a further aspect of the disclosure there is provided a pharmaceutical composition which comprises a compound of the disclosure as defined hereinbefore, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more coloring, sweetening, flavoring and/or preservative agents.

An effective amount of a compound of the present disclosure for use in therapy is an amount sufficient to treat or prevent an inflammasome related condition referred to herein, slow its progression and/or reduce the symptoms associated with the condition.

An effective amount of a compound of the present disclosure for use in therapy is an amount sufficient to treat an inflammasome related condition referred to herein, slow its progression and/or reduce the symptoms associated with the condition.

The size of the dose for therapeutic or prophylactic purposes of a compound disclosed herein will naturally vary according to the nature and severity of the conditions, the age and sex of the animal or patient and the route of administration, according to well-known principles of medicine.

METHODS OF USE

In some aspects, the present disclosure provides a method of modulating NLRP3 activity (e.g., in vitro or in vivo), comprising contacting a cell with an effective amount of a compound of the present disclosure or a pharmaceutically acceptable salt thereof.

In some aspects, the present disclosure provides a method of modulating NLRP3 activity (e.g., in vitro or in vivo), comprising contacting a cell with a compound of the present disclosure or a pharmaceutically acceptable salt thereof.

In some aspects, the present disclosure provides a method of inhibiting NLRP3 activity (e.g., in vitro or in vivo), comprising contacting a cell with an effective amount of a compound of the present disclosure or a pharmaceutically acceptable salt thereof.

In some aspects, the present disclosure provides a method of inhibiting NLRP3 activity (e.g., in vitro or in vivo), comprising contacting a cell with a compound of the present disclosure or a pharmaceutically acceptable salt thereof.

In some aspects, the present disclosure provides a method of treating or preventing a disease or disorder inhibited by NLRP3 as disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a disease or disorder inhibited by NLRP3 as disclosed herein in a subject in need thereof, comprising administering to the subject a compound of the present disclosure or a pharmaceutically acceptable salt, solvate, clathrate, hydrate, stereoisomer, tautomer, isotopically labeled compound, or prodrug thereof, or a pharmaceutical composition of the present disclosure.

In some aspects, the present disclosure provides a method of treating a disease or disorder disclosed herein in a subject in need thereof, comprising administering to the subject a compound of the present disclosure or a pharmaceutically acceptable salt, solvate, clathrate, hydrate, stereoisomer, tautomer, isotopically labeled compound, or prodrug thereof, or a pharmaceutical composition of the present disclosure. In some embodiments, the disease or disorder is a disease or disorder in which NLRP3 activity is implicated.

In some embodiments, the disease or disorder is inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease in a subject that has been determined to carry a germline or somatic non-silent mutation in NLRP3.

In some aspects, the present disclosure provides a method of treating or preventing inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease in a subject that has been determined to carry a germline or somatic non-silent mutation in NLRP3 in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease in a subject that has been determined to carry a germline or somatic non-silent mutation in NLRP3 in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease in a subject that has been determined to carry a germline or somatic non-silent mutation in NLRP3 in a subject in need thereof, comprising administering to the subject a compound of the present disclosure or a pharmaceutically acceptable salt, solvate, clathrate, hydrate, stereoisomer, tautomer, isotopically labeled compound, or prodrug thereof, or a pharmaceutical composition of the present disclosure.

In some aspects, the present disclosure provides a method of treating inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease in a subject that has been determined to carry a germline or somatic non-silent mutation in NLRP3 in a subject in need thereof, comprising administering to the subject a compound of the present disclosure or a pharmaceutically acceptable salt, solvate, clathrate, hydrate, stereoisomer, tautomer, isotopically labeled compound, or prodrug thereof, or a pharmaceutical composition of the present disclosure.

In some aspects, the present disclosure provides a compound of the present disclosure or a pharmaceutically acceptable salt, solvate, clathrate, hydrate, stereoisomer, tautomer, isotopically labeled compound, or prodrug thereof for use in modulating NLRP3 activity (e.g., in vitro or in vivo).

In some aspects, the present disclosure provides a compound of the present disclosure or a pharmaceutically acceptable salt thereof for use in inhibiting NLRP3 activity (e.g., in vitro or in vivo).

In some aspects, the present disclosure provides a compound of the present disclosure or a pharmaceutically acceptable salt thereof for use in inhibiting NLRP3 (e.g., in vitro or in vivo).

In some aspects, the present disclosure provides a compound of the present disclosure or a pharmaceutically acceptable salt thereof for use as an antagonist for NLRP3 (e.g., in vitro or in vivo).

In some aspects, the present disclosure provides a compound of the present disclosure or a pharmaceutically acceptable salt thereof for use in treating or preventing a disease or disorder disclosed herein.

In some aspects, the present disclosure provides a compound of the present disclosure or a pharmaceutically acceptable salt thereof for use in treating a disease or disorder disclosed herein.

In some aspects, the present disclosure provides use of a compound of the present disclosure or a pharmaceutically acceptable salt thereof in the manufacture of a medicament for modulating NLRP3 activity (e.g., in vitro or in vivo).

In some aspects, the present disclosure provides use of a compound of the present disclosure or a pharmaceutically acceptable salt thereof in the manufacture of a medicament for modulating NLRP3 (e.g., in vitro or in vivo).

In some aspects, the present disclosure provides use of a compound of the present disclosure or a pharmaceutically acceptable salt thereof in the manufacture of a medicament for inhibiting NLRP3 activity (e.g., in vitro or in vivo).

In some aspects, the present disclosure provides use of a compound of the present disclosure or a pharmaceutically acceptable salt thereof in the manufacture of a medicament for inhibiting NLRP3 (e.g., in vitro or in vivo).

In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides use of a compound of the present disclosure or a pharmaceutically acceptable salt thereof in the manufacture of a medicament for treating a disease or disorder disclosed herein.

In some aspects, the present disclosure provides use of a compound of the present disclosure or a pharmaceutically acceptable salt thereof for modulating NLRP3 activity (e.g., in vitro or in vivo).

In some aspects, the present disclosure provides use of a compound of the present disclosure or a pharmaceutically acceptable salt thereof for inhibiting NLRP3 activity (e.g., in vitro or in vivo).

In some aspects, the present disclosure provides use of a compound of the present disclosure or a pharmaceutically acceptable salt thereof for modulating NLRP3 (e.g., in vitro or in vivo).

In some aspects, the present disclosure provides use of a compound of the present disclosure or a pharmaceutically acceptable salt thereof for inhibiting NLRP3 (e.g., in vitro or in vivo).

In some aspects, the present disclosure provides use of a compound of the present disclosure or a pharmaceutically acceptable salt thereof for treating or preventing a disease or disorder disclosed herein.

In some aspects, the present disclosure provides use of a compound of the present disclosure or a pharmaceutically acceptable salt thereof for treating a disease or disorder disclosed herein.

Effectiveness of compounds of the disclosure can be determined by industry-accepted assays/disease models according to standard practices of elucidating the same as described in the art and are found in the current general knowledge.

In some embodiments, the disease or disorder is associated with implicated NLRP3 activity.

In some embodiments, the disease or disorder is inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease in a subject that has been determined to carry a germline or somatic non-silent mutation in NLRP3.

In some embodiments, the disease or disorder is inflammation.

In some embodiments, the disease or disorder is an auto-immune disease.

In some embodiments, the disease or disorder is a cancer.

In some embodiments, the disease or disorder is an infection.

In some embodiments, the disease or disorder is a disease or disorder of the central nervous system.

In some embodiments, the disease or disorder is a metabolic disease.

In some embodiments, the disease or disorder is a cardiovascular disease.

In some embodiments, the disease or disorder is a respiratory disease.

In some embodiments, the disease or disorder is a kidney disease.

In some embodiments, the disease or disorder is a liver disease.

In some embodiments, the disease or disorder is an ocular disease.

In some embodiments, the disease or disorder is a skin disease.

In some embodiments, the disease or disorder is a lymphatic disease.

In some embodiments, the disease or disorder is a rheumatic disease.

In some embodiments, the disease or disorder is a psychological disease.

In some embodiments, the disease or disorder is graft versus host disease.

In some embodiments, the disease or disorder is allodynia.

In some embodiments, the disease or disorder is an NLRP3-related disease.

In some embodiments, the disease or disorder of the central nervous system is Parkinson's disease, Alzheimer's disease, traumatic brain injury, spinal cord injury, amyotrophic lateral sclerosis, or multiple sclerosis.

In some embodiments, the respiratory disease is steroid-resistant asthma.

In some embodiments, the respiratory disease is severe steroid-resistant asthma.

In some embodiments, the kidney disease is an acute kidney disease, a chronic kidney disease, or a rare kidney disease.

In some embodiments, the skin disease is psoriasis, hidradenitis suppurativa (HS), or atopic dermatitis.

In some embodiments, the rheumatic disease is dermatomyositis, Still's disease, or juvenile idiopathic arthritis.

In some embodiments, the NLRP3-related disease in a subject that has been determined to carry a germline or somatic non-silent mutation in NLRP3 is cryopyrin-associated autoinflammatory syndrome.

In some embodiments, the cryopyrin-associated autoinflammatory syndrome is familial cold autoinflammatory syndrome, Muckle-Wells syndrome, or neonatal onset multisystem inflammatory disease.

In some embodiments, the compound is brain penetrant, e.g., having a Kpu,u of >0.3.

Compounds with a Kpu,u of less than or equal to 0.3 are not brain penetrant. In some embodiments, the compound is not brain penetrant.

In some embodiments, the compound has a Kpu,u of greater than 0.3 to about 10.

In some embodiments, the compound has a Kpu,u of greater than 0.3 to about 9. In some embodiments, the compound has a Kpu,u of greater than 0.3 to about 8. In some embodiments, the compound has a Kpu,u of greater than 0.3 to about 7. In some embodiments, the compound has a Kpu,u of greater than 0.3 to about 6. In some embodiments, the compound has a Kpu,u of greater than 0.3 to about 5. In some embodiments, the compound has a Kpu,u of greater than 0.3 to about 4. In some embodiments, the compound has a Kpu,u of greater than 0.3 to about 3. In some embodiments, the compound has a Kpu,u of greater than 0.3 to about 2. In some embodiments, the compound has a Kpu,u of greater than 0.3 to about 1.

In some embodiments, the compound has a Kpu,u of about 0.3. In some embodiments, the compound has a Kpu,u of about 0.4. In some embodiments, the compound has a Kpu,u of about 0.5.

In some embodiments, the compound has a Kpu,u of about 1. In some embodiments, the compound has a Kpu,u of about 1.5.

In some embodiments, the compound has a Kpu,u of about 2. In some embodiments, the compound has a Kpu,u of about 2.5.

In some embodiments, the compound has a Kpu,u of about 3. In some embodiments, the compound has a Kpu,u of about 3.5.

In some embodiments, the compound has a Kpu,u of about 4. In some embodiments, the compound has a Kpu,u of about 4.5.

In some embodiments, the compound has a Kpu,u of about 5. In some embodiments, the compound has a Kpu,u of about 5.5.

In some embodiments, the compound has a Kpu,u of about 6. In some embodiments, the compound has a Kpu,u of about 6.5.

In some embodiments, the compound has a Kpu,u of about 7. In some embodiments, the compound has a Kpu,u of about 7.5.

In some embodiments, the compound has a Kpu,u of about 8. In some embodiments, the compound has a Kpu,u of about 8.5.

In some embodiments, the compound has a Kpu,u of about 9. In some embodiments, the compound has a Kpu,u of about 9.5.

In some embodiments, the compound has a Kpu,u of about 10.

In certain embodiments, the compound is metabolically stable, e.g., having a half-life in mouse or human liver microsomes or hepatocytes of greater than 20 minutes, greater than 30 minutes, greater than 40 minutes, greater than 50 minutes, greater than 60 minutes, or between about 30 minutes to about 120 minutes.

Routes of Administration

Compounds of the present disclosure, or a pharmaceutically acceptable salt, solvate, clathrate, hydrate, stereoisomer, tautomer, isotopically labeled compound, or prodrug thereof, may be administered alone as a sole therapy or can be administered in addition with one or more other substances and/or treatments. Such conjoint treatment may be achieved by way of the simultaneous, sequential or separate administration of the individual components of the treatment.

For example, therapeutic effectiveness may be enhanced by administration of an adjuvant (i.e. by itself the adjuvant may only have minimal therapeutic benefit, but in combination with another therapeutic agent, the overall therapeutic benefit to the individual is enhanced). Alternatively, by way of example only, the benefit experienced by an individual may be increased by administering a compound of the instant disclosure with another therapeutic agent (which also includes a therapeutic regimen) that also has therapeutic benefit.

In the instances where the compound of the present disclosure is administered in combination with other therapeutic agents, the compound of the disclosure need not be administered via the same route as other therapeutic agents, and may, because of different physical and chemical characteristics, be administered by a different route. For example, the compound of the disclosure may be administered orally to generate and maintain good blood levels thereof, while the other therapeutic agent may be administered intravenously. The initial administration may be made according to established protocols known in the art, and then, based upon the observed effects, the dosage, modes of administration and times of administration can be modified by the skilled clinician.

The particular choice of other therapeutic agent will depend upon the diagnosis of the attending physicians and their judgment of the condition of the individual and the appropriate treatment protocol. According to this aspect of the disclosure there is provided a combination for use in the treatment of a disease in which inflammasome activity is implicated comprising a compound of the disclosure as defined hereinbefore, or a pharmaceutically acceptable salt thereof, and another suitable agent.

According to a further aspect of the disclosure there is provided a pharmaceutical composition which comprises a compound of the disclosure, or a pharmaceutically acceptable salt thereof, in combination with a suitable, in association with a pharmaceutically acceptable diluent or carrier.

In any of the above-mentioned pharmaceutical composition, process, method, use, medicament, and manufacturing features of the instant disclosure, any of the alternate embodiments of compounds of the present disclosure described herein also apply.

The compounds of the disclosure or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

EXEMPLARY EMBODIMENTS

Exemplary Embodiment 1. A compound of Formula (I):

(I)

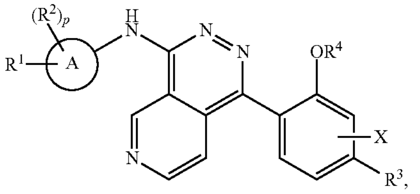

or a pharmaceutically acceptable salt, solvate, clathrate, hydrate, stereoisomer, tautomer, isotopically labeled compound, or prodrug thereof, wherein:

A is a 5- to 8-membered monocyclic heterocycloalkyl, wherein the heterocycloalkyl comprises at least one O ring atom;

$R^1$ is halogen, $C_1$-$C_6$ alkyl, or $C_1$-$C_6$ alkoxy;

$R^2$ is halogen or $C_1$-$C_6$ alkyl;

or $R^1$ and $R^2$, together with the atoms to which they are attached, form a 3- to 4-membered carbocyclic ring;

$R^3$ is —OH, halogen, $C_1$-$C_6$ alkyl, or $C_1$-$C_6$ alkoxy;

X is H, —OH, halogen, —$NH_2$, —$NH(C_1$-$C_6$ alkyl), —$N(C_1$-$C_6$ alkyl$)_2$, or $C_1$-$C_6$ alkyl; and $R^4$ is H, $C_1$-$C_6$ alkyl, or —$C(O)(C_1$-$C_6$ alkyl); and p is 0 or 1, wherein each instance of alkyl, alk-, or carbocyclic is independently substituted with 0, 1, 2, or 3 halogen atoms, and when $R^3$ is Cl, then

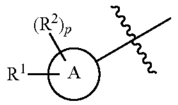

is not

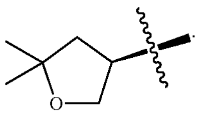

Exemplary Embodiment 2. The compound of Exemplary Embodiment 1, or a pharmaceutically acceptable salt, solvate, clathrate, hydrate, stereoisomer, tautomer, isotopically labeled compound, or prodrug thereof, wherein A is a 5-membered monocyclic heterocycloalkyl comprising one O ring atom.

Exemplary Embodiment 3. The compound of Exemplary Embodiment 1 or Exemplary Embodiment 2, or a pharmaceutically acceptable salt, solvate, clathrate, hydrate, stereoisomer, tautomer, isotopically labeled compound, or prodrug thereof, wherein A is a 6-membered monocyclic heterocycloalkyl comprising one O ring atom.

Exemplary Embodiment 4. The compound of any one of Exemplary Embodiments 1-3, or a pharmaceutically acceptable salt, solvate, clathrate, hydrate, stereoisomer, tautomer, isotopically labeled compound, or prodrug thereof, wherein p is 1.

Exemplary Embodiment 5. The compound of any one of Exemplary Embodiments 1-4, or a pharmaceutically acceptable salt, solvate, clathrate, hydrate, stereoisomer, tautomer, isotopically labeled compound, or prodrug thereof, wherein p is 1; $R^1$ is $C_1$-$C_6$ alkyl or $C_1$-$C_6$ alkoxy; and $R^2$ is $C_1$-$C_6$ alkyl.

Exemplary Embodiment 6. The compound of any one of Exemplary Embodiments 1-5, or a pharmaceutically acceptable salt, solvate, clathrate, hydrate, stereoisomer, tautomer, isotopically labeled compound, or prodrug thereof, wherein $R^3$ is not halogen.

Exemplary Embodiment 7. The compound of any one of Exemplary Embodiments 1-6, or a pharmaceutically acceptable salt, solvate, clathrate, hydrate, stereoisomer, tautomer, isotopically labeled compound, or prodrug thereof, wherein $R^3$ is $C_1$-$C_6$ alkyl or $C_1$-$C_6$ alkoxy.

Exemplary Embodiment 8. The compound of any one of Exemplary Embodiments 1-5, or a pharmaceutically acceptable salt, solvate, clathrate, hydrate, stereoisomer, tautomer, isotopically labeled compound, or prodrug thereof, wherein $R^3$ is Cl, methyl, —$CF_3$, —$CHF_2$, or —$OCHF_2$.

Exemplary Embodiment 9. The compound of any one of Exemplary Embodiments 1-8, or a pharmaceutically acceptable salt, solvate, clathrate, hydrate, stereoisomer, tautomer, isotopically labeled compound, or prodrug thereof, wherein $R^4$ is H.

Exemplary Embodiment 10. The compound of any one of Exemplary Embodiments 1-9, or a pharmaceutically acceptable salt, solvate, clathrate, hydrate, stereoisomer, tautomer, isotopically labeled compound, or prodrug thereof, wherein X is H or F.

Exemplary Embodiment 11. The compound of any one of the preceding Exemplary Embodiments, wherein the compound is of Formula (I-a) or (I-b):

(I-a)

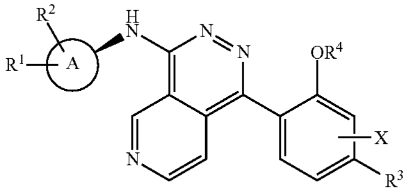

or (I-b)

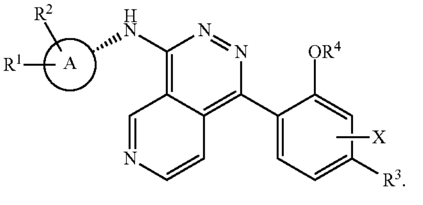

or a pharmaceutically acceptable salt, solvate, clathrate, hydrate, stereoisomer, tautomer, isotopically labeled compound, or prodrug thereof.

Exemplary Embodiment 12. The compound of any one of the preceding Exemplary Embodiments, wherein the compound is of Formula (II-a), (II-b), (II-c), (II-d), (II-e), or (II-f):

(II-a)

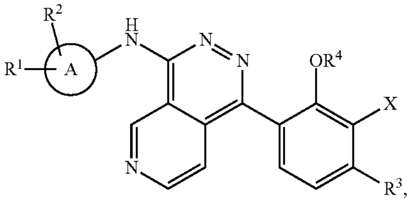

(II-b)

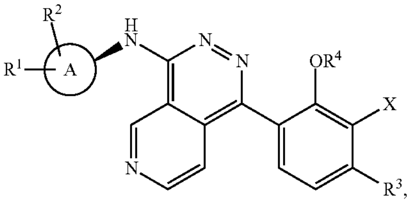

(II-c)

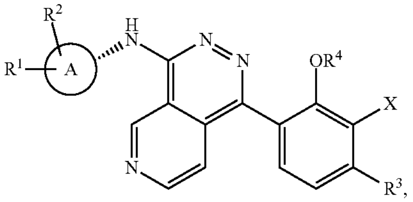

-continued (II-d)

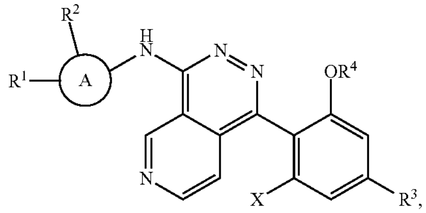

(II-e)

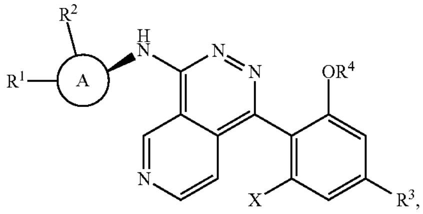

or (II-f)

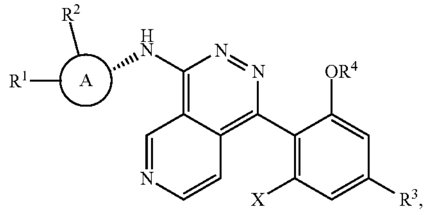

or a pharmaceutically acceptable salt, solvate, clathrate, hydrate, stereoisomer, tautomer, isotopically labeled compound, or prodrug thereof.

Exemplary Embodiment 13. The compound of any one of the preceding Exemplary Embodiments, wherein the compound is of Formula (III-a), (III-b), or (III-c):

(III-a)

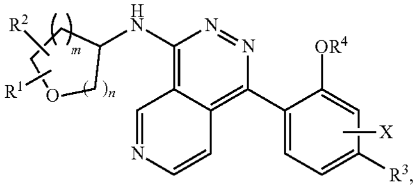

(III-b)

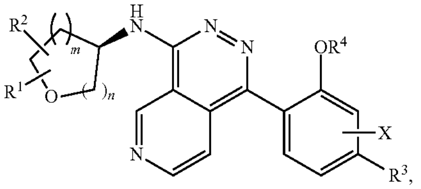

or (III-c)

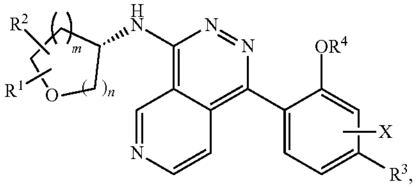

or a pharmaceutically acceptable salt, solvate, clathrate, hydrate, stereoisomer, tautomer, isotopically labeled compound, or prodrug thereof, wherein m is an integer from 0 to 2 and n is an integer from 1 to 2.

Exemplary Embodiment 14. The compound of any one of the preceding Exemplary Embodiments, wherein the compound is of Formula (III-d), (III-e), or (III-f):

(III-d)

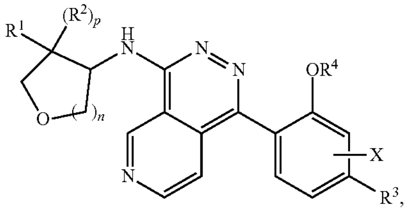

(III-e)

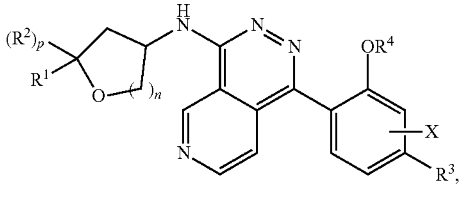

or (III-f)

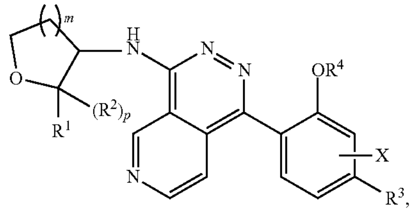

or a pharmaceutically acceptable salt, solvate, clathrate, hydrate, stereoisomer, tautomer, isotopically labeled compound, or prodrug thereof, wherein m is an integer from 0 to 2 and n is an integer from 1 to 2.

Exemplary Embodiment 15. The compound of any one of the preceding Exemplary Embodiments, wherein the compound is of Formula (IV-a), (IV-b), or (IV-c):

(IV-a)

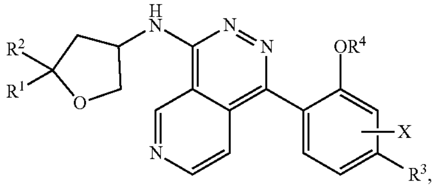

(IV-b)

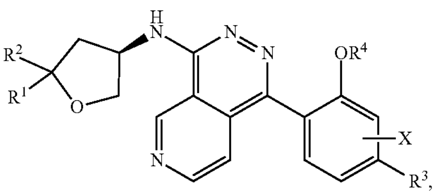

or

-continued (IV-c)

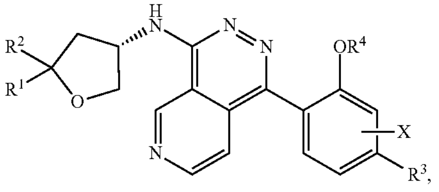

or a pharmaceutically acceptable salt, solvate, clathrate, hydrate, stereoisomer, tautomer, isotopically labeled compound, or prodrug thereof.

Exemplary Embodiment 16. The compound of any one of the preceding Exemplary Embodiments, wherein the compound is of Formula (IV-a1), (IV-b1), or (IV-c1):

(IV-a1)

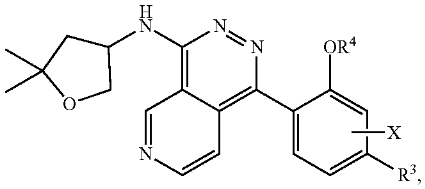

(IV-b1)

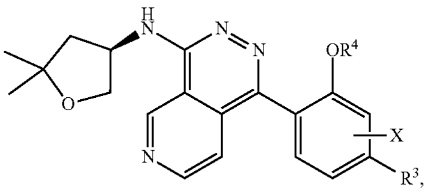

or (IV-c1)

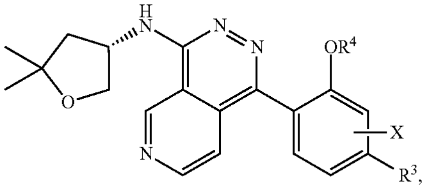

or a pharmaceutically acceptable salt, solvate, clathrate, hydrate, stereoisomer, tautomer, isotopically labeled compound, or prodrug thereof.

Exemplary Embodiment 17. The compound of any one of Exemplary Embodiments 1-13, wherein the compound is of Formula (V-a), (V-b), (V-c), (V-a'), (V-b'), or (V-c'):

(V-a)

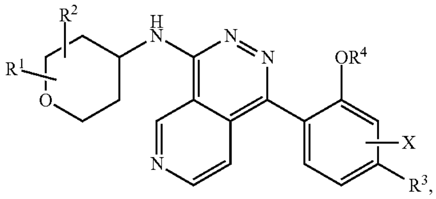

-continued (V-b)

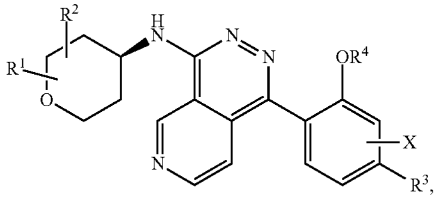

(V-c)

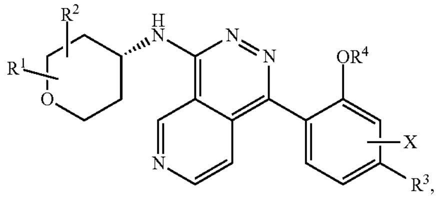

(V-a')

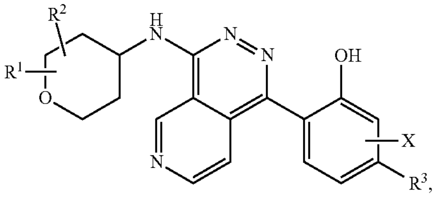

(V-b')

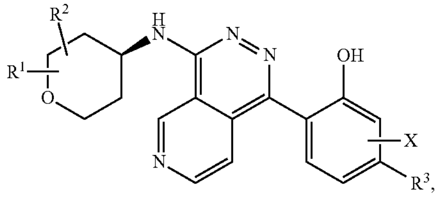

or (V-c')

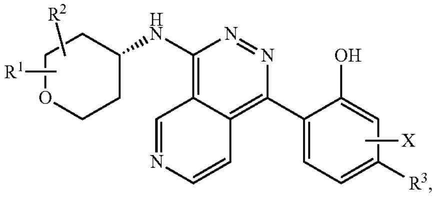

or a pharmaceutically acceptable salt, solvate, clathrate, hydrate, stereoisomer, tautomer, isotopically labeled compound, or prodrug thereof.

Exemplary Embodiment 18. The compound of any one of Exemplary Embodiments 1-13, wherein the compound is of Formula (VI-a), (VI-b), (VI-c), (VI-d), (VI-e), (VI-f), (VI-g), or (VI-h):

(VI-a)

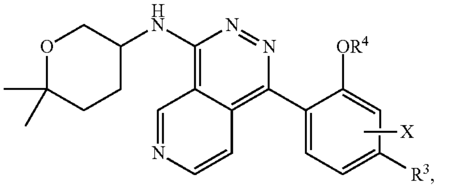

-continued (VI-b)

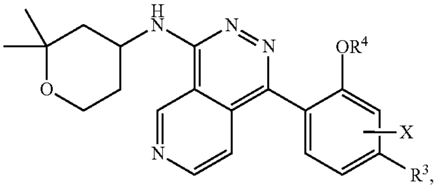

(VI-c)

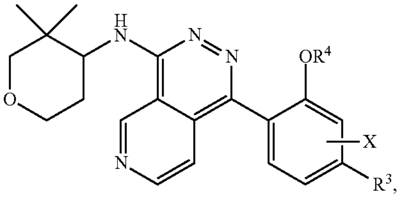

(VI-d)

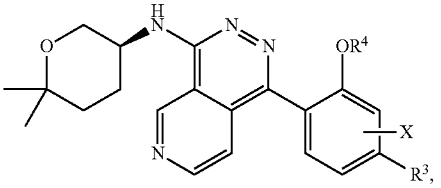

(VI-e)

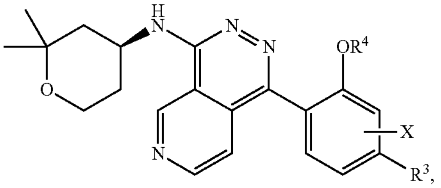

(VI-f)

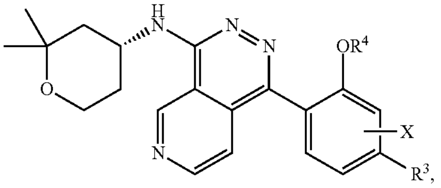

(VI-g)

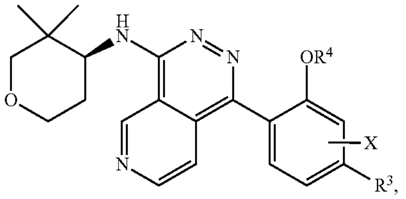

or (VI-h)

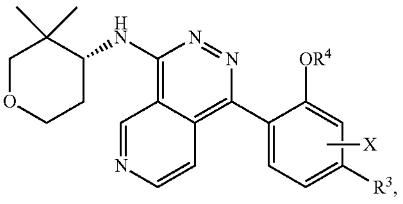

or a pharmaceutically acceptable salt, solvate, clathrate, hydrate, stereoisomer, tautomer, isotopically labeled compound, or prodrug thereof.

Exemplary Embodiment 19. The compound of Exemplary Embodiment 1 of the formula:

1A

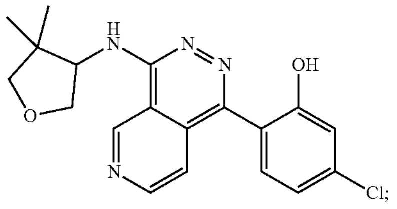

5-chloro-2-(4-((4,4-dimethyltetrahydrofuran-3-yl)amino)pyrido[3,4-d]pyridazin-1-yl)phenol

3A

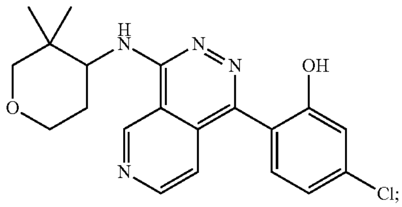

5-chloro-2-(4-((3,3-dimethyltetrahydro-2H-pyran-4-yl)amino)pyrido[3,4-d]pyridazin-1-yl)phenol

4A

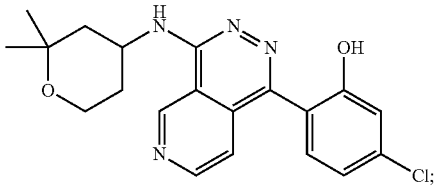

5-chloro-2-(4-((2,2-dimethyltetrahydro-2H-pyran-4-yl)amino)pyrido[3,4-d]pyridazin-1-yl)phenol

5A

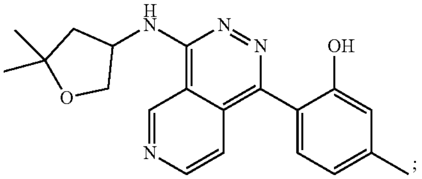

2-(4-((5,5-dimethyltetrahydrofuran-3-yl)amino)pyrido[3,4-d]pyridazin-1-yl)-5-methylphenol

9A

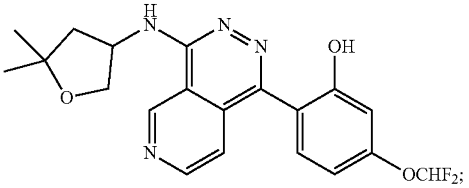

5-(difluoromethoxy)-2-(4-((5,5-dimethyltetrahydrofuran-3-yl)amino)pyrido[3,4-d]pyridazin-1-yl)phenol

10A

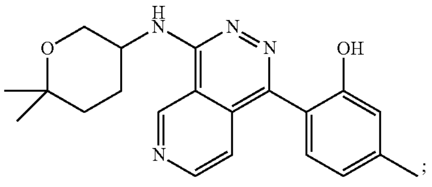

2-(4-((6,6-dimethyltetrahydro-2H-pyran-3-yl)amino)pyrido[3,4-d]pyridazin-1-yl)-5-methylphenol -continued

11A

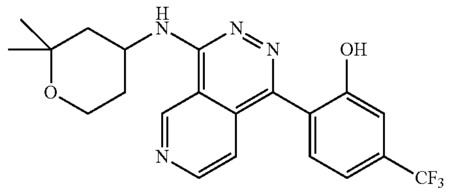

2-(4-((2,2-dimethyltetrahydro-2H-pyran-4-yl)amino)pyrido[3,4-d]pyridazin-1-yl)-5-(trifluoromethyl)phenol;

12A

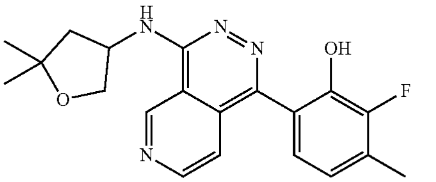

6-(4-((5,5-dimethyltetrahydrofuran-3-yl)amino)pyrido[3,4-d]pyridazin-1-yl)-2-fluoro-3-methylphenol;

13A

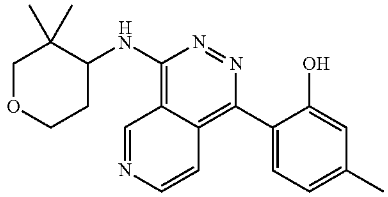

2-(4-((3,3-dimethyltetrahydro-2H-pyran-4-yl)amino)pyrido[3,4-d]pyridazin-1-yl)-5-methylphenol;

14A

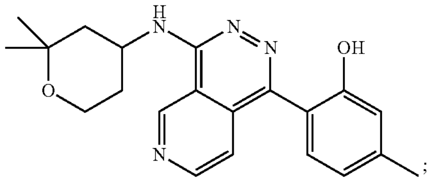

2-(4-((2,2-dimethyltetrahydro-2H-pyran-4-yl)amino)pyrido[3,4-d]pyridazin-1-yl)-5-methylphenol

15A

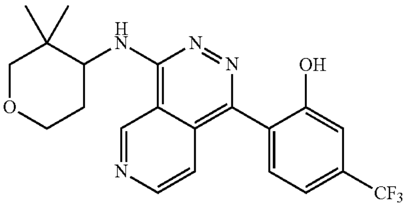

2-(4-((3,3-dimethyltetrahydro-2H-pyran-4-yl)amino)pyrido[3,4-d]pyridazin-1-yl)-5-(trifluoromethyl)phenol;

16A

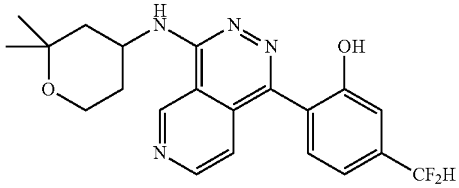

5-(difluoromethyl)-2-(4-((2,2-dimethyltetrahydro-2H-pyran-4-yl)amino)pyrido[3,4-d]pyridazin-1-yl)phenol;

-continued

17A

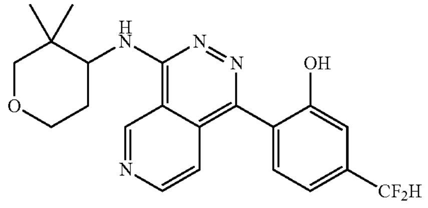

5-(difluoromethyl)-2-(4-((3,3-dimethyltetrahydro-2H-pyran-4-yl)amino)pyrido[3,4-d]pyridazin-1-yl)phenol;

18B

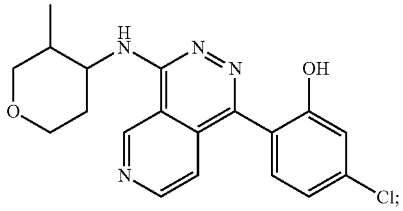

5-chloro-2-(4-((3-methyltetrahydro-2H-pyran-4-yl)amino)pyrido[3,4-d]pyridazin-1-yl)phenol

19A

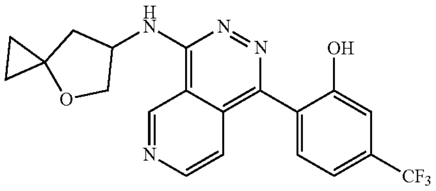

2-(4-((4-oxaspiro[2.4]heptan-6-yl)amino)pyrido[3,4-d]pyridazin-1-yl)-5-(trifluoromethyl)phenol;

20A

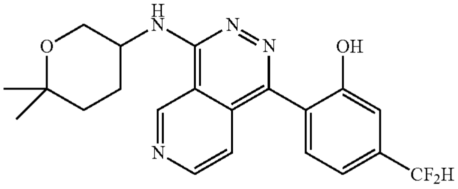

5-(difluoromethyl)-2-(4-((6,6-dimethyltetrahydro-2H-pyran-3-yl)amino)pyrido[3,4-d]pyridazin-1-yl)phenol;

21A

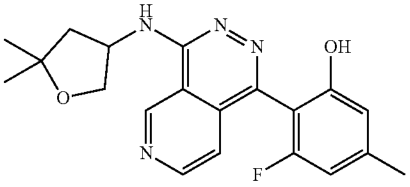

2-(4-((5,5-dimethyltetrahydrofuran-3-yl)amino)pyrido[3,4-d]pyridazin-1-yl)-3-fluoro-5-methylphenol;

22A

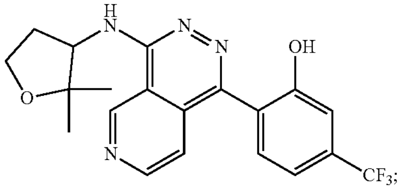

2-(4-((2,2-dimethyltetrahydrofuran-3-yl)amino)pyrido[3,4-d]pyridazin-1-yl)-5-(trifluoromethyl)phenol or a pharmaceutically acceptable salt or isotopically labeled compound thereof.

Exemplary Embodiment 20. The compound of Exemplary Embodiment 1 of the formula:

1*

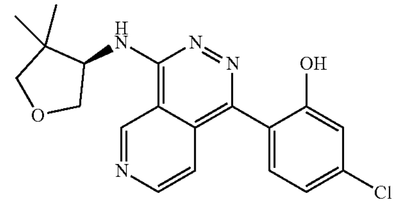

(R)-5-chloro-2-(4-((4,4-dimethyltetrahydrofuran-3-yl)amino)pyrido[3,4-d]pyridazin-1-yl)phenol;

1B*

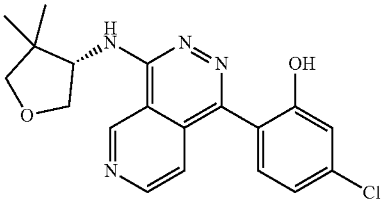

(S)-5-chloro-2-(4-((4,4-dimethyltetrahydrofuran-3-yl)amino)pyrido[3,4-d]pyridazin-1-yl)phenol;

3B*

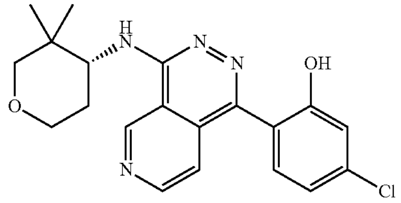

(R)-5-chloro-2-(4-((3,3-dimethyltetrahydro-2H-pyran-4-yl)amino)pyrido[3,4-d]pyridazin-1-yl)phenol;

3*

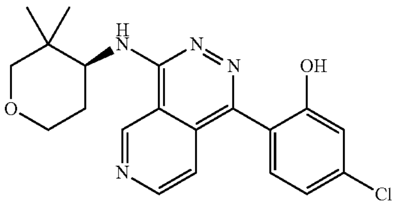

(S)-5-chloro-2-(4-((3,3-dimethyltetrahydro-2H-pyran-4-yl)amino)pyrido[3,4-d]pyridazin-1-yl)phenol;

4*

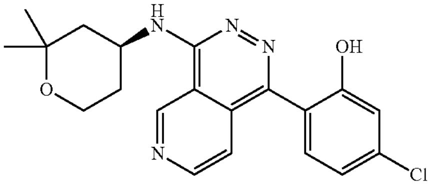

(S)-5-chloro-2-(4-((2,2-dimethyltetrahydro-2H-pyran-4-yl)amino)pyrido[3,4-d]pyridazin-1-yl)phenol;

-continued

4B*

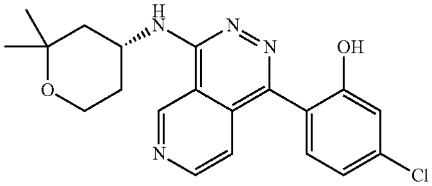

(R)-5-chloro-2-(4-((2,2-dimethyltetrahydro-2H-pyran-4-yl)amino)pyrido[3,4-d]pyridazin-1-yl)phenol;

5

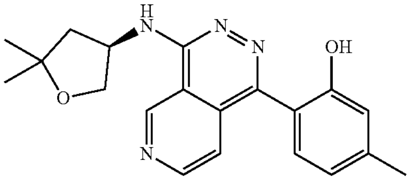

(R)-2-(4-((5,5-dimethyltetrahydrofuran-3-yl)amino)pyrido[3,4-d]pyridazin-1-yl)-5-methylphenol;

5B

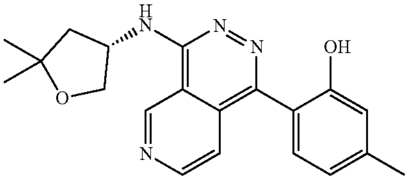

(S)-2-(4-((5,5-dimethyltetrahydrofuran-3-yl)amino)pyrido[3,4-d]pyridazin-1-yl)-5-methylphenol;

9B*

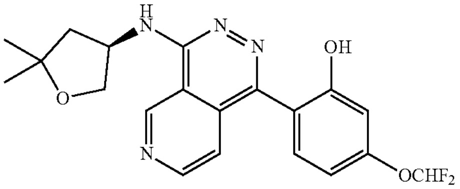

(R)-5-(difluoromethoxy)-2-(4-((5,5-dimethyltetrahydrofuran-3-yl)amino)pyrido[3,4-d]pyridazin-1-yl)phenol;

9*

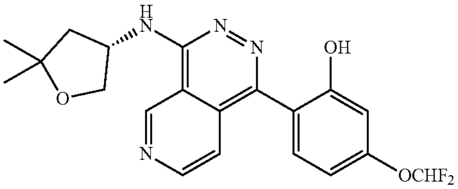

(S)-5-(difluoromethoxy)-2-(4-((5,5-dimethyltetrahydrofuran-3-yl)amino)pyrido[3,4-d]pyridazin-1-yl)phenol;

10*

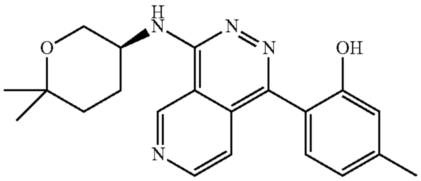

(S)-2-(4-((6,6-dimethyltetrahydro-2H-pyran-3-yl)amino)pyrido[3,4-d]pyridazin-1-yl)-5-methylphenol;

-continued

10B*

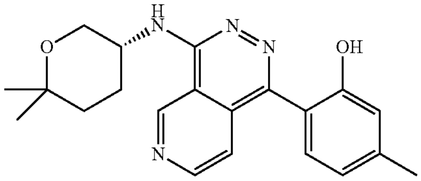

;

(R)-2-(4-((6,6-dimethyltetrahydro-2H-pyran-3-yl)amino)pyrido[3,4-d]pyridazin-1-yl)-5-methylphenol

11*

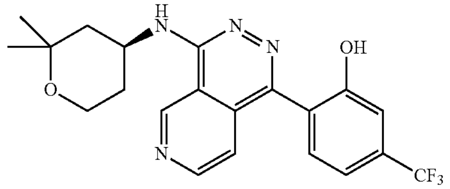

(S)-2-(4-((2,2-dimethyltetrahydro-2H-pyran-4-yl)amino)pyrido[3,4-d]pyridazin-1-yl)-5-(trifluoromethyl)phenol;

11B*

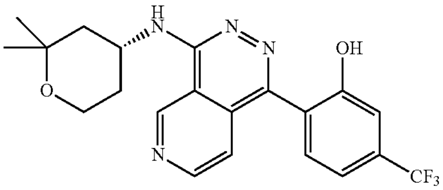

(R)-2-(4-((2,2-dimethyltetrahydro-2H-pyran-4-yl)amino)pyrido[3,4-d]pyridazin-1-yl)-5-(trifluoromethyl)phenol;

12*

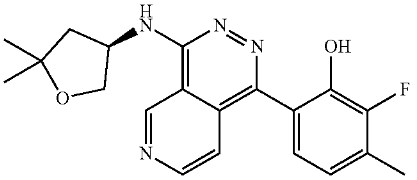

(R)-6-(4-((5,5-dimethyltetrahydrofuran-3-yl)amino)pyrido[3,4-d]pyridazin-1-yl)-2-fluoro-3-methylphenol;

12B*

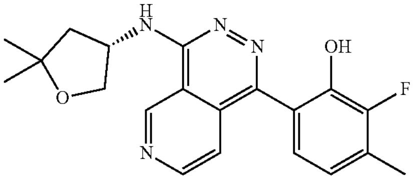

(S)-6-(4-((5,5-dimethyltetrahydrofuran-3-yl)amino)pyrido[3,4-d]pyridazin-1-yl)-2-fluoro-3-methylphenol;

13B*

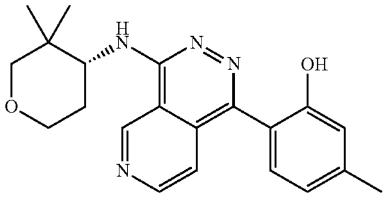

(R)-2-(4-((3,3-dimethyltetrahydro-2H-pyran-4-yl)amino)pyrido[3,4-d]pyridazin-1-yl)-5-methylphenol;

-continued

13*

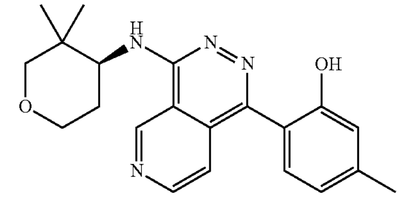

(S)-2-(4-(3,3-dimethyltetrahydro-2H-pyran-4-yl)amino)pyrido[3,4-d]pyridazin-1-yl)-5-methylphenol;

14B*

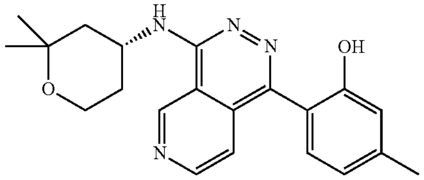

(R)-2-(4-(3,3-dimethyltetrahydro-2H-pyran-4-yl)amino)pyrido[3,4-d]pyridazin-1-yl)-5-methylphenol;

14*

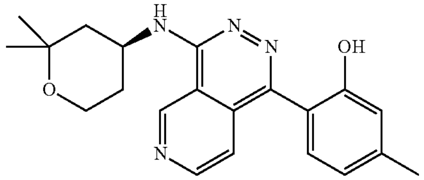

(S)-2-(4-(3,3-dimethyltetrahydro-2H-pyran-4-yl)amino)pyrido[3,4-d]pyridazin-1-yl)-5-methylphenol;

15*

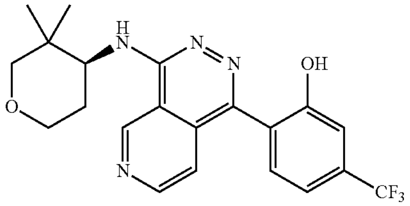

(S)-2-(4-((3,3-dimethyltetrahydro-2H-pyran-4-yl)amino)pyrido[3,4-d]pyridazin-1-yl)-5-(trifluoromethyl)phenol;

15B*

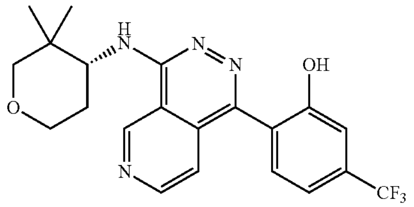

(R)-2-(4-((3,3-dimethyltetrahydro-2H-pyran-4-yl)amino)pyrido[3,4-d]pyridazin-1-yl)-5-(trifluoromethyl)phenol;

16B*

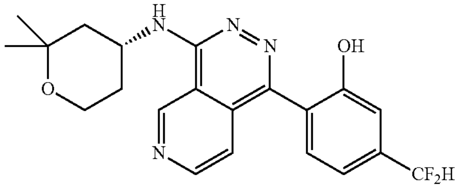

(R)-5-(difluoromethyl)-2-(4-((2,2-dimethyltetrahydro-2H-pyran-4-yl)amino)pyrido[3,4-d]pyridazin-1-yl)phenol;

-continued

16*

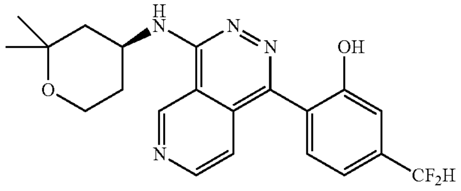

(S)-5-(difluoromethyl)-2-(4-((2,2-dimethyltetrahydro-2H-pyran-4-yl)amino)pyrido[3,4-d]pyridazin-1-yl)phenol;

17*

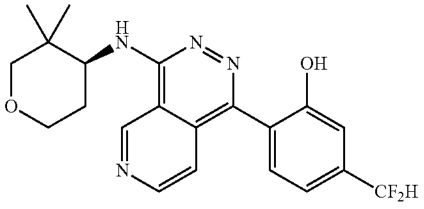

(S)-5-(difluoromethyl)-2-(4-((3,3-dimethyltetrahydro-2H-pyran-4-yl)amino)pyrido[3,4-d]pyridazin-1-yl)phenol;

17B*

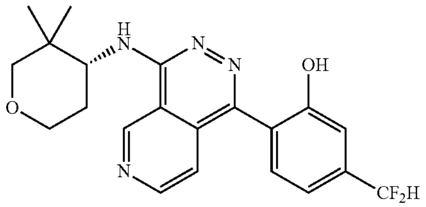

(R)-5-(difluoromethyl)-2-(4-((3,3-dimethyltetrahydro-2H-pyran-4-yl)amino)pyrido[3,4-d]pyridazin-1-yl)phenol;

18A*

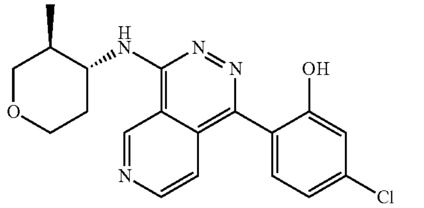

5-chloro-2-(4-(((3S,4R)-3-methyltetrahydro-2H-pyran-4-yl)amino)pyrido-[3,4-d]pyridazin-1-yl)phenol;

18*

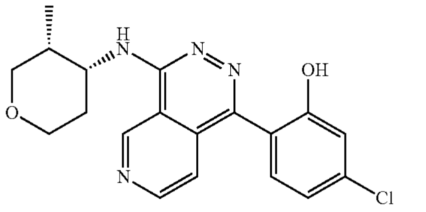

5-chloro-2-(4-(((3R,4R)-3-methyltetrahydro-2H-pyran-4-yl)amino)pyrido-[3,4-d]pyridazin-1-yl)phenol;

18C*

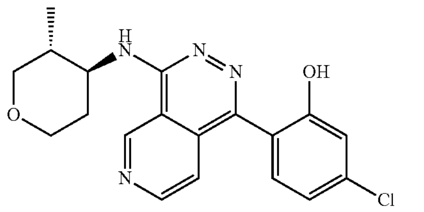

5-chloro-2-(4-(((3R,4S)-3-methyltetrahydro-2H-pyran-4-yl)amino)pyrido-[3,4-d]pyridazin-1-yl)phenol;

-continued

18D*

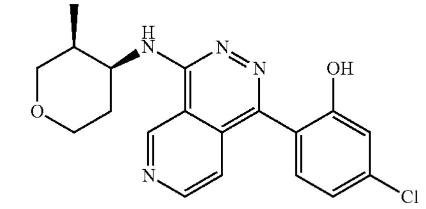

5-chloro-2-(4-(((3S,4S)-3-methyltetrahydro-2H-pyran-4-yl)amino)pyrido-[3,4-d]pyridazin-1-yl)phenol;

19B*

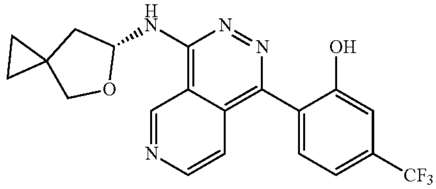

(S)-2-(4-((4-oxaspiro[2.4]heptan-6-yl)amino)pyrido[3,4-d]pyridazin-1-yl)-5-(trifluoromethyl)phenol;

19*

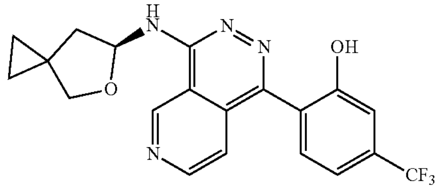

(R)-2-(4-((4-oxaspiro[2.4]heptan-6-yl)amino)pyrido[3,4-d]pyridazin-1-yl)-5-(trifluoromethyl)phenol;

20B*

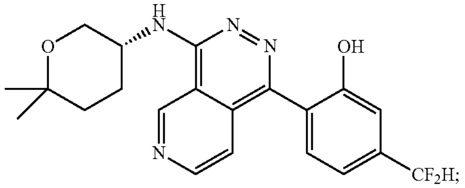

(R)-5-(difluoromethyl)-2-(4-((6,6-dimethyltetrahydro-2H-pyran-3-yl)amino)pyrido[3,4-d]pyridazin-1-yl)phenol

20*

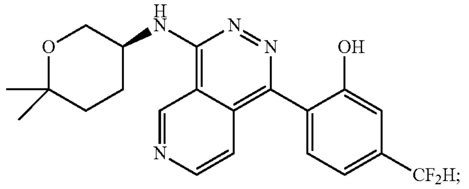

(R)-5-(difluoromethyl)-2-(4-((6,6-dimethyltetrahydro-2H-pyran-3-yl)amino)pyrido[3,4-d]pyridazin-1-yl)phenol

21*

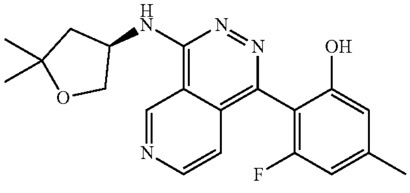

2-(4-(((R)-5,5-dimethyltetrahydrofuran-3-yl)amino)pyrido[3,4-d]pyridazin-1-yl)-3-fluoro-5-methylphenol;

-continued

21B*

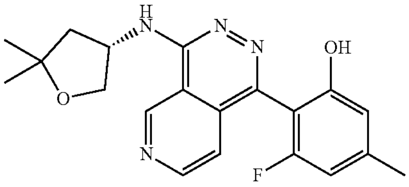

2-(4-(((S)-5,5-dimethyltetrahydrofuran-3-yl)amino)pyrido[3,4-d]pyridazin-1-yl)-3-fluoro-5-methylphenol;

22B*

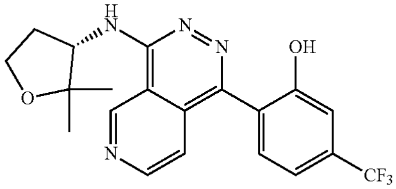

(S)-2-(4-((2,2-dimethyltetrahydrofuran-3-yl)amino)pyrido[3,4-d]pyridazin-1-yl)-5-(trifluoromethyl)phenol;

22*

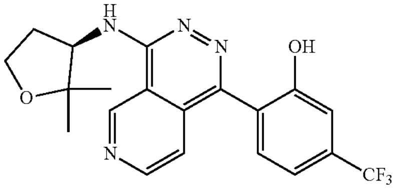

(R)-2-(4-((2,2-dimethyltetrahydrofuran-3-yl)amino)pyrido[3,4-d]pyridazin-1-yl)-5-(trifluoromethyl)phenol;

23A

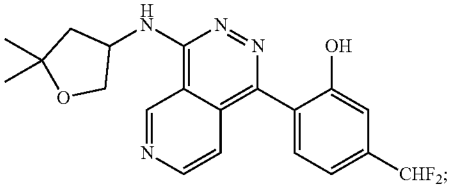

5-(difluoromethyl)-2-(4-((5,5-dimethyltetrahydrofuran-3-yl)amino)pyrido[3,4-d]pyridazin-1-yl)phenol

23*

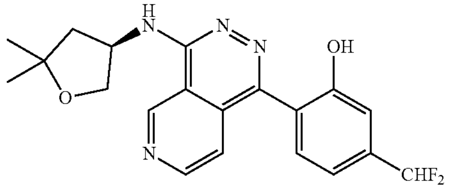

(R)-5-(difluoromethyl)-2-(4-((5,5-dimethyltetrahydrofuran-3-yl)amino)pyrido[3,4-d]pyridazin-1-yl)phenol;

23B*

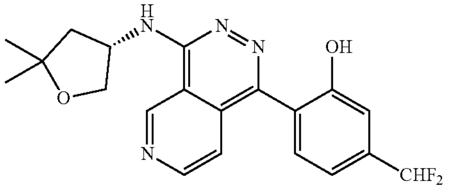

(S)-5-(difluoromethyl)-2-(4-((5,5-dimethyltetrahydrofuran-3-yl)amino)pyrido[3,4-d]pyridazin-1-yl)phenol or a pharmaceutically acceptable salt or isotopically labeled compound thereof.

Exemplary Embodiment 21. A compound of the formula:

2

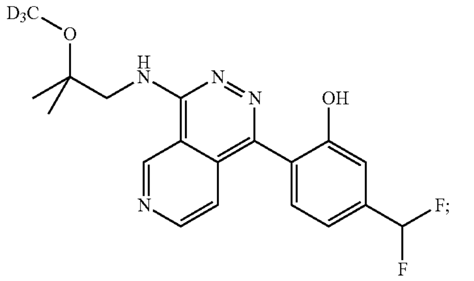

5-(difluoromethyl)-2-(4-((2-(methoxy-d3)-2-methylpropyl) amino)pyrido[3,4-d]pyridazin-1-yl)phenol

6A

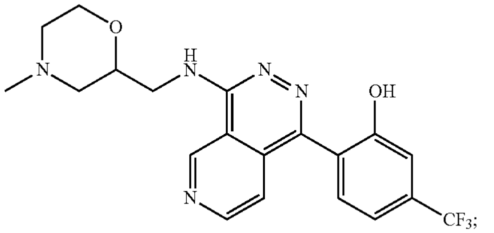

2-(4-(((4-methylmorpholin-2-yl)methyl)amino)pyrido[3,4-d] pyridazin-1-yl)-5-(trifluoromethyl)phenol or a pharmaceutically acceptable salt or isotopically labeled compound thereof.

Exemplary Embodiment 22. The compound of Exemplary Embodiment 1 of the formula:

24*

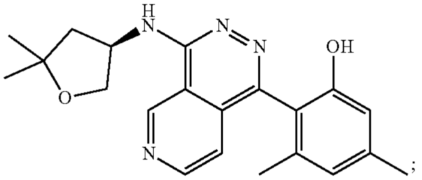

2-(4-(((R)-5,5-dimethyltetrahydrofuran-3-yl)amino)pyrido[3,4-d]pyridazin-1-yl)-3,5-dimethylphenol

24B*

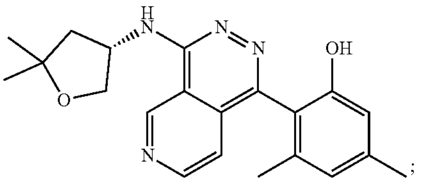

2-(4-(((S)-5,5-dimethyltetrahydrofuran-3-yl)amino)pyrido[3,4-d]pyridazin-1-yl)-3,5-dimethylphenol -continued

25A*

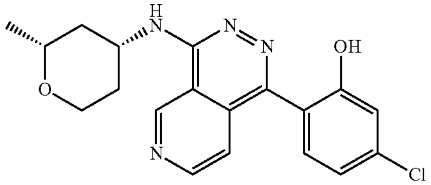

5-chloro-2-(4-(((2R,4R)-2-methyltetrahydro-2H-pyran-4-yl)amino)pyrido[3,4-d]pryidazin-1-yl)phenol;

25B*

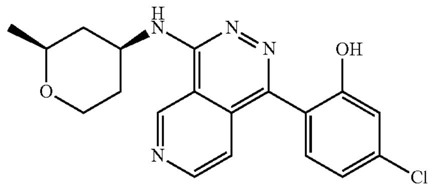

5-chloro-2-(4-(((2S,4S)-2-methyltetrahydro-2H-pyran-4-yl)amino)pyrido[3,4-d]pryidazin-1-yl)phenol;

25C*

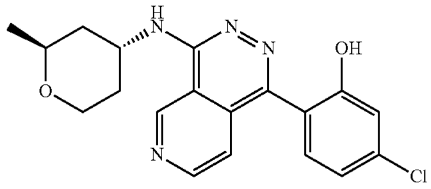

5-chloro-2-(4-(((2S,4R)-2-methyltetrahydro-2H-pyran-4-yl)amino)pyrido[3,4-d]pryidazin-1-yl)phenol;

25D*

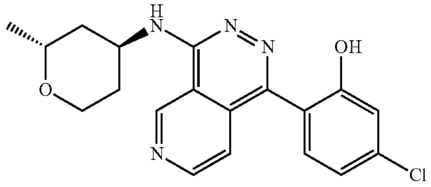

5-chloro-2-(4-(((2R,4S)-2-methyltetrahydro-2H-pyran-4-yl)amino)pyrido[3,4-d]pryidazin-1-yl)phenol;

26*

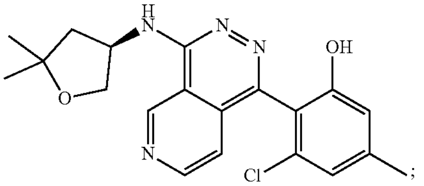

3-chloro-2-(4-(((R)-5,5-dimethyltetrahydrofuran-3-yl)amino)pyrido[3,4-d]pyridazin-1-yl)-5-methylphenol

26B*

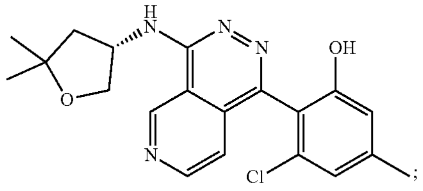

3-chloro-2-(4-(((S)-5,5-dimethyltetrahydrofuran-3-yl)amino)pyrido[3,4-d]pyridazin-1-yl)-5-methylphenol or a pharmaceutically acceptable salt or isotopically labeled compound thereof.

Exemplary Embodiment 23. The compound of Exemplary Embodiment 1, wherein the compound is not

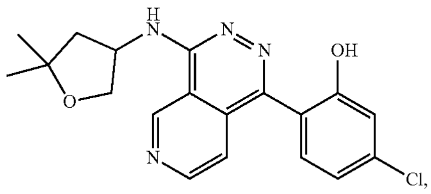 [SMILES: CC1(C)CC(Nc2nnc(-c3ccc(Cl)cc3O)c3ccncc23)CO1]

or a pharmaceutically acceptable salt, solvate, clathrate, hydrate, stereoisomer, tautomer, isotopically labeled compound, or prodrug thereof.

Exemplary Embodiment 24. The compound of Exemplary Embodiment 1, wherein the compound is not:

1A

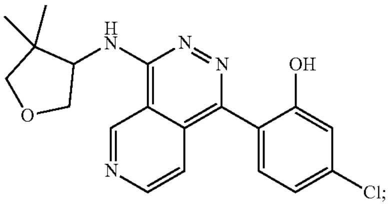

5-chloro-2-(4-((4,4-dimethyltetrahydrofuran-3-yl)amino)pyrido[3,4-d]pyridazin-1-yl)phenol

3A

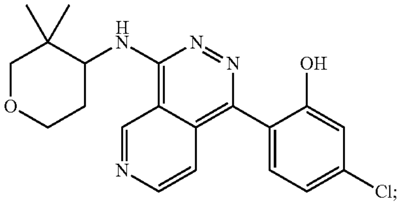

5-chloro-2-(4-((3,3-dimethyltetrahydro-2H-pyran-4-yl)amino)pyrido[3,4-d]pyridazin-1-yl)phenol

4A

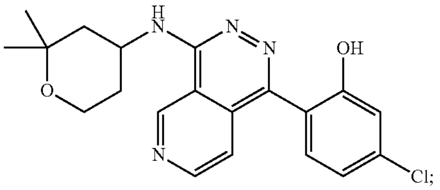

or 5-chloro-2-(4-((2,2-dimethyltetrahydro-2H-pyran-4-yl)amino)pyrido[3,4-d]pyridazin-1-yl)phenol

5A

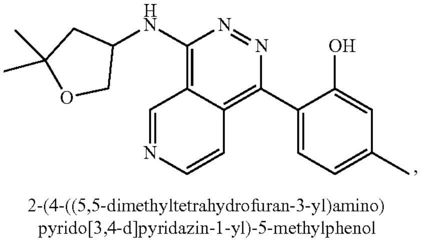

2-(4-((5,5-dimethyltetrahydrofuran-3-yl)amino)pyrido[3,4-d]pyridazin-1-yl)-5-methylphenol or a pharmaceutically acceptable salt or isotopically labeled compound thereof.

Exemplary Embodiment 25. The compound of any one of Exemplary Embodiments 1-21, 23 and 24, wherein the compound has a Kpu,u greater than 0.3.

Exemplary Embodiment 26. The compound of any one of Exemplary Embodiments 1-21, 23, or 24, wherein the compound has a Kpu,u greater than 0.3 to about 10.

Exemplary Embodiment 27. A pharmaceutical composition comprising the compound of any one of Exemplary Embodiments 1-26, or a pharmaceutically acceptable salt, solvate, clathrate, hydrate, stereoisomer, tautomer, isotopically labeled compound, or prodrug thereof, and one or more pharmaceutically acceptable carriers.

Exemplary Embodiment 28. A method of modulating NLRP3, the method comprising administering to the subject a compound of any one of Exemplary Embodiments 1-26, or a pharmaceutically acceptable salt, solvate, clathrate, hydrate, stereoisomer, tautomer, isotopically labeled compound, or prodrug thereof, or a pharmaceutical composition of Exemplary Embodiment 27.

Exemplary Embodiment 29. A method of treating or preventing a disease or disorder, the method comprising administering to the subject a compound of any one of Exemplary Embodiments 1-26, or a pharmaceutically acceptable salt, solvate, clathrate, hydrate, stereoisomer, tautomer, isotopically labeled compound, or prodrug thereof, or a pharmaceutical composition of Exemplary Embodiment 27.

Exemplary Embodiment 30. The compound of any one of Exemplary Embodiments 1-26, or a pharmaceutically acceptable salt, solvate, clathrate, hydrate, stereoisomer, tautomer, isotopically labeled compound, or prodrug thereof, or a pharmaceutical composition of Exemplary Embodiment 27, for use in treating or preventing a disease or disorder.

Exemplary Embodiment 31. Use of the compound of any one of Exemplary Embodiments 1-26, or a pharmaceutically acceptable salt, solvate, clathrate, hydrate, stereoisomer, tautomer, isotopically labeled compound, or prodrug thereof, in the manufacture of a medicament, for the treatment or prevention of a disease or disorder.

Exemplary Embodiment 32. Use of the compound of any one of Exemplary Embodiments 1-26, or a pharmaceutically acceptable salt, solvate, clathrate, hydrate, stereoisomer, tautomer, isotopically labeled compound, or prodrug thereof, for the treatment or prevention of a disease or disorder.

Exemplary Embodiment 33. The method, compound, or use of any one of Exemplary Embodiments 29-32, wherein the disease or disorder is an NLRP3-related disease or disorder.

Exemplary Embodiment 34. The method, compound, or use of any one of Exemplary Embodiments 28-33, wherein the subject is a human.

Exemplary Embodiment 35. The method, compound, or use of any one of Exemplary Embodiments 28-34, wherein the disease or disorder is inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease.

Exemplary Embodiment 36. The method, compound, or use of Exemplary Embodiment 35, wherein the disease or disorder of the central nervous system is Parkinson's disease, Alzheimer's disease, traumatic brain injury, spinal cord injury, amyotrophic lateral sclerosis, or multiple sclerosis.

Exemplary Embodiment 37. The method, compound, or use of Exemplary Embodiment 35, wherein the kidney disease is an acute kidney disease, a chronic kidney disease, or a rare kidney disease.

Exemplary Embodiment 38. The method, compound, or use of Exemplary Embodiment 35, wherein the skin disease is psoriasis, hidradenitis suppurativa (HS), or atopic dermatitis.

Exemplary Embodiment 39. The method, compound, or use of Exemplary Embodiment 35, wherein the rheumatic disease is dermatomyositis, Still's disease, or juvenile idiopathic arthritis.

Exemplary Embodiment 40. The method, compound, or use of Exemplary Embodiment 35, wherein the NLRP3-related disease is in a subject that has been determined to carry a germline or somatic non-silent mutation in NLRP3.

Exemplary Embodiment 41. The method, compound, or use of Exemplary Embodiment 40, wherein the NLRP3-related disease is in a subject that has been determined to carry a germline or somatic non-silent mutation in NLRP3 is cryopyrin-associated autoinflammatory syndrome.

Exemplary Embodiment 42. The method, compound, or use of Exemplary Embodiment 35, wherein the cryopyrin-associated autoinflammatory syndrome is familial cold auto-inflammatory syndrome, Muckle-Wells syndrome, or neonatal onset multisystem inflammatory disease.

Exemplary Embodiment 43. A compound selected from:

(R)-5-chloro-2-(4-((4,4-dimethyltetrahydrofuran-3-yl)amino)pyrido[3,4-d]pyridazin-1-yl)phenol;

5-(difluoromethyl)-2-(4-((2-(methoxy-d3)-2-methylpropyl)amino)pyrido[3,4-d]pyridazin-1-yl)phenol;

(R)-5-chloro-2-(4-((3,3-dimethyltetrahydro-2H-pyran-4-yl)amino)pyrido[3,4-d]pyridazin-1-yl)phenol;

(S)-5-chloro-2-(4-((2,2-dimethyltetrahydro-2H-pyran-4-yl)amino)pyrido[3,4-d]pyridazin-1-yl)phenol;

(R)-2-(4-((5,5-dimethyltetrahydrofuran-3-yl)amino)pyrido[3,4-d]pyridazin-1-yl)-5-methylphenol; and (S)-2-(4-(((4-methylmorpholin-2-yl)methyl)amino)pyrido[3,4-d]pyridazin-1-yl)-5-(trifluoromethyl)phenol;

and a pharmaceutically acceptable salt, solvate, clathrate, hydrate, stereoisomer, tautomer, or prodrug of any of the foregoing.

Exemplary Embodiment 44. The compound of Exemplary Embodiment 43, wherein the compound is (R)-5-chloro-2-(4-((4,4-dimethyltetrahydrofuran-3-yl)amino)pyrido[3,4-d]pyridazin-1-yl)phenol, or a pharmaceutically acceptable salt, solvate, clathrate, hydrate, stereoisomer, tautomer, isotopically labeled compound, or prodrug thereof.

Exemplary Embodiment 45. The compound of Exemplary Embodiment 43, wherein the compound is 5-(difluoromethyl)-2-(4-((2-(methoxy-d3)-2-methylpropyl)amino)pyrido[3,4-d]pyridazin-1-yl)phenol, or a pharmaceutically acceptable salt, solvate, clathrate, hydrate, stereoisomer, tautomer, isotopically labeled compound, or prodrug thereof.

Exemplary Embodiment 46. The compound of Exemplary Embodiment 43, wherein the compound is (R)-5-chloro-2-(4-((3,3-dimethyltetrahydro-2H-pyran-4-yl)amino)pyrido[3,4-d]pyridazin-1-yl)phenol, or a pharmaceutically acceptable salt, solvate, clathrate, hydrate, stereoisomer, tautomer, isotopically labeled compound, or prodrug thereof.

Exemplary Embodiment 47. The compound of Exemplary Embodiment 43, wherein the compound is (S)-5-chloro-2-(4-((2,2-dimethyltetrahydro-2H-pyran-4-yl)amino)pyrido[3,4-d]pyridazin-1-yl)phenol, or a pharmaceutically acceptable salt, solvate, clathrate, hydrate, stereoisomer, tautomer, isotopically labeled compound, or prodrug thereof.

Exemplary Embodiment 48. The compound of Exemplary Embodiment 43, wherein the compound is (R)-2-(4-((5,5-dimethyltetrahydrofuran-3-yl)amino)pyrido[3,4-d]pyridazin-1-yl)-5-methylphenol, or a pharmaceutically acceptable salt, solvate, clathrate, hydrate, stereoisomer, tautomer, isotopically labeled compound, or prodrug thereof.

Exemplary Embodiment 49. The compound of Exemplary Embodiment 43, wherein the compound is (S)-2-(4-(((4-methylmorpholin-2-yl)methyl)amino)pyrido[3,4-d]pyridazin-1-yl)-5-(trifluoromethyl)phenol, or a pharmaceutically acceptable salt, solvate, clathrate, hydrate, stereoisomer, tautomer, isotopically labeled compound, or prodrug thereof.

Exemplary Embodiment 50. A pharmaceutical composition comprising a compound of Exemplary Embodiment 43, or a pharmaceutically acceptable salt, solvate, clathrate, hydrate, stereoisomer, tautomer, isotopically labeled compound, or prodrug thereof, and a pharmaceutically acceptable carrier.

Exemplary Embodiment 51. A pharmaceutical composition comprising a compound of Exemplary Embodiment 44, or a pharmaceutically acceptable salt, solvate, clathrate, hydrate, stereoisomer, tautomer, isotopically labeled compound, or prodrug thereof, and a pharmaceutically acceptable carrier.

Exemplary Embodiment 52. A pharmaceutical composition comprising a compound of Exemplary Embodiment 45, or a pharmaceutically acceptable salt, solvate, clathrate, hydrate, stereoisomer, tautomer, isotopically labeled compound, or prodrug thereof, and a pharmaceutically acceptable carrier.

Exemplary Embodiment 53. A pharmaceutical composition comprising a compound of Exemplary Embodiment 46, or a pharmaceutically acceptable salt, solvate, clathrate, hydrate, stereoisomer, tautomer, isotopically labeled compound, or prodrug thereof, and a pharmaceutically acceptable carrier.

Exemplary Embodiment 54. A pharmaceutical composition comprising a compound of Exemplary Embodiment 47, or a pharmaceutically acceptable salt, solvate, clathrate, hydrate, stereoisomer, tautomer, isotopically labeled compound, or prodrug thereof, and a pharmaceutically acceptable carrier.

Exemplary Embodiment 55. A pharmaceutical composition comprising a compound of Exemplary Embodiment 48, or a pharmaceutically acceptable salt, solvate, clathrate, hydrate, stereoisomer, tautomer, isotopically labeled compound, or prodrug thereof, and a pharmaceutically acceptable carrier.

Exemplary Embodiment 56. A pharmaceutical composition comprising a compound of Exemplary Embodiment 49, or a pharmaceutically acceptable salt, solvate, clathrate, hydrate, stereoisomer, tautomer, isotopically labeled compound, or prodrug thereof, and a pharmaceutically acceptable carrier.

Exemplary Embodiment 57. A method of treating or preventing an NLRP3-related disease or disorder, comprising administering to the subject at least one therapeutically effective amount of the compound of Exemplary Embodiment 43, or a pharmaceutically acceptable salt, solvate, clathrate, hydrate, stereoisomer, tautomer, isotopically labeled compound, or prodrug thereof.

Exemplary Embodiment 58. The method of Exemplary Embodiment 57, wherein the NLRP3-related disease or disorder is inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease in a subject that has been determined to carry a germline or somatic non-silent mutation in NLRP3.

Exemplary Embodiment 59. The method of Exemplary Embodiment 58, wherein the compound is (R)-5-chloro-2-(4-((4,4-dimethyltetrahydrofuran-3-yl)amino)pyrido[3,4-d]pyridazin-1-yl)phenol, or a pharmaceutically acceptable salt, solvate, clathrate, hydrate, stereoisomer, tautomer, isotopically labeled compound, or prodrug thereof.

Exemplary Embodiment 60. The method of Exemplary Embodiment 58, wherein the compound is 5-(difluoromethyl)-2-(4-((2-(methoxy-d3)-2-methylpropyl)amino)pyrido[3,4-d]pyridazin-1-yl)phenol, or a pharmaceutically acceptable salt, solvate, clathrate, hydrate, stereoisomer, tautomer, isotopically labeled compound, or prodrug thereof.

Exemplary Embodiment 61. The method of Exemplary Embodiment 58, wherein the compound is (R)-5-chloro-2-(4-((3,3-dimethyltetrahydro-2H-pyran-4-yl)amino)pyrido[3,4-d]pyridazin-1-yl)phenol, or a pharmaceutically acceptable salt, solvate, clathrate, hydrate, stereoisomer, tautomer, isotopically labeled compound, or prodrug thereof.

Exemplary Embodiment 62. The method of Exemplary Embodiment 58, wherein the compound is (S)-5-chloro-2-(4-((2,2-dimethyltetrahydro-2H-pyran-4-yl)amino)pyrido[3,4-d]pyridazin-1-yl)phenol, or a pharmaceutically acceptable salt, solvate, clathrate, hydrate, stereoisomer, tautomer, isotopically labeled compound, or prodrug thereof.

Exemplary Embodiment 63. The method of Exemplary Embodiment 58, wherein the compound is (R)-2-(4-((5,5-dimethyltetrahydrofuran-3-yl)amino)pyrido[3,4-d]pyridazin-1-yl)-5-methylphenol, or a pharmaceutically acceptable salt, solvate, clathrate, hydrate, stereoisomer, tautomer, isotopically labeled compound, or prodrug thereof.

Exemplary Embodiment 64. The method of Exemplary Embodiment 58, wherein the compound is (S)-2-(4-(((4-methylmorpholin-2-yl)methyl)amino)pyrido[3,4-d]pyridazin-1-yl)-5-(trifluoromethyl)phenol, or a pharmaceutically acceptable salt, solvate, clathrate, hydrate, stereoisomer, tautomer, isotopically labeled compound, or prodrug thereof.

Exemplary Embodiment 65. A method of treating or preventing an NLRP3-related disease or disorder selected from Parkinson's disease, Alzheimer's disease, multiple sclerosis, refractory epilepsy, stroke, ALS, headache/pain, and traumatic brain injury, said method comprising administering to the subject at least one therapeutically effective amount of the compound of Exemplary Embodiment 43, or a pharmaceutically acceptable salt, solvate, clathrate, hydrate, stereoisomer, tautomer, isotopically labeled compound, or prodrug thereof.

Exemplary Embodiment 66. The method of Exemplary Embodiment 65, wherein the compound is (R)-5-chloro-2-(4-((4,4-dimethyltetrahydrofuran-3-yl)amino)pyrido[3,4-d]pyridazin-1-yl)phenol, or a pharmaceutically acceptable salt, solvate, clathrate, hydrate, stereoisomer, tautomer, isotopically labeled compound, or prodrug thereof.

Exemplary Embodiment 67. The method of Exemplary Embodiment 65, wherein the compound is 5-(difluoromethyl)-2-(4-((2-(methoxy-d3)-2-methylpropyl)amino)pyrido[3,4-d]pyridazin-1-yl)phenol, or a pharmaceutically acceptable salt, solvate, clathrate, hydrate, stereoisomer, tautomer, isotopically labeled compound, or prodrug thereof.

Exemplary Embodiment 68. The method of Exemplary Embodiment 65, wherein the compound is (R)-5-chloro-2-(4-((3,3-dimethyltetrahydro-2H-pyran-4-yl)amino)pyrido[3,4-d]pyridazin-1-yl)phenol, or a pharmaceutically acceptable salt, solvate, clathrate, hydrate, stereoisomer, tautomer, isotopically labeled compound, or prodrug thereof.

Exemplary Embodiment 69. The method of Exemplary Embodiment 65, wherein the compound is (S)-5-chloro-2-(4-((2,2-dimethyltetrahydro-2H-pyran-4-yl)amino)pyrido[3,4-d]pyridazin-1-yl)phenol, or a pharmaceutically acceptable salt, solvate, clathrate, hydrate, stereoisomer, tautomer, isotopically labeled compound, or prodrug thereof.

Exemplary Embodiment 70. The method of Exemplary Embodiment 65, wherein the compound is (R)-2-(4-((5,5-dimethyltetrahydrofuran-3-yl)amino)pyrido[3,4-d]pyridazin-1-yl)-5-methylphenol, or a pharmaceutically acceptable salt, solvate, clathrate, hydrate, stereoisomer, tautomer, isotopically labeled compound, or prodrug thereof.

Exemplary Embodiment 71. The method of Exemplary Embodiment 65, wherein the compound is (S)-2-(4-(((4-methylmorpholin-2-yl)methyl)amino)pyrido[3,4-d]pyridazin-1-yl)-5-(trifluoromethyl)phenol, or a pharmaceutically acceptable salt, solvate, clathrate, hydrate, stereoisomer, tautomer, isotopically labeled compound, or prodrug thereof.

Exemplary Embodiment 72. A method of treating or preventing an NLRP3-related disease or disorder selected from Parkinson's disease, Alzheimer's disease, multiple sclerosis, refractory epilepsy, stroke, ALS, headache/pain, and traumatic brain injury, said method comprising administering to the subject at least one therapeutically effective amount of the pharmaceutical composition of Exemplary Embodiment 50.

Exemplary Embodiment A1. A compound selected from the group consisting of:

(R)-5-chloro-2-(4-((4,4-dimethyltetrahydrofuran-3-yl)amino)pyrido[3,4-d]pyridazin-1-yl)phenol;

5-(difluoromethyl)-2-(4-((2-(methoxy-d3)-2-methylpropyl)amino)pyrido[3,4-d]pyridazin-1-yl)phenol;

(R)-5-chloro-2-(4-((3,3-dimethyltetrahydro-2H-pyran-4-yl)amino)pyrido[3,4-d]pyridazin-1-yl)phenol;

(S)-5-chloro-2-(4-((2,2-dimethyltetrahydro-2H-pyran-4-yl)amino)pyrido[3,4-d]pyridazin-1-yl)phenol;

(R)-2-(4-((5,5-dimethyltetrahydrofuran-3-yl)amino)pyrido[3,4-d]pyridazin-1-yl)-5-methylphenol; and (S)-2-(4-(((4-methylmorpholin-2-yl)methyl)amino)pyrido[3,4-d]pyridazin-1-yl)-5-(trifluoromethyl)phenol.

Exemplary Embodiment A2. The compound of Exemplary Embodiment A1, wherein the compound is (R)-5-chloro-2-(4-((4,4-dimethyltetrahydrofuran-3-yl)amino)pyrido[3,4-d]pyridazin-1-yl)phenol.

Exemplary Embodiment A3. The compound of Exemplary Embodiment A1, wherein the compound is 5-(difluoromethyl)-2-(4-((2-(methoxy-d3)-2-methylpropyl)amino)pyrido[3,4-d]pyridazin-1-yl)phenol.

Exemplary Embodiment A4. The compound of Exemplary Embodiment A1, wherein the compound is (R)-5-chloro-2-(4-((3,3-dimethyltetrahydro-2H-pyran-4-yl)amino)pyrido[3,4-d]pyridazin-1-yl)phenol.

Exemplary Embodiment A5. The compound of Exemplary Embodiment A1, wherein the compound is (S)-5-chloro-2-(4-((2,2-dimethyltetrahydro-2H-pyran-4-yl)amino)pyrido[3,4-d]pyridazin-1-yl)phenol.

Exemplary Embodiment A6. The compound of Exemplary Embodiment A1, wherein the compound is (R)-2-(4-

((5,5-dimethyltetrahydrofuran-3-yl)amino)pyrido[3,4-d]pyridazin-1-yl)-5-methylphenol.

Exemplary Embodiment A7. The compound of Exemplary Embodiment A1, wherein the compound is (S)-2-(4-(((4-methylmorpholin-2-yl)methyl)amino)pyrido[3,4-d]pyridazin-1-yl)-5-(trifluoromethyl)phenol.

Exemplary Embodiment A8. A pharmaceutical composition comprising a compound of Exemplary Embodiment A1, and a pharmaceutically acceptable carrier.

Exemplary Embodiment A9. A pharmaceutical composition comprising a compound of Exemplary Embodiment A2, and a pharmaceutically acceptable carrier.

Exemplary Embodiment A10. A pharmaceutical composition comprising a compound of Exemplary Embodiment A3, and a pharmaceutically acceptable carrier.

Exemplary Embodiment A11. A pharmaceutical composition comprising a compound of Exemplary Embodiment A4, and a pharmaceutically acceptable carrier.

Exemplary Embodiment A12. A pharmaceutical composition comprising a compound of Exemplary Embodiment A5, and a pharmaceutically acceptable carrier.

Exemplary Embodiment A13. A pharmaceutical composition comprising a compound of Exemplary Embodiment A6, and a pharmaceutically acceptable carrier.

Exemplary Embodiment A14. A pharmaceutical composition comprising a compound of Exemplary Embodiment A7, and a pharmaceutically acceptable carrier.

Exemplary Embodiment A15. A method of treating or preventing an NLRP3-related disease or disorder, comprising administering to the subject at least one therapeutically effective amount of the compound of Exemplary Embodiment A1.

Exemplary Embodiment A16. The method of Exemplary Embodiment A1, wherein the NLRP3-related disease or disorder is inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease in a subject that has been determined to carry a germline or somatic non-silent mutation in NLRP3.

Exemplary Embodiment A17. The method of Exemplary Embodiment A16, wherein the compound is (R)-5-chloro-2-(4-((4,4-dimethyltetrahydrofuran-3-yl)amino)pyrido[3,4-d]pyridazin-1-yl)phenol.

Exemplary Embodiment A18. The method of Exemplary Embodiment A16, wherein the compound is 5-(difluoromethyl)-2-(4-((2-(methoxy-d3)-2-methylpropyl)amino)pyrido[3,4-d]pyridazin-1-yl)phenol.

Exemplary Embodiment A19. The method of Exemplary Embodiment A16, wherein the compound is (R)-5-chloro-2-(4-((3,3-dimethyltetrahydro-2H-pyran-4-yl)amino)pyrido[3,4-d]pyridazin-1-yl)phenol.

Exemplary Embodiment A20. The method of Exemplary Embodiment A16, wherein the compound is (S)-5-chloro-2-(4-((2,2-dimethyltetrahydro-2H-pyran-4-yl)amino)pyrido[3,4-d]pyridazin-1-yl)phenol.

Exemplary Embodiment A21. The method of Exemplary Embodiment A16, wherein the compound is (R)-2-(4-((5,5-dimethyltetrahydrofuran-3-yl)amino)pyrido[3,4-d]pyridazin-1-yl)-5-methylphenol.

Exemplary Embodiment A22. The method of Exemplary Embodiment A16, wherein the compound is (S)-2-(4-(((4-methylmorpholin-2-yl)methyl)amino)pyrido[3,4-d]pyridazin-1-yl)-5-(trifluoromethyl)phenol.

Exemplary Embodiment A23. A method of treating or preventing an NLRP3-related disease or disorder selected from Parkinson's disease, Alzheimer's disease, multiple sclerosis, refractory epilepsy, stroke, ALS, headache/pain, and traumatic brain injury, said method comprising administering to the subject at least one therapeutically effective amount of the compound of Exemplary Embodiment A1.

Exemplary Embodiment A24. The method of Exemplary Embodiment A23, wherein the compound is (R)-5-chloro-2-(4-((4,4-dimethyltetrahydrofuran-3-yl)amino)pyrido[3,4-d]pyridazin-1-yl)phenol.

Exemplary Embodiment A25. The method of Exemplary Embodiment A23, wherein the compound is 5-(difluoromethyl)-2-(4-((2-(methoxy-d3)-2-methylpropyl)amino)pyrido[3,4-d]pyridazin-1-yl)phenol.

Exemplary Embodiment A26. The method of Exemplary Embodiment A23, wherein the compound is (R)-5-chloro-2-(4-((3,3-dimethyltetrahydro-2H-pyran-4-yl)amino)pyrido[3,4-d]pyridazin-1-yl)phenol.

Exemplary Embodiment A27. The method of Exemplary Embodiment A23, wherein the compound is (S)-5-chloro-2-(4-((2,2-dimethyltetrahydro-2H-pyran-4-yl)amino)pyrido[3,4-d]pyridazin-1-yl)phenol.

Exemplary Embodiment A28. The method of Exemplary Embodiment A23, wherein the compound is (R)-2-(4-((5,5-dimethyltetrahydrofuran-3-yl)amino)pyrido[3,4-d]pyridazin-1-yl)-5-methylphenol.

Exemplary Embodiment A29. The method of Exemplary Embodiment A23, wherein the compound is (S)-2-(4-(((4-methylmorpholin-2-yl)methyl)amino)pyrido[3,4-d]pyridazin-1-yl)-5-(trifluoromethyl)phenol.

Exemplary Embodiment A30. A method of treating or preventing an NLRP3-related disease or disorder selected from Parkinson's disease, Alzheimer's disease, multiple sclerosis, refractory epilepsy, stroke, ALS, headache/pain, and traumatic brain injury, said method comprising administering to the subject at least one therapeutically effective amount of the pharmaceutical composition of Exemplary Embodiment A8.

EXAMPLES

For exemplary purpose, neutral (free base) compounds described herein are synthesized and tested in the examples. It is understood that the neutral compounds disclosed herein may be converted to the corresponding pharmaceutically acceptable salts of the compounds using routine techniques in the art (e.g., by saponification of an ester to the carboxylic acid salt, or by hydrolyzing an amide to form a corresponding carboxylic acid and then converting the carboxylic acid to a carboxylic acid salt).

Nuclear magnetic resonance (NMR) spectra were recorded at 400 MHz as stated and at 300.3 K unless otherwise stated; the chemical shifts (6) are reported in parts per million (ppm). Spectra were recorded using a Bruker Avance 400 instrument with 8, 16 or 32 scans.

LC-MS chromatograms and spectra were recorded using a Shimadzu LCMS-2020. Injection volumes were 0.7-8.0 μl and the flow rates were typically 0.8 or 1.2 ml/min. Detection methods were diode array (DAD) or evaporative light scattering (ELSD) as well as positive ion electrospray ionization. MS range was 100-1000 Da. Solvents were gradients of water and acetonitrile both containing a modifier (typically 0.01-0.04%) such as trifluoroacetic acid or ammonium carbonate.

Abbreviations

DCM dichloromethane
DMF N,N-dimethylformamide
DMSO dimethylsulfoxide
dppf 1,1'-bis(diphenylphosphino)ferrocene
ESI electrospray ionization
EtOAc or EA ethyl acetate
EtOH ethanol
FA formic acid
h hour(s)
Hex hexanes
HPLC high-performance liquid chromatography
IPA isopropanol
LCMS Liquid Chromatography-Mass Spectrometry
MeCN or ACN acetonitrile
MeOH methanol
min minute(s)
mw microwave
m/z mass/charge
PE petroleum ether
prep-HPLC preparative high-performance liquid chromatography
rt room temperature
RT retention time
THF tetrahydrofuran
Y yield Example 1. 5-chloro-2-(4-((4,4-dimethyltetrahydrofuran-3-yl)amino)pyrido[3,4-d]pyridazin-1-yl)phenol (Compound 1A), (R)-5-chloro-2-(4-((4,4-dimethyltetrahydrofuran-3-yl)amino)pyrido[3,4-d]pyridazin-1-yl)phenol (Compound 1*) and (S)-5-chloro-2-(4-((4,4-dimethyltetrahydrofuran-3-yl)amino)pyrido[3,4-d]pyridazin-1-yl)phenol (Compound 1B*)

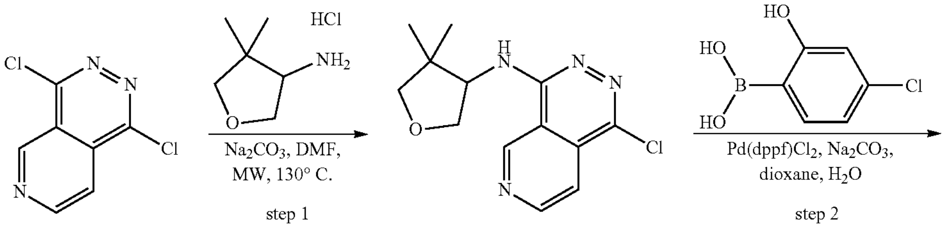

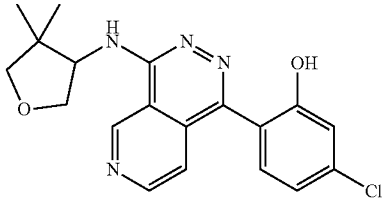

Compound 1A 5-chloro-2-(4-((4,4-dimethyltetrahydrofuran-3-yl)amino)pyrido[3,4-d]pyridazin-1-yl)phenol

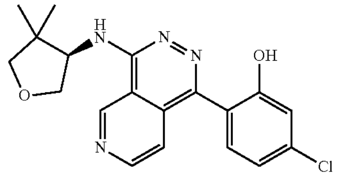

Compound 1*

(R)-5-chloro-2-(4-((4,4-dimethyltetrahydrofuran-3-yl)amino)pyrido[3,4-d]pyridazin-1-yl)phenol

+

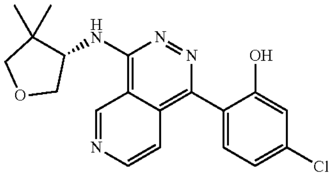

Compound 1B*

(S)-5-chloro-2-(4-((4,4-dimethyltetrahydrofuran-3-yl)amino)pyrido[3,4-d]pyridazin-1-yl)phenol Example 1 follows Protocol A.

Step 1: Synthesis of 1-chloro-N-(4,4-dimethyloxolan-3-yl)pyrido[3,4-d]pyridazin-4-amine and 4-chloro-N-(4,4-dimethyloxolan-3-yl)pyrido[3,4-d]pyridazin-1-amine. Into a 5 mL microwave tube were added 1,4-dichloropyrido[3,4-d]pyridazine (250 mg, 1.25 mmol, 1 equiv), DMF (3 mL) and $Na_2CO_3$ (423.91 mg, 4 mmol, 3.2 equiv) at 130° C. The final reaction mixture was irradiated with microwave radiation for 40 min at 130° C. After the reaction was completed, the residue was purified by reverse flash chromatography with the following conditions: column, C18 silica gel; mobile phase, acetonitrile (MeCN) in water, 0% to 100% gradient in 30 min; detector, UV 254 nm. The resulting mixture was concentrated under reduced pressure. This resulted in 1-chloro-N-(4,4-dimethyloxolan-3-yl)pyrido[3,4-d]pyridazin-4-amine and 4-chloro-N-(4,4-dimethyloxolan-3-yl)pyrido[3,4-d]pyridazin-1-amine (150 mg, mixture of two isomers) as a yellow oil. LCMS: (ES, m/z): RT=0.735 min, m/z=279[M+1]$^+$.

Step 2: 5-chloro-2-(4-((4,4-dimethyltetrahydrofuran-3-yl)amino)pyrido[3,4-d]pyridazin-1-yl)phenol (Compound 1A), (R)-5-chloro-2-(4-((4,4-dimethyltetrahydrofuran-3-yl)amino)pyrido[3,4-d]pyridazin-1-yl)phenol (Compound I*) and (S)-5-chloro-2-(4-((4,4-dimethyltetrahydrofuran-3-yl)amino)pyrido[3,4-d]pyridazin-1-yl)phenol (Compound 1B*). Into a 25 mL round-bottom flask were added a mixture of 1-chloro-N-(4,4-dimethyloxolan-3-yl)pyrido[3,4-d]pyridazin-4-amine and 4-chloro-N-(4,4-dimethyloxolan-3-yl)pyrido[3,4-d]pyridazin-1-amine (150 mg, 0.53 mmol, 1 equiv), 4-chloro-2-hydroxyphenylboronic acid (120.59 mg, 0.69 mmol, 1.3 equiv), [1,1'-Bis(diphenylphosphino)ferrocene] dichloropalladium(II) (Pd(dppf)$Cl_2$) (78.75 mg, 0.10 mmol, 0.2 equiv), $Na_2CO_3$ (171.11 mg, 1.61 mmol, 3 equiv), dioxane (6 mL) and $H_2O$ (1.2 mL) at 80° C. The final reaction mixture took 2 h at 80° C. After the reaction was completed, the reaction mixture was concentrated, and the residue was purified by reverse flash chromatography with the following conditions (column, C18 silica gel; mobile phase, acetonitrile (MeCN) in water, 0% to 100% gradient in 30 min; detector, UV 254 nm). After the reaction was completed, the reaction mixture was concentrated, and the crude product was purified by Prep-HPLC with the following conditions (2 #SHIMADZU (HPLC-01): Column, XBridge Prep Phenyl OBD Column, 19*250 mm, 5 μm; mobile phase, water (10 mmol/L $NH_4HCO_3$) and acetonitrile (MeCN) (25% MeCN up to 45% in 12 min); Detector, UV 254). This resulted in 5-chloro-2-(1-((4,4-dimethyltetrahydrofuran-3-yl)amino)pyrido[3,4-d]pyridazin-4-yl)phenol (3.2 mg, 1.5% yield) as a light yellow crude solid and 5-chloro-2-(4-{[-4,4-dimethyloxolan-3-yl]amino}pyrido[3,4-d]pyridazin-1-yl)phenol (Compound 1A) (32 mg, 15% yield) as a light yellow crude solid. 20 mg of 5-chloro-2-(4-{[-4,4-dimethyloxolan-3-yl]amino}pyrido[3,4-d]pyridazin-1-yl)phenol (Compound 1A) was then chirally separated using the following conditions (Column, Chiral ART Cellulose-SA, 4.6*50 mm, 3 um; mobile phase, methyl tert-butyl ether (MtBE) (0.2% formic acid (FA)) and isopropyl:dichloromethane (IPA:DCM)=1:1 (hold 50% IPA: DCM=1:1 in 4 min); Detector, UV 254) to provide 5-chloro-2-(4-{[(3R)-4,4-dimethyloxolan-3-yl]amino}pyrido[3,4-d]pyridazin-1-yl)phenol (also referred to herein as (R)-5-chloro-2-(4-((4,4-dimethyltetrahydrofuran-3-yl)amino)pyrido[3,4-d]pyridazin-1-yl)phenol) (Compound 1*) (RT=1.12 min, 5.4 mg, 2.69% yield) as a light yellow solid and 5-chloro-2-(4-{[(3S)-4,4-dimethyloxolan-3-yl]amino}pyrido[3,4-d]pyridazin-1-yl)phenol (also referred to herein as (S)-5-chloro-2-(4-((4,4-dimethyltetrahydrofuran-3-yl)amino)pyrido[3,4-d]pyridazin-1-yl)phenol) (Compound 1B*) (RT=2.12 min, 6.0 mg, 3% yield) as a light yellow solid. Stereochemistry arbitrarily assigned.

(R)-5-chloro-2-(4-((4,4-dimethyltetrahydrofuran-3-yl)amino)pyrido[3,4-d]pyridazin-1-yl)phenol. (Compound 1*) LCMS: (ES, m/z): RT=0.605 min, m/z=371.1 [M+1]$^+$ $^1$H NMR (400 MHz, Methanol-d4) δ 9.77 (d, J=1.0 Hz, 1H), 8.87 (d, J=5.7 Hz, 1H), 7.59-7.50 (m, 1H), 7.38 (d, J=8.0 Hz, 1H), 7.06 (d, J=7.8 Hz, 2H), 5.10-4.98 (m, 1H), 4.47-4.30 (m, 1H), 3.99-3.86 (m, 1H), 3.75 (d, J=8.4 Hz, 1H), 3.68 (d, J=8.4 Hz, 1H), 1.32 (s, 3H), 1.16 (s, 3H).

(S)-5-chloro-2-(4-((4,4-dimethyltetrahydrofuran-3-yl)amino)pyrido[3,4-d]pyridazin-1-yl)phenol. (Compound 1B*) LCMS: (ES, m/z): RT=0.605 min, m/z=371.1 [M+1]$^+$. $^1$H NMR (400 MHz, Methanol-d4) δ 9.81-9.74 (m, 1H), 8.87 (d, J=5.7 Hz, 1H), 7.57-7.51 (m, 1H), 7.38 (d, J=8.0 Hz, 1H), 7.06 (d, J=7.7 Hz, 2H), 5.13-4.98 (m, 1H), 4.50-4.33 (m, 1H), 4.00-3.87 (m, 1H), 2.45 (d, J=8.3 Hz, 1H), 2.08 (d, J=8.3 Hz, 1H), 1.32 (s, 3H), 1.16 (s, 3H).

Example 2. 5-chloro-2-(4-{[(1S,2S)-2-hydroxycyclopentyl]amino}pyrido[3,4-d]pyridazin-1-yl)phenol) (Compound 3A), (S)-5-chloro-2-(4-((3,3-dimethyltetrahydro-2H-pyran-4-yl)amino)pyrido[3,4-d]pyridazin-1-yl)phenol (Compound 3*), and (R)-5-chloro-2-(4-((3,3-dimethyltetrahydro-2H-pyran-4-yl)amino)pyrido[3,4-d]pyridazin-1-yl)phenol (Compound 3B*)

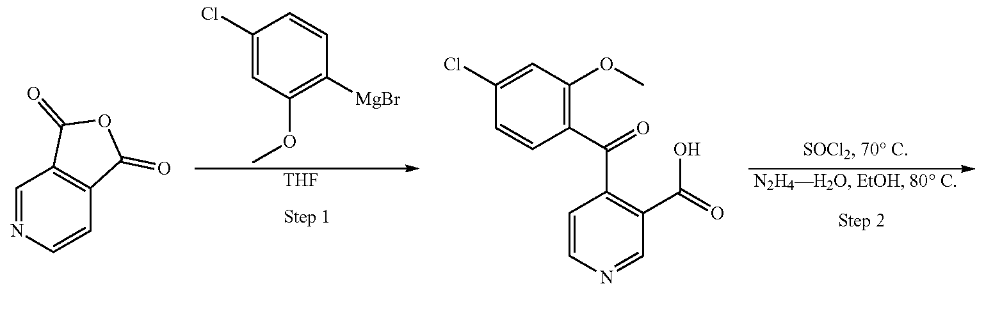

-continued

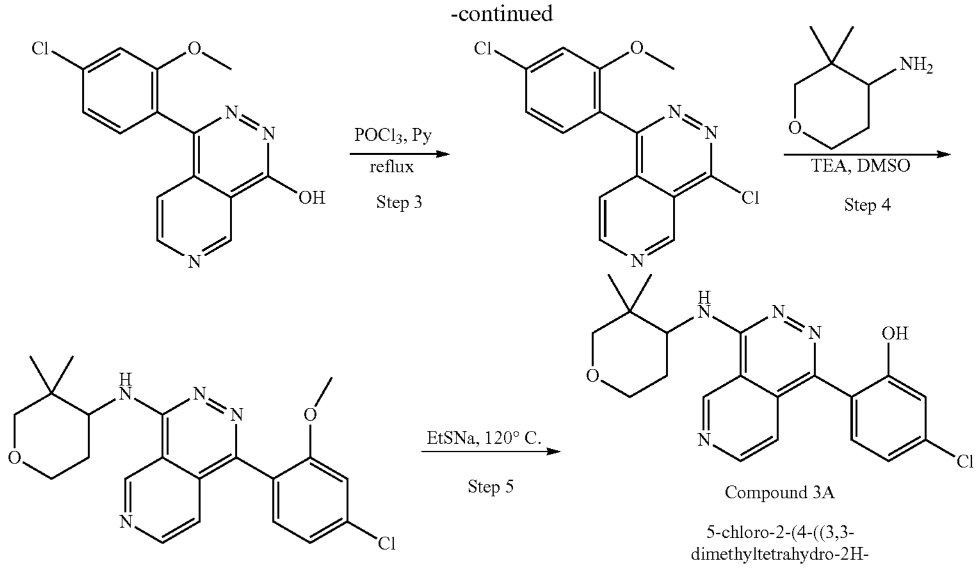

Compound 3A 5-chloro-2-(4-((3,3-dimethyltetrahydro-2H-pyran-4-yl)amino)pyrido[3,4-d]pyridazin-1-yl)phenol

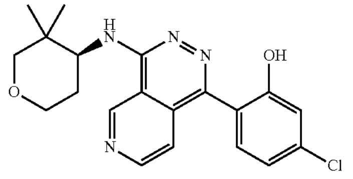

Compound 3*

(S)-5-chloro-2-(4-((3,3-dimethyltetrahydro-2H-pyran-4-yl)amino)pyrido[3,4-d]pyridazin-1-yl)phenol

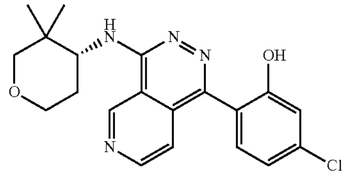

Compound 3B*

(R)-5-chloro-2-(4-((3,3-dimethyltetrahydro-2H-pyran-4-yl)amino)pyrido[3,4-d]pyridazin-1-yl)phenol Example 2 follows Protocol B.

Step 1: Synthesis of (1S,2S)-2-((1-(4-chloro-2-methoxyphenyl)pyrido[3,4-d]pyridazin-4-yl)amino)cyclopentan-1-ol. To a stirred solution of furo[3,4-c]pyridine-1,3-dione (30.0 g, 201.20 mmol, 1 equiv) and tetrahydrofuran (300 mL) was added bromo(4-chloro-2-methoxyphenyl)magnesium (0.5M in tetrahydrofuran (THF)) (241 mL, 120 mmol, 0.6 equiv) dropwise at −78° C. under nitrogen atmosphere. The resulting mixture was stirred for 2 h at 25° C. under nitrogen atmosphere. The reaction progress was monitored by LCMS. The reaction was quenched by the addition of water (150 mL) at 0° C. The precipitated solids were collected by filtration and washed with water (3×50 mL). This resulted in 4-(4-chloro-2-methoxybenzoyl)pyridine-3-carboxylic acid (20 g, 34.1% yield) as a light brown solid. LCMS (ES, m/z): RT=0.662 min, m/z=292.0[M+1]$^+$.

Step 2: Synthesis of 1-(4-chloro-2-methoxyphenyl)pyrido[3,4-d]pyridazin-4-ol. Into a 250 mL round-bottom flask were added 4-(4-chloro-2-methoxybenzoyl)pyridine-3-carboxylic acid (5 g, 17.1 mmol, 1 equiv) and $SOCl_2$ (50 mL). The resulting mixture was stirred for 2 h at 70° C. The reaction was monitored by thin layer chromatography (TLC). After the reaction was completed, the resulting mixture was concentrated under vacuum. The residue was dissolved in dichloromethane (DCM) (50 mL) and added into the solution of $NH_2NH_2{\cdot}H_2O$ (3.43 g, 68.6 mmol, 4 equiv), methanol (MeOH) (50 mL) at 0° C. The resulting mixture was stirred for 3 h at 70° C. in an oil bath. The reaction progress was monitored by LCMS. The precipitated solids were collected by filtration. The crude product (4 g, 90% purity) was purified by Prep-HPLC with the following conditions (2 #SHIMADZU (HPLC-01)): Column, XBridge Shield RP18 OBD Column, 19*250 mm, 10 μm; mobile phase, water (10 mmol/L $NH_4HCO_3$) and acetonitrile (MeCN) (hold 39% MeCN in 17 min); Detector, UV 254/220 nm. This resulted in 1-(4-chloro-2-methoxyphenyl)pyrido[3,4-d]pyridazin-4-ol (2.0 g, 40.6% yield) as an off-white solid. LCMS: (ES, m/z): RT=0.723 min, m/z=288.0 [M+H]$^+$. $^1$H NMR (400 MHz, DMSO-$d_6$) δ 12.90 (s, 1H), 9.50 (s, 1H), 8.94 (d, J=5.5 Hz, 1H), 7.41 (d, J=8.0 Hz, 1H), 7.33 (d, J=1.9 Hz, 1H), 7.23-7.15 (m, 2H), 3.75 (s, 3H).

Step 3: Synthesis of 4-chloro-1-(4-chloro-2-methoxyphenyl)pyrido[3,4-d]pyridazine. Into a 250 mL round-bottom flask were added 1-(4-chloro-2-methoxyphenyl)pyrido[3,4-d]pyridazin-4-ol (2.5 g, 8.69 mmol, 1 equiv) and $POCl_3$ (40 mL), and pyridine (4 mL). The resulting mixture was stirred for 3 h at 100° C. The reaction progress was monitored by LCMS. The reaction was quenched with 500 mL of sodium bicarbonate (aq.) and 500 mL of EtOAc at 0° C. The resulting mixture was extracted with EtOAc (3×500 mL). The combined organic layers were dried over anhydrous $Na_2SO_4$. After filtration, the filtrate was concentrated under reduced pressure. This resulted in 4-chloro-1-(4-chloro-2-methoxyphenyl)pyrido[3,4-d]pyridazine (1.5 g, 56.4% yield) as a brown solid. LCMS (ES, m/z): RT=0.845 min, m/z=306.0[M+1]$^+$. $^1$H NMR (400 MHz, DMSO-$d_6$) δ 9.84-

9.68 (m, 1H), 9.12 (d, J=5.7 Hz, 1H), 7.60-7.56 (m, 1H), 7.51 (d, J=8.1 Hz, 1H), 7.41 (d, J=1.9 Hz, 1H), 7.32-7.25 (m, 1H), 3.74 (s, 3H).

Step 4: Synthesis of 1-(4-chloro-2-methoxyphenyl)-N-(3,3-dimethyltetrahydro-2H-pyran-4-yl)pyrido[3,4-d]pyridazin-4-amine. Into a 40 mL vial were added 4-chloro-1-(4-chloro-2-methoxyphenyl)pyrido[3,4-d]pyridazine (200 mg, 0.65 mmol, 1 equiv) and 3,3-dimethyloxan-4-amine (101.28 mg, 7.84 mmol, 1.2 equiv), triethylamine (TEA) (198.32 mg, 1.96 mmol, 3 equiv), and dimethylsulfoxide (DMSO) (5 mL) at room temperature. The resulting mixture was stirred for overnight at 80° C. under nitrogen atmosphere. The reaction progress was monitored by LCMS. The resulting mixture was used in the next step directly without further purification. LCMS: (ES, m/z): RT=0.684 min, m/z=399[M+1]$^+$.

Step 5: Synthesis of 5-chloro-2-(4-{[(1S,2S)-2-hydroxycyclopentyl]amino}pyrido[3,4-d]pyridazin-1-yl)phenol) (Compound 3A), (S)-5-chloro-2-(4-((3,3-dimethyltetrahydro-2H-pyran-4-yl)amino)pyrido[3,4-d]pyridazin-1-yl)phenol (Compound 3*), and (R)-5-chloro-2-(4-((3,3-dimethyltetrahydro-2H-pyran-4-yl)amino)pyrido[3,4-d]pyridazin-1-yl)phenol (Compound 3B*). Into a 20 vial were added the reaction mixture from step 4, (ethylsulfanyl) sodium (1054.30 mg, 12.53 mmol, 25 equiv), and DMSO (8 mL) at room temperature. The resulting mixture was stirred for 2 h at 120° C. under nitrogen atmosphere. The reaction progress was monitored by LCMS. The resulting mixture was filtered, the filter cake was washed with MeCN (3×5 mL). The filtrate was concentrated under reduced pressure. The residue was purified by reverse flash chromatography with the following conditions (column, C18 gel; mobile phase, MeCN in water (10 mmol/L $NH_4HCO_3$), 0% to 100% gradient in 30 min; detector, UV 254 nm), resulting product as an off-white solid. The product (90 mg, 98.2% purity) was purified by Prep-HPLC with the following conditions (Prep-HPLC-064: Column, CHIRALPAK IG, 2*25 cm, 5 um; mobile phase, Hex and MeOH:DCM=1:1—(hold 50% MeOH:DCM=1:1—in 23 min); Detector, UV 254 nm) to afford 5-chloro-2-(4-{[(4R)-3,3-dimethyloxan-4-yl]amino}pyrido[3,4-d]pyridazin-1-yl)phenol (also referred to herein as (R)-5-chloro-2-(4-((3,3-dimethyltetrahydro-2H-pyran-4-yl)amino)pyrido[3,4-d]pyridazin-1-yl)phenol) (Compound 3B*) (RT=1.50 min, 27.8 mg, 14.3% yield) as an off-white solid and 5-chloro-2-(4-{[(4S)-3,3-dimethyloxan-4-yl]amino}pyrido[3,4-d]pyridazin-1-yl)phenol (also referred to herein as (S)-5-chloro-2-(4-((3,3-dimethyltetrahydro-2H-pyran-4-yl)amino)pyrido[3,4-d]pyridazin-1-yl)phenol) (Compound 3*) (RT=3.28 min, 24.4 mg, 12.5% yield) as an off-white solid. Stereochemistry arbitrarily assigned.

5-chloro-2-(4-{[(4R)-3,3-dimethyloxan-4-yl]amino}pyrido[3,4-d]pyridazin-1-yl)phenol (Compound 3B*). LCMS: (ES, m/z): RT=0.553 min, m/z=385.2 [M+1]$^+$. $^1$H NMR (400 MHz, DMSO-$d_6$) δ 10.24 (s, 1H), 9.89 (s, 1H), 8.86 (d, J=5.6 Hz, 1H), 7.38-7.20 (m, 3H), 7.03 (d, J=7.4 Hz, 2H), 4.81-4.70 (m, 1H), 4.05-3.89 (m, 1H), 3.54-3.42 (m, 2H), 3.25 (d, J=11.3 Hz, 1H), 1.99-1.90 (m, 1H), 1.75-1.66 (m, 1H), 1.14 (s, 3H), 0.87 (s, 3H).

5-chloro-2-(4-{[(4S)-3,3-dimethyloxan-4-yl]amino}pyrido[3,4-d]pyridazin-1-yl)phenol (Compound 3*) LCMS: (ES, m/z): RT=0.671 min, m/z=385.2 [M+1]$^+$. $^1$H NMR (400 MHz, DMSO-$d_6$) δ 10.24 (s, 1H), 9.88 (s, 1H), 8.86 (d, J=5.6 Hz, 1H), 7.40-7.17 (m, 3H), 7.03 (d, J=7.5 Hz, 2H), 4.80-4.72 (m, 1H), 4.05-3.96 (m, 1H), 3.56-3.41 (m, 2H), 3.23 (s, 1H), 2.01-1.92 (m, J=12.2, 4.8 Hz, 1H), 1.73-7.65 (m, 1H), 1.13 (s, 3H), 0.87 (s, 3H).

Example 3. 2-(4-((5,5-dimethyltetrahydrofuran-3-yl)amino)pyrido[3,4-d]pyridazin-1-yl)-5-methylphenol (Compound 5A), (R)-2-(4-((5,5-dimethyltetrahydrofuran-3-yl)amino)pyrido[3,4-d]pyridazin-1-yl)-5-methylphenol (Compound 5), and (S)-2-(4-((5,5-dimethyltetrahydrofuran-3-yl)amino)pyrido[3,4-d]pyridazin-1-yl)-5-methylphenol (Compound 5B)

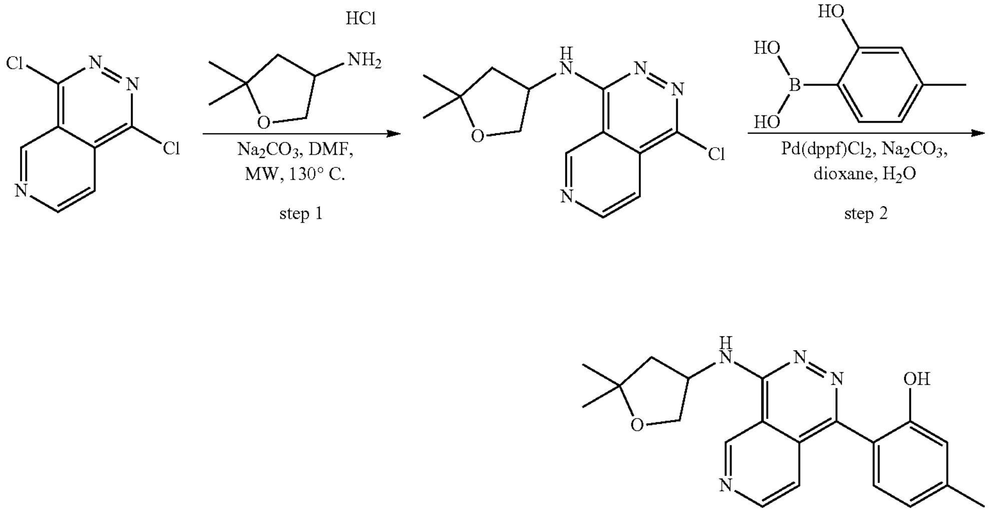

Compound 5A 2-(4-((5,5-dimethyltetrahydrofuran-3-yl)amino)pyrido[3,4-d]pyridazin-1-yl)-5-methylphenol -continued

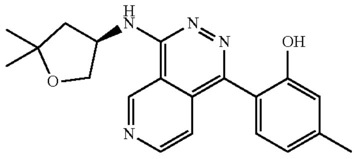

Compound 5

(R)-2-(4-((5,5-dimethyltetrahydrofuran-3-yl)amino)pyrido[3,4-d]pyridazin-1-yl)-5-methylphenol

+

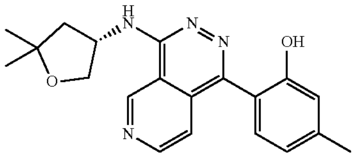

Compound 5B (S)-2-(4-((5,5-dimethyltetrahydrofuran-3-yl)amino)pyrido[3,4-d]pyridazin-1-yl)-5-methylphenol Example 3 follows Protocol A.

Into a 8 mL sealed tube were added 1-chloro-N-(5,5-dimethyloxolan-3-yl)pyrido[3,4-d]pyridazin-4-amine (120 mg, 0.430 mmol, 1 equiv), 5-methyl-2-(4,4,5,5-tetramethyl-1,3,2-dioxaborolan-2-yl)phenol (201 mg, 0.860 mmol, 2 equiv), Pd(dppf)$Cl_2$ (94.5 mg, 0.130 mmol, 0.300 equiv), dioxane (2 mL) and $H_2O$ (0.4 mL) at 80° C. The resulting mixture was stirred for 1 h at 80° C.

The reaction was monitored by LCMS. The resulting mixture was concentrated under reduced pressure, and the residue was purified by silica gel column chromatography, eluted with petroleum ether/ethyl acetate (1:1) to provide a crude product (140 mg) which was purified by Prep-HPLC (Column: Xselect CSH C18 OBD Column 30*150 mm 5 m, n; Mobile Phase A: Water (10 mmol/L $NH_4HCO_3$; Mobile Phase B: MeCN; Flow rate: 60 mL/min; Gradient: 34% B to 34% B in 11 min, 34% B; Wave Length: 254 nm; RT1(min): 10.2) to provide a mixture of Compounds 5A and 5B (65 mg), which were further purified by Prep-Chiral-HPLC (Column: CHIRAL ART Amylose-SA, 2*25 cm, 5 m; Mobile Phase A: Hexanes (Hex) HPLC, Mobile Phase B: MeOH:DCM=1:1, HPLC; Flow rate: 20 mL/min; Gradient: 20% B to 20% B in 15 min; Wave Length: 220/254 nm) to afford (R)-2-(4-((5,5-dimethyltetrahydrofuran-3-yl)amino)pyrido[3,4-d]pyridazin-1-yl)-5-methylphenol (Compound 5) (28.4 mg, 18.8% yield) (RT(min): 9.63) and (S)-2-(4-((5,5-dimethyltetrahydrofuran-3-yl)amino)pyrido[3,4-d]pyridazin-1-yl)-5-methylphenol (Compound 5B) (23.7 mg, 15.7% yield) (RT(min): 13.52). Absolute stereochemistry was determined by X-ray crystallography.

(R)-2-(4-((5,5-dimethyltetrahydrofuran-3-yl)amino)pyrido[3,4-d]pyridazin-1-yl)-5-methylphenol (Compound 5). LCMS (ES, m/z): RT=1.23 mi, m/z=351.1 $[M+H]^+$. $^1H$ NMR (400 MHz, Methanol-$d_4$) δ 9.70 (d, J=1.0 Hz, 1H), 8.85 (d, J=5.7 Hz, 1H), 7.57 (m, J=5.7, 1.0 Hz, 1H), 7.28 (d, J=7.7 Hz, 1H), 6.91-6.83 (m, 2H), 5.05-4.97 (m, 1H), 4.41 (m, J=9.1, 6.7 Hz, 1H), 3.92 (m, J=9.1, 5.9 Hz, 1H), 2.45 (m, J=12.8, 8.1 Hz, 1H), 2.40 (s, 3H), 2.08 (m, J=12.7, 6.8 Hz, 1H), 1.45 (s, 3H), 1.35 (s, 3H).

(S)-2-(4-((5,5-dimethyltetrahydrofuran-3-yl)amino)pyrido[3,4-d]pyridazin-1-yl)-5-methylphenol (Compound 5B) LCMS (ES, m/z): RT=1.23 min, m/z=351.1 $[M+H]^+$. $^1H$ NMR (400 MHz, Methanol-$d_4$) δ 9.70 (d, J=1.0 Hz, 1H), 8.85 (d, J=5.7 Hz, 1H), 7.57 (m, J=5.7, 1.0 Hz, 1H), 7.28 (d, J=7.7 Hz, 1H), 6.91-6.83 (m, 2H), 5.07-4.97 (m, 1H), 4.41 (m, J=9.1, 6.6 Hz, 1H), 3.92 (m, J=9.1, 5.8 Hz, 1H), 2.45 (m, J=12.8, 8.0 Hz, 1H), 2.40 (s, 3H), 2.08 (m, J=12.7, 6.8 Hz, 1H), 1.45 (s, 3H), 1.35 (s, 3H).

Table A shows the protocol by which the compounds of the instant disclosure were prepared, and Table B provides the NMR data.

TABLE A

| Cmp, # | Structure | MS (ESI; m/z; M + H) | Protocol |
|---|---|---|---|
| 1* | 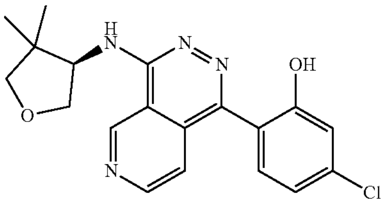 [SMILES: CC1(C)COC[C@@H]1Nc1nnc(-c2ccc(Cl)cc2O)c2ccncc12] (R)-5-chloro-2-(4-((4,4-dimethyltetrahydrofuran-3-yl)amino)pyrido[3,4-d]pyridazin-1-yl)phenol | 371.1 | Protocol A (Example 1) |

TABLE A-continued

| Cmp, # | Structure | MS (ESI; m/z; M + H) | Protocol |
|---|---|---|---|
| 1A* | 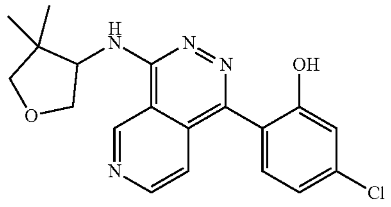 [SMILES: CC1(C)COCC1Nc1nnc(-c2ccc(Cl)cc2O)c2ccncc12]<br>5-chloro-2-(4-((4,4-dimethyltetrahydrofuran-3-yl)amino)pyrido[3,4-d]pyridazin-1-yl)phenol | 371.1 | Protocol A (Example 1) |
| 1B* | 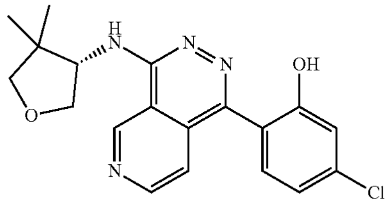 [SMILES: CC1(C)COC[C@H]1Nc1nnc(-c2ccc(Cl)cc2O)c2ccncc12]<br>(S)-5-chloro-2-(4-((4,4-dimethyltetrahydrofuran-3-yl)amino)pyrido[3,4-d]pyridazin-1-yl)phenol | 371.1 | Protocol A (Example 1) |
| 2 | 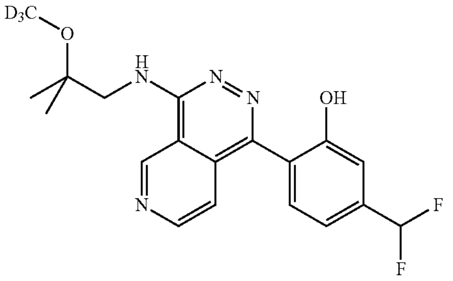 [SMILES: [2H]C([2H])([2H])OC(C)(C)CNc1nnc(-c2ccc(C(F)F)cc2O)c2ccncc12]<br>5-(difluoromethyl)-2-(4-((2-(methoxy-d3)-2-methylpropyl)amino)pyrido[3,4-d]pyridazin-1-yl)phenol | 378.2 | Protocol A |
| 3B* | 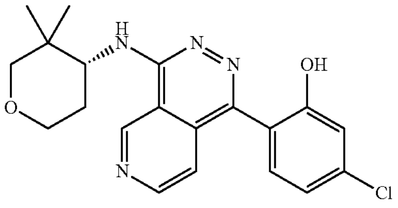 [SMILES: CC1(C)COCC[C@H]1Nc1nnc(-c2ccc(Cl)cc2O)c2ccncc12]<br>(R)-5-chloro-2-(4-((3,3-dimethyltetrahydro-2H-pyran-4-yl)amino)pyrido[3,4-d]pyridazin-1-yl)phenol | 385.2 | Protocol B (Example 2) |
| 3A | 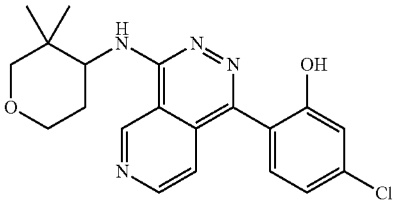 [SMILES: CC1(C)COCCC1Nc1nnc(-c2ccc(Cl)cc2O)c2ccncc12]<br>5-chloro-2-(4-((3,3-dimethyltetrahydro-2H-pyran-4-ylamino)pyrido[3,4-d]pyridazin-1-yl)phenol | 385.2 | Protocol B (Example 2) |

TABLE A-continued

| Cmp, # | Structure | MS (ESI; m/z; M + H) | Protocol |
|---|---|---|---|
| 3* | 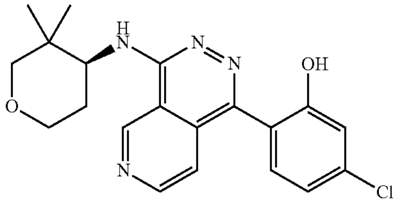 [SMILES: CC1(C)COCC[C@@H]1Nc1nnc(-c2ccc(Cl)cc2O)c2ccncc12] (S)-5-chloro-2-(4-((3,3-dimethyltetrahydro-2H-pyran-4-yl)amino)pyrido[3,4-d]pyridazin-1-yl)phenol | 385.2 | Protocol B (Example 2) |
| 4* | 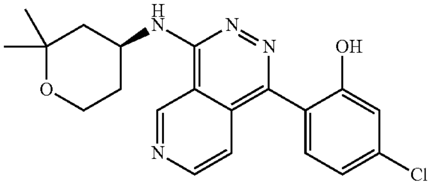 [SMILES: CC1(C)C[C@@H](Nc2nnc(-c3ccc(Cl)cc3O)c3ccncc23)CCO1] (S)-5-chloro-2-(4-((2,2-dimethyltetrahydro-2H-pyran-4-ylamino)pyrido[3,4-d]pyridazin-1-yl)phenol | 385.1 | Protocol B Compound 4*: Column, CHIRALPAK IE, 2*25 cm, 5 um; mobile phase: Hexanes and MeOH:DCM = 1:1 (hold 25% MeOH:DCM = 1:1 in 17 min); Detector, UV 254. RT = 2.45 min |
| 4A | 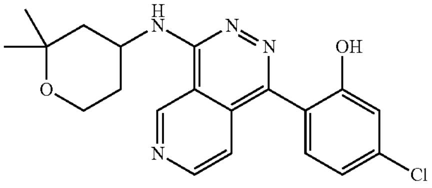 [SMILES: CC1(C)CC(Nc2nnc(-c3ccc(Cl)cc3O)c3ccncc23)CCO1] 5-chloro-2-(4-((2,2-dimethyltetrahydro-2H-pyran-4-yl)amino)pyrido[3,4-d]pyridazin-1-yl)phenol | 385.1 | Protocol B Compounds 4*, 4A, and 4B* were synthesized following Protocol B and Example 2 using 2,2-dimethyl tetrahydro-2H-pyran-4-amine as the step 4 amine (i) reagent. |
| 4B* | 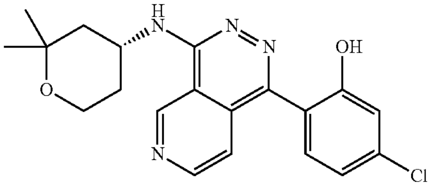 [SMILES: CC1(C)C[C@H](Nc2nnc(-c3ccc(Cl)cc3O)c3ccncc23)CCO1] (R)-5-chloro-2-(4-((2,2-dimethyltetrahydro-2H-pyran-4-ylamino)pyrido[3,4-d]pyridazin-1-yl)phenol | 385.1 | Protocol B Compound 4B*: Column, CHIRALPAK IE, 2*25 cm, 5 um; mobile phase, Hex- and MeOH:DCM = 1:1- (hold 25% MeOH:DCM = 1:1- in 17 min); Detector, UV 254. RT = 3.12 min |
| 5 | 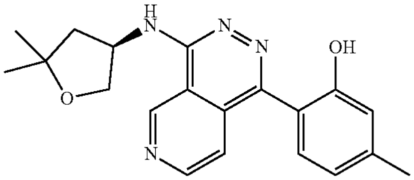 (R)-2-(4-((5,5-dimethyltetrahydrofuran-3-yl)amino)pyrido[3,4-d]pyridazin-1-yl)-5-methylphenol | 351.1 | Protocol A (Example 3) |
| 5A | 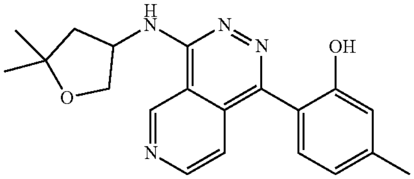 2-(4-((5,5-dimethyltetrahydrofuran-3-yl)amino)pyrido[3,4-d]pyridazin-1-yl)-5-methylphenol | 351.1 | Protocol A (Example 3) |

TABLE A-continued

| Cmp, # | Structure | MS (ESI; m/z; M + H) | Protocol |
|---|---|---|---|
| 5B | 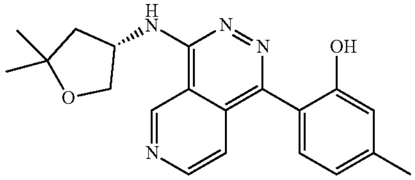 (S)-2-(4-((5,5-dimethyltetrahydrofuran-3-yl)amino)pyrido[3,4-d]pyridazin-1-yl)-5-methylphenol | 351.1 | Protocol A (Example 3) |
| 6* | 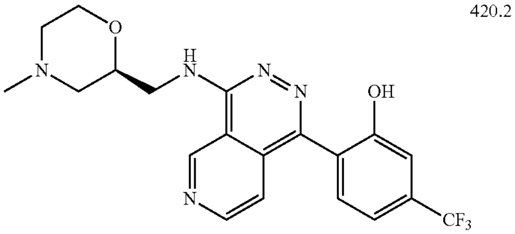 (S)-2-(4-(((4-methylmorpholin-2-yl)methyl)amino)pyrido[3,4-d]pyridazin-1-yl)-5-(trifluoromethyl)phenol | 420.2 | Protocol A Compound 6*: Column: CHIRALPAK IG, 2*25 cm, 5 μm; Mobile Phase A: Hexanes (Hex) (0.5% 2M $NH_3$—MeOH), Mobile Phase B: EtOH: DCM = 1:1; Flow rate: 20 mL/min; Gradient: 50% B to 50% B in 8 min; Wave Length: 220/254 nm RT(min): 5.27 |
| 6A | 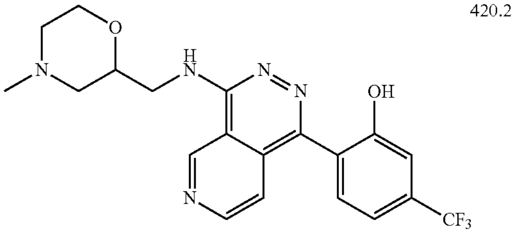 2-(4-(((4-methylmorpholin-2-yl)methyl)amino)pyrido[3,4-d]pyridazin-1-yl)-5-(trifluoromethyl)phenol | 420.2 | Protocol A Compounds 6*, 6A, and 6B* were synthesized following Protocol A and Example 1 using (4-methylmorpholin-2-yl) methanamine as the step 1 amine (i) reagent. |
| 6B* | 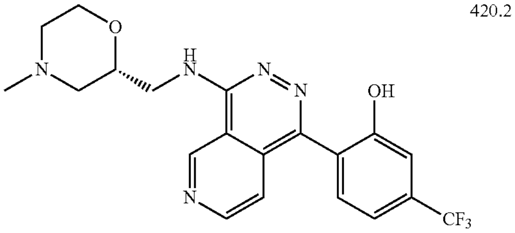 (R)-2-(4-(((4-methylmorpholin-2-yl)methyl)amino)pyrido[3,4-d]pyridazin-1-yl)-5-(trifluoromethyl)phenol | 420.2 | Protocol A Compound 6B*: Column: CHIRALPAK IG, 2*25 cm, 5 μm; Mobile Phase A: Hexanes (0,5% 2M $NH_3$—MeOH), Mobile Phase B: EtOH: DCM = 1:1; Flow rate: 20 mL/min; Gradient: 50% B to 50% B in 8 min; Wave Length: 220/254 nm; RT(min): 7.30 |
| 7* | 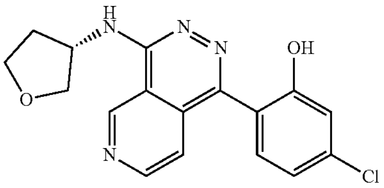 [SMILES: Oc1cc(Cl)ccc1-c1nnc(N[C@H]2CCOC2)c2cnccc12] (S)-5-chloro-2-(4-((tetrahydrofuran-3-yl)amino)pyrido[3,4-d]pyridazin-1-yl)phenol Comparative Example 1 USSN 17/528,928 | 343.1 | Protocol A |

TABLE A-continued

| Cmp, # | Structure | MS (ESI; m/z; M + H) | Protocol |
|---|---|---|---|
| 8 | 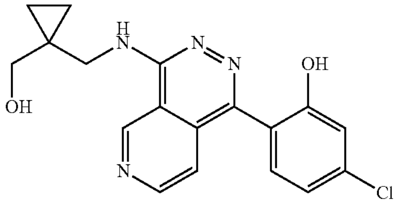 [SMILES: OCC1(CNc2nnc(-c3ccc(Cl)cc3O)c3ccncc23)CC1]<br>5-chloro-2-(4-(((1-(hydroxymethyl)cyclopropyl)methyl)amino)pyrido[3,4-dipyridazin-1-yl)phenol<br>Comparative Example 2<br>USSN 17/528,928 | 357.0 | Protocol A |

TABLE B

| $^1$H NMR table | |
|---|---|
| Cmp. # | $^1$H NMR |
| 1* | 1H NMR (400 MHz, Methanol-$d_4$) δ 9.77 (d, J = 1.0 Hz, 1H), 8.87 (d, J = 5.7 Hz, 1H), 7.59-7.50 (m, 1H), 7.38 (d, J = 8.0 Hz, 1H), 7.06 (d, J = 7.8 Hz, 2H), 5.10-4.98 (m, 1H), 4.47-4.30 (m, 1H), 3.99-3.86 (m, 1H), 3.75 (d, J = 8.4 Hz, 1H), 3.68 (d, J = 8.4 Hz, 1H), 1.32 (s, 3H), 1.16 (s, 3H). |
| 1B* | $^1$H NMR (400 MHz, Methanol-$d_4$) δ 9.81-9.74 (m, 1H), 8.87 (d, J = 5.7 Hz, 1H), 7.57-7.51 (m, 1H), 7.38 (d, J = 8.0 Hz, 1H), 7.06 (d, J = 7.7 Hz, 2H), 5.13-4.98 (m, 1H), 4.50-4.33 (m, 1H), 4.00-3.87 (m, 1H), 2.45 (d, J = 8.3 Hz, 1H), 2.08 (d, J = 8.3 Hz, 1H), 1.32 (s, 3H), 1.16 (s, 3H). |
| 2* | $^1$H NMR (400 MHz, DMSO-$d_6$) δ 10.18 (s, 1H), 9.84 (s, 1H), 8.86 (d, J = 5.6 Hz, 1H), 7.69 (t, J = 6.0 Hz, 1H), 7.47 (d, J = 7.7 Hz, 1H), 7.30 (d, J = 5.6 Hz, 1H), 7.26-6.90 (m, 3H), 3.82 (d, J = 5.9 Hz, 2H), 1.25 (s, 6H). |
| 3B* | $^1$H NMR (400 MHz, DMSO-$d_6$) δ 10.24 (s, 1H), 9.89 (s, 1H), 8.86 (d, J = 5.6 Hz, 1H), 7.38-7.20 (m, 3H), 7.03 (d, J = 7.4 Hz, 2H), 4.81-4.70 (m, 1H), 4.05-3.89 (m, 1H), 3.54-3.42 (m, 2H), 3.25 (d, J = 11.3 Hz, 1H), 1.99-1.90 (m, 1H), 1.75-1.66 (m, 1H), 1.14 (s, 3H), 0.87 (s, 3H). |
| 3* | $^1$H NMR (400 MHz, DMSO-$d_6$) δ 10.24 (s, 1H), 9.88 (s, 1H), 8.86 (d, J = 5.6 Hz, 1H), 7.40-7.17 (m, 3H), 7.03 (d, J = 7.5 Hz, 2H), 4.80-4.72 (m, 1H), 4.05-3.96 (m, 1H), 3.56-3.41 (m, 2H), 3.23 (s, 1H), 2.01-1.92 (m, J = 12.2, 4.8 Hz, 1H), 1.73-7.65 (m, 1H), 1.13 (s, 3H), 0.87 (s, 3H). |
| 4* | $^1$H NMR (400 MHz, Methanol-$d_4$) δ 9.70 (s, 1H), 8.86 (d, J = 5.7 Hz, 1H), 7.56-7.50 (m, 1H), 7.38 (d, J = 8.0 Hz, 1H), 7.06 (d, J = 8.0 Hz, 2H), 4.80-4.71 (m, 1H), 3.95-3.80 (m, 2H), 2.23-2.10 (m, 2H), 1.70-1.57 (m, 2H), 1.40 (s, 3H), 1.31 (s, 3H). |
| 4B* | $^1$H NMR (400 MHz, Methanol-$d_4$) δ 9.68 (d, J = 1.0 Hz, 1H), 8.85 (d, J = 5.7 Hz, 1H), 7.52-7.50 (m, 1H), 7.38 (d, J = 7.9 Hz, 1H), 7.12-7.01 (m, 2H), 4.84-4.76 (m, 1H), 3.97-3.80 (m, 2H), 2.21-2.13 (m, 2H), 1.70-1.57 (m, 2H), 1.41 (s, 3H), 1.31 (s, 3H). |
| 5 | $^1$H NMR (400 MHz, Methanol-$d_4$) δ 9.70 (d, J = 1.0 Hz, 1H), 8.85 (d, J = 5.7 Hz, 1H), 7.57 (m, J = 5.7, 1.0 Hz, 1H), 7.28 (d, J = 7.7 Hz, 1H), 6.91-6.83 (m, 2H), 5.05-4.97 (m, 1H), 4.41 (m, J = 9.1, 6.7 Hz, 1H), 3.92 (m, J = 9.1, 5.9 Hz, 1H), 2.45 (m, J = 12.8, 8.1 Hz, 1H), 2.40 (s, 3H), 2.08 (m, J = 12.7, 6.8 Hz, 1H), 1.45 (s, 3H), 1.35 (s, 3H). |
| 5B | $^1$H NMR (400 MHz, Methanol-$d_4$) δ 9.70 (d, J = 1.0 Hz, 1H), 8.85 (d, J = 5.7 Hz, 1H), 7.57 (m, J = 5.7, 1.0 Hz, 1H), 7.28 (d, J = 7.7 Hz, 1H), 6.91-6.83 (m, 2H), 5.07-4.97 (m, 1H), 4.41 (m, J = 9.1, 6.6 Hz, 1H), 3.92 (m, J = 9.1, 5.8 Hz, 1H), 2.45 (m, J = 12.8, 8.0 Hz, 1H), 2.40 (s, 3H), 2.08 (m, J = 12.7, 6.8 Hz, 1H), 1.45 (s, 3H), 1.35 (s, 3H). |
| 6* | $^1$H NMR (400 MHz, Methanol-$d_4$) δ 9.66 (s, 1H), 8.87 (d, J = 5.7 Hz, 1H), 7.59 (d, J = 7.9 Hz, 1H), 7.50 (d, J = 5.7 Hz, 1H), 7.34 (d, J = 8.0 Hz, 1H), 7.28 (s, 1H), 4.03 (d, J = 8.0 Hz, 1H), 3.99-3.92 (m, 1H), 3.87 (dd, J = 13.8, 4.7 Hz, 1H), 3.82-3.65 (m, 2H), 3.00 (d, J = 11.4 Hz, 1H), 2.74 (d, J = 11.7 Hz, 1H), 2.34 (s, 3H), 2.23 (td, J = 11.7, 3.4 Hz, 1H), 2.04 (t, J = 10.9 Hz, 1H). |
| 6B* | $^1$H NMR (400 MHz, Methanol-$d_4$) δ 9.66 (s, 1H), 8.87 (d, J = 5.7 Hz, 1H), 7.59 (d, J = 7.9 Hz, 1H), 7.50 (d, J = 5.7 Hz, 1H), 7.34 (d, J = 8.0 Hz, 1H), 7.28 (s, 1H), 4.04 (s, 1H), 4.02-3.92 (m, 1H), 3.87 (m, 1H), 3.83-3.65 (m, 2H), 3.00 (d, J = 11.3 Hz, 1H), 2.74 (d, J = 11.8 Hz, 1H), 2.35 (s, 3H), 2.24 (td, J = 11.6, 3.4 Hz, 1H), 2.05 (t, J = 10.8 Hz, 1H). |
| 7*<br>Comp Ex 1 | $^1$H NMR (400 MHz, DMSO-$d_6$) δ 9.82 (s, 1H), 8.87 (d, J = 5.6 Hz, 1H), 7.94 (d, J = 5.8 Hz, 1H), 7.43-7.27 (m, 2H), 7.04 (d, J = 7.1 Hz, 2H), 4.87-4.80 (m, 1H), 4.11-3.91 (m, 2H), 3.85-3.72 (m, 2H), 2.40-2.26 (m, 1H), 2.22-2.06 (m, 1H). |
| 8<br>Comp Ex 2 | $^1$H NMR (400 MHz, DMSO-d6) δ 9.90 (d, J = 0.9 Hz, 1H), 9.13 (d, J = 5.5 Hz, 1H), 7.67-7.65 (m, 1H), 7.40 (d, J = 8.1 Hz, 1H), 7.18-7.02 (m, 2H), 3.77 (s, 2H), 3.62 (s, 2H), 0.86-0.63 (m, 4H). |

Example 4. 5-(difluoromethoxy)-2-(4-((5,5-dimethyltetrahydrofuran-3-yl)amino)pyrido[3,4-d]pyridazin-1-yl)phenol (Compound 9A), (S)-5-(difluoromethoxy)-2-(4-((5,5-dimethyltetrahydrofuran-3-yl)amino)pyrido[3,4-d]pyridazin-1-yl)phenol (Compound 9*), and (R)-5-(difluoromethoxy)-2-(4-((5,5-dimethyltetrahydrofuran-3-yl)amino)pyrido[3,4-d]pyridazin-1-yl)phenol (Compound 9B*)

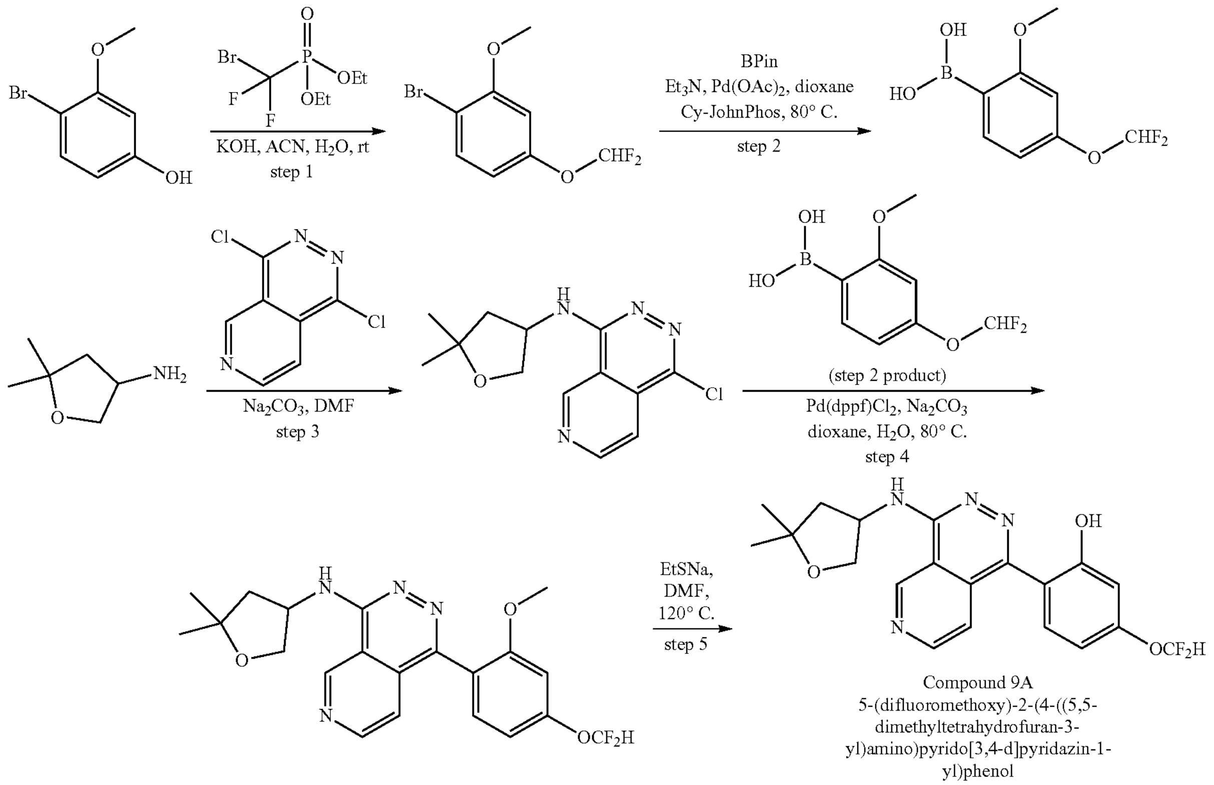

Compound 9A
5-(difluoromethoxy)-2-(4-((5,5-dimethyltetrahydrofuran-3-yl)amino)pyrido[3,4-d]pyridazin-1-yl)phenol

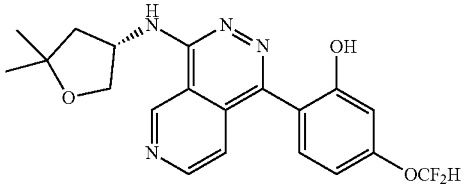

Compound 9*
(S)-5-(difluoromethoxy)-2-(4-((5,5-dimethyltetrahydrofuran-3-yl)amino)pyrido[3,4-d]pyridazin-1-yl)phenol

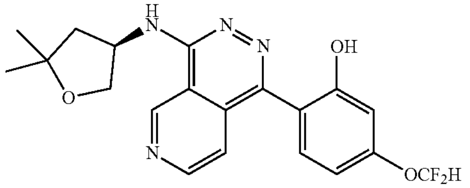

Compound 9B*
(R)-5-(difluoromethoxy)-2-(4-((5,5-dimethyltetrahydrofuran-3-yl)amino)pyrido[3,4-d]pyridazin-1-yl)phenol Example 4 follows Protocol A.

Step 1. Synthesis of 1-bromo-4-(difluoromethoxy)-2-methoxybenzene. Into a 100 mL round-bottom flask were added 4-bromo-3-methoxyphenol (5 g, 24.62 mmol, 1 equiv), acetonitrile (MeCN) (10 mL), diethyl bromodifluoromethylphosphonate (13.15 g, 49.25 mmol, 2 equiv) and KOH (2.76 g, 49.25 mmol, 2 equiv), $H_2O$ (10 mL) at room temperature. The resulting mixture was stirred for 1 h at room temperature. The reaction was monitored by gas chromatography/mass spectrometry (GCMS). The reaction was quenched with water (10 mL) at 0° C. The resulting mixture was extracted with EtOAc (3×10 mL). The combined organic layers were washed with brine (1×10 mL), dried over anhydrous $Na_2SO_4$. After filtration, the filtrate was concentrated under reduced pressure. The residue was purified by silica gel column chromatography, eluted with petroleum ether/ethyl acetate (PE/EA) (4:1) to afford the title compound (3.9 g, 61.3% yield). LCMS, ESI: RT=1.35 min, m/z=253[M+H]$^+$.

Step 2. Synthesis of (4-(difluoromethoxy)-2-methoxyphenyl)boronic acid. To a stirred solution of 1-bromo-4-(difluoromethoxy)-2-methoxybenzene (2200 mg, 8.69 mmol, 1 equiv) in dioxane (25 mL) was added triethylamine (2639.37 mg, 26.08 mmol, 3 equiv) and 4,4,5,5-tetramethyl-1,3,2-dioxaborolane (5563.40 mg, 43.47 mmol, 5 equiv) at room temperature. The resulting mixture was stirred for 0.5 h at room temperature under nitrogen atmosphere. To the above mixture was added $Pd(OAc)_2$ (195.19 mg, 0.86 mmol, 0.1 equiv) and 2-(dicyclohexylphosphino)biphenyl, (2-Biphenyl)dicyclohexylphosphine (Cy-JohnPhos) (609.44 mg, 1.73 mmol, 0.2 equiv) in dioxane (2 mL) at room temperature. The resulting mixture was stirred for additional 2 h at 80° C. under nitrogen atmosphere. The reaction was monitored by LCMS. The reaction was quenched with water (10 mL) at 0° C. The resulting mixture was extracted with EtOAc (2×20 mL). The combined organic layers were washed with brine (1×20 mL), dried over anhydrous $Na_2SO_4$. After filtration, the filtrate was concentrated under reduced pressure to provide the crude title compound, which was used in the next step directly. LCMS, ESI: RT=0.75 min, m/z=219[M+H]$^+$.

Step 3. Synthesis of 1-chloro-N-(5,5-dimethyloxolan-3-yl)pyrido[3,4-d]pyridazin-4-amine. Into 20 mL sealed tube were added 1,4-dichloropyrido[3,4-d]pyridazine (800 mg, 3.99 mmol, 1 equiv), 5,5-dimethyloxolan-3-amine (552.79 mg, 4.79 mmol, 1.2 equiv), $Na_2CO_3$ (1270.94 mg, 11.99 mmol, 3 equiv) and dimethylformamide (10 mL). The final reaction mixture was irradiated with microwave radiation for 30 min at 130° C. The reaction was monitored by LCMS. The reaction was repeated for 5 times. The combined resulting mixture was filtered, the filter cake was washed with EtOAc (3×20 mL). The filtrate was concentrated under reduced pressure. The crude product was purified by Prep-HPLC (2 #SHIMADZU (HPLC-01): Column, XBridge Prep Phenyl OBD Column, 19*250 mm, 5 μm; mobile phase, water (50 mmol/L $NH_4HCO_3$) and acetonitrile (MeCN) (12% MeCN up to 22% in 10 min, hold 22% in 2 min); Detector, UV254 nm) to provide 1-chloro-N-(5,5-dimethyloxolan-3-yl)pyrido[3,4-d]pyridazin-4-amine (2 g, 32.3% yield). LCMS, ESI: RT=0.73 min, m/z=279.1 [M+H]$^+$; $^1$H NMR (400 MHz, DMSO-$d_6$) δ 9.83 (d, J=1.0 Hz, 1H), 9.07 (d, J=5.6 Hz, 1H), 8.07 (d, J=5.8 Hz, 1H), 7.88 (dd, J=5.6, 0.9 Hz, 1H), 4.85-4.77 (m, 1H), 4.20-4.16 (m, 1H), 3.78-3.74 (m, 1H), 2.30-2.25 (m, 1H), 1.98-1.93 (m, 1H), 1.34 (s, 3H), 1.24 (s, 3H).

Step 4. Synthesis of 1-(4-(difluoromethoxy)-2-methoxyphenyl)-N-(5,5-dimethyltetrahydrofuran-3-yl)pyrido[3,4-d]pyridazin-4-amine. To a stirred solution of 1-chloro-N-(5,5-dimethyloxolan-3-yl)pyrido[3,4-d]pyridazin-4-amine (1400 mg, 5.02 mmol, 1 equiv) and 4-(difluoromethoxy)-2-methoxyphenylboronic acid (3284.18 mg, 15.06 mmol, 3 equiv) in dioxane (12 mL) and water (2.4 mL) was added $Na_2CO_3$ (1596.36 mg, 15.06 mmol, 3 equiv) and Pd(dppf)$Cl_2$ (735.02 mg, 1 mmol, 0.2 equiv) at room temperature. The resulting mixture was stirred for 2 h at 80° C. under nitrogen atmosphere. The reaction was monitored by LCMS. The resulting mixture was concentrated under vacuum. The residue was purified by reversed-phase flash chromatography (column, C18 silica gel; mobile phase, acetonitrile (MeCN) in water, 40% to 50% gradient in 10 min; detector, UV 254 nm) to provide the title compound (1.20 g, 57% yield). LCMS, ESI: RT=0.66 min, m/z=417.1 [M+H]$^+$.

Step 5. Synthesis of 5-(difluoromethoxy)-2-(4-((5,5-dimethyltetrahydrofuran-3-yl)amino)pyrido[3,4-d]pyridazin-1-yl)phenol. To a stirred solution of 1-(4-(difluoromethoxy)-2-methoxyphenyl)-N-(5,5-dimethyltetrahydrofuran-3-yl)pyrido[3,4-d]pyridazin-4-amine (1100 mg, 2.64 mmol, 1 equiv) in dimethylformamide (10 mL) was added (ethylsulfanyl)sodium (666.53 mg, 7.92 mmol, 3 equiv) at room temperature. The resulting mixture was stirred for 1 h at 120° C. The reaction was monitored by LCMS. The resulting mixture was filtered, the filter cake was washed with MeOH (3×5 mL). The filtrate was concentrated under reduced pressure. The crude product was purified by Prep-HPLC (Column: Xselect CSH C18 OBD Column 30*150 mm 5 m, n; Mobile Phase A: Water (0.05% trifluoroacetic acid (TFA)), Mobile Phase B: MeCN; Flow rate: 60 mL/min; Gradient: 18% B to 28% B in 10 min, 28% B; Wave Length: 254 nm; RT(min): 8.4) to provide the title compound (Compound 9A) (751.6 mg, 55.1% yield). LCMS, ESI: RT=0.67 min, m/z=403.1[M+H]$^+$; $^1$H NMR (400 MHz, Methanol-$d_4$) δ 10.01 (d, J=1.0 Hz, 1H), 9.15 (d, J=5.5 Hz, 1H), 7.72 (dd, J=5.6, 1.0 Hz, 1H), 7.47 (d, J=8.4 Hz, 1H), 7.24-6.73 (m, 3H), 4.85-4.76 (m, 1H), 4.36-4.32 (m, 1H), 4.11-4.07 (m, 1H), 2.53-2.48 (m, 1H), 2.18-2.13 (m, 1H), 1.46 (s, 3H), 1.37 (s, 3H). Compound 9* and Compound 9B* were then isolated via chiral HPLC, and stereochemistry was assigned based on extrapolation from Compound 5 and Compound 5B stereochemical assignments.

Isolation of (S)-5-(difluoromethoxy)-2-(4-((5,5-dimethyltetrahydrofuran-3-yl)amino)pyrido[3,4-d]pyridazin-1-yl)phenol (Compound 9*). Prep-Chiral-HPLC (Column: CHIRALPAK IF, 2*25 cm, 5 m; Mobile Phase A: Hexanes (0.1% trifluoroacetic acid (TFA)), Mobile Phase B: EtOH: DCM=1:1; Flow rate: 20 mL/min; Gradient: 60% B to 60% B in 11 min; Wave Length: 220/254 nm; RT(min): 6.39; $^1$H NMR (400 MHz, Methanol-d4) δ 9.99 (d, J=1.3 Hz, 1H), 9.14 (d, J=5.5 Hz, 1H), 7.72-7.71 (m, 1H), 7.47 (d, J=8.4 Hz, 1H), 7.17-6.76 (m, 3H), 4.83-4.75 (m, 1H), 4.35-4.31 (m, 1H), 4.09-4.06 (m, 1H), 2.53-2.47 (m, 1H), 2.17-2.13 (m, 6.0 Hz, 1H), 1.46 (s, 3H), 1.37 (s, 3H); LCMS: 403.5 [M+H]$^+$.

Isolation of (R)-5-(difluoromethoxy)-2-(4-((5,5-dimethyltetrahydrofuran-3-yl)amino)pyrido[3,4-d]pyridazin-1-yl)phenol (Compound 9B*). Prep-Chiral-HPLC (Column: CHIRALPAK IF, 2*25 cm, 5 m; Mobile Phase A: Hexanes (0.1% TFA), Mobile Phase B: EtOH:DCM=1:1; Flow rate: 20 mL/min; Gradient: 60% B to 60% B in 11 min; Wave Length: 220/254 nm; RT(min): 9.83; $^1$H NMR (400 MHz, Methanol-$d_4$) δ 10.03-9.98 (m, 1H), 9.14-9.13 (m, 1H), 7.72-7.71 (m, 1H), 7.47 (d, J=8.4 Hz, 1H), 7.16-6.79 (m, 3H), 4.83-4.75 (m, 1H), 4.35-4.31 (m, 1H), 4.10-4.06 (m, 1H), 2.53-2.47 (m, 1H), 2.18-2.13 (m, 1H), 1.46 (s, 3H), 1.37 (s, 3H); LCMS: 403.5 [M+H]$^+$.

Example 5. 2-(4-((6,6-dimethyltetrahydro-2H-pyran-3-yl)amino)pyrido[3,4-d]pyridazin-1-yl)-5-methylphenol (Compound 10A), (S)-2-(4-((6,6-dimethyltetrahydro-2H-pyran-3-yl)amino)pyrido[3,4-d]pyridazin-1-yl)-5-methylphenol (Compound 10*), and (R)-2-(4-((6,6-dimethyltetrahydro-2H-pyran-3-yl)amino)pyrido[3,4-d]pyridazin-1-yl)-5-methylphenol (Compound 10B*)

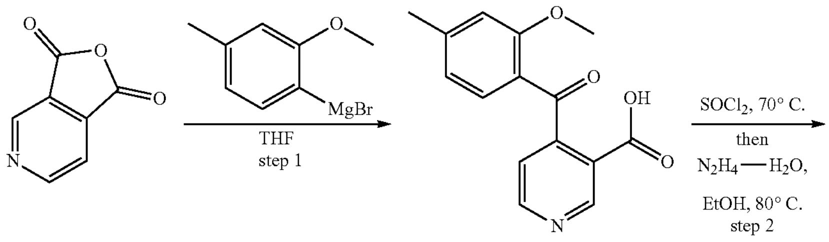

-continued

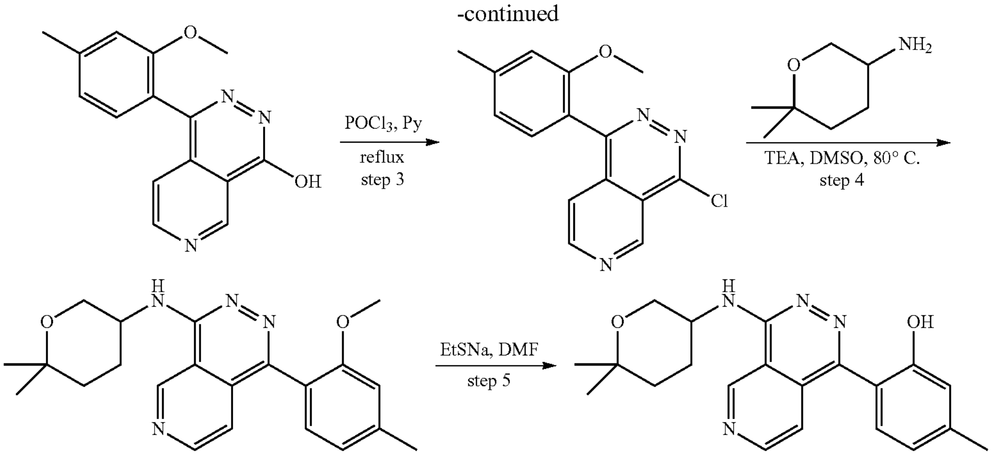

Compound 10A
2-(4-((6,6-dimethyltetrahydro-2H-pyran-3-yl)amino)pyrido[3,4-d]pyridazin-1-yl)-5-methylphenol

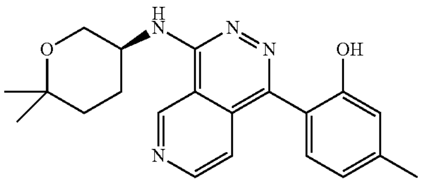

Compound 10*
(S)-2-(4-((6,6-dimethyltetrahydro-2H-pyran-3-yl)amino)pyrido[3,4-d]pyridazin-1-yl)-5-methylphenol

+

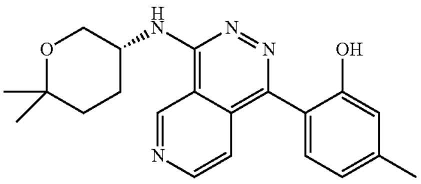

Compound 10B*
(R)-2-(4-((6,6-dimethyltetrahydro-2H-pyran-3-yl)amino)pyrido[3,4-d]pyridazin-1-yl)-5-methylphenol Example 5 follows Protocol B.

Step 1. Synthesis of 4-(2-methoxy-4-methylbenzoyl)pyridine-3-carboxylic acid. Into a 250 mL 3-necked round-bottom flask were added furo[3,4-c]pyridine-1,3-dione (10 g, 67.06 mmol, 1 equiv), THF (100 mL) and bromo(2-methoxy-4-methylphenyl)magnesium (9 g, 40.24 mmol, 0.6 equiv) was added by dropwise at −78° C. The resulting mixture was stirred for 1 h at room temperature under nitrogen atmosphere. The reaction progress was monitored by LCMS. The reaction was quenched by the addition of ice/water (50 mL) at room temperature. The resulting mixture was extracted with EtOAc (3×50 mL), dried over anhydrous $Na_2SO_4$, filtered, and the filtrate concentrated under reduced pressure to provide the title compound (6 g, 33% yield). LCMS: (ES, m/z): RT=0.570 min, m/z=272 $[M+1]^+$.

Step 2. Synthesis of 1-(2-methoxy-4-methylphenyl)pyrido[3,4-d]pyridazin-4-ol. Into a 250 mL round-bottom flask were added 4-(2-methoxy-4-methylbenzoyl)pyridine-3-carboxylic acid (2 g, 7.37 mmol, 1 equiv), and $SOCl_2$ (20 mL). The resulting mixture was stirred for 2 h at 70° C., and the reaction was monitored by TLC. After the reaction was completed, the resulting mixture was concentrated under vacuum. The residue was dissolved in DCM (50 mL) and added into the solution of hydrazine hydrate (1.70 g, 33.99 mmol, 4.61 equiv) and EtOH (10 mL) at 0° C. The resulting mixture was stirred for 3 h at 70° C. in an oil bath. The reaction progress was monitored by LCMS. The precipitated solids were collected by filtration. The crude product (2.0 g, 80% purity) was purified by Prep-HPLC ((Prep-HPLC-059): Column, CHIRAL ART Cellulose-SC, 2*25 cm, 5 um; mobile phase, Hex (0.5% 2M $NH_3$-MeOH) and MeOH: DCM=1:1 (hold 60% MeOH:DCM=1:1—in 10 min); Detector, UV 254) to provide the title compound (1.30 g, 66% yield). LCMS: (ES, m/z): RT=0.880 min, m/z=268[M+1]+ 1H NMR (400 MHz, DMSO-d6) δ 12.75 (s, 1H), 9.49 (d, J=0.9 Hz, 1H), 8.93 (d, J=5.5 Hz, 1H), 7.25 (d, J=7.6 Hz, 1H), 7.17 (d, J=5.5, 0.9 Hz, 1H), 7.06 (s, 1H), 6.98-6.91 (m, 1H), 3.70 (s, 3H), 2.43 (s, 3H).

Step 3. Synthesis of 4-(2-methoxy-4-methylbenzoyl)pyridine-3-carboxylic acid. Into a 250 mL round-bottom flask were added 1-(2-methoxy-4-methylphenyl)pyrido[3,4-d]pyridazin-4-ol (800 mg, 2.99 mmol, 1 equiv), $POCl_3$ (10 mL), and pyridine (1 mL) at room temperature. The resulting mixture was stirred for 2 h at 110° C. under nitrogen atmosphere. The reaction progress was monitored by LCMS. The reaction was quenched by the addition into aqueous of $NaHCO_3$ (500 mL) and ethyl acetate (EtOAc) (500 mL) at 0° C. The resulting mixture was extracted with EtOAc (3×500 mL). The combined organic layers were washed with $H_2O$ (1×500 mL), dried over anhydrous $Na_2SO_4$, filtered, and the filtrate was then concentrated under reduced pressure to provide the title compound (300 mg, 35.1% yield). LCMS: (ES, m/z): RT=0.837 min, m/z=286[M+1]+ 1H NMR (300 MHz, DMSO-d6) δ 9.74 (d, J=1.0 Hz, 1H), 9.10 (d, J=5.7 Hz, 1H), 7.59-7.46 (m, 1H), 7.35 (d, J=7.6 Hz, 1H), 7.14 (d, J=1.4 Hz, 1H), 7.08-6.95 (m, 1H), 3.69 (s, 3H), 2.47 (s, 3H).

Step 4. Synthesis of N-(6,6-dimethyloxan-3-yl)-1-(2-methoxy-4-methylphenyl)pyrido[3,4-d]pyridazin-4-amine. To a stirred solution of 4-chloro-1-(2-methoxy-4-methylphenyl)pyrido[3,4-d]pyridazine (149.6 mg, 0.525 mmol, 1 equiv) in DMSO (4.5 mL) was added 6,6-dimethyloxan-3-amine (81.39 mg, 0.630 mmol, 1.2 equiv) and triethylamine (TEA) (159.4 mg, 1.58 mmol, 3 equiv). The resulting mixture was stirred for 2 h at 80° C. The reaction was monitored by LCMS. After the reaction was completed, the resulting mixture was concentrated under vacuum and purified by reverse flash chromatography (column, C18 silica gel; mobile phase, MeCN in Water (0.1% FA), 10% to 50% gradient in 10 min; detector, UV 254 nm) to provide the title compound (180 mg, 77.5% yield). LCMS: (ES, m/z): RT=0.663 min, m/z=378[M+H]$^+$.

Step 5. Synthesis of 2-(4-((6,6-dimethyltetrahydro-2H-pyran-3-yl)amino)pyrido[3,4-d]pyridazin-1-yl)-5-methylphenol (Compound 10A), (S)-2-(4-((6,6-dimethyltetrahydro-2H-pyran-3-yl)amino)pyrido[3,4-d]pyridazin-1-yl)-5-methylphenol (Compound 10*), and (R)-2-(4-((6,6-dimethyltetrahydro-2H-pyran-3-yl)amino)pyrido[3,4-d]pyridazin-1-yl)-5-methylphenol (Compound 10B*). To a stirred solution of N-(6,6-dimethyloxan-3-yl)-1-(2-methoxy-4-methylphenyl)pyrido[3,4-d]pyridazin-4-amine (50 mg, 0.026 mmol, 1 equiv) in DMF (1.5 mL) was added (ethylsulfanyl)sodium (166.3 mg, 1.98 mmol, 15 equiv). The resulting mixture was stirred for 1 h at 120° C. The reaction was monitored by LCMS. After the reaction was completed, the resulting mixture was cooled to room temperature, filtered, the filter cake was washed with EtOAc (2×10 mL) and concentrated under vacuum. The product was purified by Prep-HPLC (Column: YMC-Actus Triart C18 ExRS, 30*150 mm, 5 μm; Mobile Phase A: Water (10 mmol/L $NH_4HCO_3$), Mobile Phase B: MeCN; Flow rate: 60 mL/min; Gradient: 33% B to 43% B in 10 min, 43% B; Wave Length: 254 nm; RT1(min): 9.5) to provide the title compound (Compound 10A). Compound 10* and Compound 10B* were then isolated via chiral HPLC. Stereochemistry arbitrarily assigned.

Isolation of (S)-2-(4-((6,6-dimethyltetrahydro-2H-pyran-3-yl)amino)pyrido[3,4-d]pyridazin-1-yl)-5-methylphenol (Compound 10*). Column: Lux 5 um Celluloes-3, 2.12*25 cm, 5 m; Mobile Phase A: Hexanes (0.2% formic acid (FA)), Mobile Phase B: MeOH:EtOH=1:1; Flow rate: 20 mL/min; Gradient: 15% B to 15% B in 12.5 min; Wave Length: 220/254 nm; RT(min): 2.81; (13.3 mg, 27.6% yield). LCMS: (ES, m/z): RT=1.372 min, m/z=365 [M+H]$^+$; $^1$H NMR (400 MHz, DMSO-d6) δ 9.74 (s, 1H), 9.65 (s, 1H), 8.85 (dd, J=5.8, 2.2 Hz, 1H), 7.53 (d, J=7.6 Hz, 1H), 7.32 (d, J=5.7 Hz, 1H), 7.20 (d, J=7.6 Hz, 1H), 6.81 (q, J=7.7, 6.7 Hz, 2H), 4.39 (s, 1H), 3.91-3.82 (m, 1H), 3.53 (dd, J=11.1, 9.6 Hz, 1H), 2.34 (s, 3H), 1.97-1.85 (m, 2H), 1.76-1.68 (m, 1H), 1.64-1.53 (m, 1H), 1.28 (s, 3H), 1.22 (s, 3H).

(R)-2-(4-((6,6-dimethyltetrahydro-2H-pyran-3-yl)amino)pyrido[3,4-d]pyridazin-1-yl)-5-methylphenol (Compound 10B*). Column: Lux 5 um Celluloes-3, 2.12*25 cm, 5 m; Mobile Phase A: Hexanes (0.2% FA), Mobile Phase B: MeOH:EtOH=1:1; Flow rate: 20 mL/min; Gradient: 15% B to 15% B in 12.5 min; Wave Length: 220/254 nm; RT(min): 3.82; (5.4 mg, 11.2% yield). LCMS: (ES, m/z): RT=1.36 min, m/z=365 [M+H]$^+$; $^1$H NMR (400 MHz, DMSO-d6) δ 9.75 (s, 1H), 9.64 (s, 1H), 8.85 (d, J=5.6 Hz, 1H), 7.53 (d, J=7.6 Hz, 1H), 7.32 (d, J=5.6 Hz, 1H), 7.20 (d, J=7.6 Hz, 1H), 6.84-6.76 (m, 2H), 4.39 (s, 1H), 3.87 (dd, J=11.4, 4.7 Hz, 1H), 3.53 (t, J=10.5 Hz, 1H), 2.34 (s, 3H), 1.95-1.87 (m, 2H), 1.76-1.67 (m, 1H), 1.64-1.52 (m, 1H), 1.28 (s, 3H), 1.22 (s, 3H).

Example 6. 2-(4-((2,2-dimethyltetrahydro-2H-pyran-4-yl)amino)pyrido[3,4-d]pyridazin-1-yl)-5-(trifluoromethyl)phenol (Compound 11A), (S)-2-(4-((2,2-dimethyltetrahydro-2H-pyran-4-yl)amino)pyrido[3,4-d]pyridazin-1-yl)-5-(trifluoromethyl)phenol (Compound 11*) and (R)-2-(4-((2,2-dimethyltetrahydro-2H-pyran-4-yl)amino)pyrido[3,4-d]pyridazin-1-yl)-5-(trifluoromethyl)phenol (Compound 11B*)

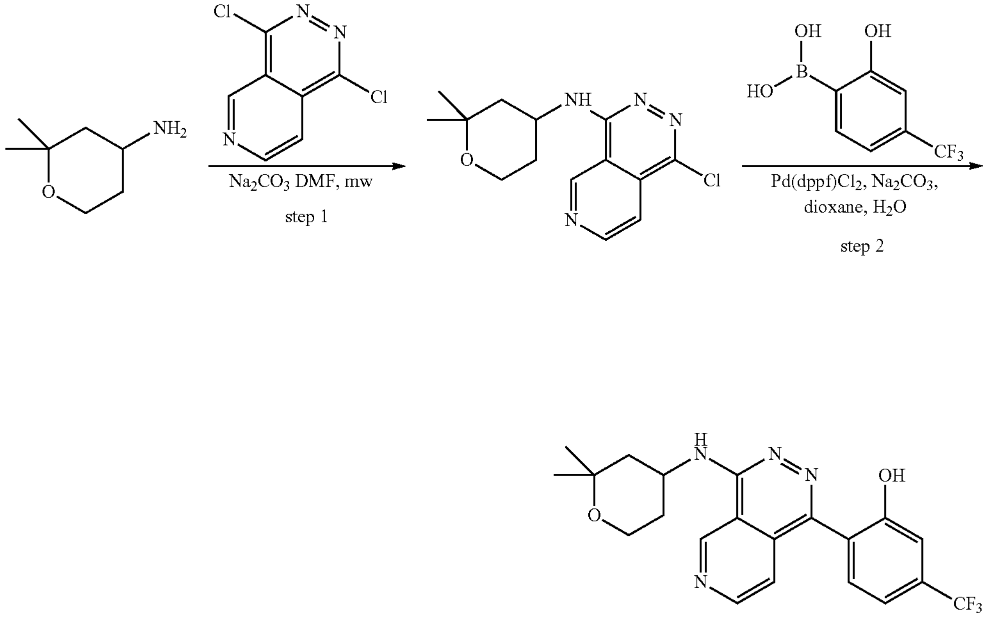

Compound 11A*

2-(4-((2,2-dimethyltetrahydro-2H-pyran-4-yl)amino)pyrido[3,4-d][pyridazin-1-yl)-5-(trifluoromethyl)phenol -continued

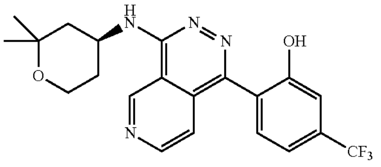

Compound 11*

(S)-2-(4-((2,2-dimethyltetrahydro-2H-pyran-4-yl)amino)pyrido[3,4-d][pyridazin-1-yl)-5-(trifluoromethyl)phenol

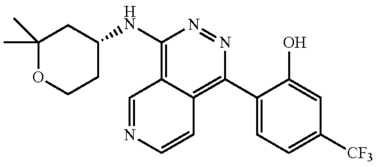

Compound 11B*

(R)-2-(4-((2,2-dimethyltetrahydro-2H-pyran-4-yl)amino)pyrido[3,4-d][pyridazin-1-yl)-5-(trifluoromethyl)phenol Example 6 follows Protocol A.

Step 1. Synthesis of 1-chloro-N-(2,2-dimethyloxan-4-yl) pyrido[3,4-d] pyridazin-4-amine. Into a 100 mL sealed tube were added 2,2-dimethyloxan-4-amine (2 g, 15.5 mmol, 1 equiv), $Na_2CO_3$ (4921 mg, 46.44 mmol, 3 equiv), and DMF (20 mL). The final reaction mixture was irradiated with microwave radiation for 1 h at 130° C. The reaction progress was monitored by LCMS. The resulting mixture was filtered, the filter cake was washed with DMF (3×10 mL). The filtrate was concentrated under reduced pressure. The residue was purified by reverse flash chromatography (column, C18 silica gel; mobile phase, MeCN in Water, 100% to 60% gradient in 30 min; detector, UV 254 nm) to provide the title compound (1.80 g, 39.3% yield). LCMS: (ES, m/z): RT=0.93 min, m/z=293.0$[M+H]^+$.

Step 2. Synthesis of 2-(4-((2,2-dimethyltetrahydro-2H-pyran-4-yl)amino)pyrido[3,4-d]pyridazin-1-yl)-5-(trifluoromethyl)phenol (Compound 11A), (S)-2-(4-((2,2-dimethyltetrahydro-2H-pyran-4-yl)amino)pyrido[3,4-d]pyridazin-1-yl)-5-(trifluoromethyl)phenol (Compound 11*) and (R)-2-(4-((2,2-dimethyltetrahydro-2H-pyran-4-yl)amino)pyrido [3,4-d]pyridazin-1-yl)-5-(trifluoromethyl)phenol (Compound 11B*). Into a 20 mL vial were added 1-chloro-N-(2,2-dimethyloxan-4-yl) pyrido[3,4-d]pyridazin-4-amine (250 mg, 0.85 mmol, 1 equiv), $Na_2CO_3$ (271.51 mg, 2.56 mmol, 3 equiv), $Pd(dppf)Cl_2$ (187.44 mg, 0.25 mmol, 0.3 equiv), dioxane (2.5 mL), and $H_2O$ (0.5 mL). The resulting mixture was stirred for 1 h at 80° C. under nitrogen atmosphere. The reaction progress was monitored by LCMS. The resulting mixture was extracted with EtOAc (3×40 mL). The combined organic layers was dried over anhydrous $Na_2SO_4$. After filtration, the filtrate was concentrated under reduced pressure. The residue was purified by reverse flash chromatography (column, C18 silica gel; mobile phase, MeCN in water, 30% to 60% gradient in 10 min; detector, UV 254 nm) to provide the crude product, Compound 11A (200 mg, 80% purity), which was purified by Prep-HPLC (Column, YMC-Actus Triart C18 ExRS, 30*150 mm, 5 μm; mobile phase, water (10 mmol/L $NH_4HCO_3$) and MeCN (35% MeCN up to 45% in 10 min); Detector, UV 254 nm) to provide purified Compound 11A (120 mg, 98% purity) was further purified by Chiral-Prep-HPLC (Column, CHIRALPAK ID, 2*25 cm, 5 um; mobile phase, hexanes (0.2% formic acid) and ethanol (EtOH) (hold 10% EtOH— in 20 min); Detector, UV 254 nm) to provide (S)-2-(4-((2,2-dimethyltetrahydro-2H-pyran-4-yl)amino) pyrido[3,4-d]pyridazin-1-yl)-5-(trifluoromethyl)phenol (26.5 mg, 7.25% yield) (Compound 11*) with a RT of 1.66 min; and (R)-2-(4-((2,2-dimethyltetrahydro-2H-pyran-4-yl) amino)pyrido[3,4-d]pyridazin-1-yl)-5-(trifluoromethyl)phenol (24.3 mg, 5.33% yield) (Compound 11B*) with a RT of 2.37 min. Stereochemistry arbitrarily assigned.

(S)-2-(4-((2,2-dimethyltetrahydro-2H-pyran-4-yl)amino) pyrido[3,4-d]pyridazin-1-yl)-5-(trifluoromethyl)phenol (Compound 11*): LCMS: (ES, m/z): RT=1.21 min, m/z=419.0$[M+H]^+$; $^1H$ NMR (400 MHz, Methanol-$d_4$) δ 9.71 (d, J=1.0 Hz, 1H), 8.86 (d, J=5.7 Hz, 1H), 7.60 (d, J=7.9 Hz, 1H), 7.52-7.46 (m, 1H), 7.37-7.31 (m, 1H), 7.28 (d, J=1.7 Hz, 1H), 4.86-4.75 (m, 1H), 3.99-3.88 (m, 1H), 3.91-3.82 (m, 1H), 2.24-2.10 (m, 2H), 1.75-1.64 (m, 1H), 1.67-1.58 (m, 1H), 1.41 (s, 3H), 1.32 (s, 3H).

(R)-2-(4-((2,2-dimethyltetrahydro-2H-pyran-4-yl)amino) pyrido[3,4-d]pyridazin-1-yl)-5-(trifluoromethyl)phenol (Compound 11B*): LCMS: (ES, m/z): RT=1.21 min, m/z=419.0$[M+H]^+$; $^1H$ NMR (400 MHz, Methanol-$d_4$) δ 9.71 (d, J=1.0 Hz, 1H), 8.86 (d, J=5.7 Hz, 1H), 7.59 (d, J=7.9 Hz, 1H), 7.52-7.46 (m, 1H), 7.37-7.31 (m, 1H), 7.28 (d, J=1.7 Hz, 1H), 4.86-4.74 (m, 1H), 3.99-3.81 (m, 2H), 2.24-2.10 (m, 2H), 1.75-1.58 (m, 2H), 1.41 (s, 3H), 1.32 (s, 3H).

Example 7. 5-(difluoromethyl)-2-(4-((2,2-dimethyltetrahydro-2H-pyran-4-yl)amino)pyrido[3,4-d] pyridazin-1-yl)phenol (Compound 16A), (S)-5-(difluoromethyl)-2-(4-((2,2-dimethyltetrahydro-2H-pyran-4-yl)amino)pyrido[3,4-d]pyridazin-1-yl) phenol (Compound 16*), and (R)-5-(difluoromethyl)-2-(4-((2,2-dimethyltetrahydro-2H-pyran-4-yl)amino)pyrido[3,4-d]pyridazin-1-yl) phenol (Compound 16B*)

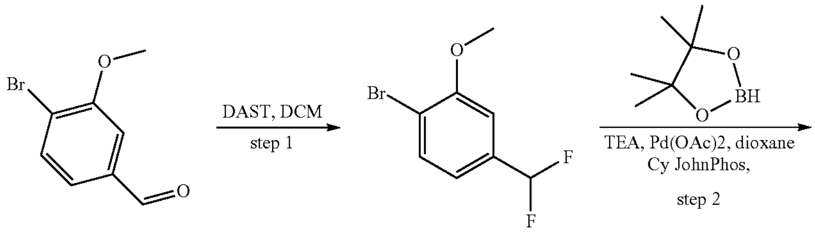

-continued

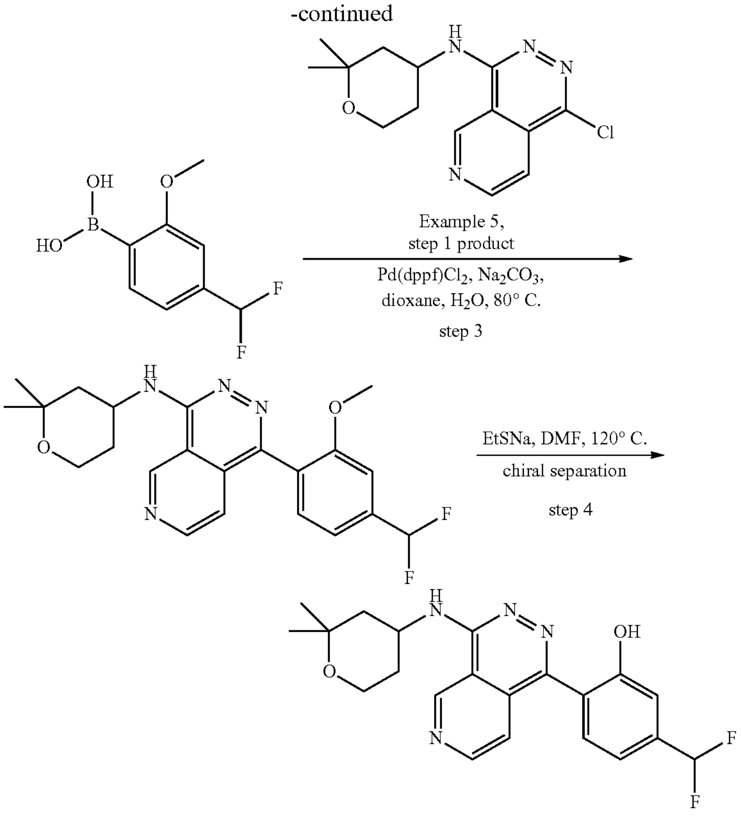

Compound 16A*

5-(difluoromethyl)-2-(4-((2,2-dimethyltetrahydro-2H-pyran-4-yl)amino)pyrido[3,4-d]pyridazin-1-yl)phenol

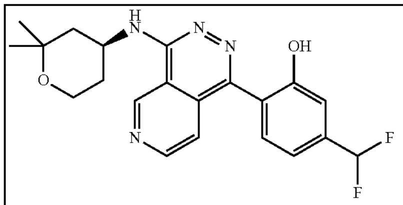

Compound 16*

(S)-5-(difluoromethyl)-2-(4-((2,2-dimethyltetrahydro-2H-pyran-4-yl)amino)pyrido[3,4-d]pyridazin-1-yl)phenol

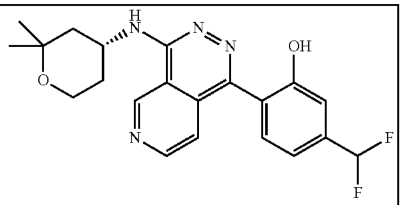

Compound 16B*

(R)-5-(difluoromethyl)-2-(4-((2,2-dimethyltetrahydro-2H-pyran-4-yl)amino)pyrido[3,4-d]pyridazin-1-yl)phenol Example 7 follows Protocol A.

Step 1. Synthesis of 1-bromo-4-(difluoromethyl)-2-methoxybenzene. To a stirred solution of 4-bromo-3-methoxybenzaldehyde (1 g, 4.65 mmol, 1 equiv) in DCM (10 mL) was added diethylaminosulfur trifluoride (DAST) (3.75 g, 23.25 mmol, 5 equiv). The resulting mixture was stirred for 2 h at room temperature under air atmosphere. The reaction was quenched with ice water (20 mL) at 0° C. The aqueous layer was extracted with EtOAc (3×10 mL). The resulting mixture was concentrated under reduced pressure. The residue was purified by silica gel column chromatography, eluted with dichloromethane/petroleum ether (DCM/PE) (1:1) to afford the title compound (1.03 g, 93% yield).

Step 2. Synthesis of (4-(difluoromethyl)-2-methoxyphenyl)boronic acid. A solution of 1-bromo-4-(difluoromethyl)-2-methoxybenzene (400 mg, 1.68 mmol, 1 equiv) in dioxane (10 mL) was treated with triethylamine (512.27 mg, 5.04 mmol, 3 equiv) for 30 min at room temperature under nitrogen atmosphere followed by the addition of Pd$(OAc)_2$ (37.88 mg, 0.17 mmol, 0.1 equiv) and 2-(dicyclohexylphosphino)biphenyl, (2-Biphenyl)dicyclohexylphosphine (CyJohnPhos) (118.29 mg, 0.33 mmol, 0.2 equiv) was added. The resulting mixture was stirred for 2 h at 80° C. under nitrogen atmosphere. The reaction was quenched with ice/water (10 mL) at 0° C. The aqueous layer was extracted with EtOAc (50 mL×3). The resulting mixture was concentrated under reduced pressure. The resulting mixture was concentrated under vacuum to afford the title compound (1 g crude), which was used for next step directly without further purification. GCMS: m/z=202.06.

Step 3. Synthesis of 1-[4-(difluoromethyl)-2-methoxyphenyl]-N-(2,2-dimethyloxan-4-yl)pyrido[3,4-d]pyridazin-4-amine. To a stirred solution of 2-[4-(difluoromethyl)-2-methoxyphenyl]-4,4,5,5-tetramethyl-1,3,2-dioxaborolane (135.86 mg, 0.47 mmol, 1 equiv) in 1,4-dioxane (9 mL) and $H_2O$ (1.8 mL) was added $Na_2CO_3$ (152.05 mg, 1.43 mmol, 3 equiv) and Pd(dppf)$Cl_2$ (104.97 mg, 0.14 mmol, 0.3 equiv). The resulting mixture was stirred for 2 h at 80° C. under nitrogen atmosphere. The reaction was diluted with water (20 mL) at 0° C. The aqueous layer was extracted with EtOAc (3×50 mL). The resulting mixture was concentrated under reduced pressure. The residue was purified by reverse flash chromatography (column, C18 silica gel; mobile phase, MeCN in water, 10% to 50% gradient in 10 min; detector, UV 254 nm) to provide the title compound (176 mg, 88.8% yield). LCMS: (ES, m/z): RT=0.65 min, m/z=415.40[M+H]+; 1H NMR (400 MHz, DMSO-d6) δ 9.78 (s, 1H), 8.84 (d, J=5.60 Hz, 1H), 7.67 (d, J=6.90 Hz, 1H), 7.52 (d, J=7.70 Hz, 1H), 7.40 (s, 1H), 7.34 (d, J=7.9 Hz, 1H), 7.21-7.12 (m, 1H), 6.44 (q, J=7.0 Hz, 1H), 3.76 (d, J=5.50 Hz, 3H), 3.74 (s, 2H), 1.91 (d, J=12.90 Hz, 4H), 1.27-1.14 (m, 6H).

Step 4. Synthesis of 5-(difluoromethyl)-2-(4-((2,2-dimethyltetrahydro-2H-pyran-4-yl)amino)pyrido[3,4-d]pyridazin-1-yl)phenol (Compound 16A), (S)-5-(difluoromethyl)-2-(4-((2,2-dimethyltetrahydro-2H-pyran-4-yl)amino)pyrido[3,4-d]pyridazin-1-yl)phenol (Compound 16*), and (R)-5-(difluoromethyl)-2-(4-((2,2-dimethyltetrahydro-2H-pyran-4-yl)amino)pyrido[3,4-d]pyridazin-1-yl)phenol (Compound 16B*). To a stirred solution of 1-[4-(difluoromethyl)-2-methoxyphenyl]-N-(2,2-dimethyloxan-4-yl)pyrido[3,4-d]pyridazin-4-amine (150 mg, 0.36 mmol, 1 equiv) in DMF (1.5 mL) was added sodium ethanethiolate (EtSNa) (457 mg, 5.43 mmol, 15 equiv). The final reaction mixture was stirred for 2 h at 120° C. The reaction progress was monitored by LCMS. The resulting mixture was filtered, the filter cake was washed with EtOAc (3×5 mL). The filtrate was concentrated under reduced pressure. The residue was purified by reverse flash chromatography (column, C18 silica gel; mobile phase, MeCN in water (10 mmol/L $NH_4HCO_3$), 25% to 45% gradient in 10 min; detector, UV 254 nm) to provide Compound 16A (43 mg, 96% purity, 88.8% yield), which was further purified by Prep-Chiral-HPLC (Column: CHIRAL ART Cellulose-SB, 2*25 cm, 5 m; Mobile Phase A: Hex (0.2% FA), Mobile Phase B: IPA:DCM=1:1; Flow rate: 20 mL/min; Gradient: 30% B to 30% B in 15 min; Wave Length: 254/220 nm; RT1(min): 10.29) to afford (R)-5-(difluoromethyl)-2-(4-((3,3-dimethyltetrahydro-2H-pyran-4-yl)amino)pyrido[3,4-d]pyridazin-1-yl)phenol (Compound 16B*) with a RT of 14.32 min (16.5 mg, 11.4% yield) and (S)-5-(difluoromethyl)-2-(4-((3,3-dimethyltetrahydro-2H-pyran-4-yl)amino)pyrido[3,4-d]pyridazin-1-yl)phenol (Compound 16*) with a RT of 10.29 min (18.5 mg, 12.3% yield). Stereochemistry arbitrarily assigned.

(R)-5-(difluoromethyl)-2-(4-((3,3-dimethyltetrahydro-2H-pyran-4-yl)amino)pyrido[3,4-d]pyridazin-1-yl)phenol. (Compound 16B*): LCMS: (ES, m/z): RT=1.12 min, m/z=401.20[M+H]$^+$; $^1$H NMR (400 MHz, DMSO-d6) δ 10.14 (s, 1H), 9.78 (s, 1H), 8.85 (d, J=5.6 Hz, 1H), 7.66 (s, 1H), 7.46 (d, J=7.60 Hz, 1H), 7.29 (d, J=5.6 Hz, 1H), 7.24-6.91 (m, 3H), 4.85-4.59 (m, 1H), 3.79-3.69 (m, 2H), 2.03 (s, 2H), 1.65-1.47 (m, 2H), 1.30 (s, 3H), 1.22 (s, 3H).

(S)-5-(difluoromethyl)-2-(4-((3,3-dimethyltetrahydro-2H-pyran-4-yl)amino)pyrido[3,4-d]pyridazin-1-yl)phenol (Compound 16*): LCMS: (ES, m/z): RT=1.12 min, m/z=401.20[M+H]$^+$; $^1$H NMR (400 MHz, DMSO-d6) δ 10.14 (s, 1H), 9.78 (s, 1H), 8.85 (d, J=5.6 Hz, 1H), 7.66 (s, 1H), 7.46 (d, J=7.60 Hz, 1H), 7.29 (d, J=5.6 Hz, 1H), 7.24-6.91 (m, 3H), 4.85-4.59 (m, 1H), 3.79-3.69 (m, 2H), 2.03 (s, 2H), 1.65-1.47 (m, 2H), 1.30 (s, 3H), 1.22 (s, 3H).

Example 8. 5-chloro-2-(4-((3-methyltetrahydro-2H-pyran-4-yl)amino)pyrido[3,4-d]pyridazin-1-yl)phenol (Compound 18B*), 5-chloro-2-(4-(((3R,4S)-3-methyltetrahydro-2H-pyran-4-yl)amino)pyrido[3,4-d]pyridazin-1-yl)phenol (Compound 18C*), 5-chloro-2-(4-(((3S,4R)-3-methyltetrahydro-2H-pyran-4-yl)amino)pyrido[3,4-d]pyridazin-1-yl)phenol (Compound 18A*), 5-chloro-2-(4-(((3R,4R)-3-methyltetrahydro-2H-pyran-4-yl)amino)pyrido[3,4-d]pyridazin-1-yl)phenol (Compound 18*), 5-chloro-2-(4-(((3S,4S)-3-methyltetrahydro-2H-pyran-4-yl)amino)pyrido[3,4-d]pyridazin-1-yl)phenol (Compound 18D*)

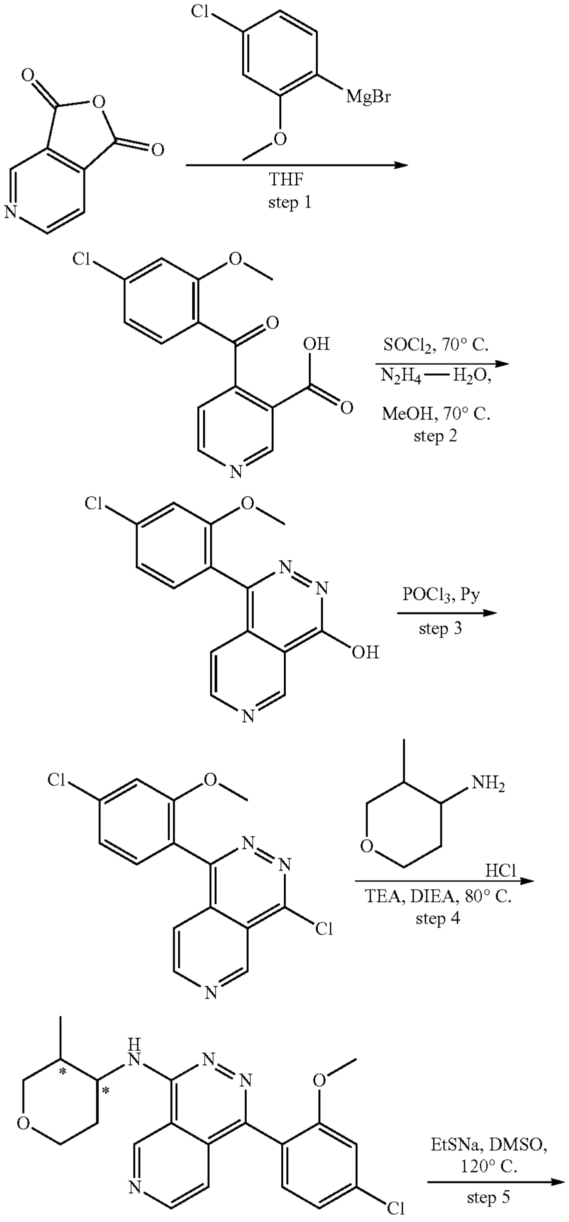

1-(4-chloro-2-methoxyphenyl)-N-(3-methyltetrahydro-2H-pyran-4-yl)pyrido[3,4-d]pyridazin-4-amine -continued

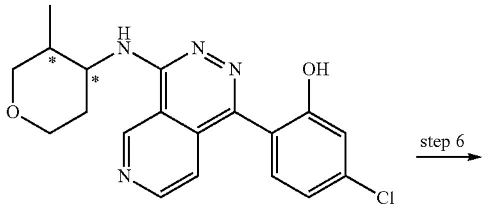

Compound 18B*
5-chloro-2-(4-((3-methyltetrahydro-2H-pyran-4-yl)amino)pyrido[3,4-d]pyridazin-1-yl)phenol
(cis and trans isomers)

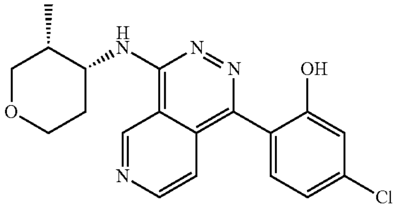

Compound 18*
5-chloro-2-(4-(((3R,4R)-3-methyltetrahydro-2H-pyran-4-yl)amino)pyrido[3,4-d]pyridazin-1-yl)phenol

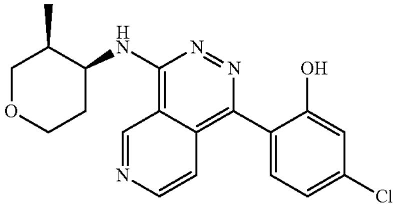

Compound 18D*
5-chloro-2-(4-(((3S,4S)-3-methyltetrahydro-2H-pyran-4-yl)amino)pyrido[3,4-d]pyridazin-1-yl)phenol

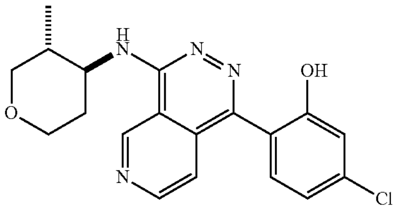

Compound 18′*
assumed trans mixture

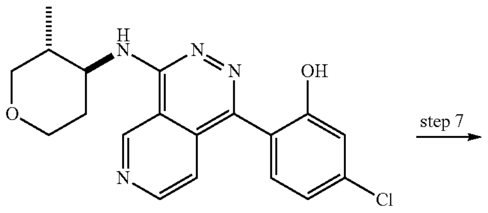

Compound 18′*
assumed trans mixture

-continued

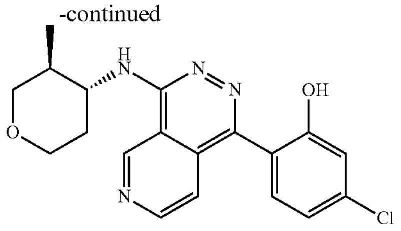

Compound 18A*
5-chloro-2-(4-(((3S,4R)-3-methyltetrahydro-2H-pyran-4-yl)amino)pyrido[3,4-d]pyridazin-1-yl)phenol

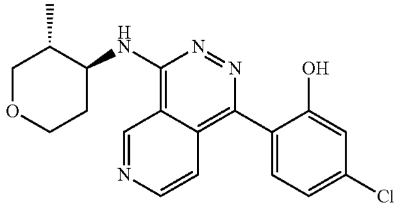

Compound 18C*
5-chloro-2-(4-(((3R,4S)-3-methyltetrahydro-2H-pyran-4-yl)amino)pyrido[3,4-d]pyridazin-1-yl)phenol Example 8 follows Protocol B.

Step 1: Synthesis of 4-(4-chloro-2-methoxybenzoyl)pyridine-3-carboxylic acid. To a stirred solution of furo[3,4-c]pyridine-1,3-dione (30.0 g, 201.20 mmol, 1 equiv) and tetrahydrofuran (300 mL) was added bromo(4-chloro-2-methoxyphenyl)magnesium (0.5M in THF) (241 mL, 120 mmol, 0.60 equiv) dropwise at −78° C. under nitrogen atmosphere. The resulting mixture was stirred for 2 h at 25° C. under nitrogen atmosphere. The reaction progress was monitored by LCMS. The reaction was quenched by the addition of water (150 mL) at 0° C. The precipitated solids were collected by filtration and washed with water (3×50 mL). This resulted in the title compound (20 g, 34.1% yield). LCMS (ES, m/z): RT=0.662 min, m/z=292.0[M+1]$^+$.

Step 2: Synthesis of 1-(4-chloro-2-methoxyphenyl)pyrido[3,4-d]pyridazin-4-ol. Into a 250 mL round-bottom flask were added 4-(4-chloro-2-methoxybenzoyl)pyridine-3-carboxylic acid (5 g, 17.1 mmol, 1 equiv) and $SOCl_2$ (50 mL). The resulting mixture was stirred for 2 h at 70° C. The reaction was monitored by TLC. After the reaction was completed, the resulting mixture was concentrated under vacuum. The residue was dissolved in DCM (50 mL) and added into the solution of $NH_2NH_2 \cdot H_2O$ (3.43 g, 68.6 mmol, 4 equiv), MeOH (50 mL) at 0° C. The resulting mixture was stirred for 3 h at 70° C. in an oil bath. The reaction progress was monitored by LCMS. The precipitated solids were collected by filtration. The crude product (4 g, 90% purity) was purified by Prep-HPLC (2 #SHIMADZU (HPLC-01): Column, XBridge Shield RP18 OBD Column, 19*250 mm, 10 μm; mobile phase, water (10 mmol/L $NH_4HCO_3$) and MeCN (hold 39% MeCN in 17 min); Detector, UV 254/220 nm) to provide the title compound (2.0 g, 40.6% yield). LCMS: (ES, m/z): RT=0.723 min, m/z=288.0 [M+H]$^+$. $^1$H NMR (400 MHz, DMSO-$d_6$) δ 12.90 (s, 1H), 9.50 (s, 1H), 8.94 (d, J=5.5 Hz, 1H), 7.41 (d, J=8.0 Hz, 1H), 7.33 (d, J=1.9 Hz, 1H), 7.23-7.15 (m, 2H), 3.75 (s, 3H).

Step 3: Synthesis of 4-chloro-1-(4-chloro-2-methoxyphenyl)pyrido[3,4-d]pyridazine. Into a 250 mL round-bottom flask were added 1-(4-chloro-2-methoxyphenyl)pyrido[3,4-d]pyridazin-4-ol (2.5 g, 8.69 mmol, 1 equiv) and $POCl_3$ (40 mL), and pyridine (4 mL). The resulting mixture was stirred for 3 h at 100° C. The reaction progress was monitored by LCMS. The reaction was quenched with 500 mL of sodium bicarbonate (aq.) and 500 mL of EtOAc at 0° C. The resulting mixture was extracted with EtOAc (3×500 mL). The combined organic layers were dried over anhydrous $Na_2SO_4$. After filtration, the filtrate was concentrated under reduced pressure to provide the title compound (1.50 g, 56.4% yield). LCMS (ES, m/z): RT=0.845 min, m/z=306.0 $[M+1]^+$. $^1H$ NMR (400 MHz, DMSO-$d_6$) δ 9.84-9.68 (m, 1H), 9.12 (d, J=5.7 Hz, 1H), 7.60-7.56 (m, 1H), 7.51 (d, J=8.1 Hz, 1H), 7.41 (d, J=1.9 Hz, 1H), 7.32-7.25 (m, 1H), 3.74 (s, 3H).

Step 4: Synthesis 1-(4-chloro-2-methoxyphenyl)-N-(3-methyltetrahydro-2H-pyran-4-yl)pyrido[3,4-d]pyridazin-4-amine. Into a 20 mL vial were added 3-methyloxan-4-amine hydrochloride (200 mg, 1.31 mmol, 3 equiv), DMSO (3 mL), 4-chloro-1-(4-chloro-2-methoxyphenyl)pyrido[3,4-d]pyridazine (134.60 mg, 0.44 mmol, 1 equiv) and DIEA (170.48 mg, 1.31 mmol, 3 equiv) at room temperature. The resulting mixture was stirred for overnight at 80 C under nitrogen atmosphere. The reaction progress was monitored by LCMS. The residue was purified by reverse flash chromatography (column, C18 gel; mobile phase, MeCN in water, 0% to 100% gradient in 30 min; detector, UV 254 nm) to provide the title compound as a mixture of cis and trans stereoisomers (150 mg, 88.7% yield). LCMS: (ES, m/z): RT=0.688 min, m/z=385$[M+1]^+$.

Step 5: Synthesis of 5-chloro-2-(4-((3-methyltetrahydro-2H-pyran-4-yl)amino)pyrido[3,4-d]pyridazin-1-yl)phenol (Compound 18B*). Into a 20 mL vial were added the cis/trans mixture of (1-(4-chloro-2-methoxyphenyl)-N-(3-methyltetrahydro-2H-pyran-4-yl)pyrido[3,4-d]pyridazin-4-amine (90 mg, 0.24 mmol, 1 equiv), DMSO (3 mL) and (ethylsulfanyl)sodium (204.14 mg, 2.43 mmol, 10 equiv) at room temperature. The resulting mixture was stirred for 1 h at 120° C. under nitrogen atmosphere. The reaction progress was monitored by LCMS. The residue was purified by reversed-phase flash chromatography (column, C18 gel; mobile phase, MeCN in water, 0% to 100% gradient in 30 min; detector, UV 254 nm) to provide a crude mixture of stereoisomers (70 mg, 90% purity).

Step 6: Isolation of cis diastereomers: 5-chloro-2-(4-(((3R,4R)-3-methyltetrahydro-2H-pyran-4-yl)amino)pyrido[3,4-d]pyridazin-1-yl)phenol (Compound 18*), 5-chloro-2-(4-{3-methyloxan-4-yl]amino}pyrido[3,4-d]pyridazin-1-yl)phenol (Compound 18'*) and 5-chloro-2-(4-(((3S,4S)-3-methyltetrahydro-2H-pyran-4-yl)amino)pyrido[3,4-d]pyridazin-1-yl)phenol (Compound 18D*). The crude mixture was purified using Chiral-Prep-HPLC with the following conditions: Column, Chiral ART Cellulose-SA, 2*25 cm, 5 um; mobile phase, Hex (0.2% FA)- and EtOH:DCM=1:1 (hold 30% EtOH:DCM=1:1—in 15.5 min); Detector, UV 254 nm. This resulted in 5-chloro-2-(4-{[(3R,4R)-3-methyloxan-4-yl]amino}pyrido[3,4-d]pyridazin-1-yl)phenol (also referred to as 5-chloro-2-(4-(((3R,4R)-3-methyltetrahydro-2H-pyran-4-yl)amino)pyrido[3,4-d]pyridazin-1-yl)phenol) (Compound 18*) (9.30 mg, 10.3% yield, RT=1.47 on 4.6*50 mm column) as a light yellow solid and 5-chloro-2-(4-{3-methyloxan-4-yl]amino}pyrido[3,4-d]pyridazin-1-yl)phenol (also referred to as 5-chloro-2-(4-{3-methyloxan-4-yl]amino}pyrido[3,4-d]pyridazin-1-yl)phenol) (Compound 18'*) as an assumed mixture of trans isomers (30 mg, 34.6% yield, RT=2.39 on 4.6*50 mm column) as a light yellow solid and 5-chloro-2-(4-{[(3S,4S)-3-methyloxan-4-yl]amino}pyrido[3,4-d]pyridazin-1-yl)phenol (also referred to as 5-chloro-2-(4-(((3S,4S)-3-methyltetrahydro-2H-pyran-4-yl)amino)pyrido[3,4-d]pyridazin-1-yl)phenol) (Compound 18D*) (7.50 mg, 8.3% yield, RT=3.11 on 4.6*50 mm column) as a light yellow solid (cis and trans isomers and stereochemistry arbitrarily assigned).

5-chloro-2-(4-(((3R,4R)-3-methyltetrahydro-2H-pyran-4-yl)amino)pyrido[3,4-d]pyridazin-1-yl)phenol (Compound 18*): LCMS: (ES, m/z): RT=0.631 min, m/z=371$[M+1]^+$; $^1H$ NMR (400 MHz, Methanol-$d_4$) δ 9.72 (d, J=1.0 Hz, 1H), 8.86 (d, J=5.7 Hz, 1H), 7.52 (d, J=5.7 Hz, 1H), 7.45-7.32 (m, 1H), 7.05 (d, J=7.3 Hz, 2H), 4.43-4.31 (m, 1H), 4.11-3.93 (m, 2H), 3.72-3.57 (m, 1H), 3.30-3.15 (m, 1H), 2.23-2.12 (m, 1H), 2.12-1.97 (m, 1H), 1.85-1.61 (m, 1H), 0.99 (d, J=6.6 Hz, 3H).

5-chloro-2-(4-(((3S,4S)-3-methyltetrahydro-2H-pyran-4-yl)amino)pyrido[3,4-d]pyridazin-1-yl)phenol (Compound 18D*): LCMS: (ES, m/z): RT=1.202 min, m/z=371$[M+1]^+$; $^1H$ NMR (400 MHz, Methanol-$d_4$) δ 9.72 (d, J=1.0 Hz, 1H), 8.86 (d, J=5.7 Hz, 1H), 7.56-7.45 (m, 1H), 7.45-7.36 (m, 1H), 7.14-6.99 (m, 2H), 4.43-4.31 (m, 1H), 4.10-3.94 (m, 2H), 3.70-3.59 (m, 1H), 3.31-3.16 (m, 1H), 2.25-2.14 (m, 1H), 2.14-1.94 (m, 1H), 1.80-1.60 (m, 1H), 1.00 (d, J=6.6 Hz, 3H). Step 7:

Isolation of trans diastereomers: 5-chloro-2-(4-(((3R,4S)-3-methyltetrahydro-2H-pyran-4-yl)amino)pyrido[3,4-d]pyridazin-1-yl)phenol (Compound 18C*) and 5-chloro-2-(4-(((3S,4R)-3-methyltetrahydro-2H-pyran-4-yl)amino)pyrido[3,4-d]pyridazin-1-yl)phenol (Compound 18A*). The assumed trans mixture (30 mg, 98% purity) was separated by Chiral-Prep-HPLC with the following conditions: Column, Chiral ART Cellulose-SA, 2*25 cm, 5 um; mobile phase, Hex (0.2% FA)- and EtOH:DCM=1:1—(hold 30% EtOH:DCM=1:1—in 18.2 min); Detector, UV 254 nm. This resulted in 5-chloro-2-(4-{[(3R,4S)-3-methyloxan-4-yl]amino}pyrido[3,4-d]pyridazin-1-yl)phenol (also referred to as 5-chloro-2-(4-(((3R,4S)-3-methyltetrahydro-2H-pyran-4-yl)amino)pyrido[3,4-d]pyridazin-1-yl)phenol) (Compound 18C*) (13.9 mg, 39.6% yield, RT=4.880 on 4.6*50 mm column) and 5-chloro-2-(4-{[(3S,4R)-3-methyloxan-4-yl]amino}pyrido[3,4-d]pyridazin-1-yl)phenol (also referred to as 5-chloro-2-(4-(((3S,4R)-3-methyltetrahydro-2H-pyran-4-yl)amino)pyrido[3,4-d]pyridazin-1-yl)phenol) (Compound 18A*) (14.0 mg, 40.0% yield, RT=3.50 on 4.6*50 mm column). Stereochemistry arbitrarily assigned.

5-Chloro-2-(4-(((3R,4S)-3-methyltetrahydro-2H-pyran-4-yl)amino)pyrido[3,4-d]pyridazin-1-yl)phenol (Compound 18C*): LCMS: (ES, m/z): RT=1.032 min, m/z=371$[M+1]^+$; $^1H$ NMR (400 MHz, Methanol-$d_4$) δ 9.78 (d, J=1.0 Hz, 1H), 8.86 (d, J=5.7 Hz, 1H), 7.42-7.33 (m, 1H), 7.38 (d, J=8.0 Hz, 1H), 7.11-7.01 (m, 2H), 4.74-4.66 (m, 1H), 4.11-4.02 (m, 1H), 3.86-3.72 (m, 2H), 3.66 (d, J=2.7 Hz, 1H), 2.58-2.47 (m, 1H), 2.29-2.12 (m, 1H), 1.83-1.72 (m, 1H), 1.13 (d, J=7.1 Hz, 3H).

5-Chloro-2-(4-(((3S,4R)-3-methyltetrahydro-2H-pyran-4-yl)amino)pyrido[3,4-d]pyridazin-1-yl)phenol (Compound 18A*): LCMS: (ES, m/z): RT=1.032 min m/z=371$[M+1]^+$; $^1H$ NMR (400 MHz, Methanol-$d_4$) δ 9.78 (d, J=1.0 Hz, 1H), 8.86 (d, J=5.7 Hz, 1H), 7.59-7.48 (m, 1H), 7.38 (d, J=7.9 Hz, 1H), 7.10-6.97 (m, 2H), 4.79-4.52 (m, 1H), 4.07 (d, J=11.9 Hz, 1H), 3.86-3.71 (m, 2H), 3.70-3.56 (m, 1H), 2.53 (s, 1H), 2.25-2.14 (m, 1H), 1.86-1.71 (m, 1H), 1.13 (d, J=7.1 Hz, 3H).

Additional compounds provided in Table C below follow the Protocols and Examples described herein.

TABLE C

| Cmpd. # | Structure/Name | MS (ESI; m/z; M + H) | $^1$H NMR | Protocol |
|---|---|---|---|---|
| 12A | 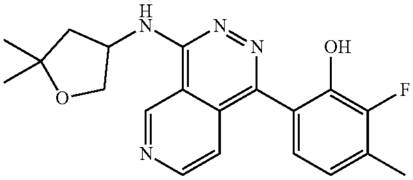 [SMILES: Cc1ccc(-c2nnc(NC3COC(C)(C)C3)c3cnccc23)c(O)c1F] 6-(4-(15,5-dimethyltetrahydrofuran-3-yl)amino)pyrido[3,4-d]pyridazin-1-yl)-2-fluoro-3-methylphenol | 369.15 | | Protocol A Compounds 12*, 12A, and 12B* were synthesized following Protocol A and Examples 1, 3, 4, 6, and 7 using 5,5-dimethyltetrahydrofuran-3-amine as the step 1 amine (i) reagent. |
| 12* | 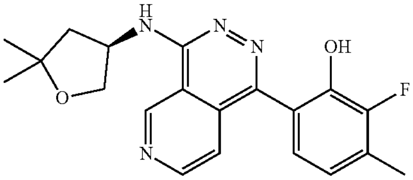 [SMILES: Cc1ccc(-c2nnc(N[C@H]3COC(C)(C)C3)c3cnccc23)c(O)c1F] (R)-6-(4-((5,5-dimethyltetrahydrofuran-3-ylamino)pyrido[3,4-d]pyridazin-1-yl)-2-fluoro-3-methylphenol | 369.15 | $^1$H NMR (400 MHz, DMSO-$d_6$) δ 9.82 (s, 1H), 9.74 (s, 1H), 8.87 (d, J = 5.6 Hz, 1H), 7.97 (s, [H), 7.34 (d, J = 5.6 Hz, 1H), 7.06 - 7.04 (m, 1H), 6.88 - 6.85 (m, 1H), 4.96 - 4.87 (m, 1H), 4.28 - 4.19 (m, 1H), 3.81 - 3.77 (m, 1H), 2.36 - 2.26 (m, 4H), 2.01 - 1.96 (mn, 1H), 1.36 (s, 3H), 1.26 (s, 3H). | Protocol A Column: Chiral ART Cellulose-SA, 2*25 cm, 5 μm; Mobile Phase A: Hexanes (0.2% formic acid (FA)), Mobile Phase B: MeOH: DCM = 1:1; Flow rate: 20 mL/min; Gradient: 25% B to 25% B in 20 min; Wave Length: 220/254 nm; RT(min): 12.07 |
| 12B* | 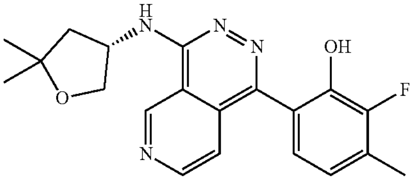 (S)-6-(4-((5,5-dimethyltetrahydrofuran-3-yl)amino)pyrido[3,4-d]pyridazin-1-yl)-2-fluoro-3-methylphenol | 369.15 | $^1$H NMR (400 MHz, DMSO-$d_6$) δ 9.82 (s, 1H), 9.74 (s, [H), 8.87 (d, J = 5.6 Hz, 1H), 7.93 (d, J = 5.8 Hz, 1H), 7.33 (d, J = 5.6 Hz, 1H), 7.06 - 7.04 (m, 1H), 6.88 6.85 (m, 1H), 4.96 - 4.87 (m, 1H), 4.25 - 4.21 (m, 1H), 3.80 - 3.77 (m, 1H), 2.36 - 2.26 (m, 4H), 2.03 - 1.94 (m, [H), 1.36 (s, 3H), 1.26 (s, 3H). | Protocol A Column: Chiral ART Cellulose-SA, 2*25 cm, 5 μm; Mobile Phase A: Hex (0.2% FA), Mobile Phase B: MeOH: DCM = 1: 1; Flow rate: 20 mL/min; Gradient: 25% B to 25% B in 20 min; Wave Length: 220/254 nm; RT(min): 17.03 |
| 13A | 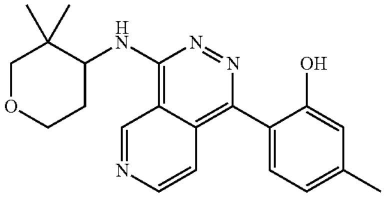 [SMILES: Cc1ccc(-c2nnc(NC3CCOCC3(C)C)c3cnccc23)c(O)c1] 2-(4-((3,3-dimethyltetrahydro-2H-pyran-4-yl)amino)pyrido[3,4-d]pyridazin-1-yl)-5-methylphenol | 365.10 | | Protocol B Compounds 13*, 13A, and 13B* were synthesized following Protocol B and Example 2 using 3,3-dimethyltetrahydro-2H-pyran-4-amine as the step 4 amine (i) reagent. |
| 13B* | 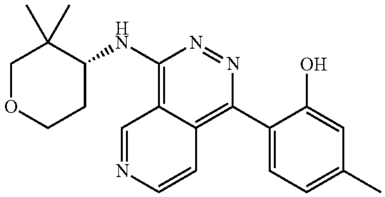 [SMILES: Cc1ccc(-c2nnc(N[C@@H]3CCOCC3(C)C)c3cnccc23)c(O)c1] (R)-2-(4-((3,3-dimethyltetrahydro-2H-pyran-4-yl)amino)pyrido[3,4-d]pyridazin-1-yl)-5-methylphenol | 365.10 | $^1$H NMR (400 MHz, DMSO-$d_6$) δ 9.88 (s, 1H), 9.65 (s, 1H), 8.86 (d, J = 5.6 Hz, 1H), 7.39 - 7.10 (m, 3H), 6.85 - 6.75 (m, 2H), 4.80 - 4.71 (m, [H), 4.02 - 3.93 (m, 1H), 3.56 - 3.41 (m, 2H), 3.25 (d, J = 11.3 Hz, 1H), 2.34 (s, 3H), 1.99 - 1.90 (m, 1H), 1.75 - 1.67 (m, 1H), 1.14 (s, 3H), 0.87 (s, 3H). | Protocol B Column, CHIRALPAK IE, 2*25 cm, 5 um; mobile phase, Hex(0.2% FA)- and MeOH:DCM = 1:1- (hold 50% MeOH:DCM = 1:1- in 12 min); Detector, UV 254 nm; RT(min): 1.59 |

TABLE C-continued

| Cmpd. # | Structure/Name | MS (ESI; m/z; M + H) | $^1$H NMR | Protocol |
|---|---|---|---|---|
| 13* | 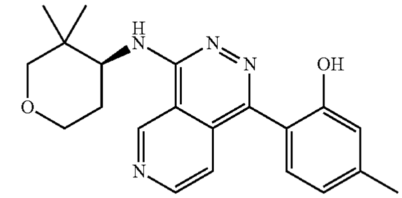 [SMILES: Cc1ccc(-c2nnc(N[C@H]3CCOCC3(C)C)c3cnccc23)c(O)c1] (S)-2-(4-((3,3-dimethyltetrahydro-2H-pyran-4-yl)amino)pyrido[3,4-d]pyridazin-1-yl)-5-methylphenol | 365.10 | $^1$H NMR (400 MHz, DMSO-$d_6$) δ 9.88 (s, 1H), 9.64 (s. 1H), 8.86 (d, J = 5.6 Hz, 1H), 7.33 (d, J = 5.6 Hz, 1H), 7.21 (d, J = 7.6 Hz, 2H), 6.84 – 6.77 (m, 2H), 4.70 4.61 (m, 1H), 3.97 (m, 1H), 3,60 – 3.42 (m, 2H), 3.25 (d, J = 11.3 Hz, 1H), 2.34 (s, 3H), 1.95 – 1.88 (m, 1H), 1.75 – 1.67 (m, 1H), 1.14 (s, 3H), 0.87 (s, 3H) | Protocol B Column, CHIRALPAK IE, 2*25 cm, 5 μm; mobile phase, Hex(0.2% FA)- and MeOH:DCM = 1:1- (hold 50% MeOH:DCM = 1:1- in 12 min); Detector, UV 254 nm; RT(min): 1.85 |
| 14A | 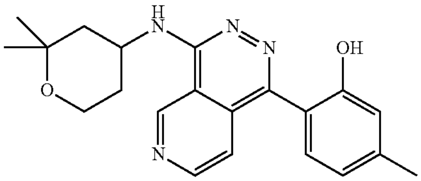 2-(4-((2,2-dimethyltetrahydro-2H-pyran-4-yl)amino)pyrido[3,4-d]pyridazin-1-yl)-5-methylphenol | 365.20 | | Protocol B Compounds 14*, 14A, and 14B* were synthesized following Protocol B and Examples 2 and 5 using 2,2-dimethyltetrahydro-2H-pyran-4-amine as the step 4 amine (i) reagent. |
| 14B* | 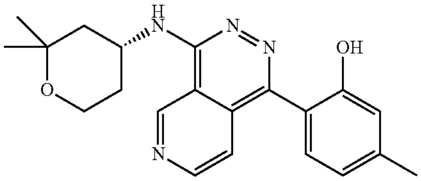 (R)-2-(4-((2,2-dimethyltetrahydro-2H-pyran-4-yl)amino)pyrido[3,4-d]pyridazin-1-yl)-5-methylphenol | 365.20 | $^1$H NMR (400 MHz, DMSO-$d_6$) δ 9.82 (s. 1H), 9.74 (s, 1H), 8.87 (d, J = 5.6 Hz, 1H), 7.97 (s, 1H), 7.34 (d, J = 5.6 Hz, 1H), 7.06 – 7.04 (m, 1H), 6.88 – 6.85 (m, 1H), 4.96 – 4.87 (m, 1H), 4.28 – 4.19 (m, 1H), 3.81 – 3.77 (m, [H), 2.36 – 2.26 (mt, 4H), 2.01 – 1.96 (m, 1H), 1.36 (s, 3H), 1.26 (s, 3H). | Protocol B Column, CHIRALPAK IE, 2*25 cm, 5 μm; mobile phase, Hex(0.5% 2M $NH_3$-MeOH)- and EtOH:DCM = 1:1- (hold 30% EtOH:DCM = 1:1- in 23 min); Detector, UV 254; RT(min): 2.75 |
| 14* | 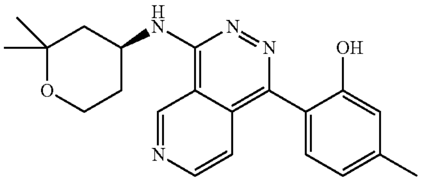 (S)-2-(4-((2,2-dimethyltetrahydro-2H-pyran-4-yl)amino)pyrido[3,4-dipyridazin-1-yl)-5-methylphenol | 365.20 | $^1$H NMR (400 MHz, Methanol-$d_4$) δ 9.67 (d, J = 1.0 Hz, 1H), 8.83 (d, J = 5.7 Hz, 1H), 7.56 (d, J = 5.7 Hz, 1H), 7.28 (d, J = 7.6 Hz, 1H), 6.91 – 6.83 (m, 2H), 4.76 (d, J = 11.9, [H), 3.92 (d, J = 12.3 Hz, 2H), 2.40 (s, 3H), 2.16 (d, J = 22.5 Hz, 2H), 1.73 – 1.56 (m, 2H), 1.40 (s, 3H), 1.31 (s. 3H). | Protocol B Column, CHIRALPAK IE, 2*25 cm, 5 μm; mobile phase, Hex(0.5% 2M NH3-MeOH)- and EtOH:DCM = 1:1- (hold 30% EtOH:DCM = 1:1- in 23 min); Detector, UV 254; RT(min): 4.16 |

TABLE C-continued

| Cmpd. # | Structure/Name | MS (ESI; m/z; M + H) | $^1$H NMR | Protocol |
|---|---|---|---|---|
| 15A | 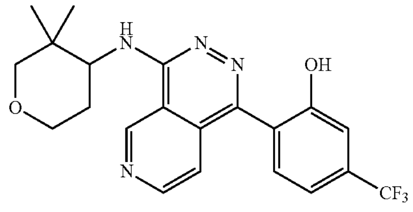 [SMILES: CC1(C)COCCC1Nc1nnc(-c2ccc(C(F)(F)F)cc2O)c2ccncc12] 2-(4-((3,3-dimethyltetrahydro-2H-pyran-4-yl)amino)pyrido[3,4-d]pyridazin-1-yl)-5-(trifluoromethyl)phenol | 419.10 | | Protocol A Compounds 15*, 15A, and 15B* were synthesized following Protocol A and Examples 1, 3, 4, 6, and 7 using 3,3-dimethyltetrahydro-2H-pyran-4-amine as the step 1 amine (i) reagent. |
| 15* | 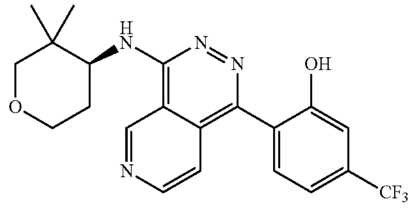 [SMILES: CC1(C)COCC[C@@H]1Nc1nnc(-c2ccc(C(F)(F)F)cc2O)c2ccncc12] (S)-2-(4-((3,3-dimethyltetrahydro-2H-pyran-4-yl)amino)pyrido[3,4-d]pyridazin-1-yl)-5-(trifluoromethyl)phenol | 419.10 | $^1$H NMR (400 MHz, Methanol-$d_4$) δ 9.78 (d, J = 1.0 Hz, 1H), 8.87 (d, J = 5.7 Hz, 1H), 7.60 (d, J = 8.2 Hz, 1H), 7.49 – 7.35 (m, 1H), 7.34 – 7.29 (m, 1H), 7.28 (d, J = 1.7 Hz, 1H), 4.86 – 4.79 (m, 1H), 4.09-4.01 (m, 1H), 3.68 – 3.56 (m, 2H), 3.38 (d, J = 11.4 Hz, 1H), 2.09-1.96 (m, 1H), 1.87 – 1.77 (m, 1H), 1.23 (s, 3H), 0.97 (s, 3H). | Protocol A Column: CHIRAL ART Amylose-SA, 2*25 cm, 5 μm; Mobile Phase A: Hex (0.2% FA), Mobile Phase B: EtOH: DCM = 1:1; Flow rate: 20 mL/min; Gradient: 25% B to 25% B in 19 min; Wave Length: 220/254 nm; RT (min): 2.27 |
| 15B* | 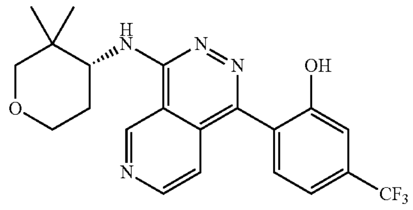 [SMILES: CC1(C)COCC[C@H]1Nc1nnc(-c2ccc(C(F)(F)F)cc2O)c2ccncc12] (R)-2-(4-((3,3-dimethyltetrahydro-2H-pyran-4-yl)amino)pyrido[3,4-d]pyridazin-1-yl)-5-(trifluoromethyl)phenol | 419.10 | $^1$H NMR (400 MHz, Methanol-d4) δ 9.78 (d, J = 1.0 Hz, 1H). 8.87 (d, J = 5.7 Hz, 1H), 7.60 (d, J = 7.8 Hz, 1H), 7.49 – 7.37 (m. 1H), 7.34 – 7.29 (m, 1H), 7.28 (d, J = 1.7 Hz, 1H), 4.82 (d, J = 4.4 Hz, 1H), 4.08 3.96 (m, 1H), 3.68 – 3.55 (m, 2H), 3.38 – (d. J = 11.4 Hz, 1H), 2.09 – 1.98 (m, 1H), 1.82 – 1.67 (m, 1H), 1.23 (s, 3H), 0.97 (s, 3H). | Protocol A Column: CHIRAL ART Amylose-SA, 2*25 cm, 5 μm; Mobile Phase A: Hex (0.2% FA), Mobile Phase B: EtOH: DCM = 1: 1; Flow rate: 20 mL/min; Gradient: 25% B to 25% B in 19 min; Wave Length: 220/254 nm; RT (min): 3.37 |
| 17A | 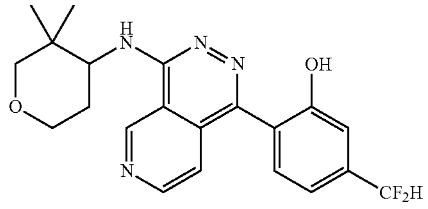 [SMILES: CC1(C)COCCC1Nc1nnc(-c2ccc(C(F)F)cc2O)c2ccncc12] 5-(difluoromethyl)-2-(4-((3,3-dimethyltetrahydro-2H-pyran-4-yl)amino)pyrido[3,4-d]pyridazin-1-yl)phenol | 401.15 | | Protocol A Compounds 17*, 17A, and 17B* were synthesized following Protocol A and Examples 1, 3, 4, 6, and 7 using 3,3-dimethyltetrahydro-2H-pyran-4-amine as the step 1 amine (i) reagent. |

TABLE C-continued

| Cmpd. # | Structure/Name | MS (ESI; m/z; M + H) | $^1$H NMR | Protocol |
|---|---|---|---|---|
| 17* | 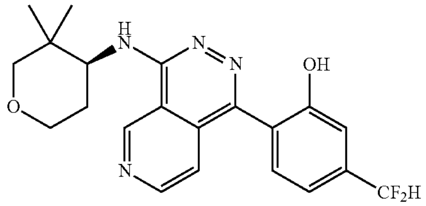 [SMILES: CC1(C)COCC[C@@H]1Nc1nnc(-c2ccc(C(F)F)cc2O)c2ccncc12] (S)-5-(difluoromethyl)-2-(4-((3,3-dimethyltetrahydro-2H-pyran-4-yl)amino)pyrido[3,4-d]pyridazin-1-yl)phenol | 401.15 | $^1$H NMR (400 MHz, Methanol-$d_4$) δ 10.04 (d, J = 0,9 Hz, 1H), 9.13 (d, J = 5.5 Hz, 1H), 7.67 – 7.60 (m 1H), 7.56 (d, J = 7.8 Hz, 1H), 7.34 – 7.19 (m, 2H), 6.84 (t, J = 56.1 Hz, 1H), 4.40 – 4.33 (m, 1H), 4.13 – 4.06 (m, 1H), 3.76 – 3.57 (m, 2H), 3.39 (d, J = 11.6 Hz, 1H), 2.38 – 2.22 (m, 1H), 1.86 – 1.80 (m, 1H), 1.26 (s, 3H), 1.02 (s, 3H) | Protocol A Column, CHIRAL ART Amylose-SA , 2*25 cm, 5 μm; mobile phase, Hex (0.1% TFA)- and EtOH:DCM = 1:1 (hold 30% EtOH:DCM = 1:1 in 15 min); RT(min): 2.25 |
| 17B* | 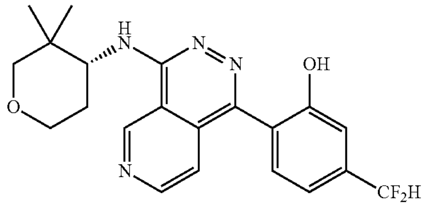 [SMILES: CC1(C)COCC[C@H]1Nc1nnc(-c2ccc(C(F)F)cc2O)c2ccncc12] (R)-5-(difluoromethyl)-2-(4-((3,3-dimethyltetrahydro-2H-pyran-4-ylamino)pyrido [3,4-d]pyridazin-1-yl)phenol | 401.15 | $^1$H NMR (400 MHz, Methanol-$d_4$) δ 10.15 – 9.94 (m), 1H), 9,25 – 8.99 (m. 1H), 7.67 (d, J = 5.5 Hz, 1H), 7.56 (d, J = 7.8 Hz, 1H), 7.37 – 7.21 (m, 2H), 6.84 (t, J = 56.1 Hz, 1H), 4.55 – 4.39 (m, 1H), 4.13 – 4.01 (m, 1H), 3.61 – 3.50 (m, 2H), 3.39 (d, J = 11.6 Hz, 1H), 2.27 – 2.10 (m, 1H), 2.06 – 1.78 (m, 1H), 1.26 (s, 2H), 1.02 (s, 2H). | Protocol A Column, CHIRAL ART Amylose-SA, 2*25 cm, 5 μm; mobile phase, Hex (0.1% TFA)- and EIOH:DCM = 1:1 (hold 30% EtOH:DCM = 1:1 in 15 min); RT(min): 2.97 |
| 19A | 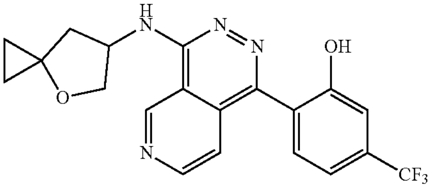 [SMILES: Oc1cc(C(F)(F)F)ccc1-c1nnc(NC2COC3(CC3)C2)c2cnccc12] 2-(4-((4-oxaspiro[2.4]heptan-6-ylamino)pyrido[3,4-d]pyridazin-1-yl)-5-(trifluoromethyl)phenol | 403.10 | | Protocol A Compounds 19*, 19A, and 19B* were synthesized following Protocol A and Examples 1, 3, 4, 6, and 7 using 4-oxaspiro[2.4]heptan-6-amine as the step 1 amine (i) reagent. |
| 19B* | 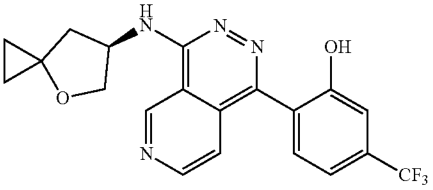 [SMILES: Oc1cc(C(F)(F)F)ccc1-c1nnc(N[C@H]2COC3(CC3)C2)c2cnccc12] (S)-2-(4-((4-oxaspiro[2.4]heptan-6-yl)amino)pyrido[3,4-d]pyridazin-1-yl)-5-(trifluoromethyl)phenol | 403.10 | $^1$H NMR (400 MHz Methanol-$d_4$) δ 9.77 (d, J = 1.0 Hz, 1H), 8.88 (d, J = 5.6 Hz, 1H), 7.60 (d, J = 7.9 Hz, 1H), 7.54 – 7.50 (m, 1H), 7.39 – 7,32 (m, 1H), 7.29 (d, J = 1.7 Hz, 1H), 5.12 – 5.09 (m, 1H), 4.34 – 4.31 (m, 1H), 4.02 – 3.97 (m, 1H), 2.57 – 2.51 (m, 1H), 2.35 – 2.33 (m, 1H), 0.98 – 0.93 (m, 1H), 0.87 – 0.84 (m, 1H), 0.74 – 0.71 (m, 1H), 0.65 – 0.58 (m, 1H). | Protocol A Column, CHIRAL ART Amylose-SA, 2*25 cm, 5 μm; mobile phase, Hex(0.5% 2M $NH_3$-MeOH)— and MeOH:DCM = 1:1-(hold 25% MeOH:DCM = 1:1- in 11.5 min); Detector, UV 254. RT(min): 1.64 |

TABLE C-continued

| Cmpd. # | Structure/Name | MS (ESI; m/z; M + H) | $^1$H NMR | Protocol |
|---|---|---|---|---|
| 19* | 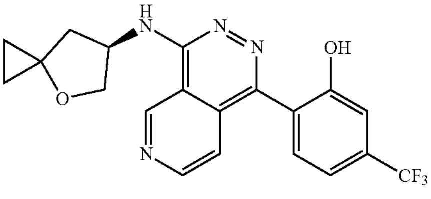 [SMILES: Oc1cc(C(F)(F)F)ccc1-c1nnc(N[C@H]2COC3(CC3)C2)c2cnccc12] (R)-2-(4-((4-oxaspiro[2.4]heptan-6-yl)amino)pyrido[3,4-dipyridazin-1-yl)-5-(trifluoromethyl)phenol | 403.10 | $^1$H NMR (400 MHz, Methanol-$d_4$) δ 9.77 (d, J = 1.0 Hz, 1H), 8.88 (d, J = 5.7 Hz, 1H), 7.60 (d, J = 7.9 Hz, 1H), 7.52 - 7.49 (m, 1H), 7.37 - 7,32 (m, 1H), 7.29 (d, J = 1.7 Hz, 1H), 5.17 - 5.07 (m, 1H), 4.36 - 4.32 (m, 1H), 4.02 - 3.98 (m, 1H), 2.59 - 2.53 (m, 1H), 2.36 - 2.31 (m, 1H), 1.01 0.92 (m, 1H), 0.87 - 0.84 (m, 1H), 0.76 - 0.71 (m, 1H), 0.64 - 0.56 (m, 1H). | Protocol A Column, CHIRAL ART Amylose-SA, 2*25 cm, 5 μm; mobile phase, Hex (0.5% 2M $NH_3$-MeOH) and MeOH:DCM =1:1 (hold 25% MeOH:DCM = 1:1 in 11.5 min); Detector, UV 254. RT(min): 1.25 |
| 20A | 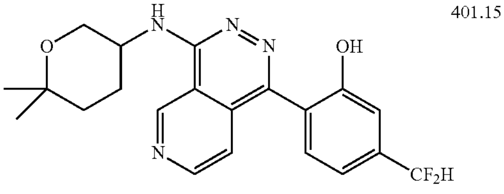 5-(difluoromethyl)-2-(4-((6,6-dimethyltetrahydro-2H-pyran-3-yl)amino)pyrido[3,4-d]pyridazin-1-yl)phenol | 401.15 | | Protocol A Compounds 20*, 20A, and 20B* were synthesized following Protocol A and Examples 1, 3, 4, 6, and 7 using 6,6-dimethyltetrahydro-2H-pyran-3-amine as the step 1 amine (i) reagent. |
| 20B* | 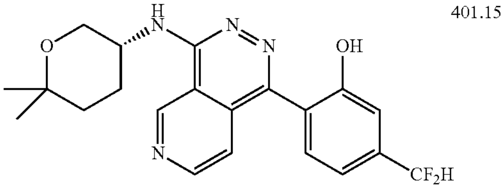 (R)-5-(difluoromethyl)-2-(4-((6,6-dimethyltetrahydro-2H-pyran-3-yl)amino)pyrido[3,4-d]pyridazin-1-yl)phenol | 401.15 | $^1$H NMR (400 MHz, Methanol-$d_4$) δ 9.72 (d, J = 1.0 Hz, 1H), 8.86 (d, J = 5.7 Hz, 1H), 7.55 - 7.48 (m, 2H), 7.25 - 7.16 (m, 2H), 6.96-6.67(m, 1H), 4.49 (tt, J = 9.2, 4.5 Hz, 1H), 4.07 (ddd, J = 11.3, 4.6, 1.6 Hz. 1H), 3.72 (dd, J = 11.4, 9.0 Hz, 1H), 2.15 (dd, J = 13.4, 5.1 Hz, 1H), 2.11 - 1.96 (m, 1H), 1.82 (dt, J = 13.6, 4.6 Hz, 1H), 1.77 - 1.66 (m, 1H), 1.37 (s, 3H), 1.32 (s, 3H) | Protocol A Column: CHIRALPAK IE-3, 4.6*50 mm; 3 μm; Mobile Phase A: Hex(0.2% DEA): (EIOH: DCM = 1:1) = 60:40; Flow rate: 1 mL/min; Gradient: 0% B to 0% B; Injection Volume: 5 ul mL) RT(min): 4.10 |
| 20* | 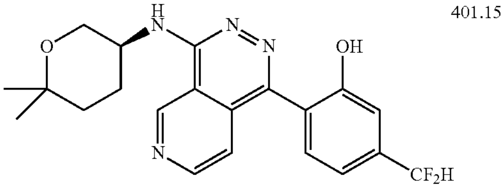 (S)-5-(difluoromethyl)-2-(4-((6,6-dimethyltetrahydro-2H-pyran-3-ylamino)pyrido[3,4-d]pyridazin-1-yl)phenol | 401.15 | $^1$H NMR (400 MHz, Methanol-d4) δ 9.72 (d, J = 1.0 Hz, 1H), 8.86 (d, J = 5.6 Hz, 1H), 7.55 - 7.48 (m, 2H), 7.25 - 7.17 (m, 2H), 6.95-6.67(m, 1H), 4.50 (tt, J = 9.2, 4.5 Hz, 1H), 4.07 (ddd, J = 11.4, 4.5, 1.6 Hz, 1H), 3.72 (dd, J = 11.4, 9.0 Hz, 1H), 2.19 - 2.11 (m, 1H), 2.11-1.96 (m, 1H), 1.82 (dt, J = 13.6, 4.6 Hz, 1H), 1.77 - 1.66 (m, 1H), 1.37 (s, 3H), 1.31 (s, 3H). | Protocol A Column: CHIRALPAK IE-3, 4.6*50 mm; 3 μm; Mobile Phase A: Hex(0,2% DEA): (EtOH: DCM = 1:1) = 60:40; Flow rate: 1 mL/min; Gradient: 0% B to 0% B; Injection Volume: 5 ul mL) RT(min): 2.87 |

TABLE C-continued

| Cmpd. # | Structure/Name | MS (ESI; m/z; M + H) | $^1$H NMR | Protocol |
|---|---|---|---|---|
| 21A | 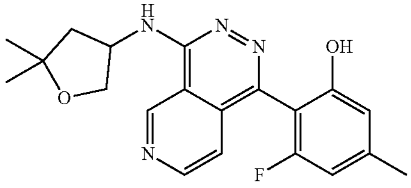 2-(4-((5,5-dimethyltetrahydrofuran-3-yl)amino)pyrido[3,4-d]pyridazin-1-yl)-3-fluoro-5-methylphenol | 369.10 | | Protocol A Compounds 21*, 21A, and 21B* were synthesized following Protocol A and Examples 1, 3, 4, 6, and 7 using 5,5-dimethyltetrahydrofuran-3-amine as the step 1 amine (i) reagent |
| 21B* | 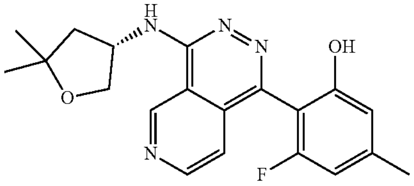 2-(4-(((S)-5,5-dimethyltetrahydrofuran-3-ylamino)pyrido[3,4-d]pyridazin-1-yl)-3-fluoro-5-methylphenol | | $^1$H NMR (400 MHz, Methanol-d4) δ 9.72 (d, J = 1.0 Hz, 1H), 8.86 (d, J = 5.6 Hz, 1H), 7.41 (d, J = 5.7 Hz, 1H), 6.69 – 6.61 (m, 2H), 5.08 – 5.00 (m, 1H), 4.41-4.25 (m, 1H), 3.93-3.82 (m. 1H), 2.49 – 2.43 (m, 1H), 2.40 (s, 3H), 2.08-1.95 (m, 1H), 1.45 (s, 3H), 1.35 (s. 3H). | Protocol A Column: CHIRALPAK IG, 4.6*50 mm, 3 µm; Mobile Phase A: Hex(0.2% DEA), Mobile Phase B: MeOH: DCM = 1: 1; Flow rate: 1 mL/min; (hold 35% MeOH:DCM = 1:1- in 4 min); Wave Length: 220/254 nm; RT(min): 2.54 |
| 21* | 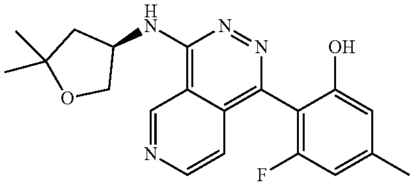 2-(4-(((R)-5,5-dimethyltetrahydrofuran-3-yl)amino)pyrido[3,4-d]pyridazin-1-yl)-3-fluoro-5-methylphenol | 369.10 | $^1$H NMR (400 MHz, Methanol-d4) δ 9.72 (s, 1H), 8.85 (d, J = 5.7 Hz, 1H), 7.46 – 7.37 (m, 1H), 6.68 – 6.60 (m, 2H), 5.08 – 4.99 (m, 1H), 4.41-4.36 (m, 1H), 3.93-3.80 (m, 1H), 2.50 – 2.43 (m, 1H), 2.39 (s, 3H), 2.10 (d, J = 6.9 Hz, 1H), 1.45 (S, 3H), 1.35 (s, 3H). | Protocol A Column: CHIRALPAK IG, 4.6*50 mm, 3 µm; Mobile Phase A: Hex(0.2% DEA), Mobile Phase B: MeOH: DCM = 1: 1; Flow rate: 1 mL/min; (hold 35% MeOH:DCM = 1:1- in 4 min); Wave Length: 220/254 nm; RT(min): 1.70 |
| 22A | 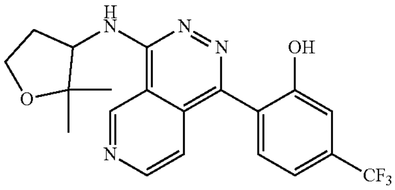 2-(4-((2,2-dimethyltetrahydrofuran-3-ylamino)pyrido[3,4-d]pyridazin-1-yl)-5-(trifluoromethyl)phenol | 405.15 | | Protocol A Compounds 22*, 22A, and 22B* were synthesized following Protocol A and Examples 1, 3, 4, 6, and 7 using 2,2-dimethyltetrahydrofuran-3-amine as the step 1 amine (i) reagent. |
| 22B* | 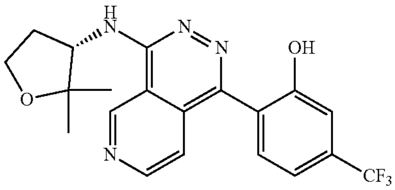 [SMILES: CC1(C)OCC[C@@H]1Nc1nnc(-c2ccc(C(F)(F)F)cc2O)c2ccncc12] (S)-2-(4-((2,2-dimethyltetrahydrofuran-3-ylamino)pyrido[3,4-d]pyridazin-1-yl)-5-(trifluoromethyl)phenol | 405.15 | $^1$H NMR (400 MHz, DMSO-$d_6$) δ 10.43 (s, 1H), 9.90 (s, 1H), 8.87 (d, J = 5.6 Hz, 1H), 7.73 (d, J = 8.1 Hz, 1H), 7.58 (d, J = 7.8 Hz, 1H), 7.36 – 7.27 (m, 3H), 4.94 (d, J = 7.8 Hz, 1H), 3.97 (s, 1H), 3.79 (d, J = 7.8 Hz, 1H), 2.43 (d, J = 12.6, 7.9, 3.9 Hz, [H), 2.25 – 2.12 (m, 1H), 1.37 (s, 3H), 1.17 (s, 3H). | Protocol A Column, CHIRAL ART Amylose-SA, 4.6*50 mm, 3 µm; mobile phase, Hex(0.2% DEA)- and MeOH:DCM = 1:1- (hold 40% MeOH:DCM = 1:1- in 4 min); Detector, UV 254 nm; RT(min): 3.14 |

TABLE C-continued

| Cmpd. # | Structure/Name | MS (ESI; m/z; M + H) | $^1$H NMR | Protocol |
|---|---|---|---|---|
| 22* | 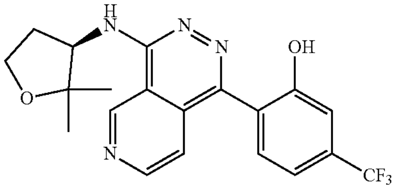 [SMILES: CC1(C)OCC[C@H]1Nc1nnc(-c2ccc(C(F)(F)F)cc2O)c2ccncc12]<br>(R)-2-(4-((2,2-dimethyltetrahydrofuran-3-yl)amino)pyrido[3,4-d]pyridazin-1-yl)-5-(trifluoromethyl)phenol | 405.15 | $^1$H NMR (400 MHz, DMSO-$d_6$) δ 10.43 (s, 1H), 9.90 (s, 1H), 8.87 (d, J = 5.6 Hz, 1H), 7.73 (d. J = 8.1 Hz, 1H), 7.58 (d, J = 7.8 Hz, 1H), 7.36 – 7.27 (m, 3H), 4.94 (d, J = 7.8 Hz, 1H), 3.97 (d, J = 8.4, 4.6 Hz, 1H), 3.79 (s, 1H), 2.42 (s, 1H), 2.25 – 2.12 (m, 1H), 1.37 (s, 3H), 1.17 (5, 3H). | Protocol A<br>Column, CHIRAL ART Amylose-SA , 4.6*50 mm, 3 um; mobile phase, Hex(0.2% DEA)- and MeOH:DCM = 1:1- (hold 40% MeOH:DCM = 1:1- in 4 min); Detector, UV 254 nm; RT(min): 0.98 |
| 23A | 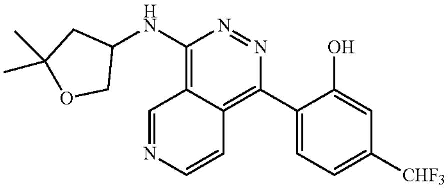<br>5-(difluoromethyl)-2-(4-((5,5-dimethyltetrahydrofuran-3-yl)amino)pyrido[3,4-d]pyridazin-1-yl)phenol | 387.15 | | Protocol A<br>Compounds 23*, 23A, and 23B* were synthesized following Protocol A and Examples 1, 3, 4, 6, and 7 using 2,2-dimethyltetrahydrofuran-3-amine as the step 1 |
| 23* | 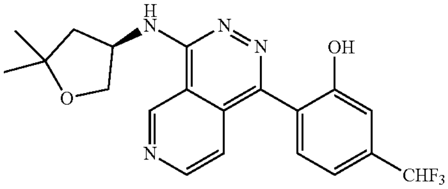<br>(R)-5-(difluoromethyl)-2-(4-((5,5-dimethyltetrahydrofuran-3-yl)amino)pyrido[3,4-d]pyridazin-1-yl)phenol | 387.15 | $^1$H NMR (400 MHz, DMSO-$d_6$) δ 10.15 (s, 1H), 9.82 (s, 1H), 8.86 (d, J = 5.6 Hz, 1H), 7.95 (d, J = 5.8 Hz, 1H), 7.47 (d, J = 7.6 Hz, 1H), 7.30 (d, J = 5.6 Hz, 1H), 7.24 – 6.90 (m, 3H), 4.92 (m, 1H), 4.29 – 4.20 (m, 1H), 3.85 – 3,78 (m. 1H), 2.39 – 2.30 (m, 1H), 2.05 – 1.95 (m, 1H), 1.36 (s, 3H), 1.26 (s, 3H). | Protocol A<br>Column: CHIRALPAK IA-3, 4.6*50 mm; 3 um; Mobile Phase, Hex: (MeOH: DCM = 1: 1) = 70:30 in 4 min; RT(min): 2.00 |
| 23B* | 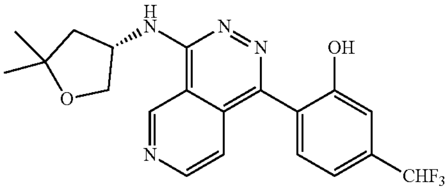<br>(S)-5-(difluoromethyl)-2-(4-((5,5-dimethyltetrahydrofuran-3-yl)amino)pyrido[3,4-d]pyridazin-1-yl)phenol | 387.15 | $^1$H NMR (400 MHz, DMSO-$d_6$) δ 10.16 (s, 1H), 9.82 (s, 1H), 8.87 (d, J = 5.6 Hz, 1H), 7.95 (d, J = 5.8 Hz, 1H), 7.47 (d, J = 7.6 Hz, 1H), 7.30 (d, J = 5.6 Hz, 1H), 7.23 – 7.05 (m, 3H), 4.92 (m, 1H), 4.29 – 4.20 (m, 1H), 3.85 – 3.75 (m, 1H), 2.37 – 2.29 (m, 1H), 2.04 – 1,95 (m, 1H), 1.36 (s, 3H), 1.26 (s, 3H). | Protocol A<br>Column: CHIRALPAK IA-3, 4.6*50 mm; 3 um; Mobile Phase, Hex: (MeOH:DCM = 1; 1) = 70:30 in 4 min; RT(min): 1.45 |

Example 9. 2-(4-(((R)-5,5-dimethyltetrahydrofuran-3-yl)amino)pyrido[3,4-d]pyridazin-1-yl)-3,5-dimethylphenol (Compound 24*) and 2-(4-(((S)-5,5-dimethyltetrahydrofuran-3-yl)amino)pyrido[3,4-d]pyridazin-1-yl)-3,5-dimethylphenol (Compound 24B*)

Scheme 9A

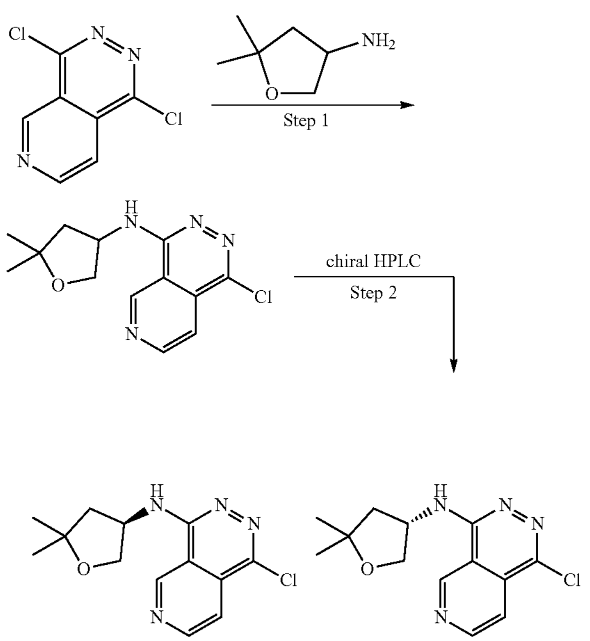

Intermediate A*

(R)-1-chloro-N-(5,5-dimethyltetrahydrofuran-3-yl)pyrido[3,4-d]pyridazin-4-amine

Intermediate B*

(S)-1-chloro-N-(5,5-dimethyltetrahydrofuran-3-yl)pyrido[3,4-d]pyridazin-4-amine

Scheme 9B

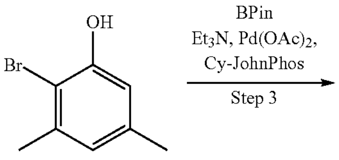

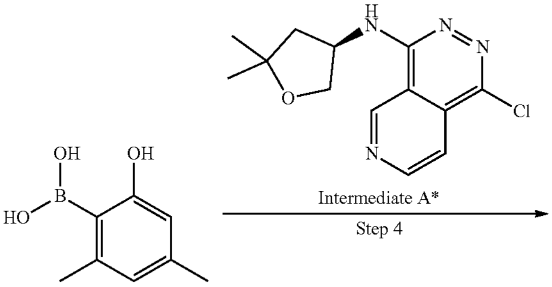

-continued

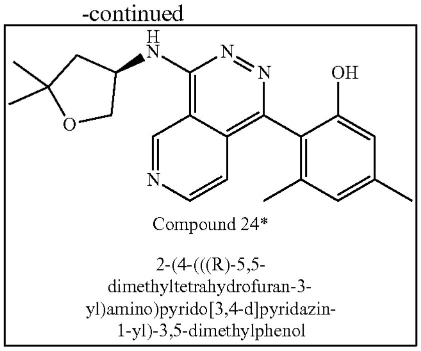

Compound 24*

2-(4-(((R)-5,5-dimethyltetrahydrofuran-3-yl)amino)pyrido[3,4-d]pyridazin-1-yl)-3,5-dimethylphenol Scheme 9C

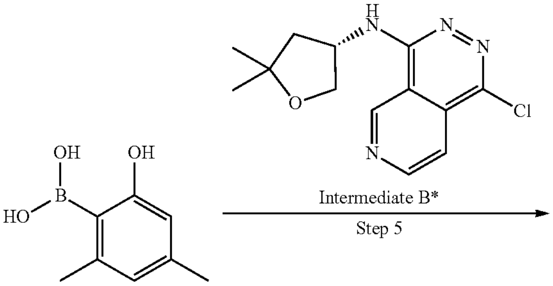

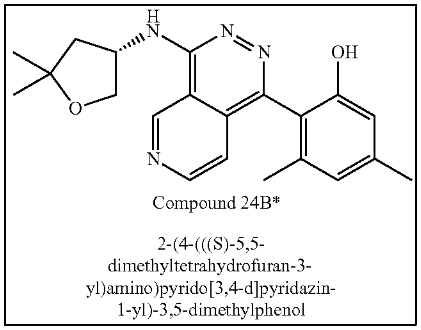

Compound 24B*

2-(4-(((S)-5,5-dimethyltetrahydrofuran-3-yl)amino)pyrido[3,4-d]pyridazin-1-yl)-3,5-dimethylphenol Example 9 follows Protocol A.

Step 1: Into 20 ml sealed tube were added 1,4-dichloropyrido[3,4-d]pyridazine (500 mg, 2.50 mmol, 1 equiv), 5,5-dimethyloxolan-3-amine (201.53 mg, 1.75 mmol, 0.7 equiv), $Na_2CO_3$ (802.39 mg, 7.50 mmol, 3 equiv) and DMF (5 mL). The final reaction mixture was irradiated with microwave radiation for 30 min at 130° C. The reaction was repeated for four times. The reaction was monitored by LCMS. The resulting mixture was filtered, the filter cake was washed with methanol (MeOH). The filtrate was concentrated under reduced pressure. The residue was purified by reverse flash chromatography with the following conditions: column, C18 silica gel; mobile phase, acetonitrile (MeCN) in water, 10% to 80% gradient in 25 min; detector, UV 254 nm, to provide a crude product, which was purified by Prep-HPLC with the following conditions (2 #SHIMADZU (HPLC-01)): Column, XBridge Shield RP18 OBD Column, 30*150 mm, 5 μm; mobile phase, water (10 mmol/L $NH_4HCO_3$) and acetonitrile (23% up to 35% in 8 min); Detector, UV 254 nm to provide 1-chloro-N-(5,5-dimethyloxolan-3-yl)pyrido[3,4-d]pyridazin-4-amine as a mixture of R and S stereoisomers (1.2 g, 28% yield). LCMS: (ES, m/z): RT=0.62 min, m/z=279.0$[M+H]^+$.

Step 2: The stereoisomeric mixture from Step 1 was purified by Chiral-HPLC with the following conditions:

Column: CHIRALPAK IG, 2*25 cm, 5 m; Mobile Phase A: hexanes (0.5% 2M $NH_3$ in methanol), Mobile Phase B: isopropanol/dichloromethane (1:1); Flow rate: 20 mL/min; Gradient: 70% B to 70% B in 14.5 min; Wave Length: 254/220 nm; RT1(min) ((R)-1-chloro-N-(5,5-dimethyltetrahydrofuran-3-yl)pyrido[3,4-d]pyridazin-4-amine): 4.81; RT2(min): 11.33 (S)-1-chloro-N-(5,5-dimethyltetrahydrofuran-3-yl)pyrido[3,4-d]pyridazin-4-amine; Sample Solvent: methanol/dichloromethane (1:1); Injection Volume: 1 mL, to provide (R)-1-chloro-N-(5,5-dimethyltetrahydrofuran-3-yl)pyrido[3,4-d]pyridazin-4-amine (Intermediate A*) (120 mg, 39% yield; LCMS: (ES, m/z): RT=0.78 min, m/z=279.1[M+H]$^+$) and (S)-1-chloro-N-(5,5-dimethyltetrahydrofuran-3-yl)pyrido[3,4-d]pyridazin-4-amine (Intermediate B*) (121 mg, 39% yield; LCMS: (ES, m/z): RT=0.78 min, m/z=279.1[M+H]$^+$), stereochemistry arbitrarily assigned.

Step 3: Into a 20 mL vial was added 2-bromo-3,5-dimethylphenol (600 mg, 2.98 mmol, 1 equiv) and dioxane (6 mL), triethylamine (905.92 mg, 8.95 mmol, 3 equiv), and 4,4,5,5-tetramethyl-1,3,2-dioxaborolane (1909.55 mg, 14.92 mmol, 5 equiv). The resulting mixture was stirred for 30 min at room temperature under nitrogen atmosphere. To the above mixture was added palladium (II) acetate ($Pd(OAc)_2$) (67 mg, 0.29 mmol, 0.1 equiv), 2-(dicyclohexylphosphino) biphenyl (Cy-JohnPhos) (209.18 mg, 0.59 mmol, 0.2 equiv). The resulting mixture was stirred for 1 h at 80° C. under nitrogen atmosphere. The reaction progress was monitored by GCMS. The reaction was quenched with water (10 mL). The resulting mixture was extracted with ethyl acetate (EtOAc) (3x10 mL), dried over anhydrous $Na_2SO_4$. After filtration, the filtrate was concentrated under reduced pressure to afford 2-hydroxy-4,6-dimethylphenylboronic acid (800 mg, 81% yield), which was used in the next step directly without further purification.

Step 4. Into a 8 mL vial were added 2-hydroxy-4,6-dimethylphenylboronic acid (214.37 mg, 1.29 mmol, 3 equiv) and Intermediate A* (120 mg, 0.43 mmol, 1 equiv), water (0.2 mL), $Na_2CO_3$ (138.19 mg, 1.29 mmol, 3 equiv), [1,1'-bis(diphenylphosphino)ferrocene]dichloropalladium (II), complex with dichloromethane ($Pd(dppf)Cl_2CH_2Cl_2$) (94.50 mg, 0.12 mmol, 0.3 equiv), and dioxane (1 mL). The resulting mixture was stirred for 2 h at 80° C. under nitrogen atmosphere. The reaction progress was monitored by LCMS. The resulting mixture was concentrated under reduced pressure. The residue was purified by reversed-phase flash chromatography with the following conditions: column, C18 silica gel; mobile phase, acetonitrile in water, 10% to 50% gradient in 10 min; detector, UV 254 nm, to provide the crude product (70 mg), which was purified by Prep-HPLC with the following conditions: Column: XBridge Shield RP18 OBD Column, 30*150 mm, 5 μm; Mobile Phase A: water (10 mmol/L $NH_4HCO_3$), Mobile Phase B: acetonitrile; Flow rate: 60 mL/min; Gradient: 25% B to 35% B in 10 min, 35% B; Wave Length: 254 nm; RT1(min): 9.5, to provide 2-(4-(((R)-5,5-dimethyltetrahydrofuran-3-yl)amino)pyrido[3,4-d]pyridazin-1-yl)-3,5-dimethylphenol (Compound 24*) (41.90 mg, 27% yield). Stereochemistry was arbitrarily assigned. LCMS: (ES, m/z): $RT_1$=1.43 min, m/z=365.2[M+H]$^+$. $^1H$ NMR (400 MHz, DMSO-$d_6$) δ 9.81 (d, J=0.9 Hz, 1H), 9.21 (d, J=2.3 Hz, 1H), 8.82 (d, J=5.6 Hz, 1H), 7.84-7.82 (m, 1H), 7.13-7.03 (m, 1H), 6.65 (d, J=6.9 Hz, 2H), 4.98-4.88 (m, 1H), 4.30-4.18 (m, 1H), 3.87-3.71 (m, 1H), 2.38-2.26 (m, 4H), 2.05-1.90 (m, 1H), 1.87 (d, J=3.1 Hz, 3H), 1.37 (d, J=3.2 Hz, 3H), 1.26 (s, 3H).

Step 5. Into a 8 mL vial was added 2-hydroxy-4,6-dimethylphenylboronic acid (214.37 mg, 1.29 mmol, 3 equiv), Intermediate B* (120 mg, 0.43 mmol, 1 equiv), water (0.2 mL), $Na_2CO_3$ (138.19 mg, 1.29 mmol, 3 equiv), [1,1'-bis(diphenylphosphino)ferrocene]dichloropalladium (II), complex with dichloromethane ($Pd(dppf)Cl_2CH_2Cl_2$) (94.50 mg, 0.12 mmol, 0.3 equiv), and dioxane (1 mL). The resulting mixture was stirred for 2 h at 80° C. under nitrogen atmosphere. The reaction progress was monitored by LCMS. The resulting mixture was concentrated under reduced pressure. The residue was purified by reversed-phase flash chromatography with the following conditions: column, C18 silica gel; mobile phase, acetonitrile in water, 10% to 50% gradient in 10 min; detector, UV 254 nm, to provide the crude product (70 mg), which was purified by Prep-HPLC with the following conditions: Column: XBridge Shield RP18 OBD Column, 30*150 mm, 5 μm; Mobile Phase A: water (10 mmol/L $NH_4HCO_3$), Mobile Phase B: acetonitrile; Flow rate: 60 mL/min; Gradient: 25% B to 35% B in 10 min, 35% B; Wave Length: 254 nm; RT1(min): 9.5, to provide 2-(4-(((S)-5,5-dimethyltetrahydrofuran-3-yl)amino)pyrido[3,4-d]pyridazin-1-yl)-3,5-dimethylphenol (Compound 24B*) (40.4 mg, 26% yield). Stereochemistry was arbitrarily assigned. LCMS: (ES, m/z): $RT_1$=1.43 min, m/z=365.2[M+H]$^+$. $^1H$ NMR (400 MHz, DMSO-$d_6$) δ 9.81 (d, J=0.9 Hz, 1H), 9.21 (d, J=2.3 Hz, 1H), 8.82 (d, J=5.6 Hz, 1H), 7.84-7.82 (m, 1H), 7.13-7.03 (m, 1H), 6.65 (d, J=6.9 Hz, 2H), 4.98-4.88 (m, 1H), 4.30-4.18 (m, 1H), 3.87-3.71 (m, 1H), 2.38-2.26 (m, 4H), 2.05-1.90 (m, 1H), 1.87 (d, J=3.1 Hz, 3H), 1.37 (d, J=3.2 Hz, 3H), 1.26 (s, 3H).

Example 10. Synthesis of 5-chloro-2-(4-(((2R,4R)-2-methyltetrahydro-2H-pyran-4-yl)amino)pyrido[3,4-d]pyridazin-1-yl)phenol (Compound 25A*), 5-chloro-2-(4-(((2S,4S)-2-methyltetrahydro-2H-pyran-4-yl)amino)pyrido[3,4-d]pyridazin-1-yl)phenol (Compound 25B*), 5-chloro-2-(4-(((2S,4R)-2-methyltetrahydro-2H-pyran-4-yl)amino)pyrido[3,4-d]pyridazin-1-yl)phenol (Compound 25C*), and 5-chloro-2-(4-(((2R,4S)-2-methyltetrahydro-2H-pyran-4-yl)amino)pyrido[3,4-d]pyridazin-1-yl)phenol (Compound 25D*)

Scheme 10A

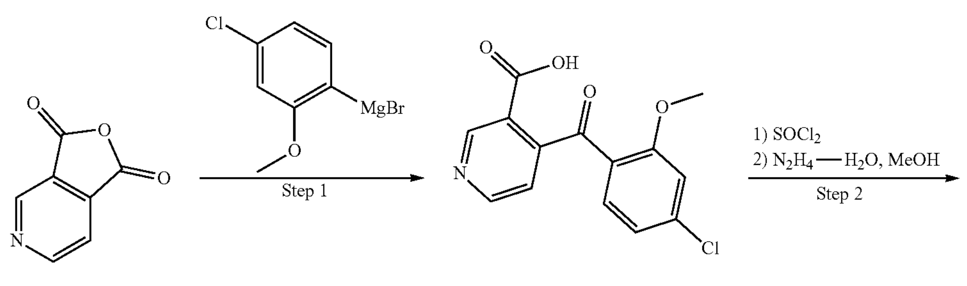

-continued

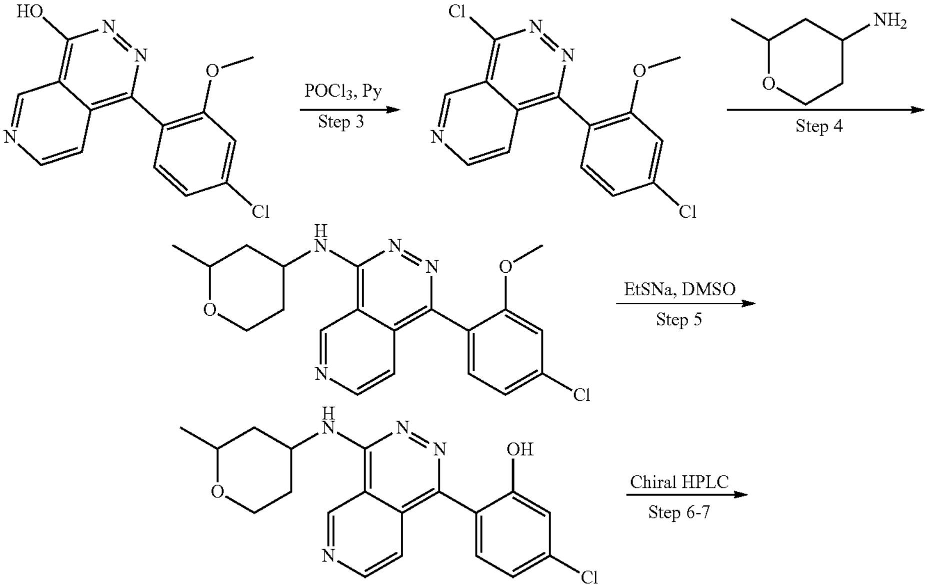

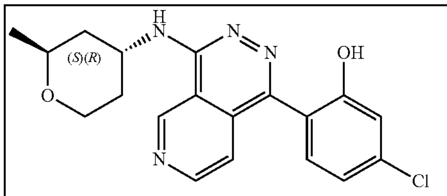

Compound 25C*

5-chloro-2-(4-(((2S,4R)-2-methyltetrahydro-2H-pyran-4-yl)amino)pyrido[3,4-d]pyridazin-1-yl)phenol

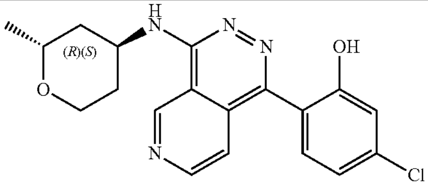

Compound 25D*

5-chloro-2-(4-(((2R,4S)-2-methyltetrahydro-2H-pyran-4-yl)amino)pyrido[3,4-d]pyridazin-1-yl)phenol

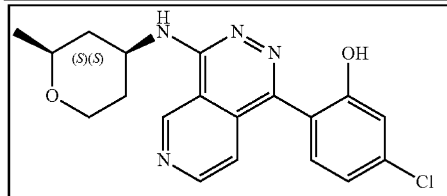

Compound 25B*

5-chloro-2-(4-(((2S,4S)-2-methyltetrahydro-2H-pyran-4-yl)amino)pyrido[3,4-d]pyridazin-1-yl)phenol

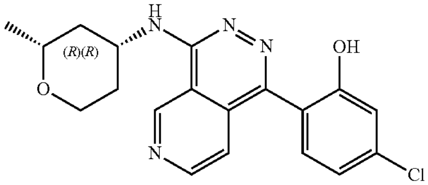

Compound 25A*

5-chloro-2-(4-(((2R,4R)-2-methyltetrahydro-2H-pyran-4-yl)amino)pyrido[3,4-d]pyridazin-1-yl)phenol Example 10 follows Protocol B.

Step 1: Into a 250 mL 3-necked round-bottom flask were added furo[3,4-c]pyridine-1,3-dione (3 g, 20.12 mmol, 1 equiv), tetrahydrofuran (THF) (30 mL), and bromo(4-chloro-2-methoxyphenyl)magnesium (0.5 mol/L) (24.16 mL, 12.07 mmol, 0.6 equiv) at −78° C. The resulting mixture was stirred for 2 h at room temperature under nitrogen atmosphere. The reaction progress was monitored by LCMS. The reaction was quenched by the addition of ice water (300 mL) at 0° C. The resulting mixture was concentrated under vacuum. The precipitated solids were collected by filtration and washed with water (3×20 mL), and dried under vacuum, to provide 4-(4-chloro-2-methoxybenzoyl)pyridine-3-carboxylic acid (2.5 g, 43% yield). LCMS: (ES, m/z): RT=0.633 min, m/z=292.0[M+1]$^+$.

Step 2: Into a 250 mL round-bottom flask were added 4-(4-chloro-2-methoxybenzoyl)pyridine-3-carboxylic acid (2.5 g, 8.56 mmol, 1 equiv) and $SOCl_2$ (25 mL). The resulting mixture was stirred for 2 h at 70° C. The reaction progress was monitored by LCMS. The resulting mixture was concentrated under vacuum. The residue was dissolved in dichloromethane (DCM) (30 mL) and added into the solution of $NH_2NH_2 \cdot H_2O$ (80%) (2.39 g, 34.24 mmol, 4 equiv) in methanol (MeOH) (50 mL) at 0° C. The resulting mixture was stirred for 1 h at 80° C. in an oil bath. The reaction progress was monitored by LCMS. The precipitated solids were collected by filtration. The crude product (2 g, 73% purity) was purified by Prep-HPLC with the following conditions (2 #SHIMADZU (HPLC-01)): Column, XBridge Shield RP18 OBD Column, 19*250 mm, 10 μm; mobile phase, Water (10 mmol/L $NH_4HCO_3$) and acetonitrile (hold 41% in 19 min); Detector, UV 254/220 nm, to provide 1-(4-chloro-2-methoxyphenyl)pyrido[3,4-d]pyridazin-4-ol (1.2 g, 49% yield). LCMS: (ES, m/z): RT=0.678 min, m/z=288.0[M+1]$^+$.

Step 3: Into a 250 mL round-bottom flask were added 1-(4-chloro-2-methoxyphenyl)pyrido[3,4-d]pyridazin-4-ol (1.2 g, 4.16 mmol, 1 equiv) and $POCl_3$ (25 mL), and pyridine (2.5 mL). The resulting mixture was stirred for 2 h at 110° C. The reaction progress was monitored by LCMS. The resulting mixture was diluted with ethyl acetate (EtOAc) (20 mL). The resulting mixture was poured into the mixture of EtOAc (1 L) and sat. sodium bicarbonate (aq.)(1 L) slowly at 0° C. The aqueous layer was extracted with EtOAc (2×1 L). The combined organic layers were dried over anhydrous $Na_2SO_4$. After filtration, the filtrate was concentrated under reduced pressure to provide 4-chloro-1-(4-chloro-2-methoxyphenyl)pyrido[3,4-d]pyridazine (800 mg, 63% yield). LCMS: (ES, m/z): RT=0.801 min, m/z=306.0[M+1]$^+$.

Step 4. Into a 20 mL sealed tube were added 4-chloro-1-(4-chloro-2-methoxyphenyl)pyrido[3,4-d]pyridazine (200 mg, 0.65 mmol, 1 equiv), 2-methyloxan-4-amine (150.48 mg, 1.30 mmol, 2 equiv), triethylamine (198.32 mg, 1.95 mmol, 3 equiv) and DMSO (6 mL) at room temperature. The resulting mixture was stirred for 12 h at 80° C. under air atmosphere. The reaction was monitored by LCMS. The crude product, a mixture of cis and trans stereoisomers of 5-chloro-2-{4-[(2-methyloxan-4-yl)amino]pyrido[3,4-d]pyridazin-1-yl}phenol, was used in the next step directly without further purification. LCMS: RT=0.85 min, m/z=385 [M+H]$^+$.

Step 5. Sodium ethanethiolate (EtSNa) (654.78 mg, 7.80 mmol, 15 equiv) was added directly into the reaction solution from Step 4. The resulting mixture was stirred for 1 h at 120° C. under air atmosphere. The reaction was monitored by LCMS. The residue was purified by reverse flash chromatography with the following conditions: column, C18 silica gel; mobile phase, acetonitrile in water, 15% to 18% gradient in 15 min; detector, UV 254 nm and 220 nm, to provide a mixture of cis and trans isomers of 5-chloro-2-{4-[(2-methyloxan-4-yl)amino]pyrido[3,4-d]pyridazin-1-yl}phenol (150 mg, 78% yield). The crude product (150 mg) was purified by Prep-HPLC with the following conditions (Column: XSelect CSH Prep C18 OBD Column, 19*250 mm, 5 m; Mobile Phase A: Water (0.05% trifluoroacetic acid), Mobile Phase B: methanol; Flow rate: 20 mL/min; Gradient: 40% B to 45% B in 8 min; Wave Length: 254 nm; RT1(min): 10) to afford 5-chloro-2-{4-[(2-methyloxan-4-yl)amino]pyrido[3,4-d]pyridazin-1-yl}phenol as a mixture of cis and trans isomers (120 mg, 99% purity). LCMS: RT=0.62 min, m/z=371 [M+H]$^+$.

Step 6. The mixture of isomers of 5-chloro-2-{4-[(2-methyloxan-4-yl)amino]pyrido[3,4-d]pyridazin-1-yl}phenol (120 mg) was purified by Prep-Chiral HPLC with the following conditions (Column: CHIRALPAK IG, 2*25 cm, 5 m; Mobile Phase A: hexanes (0.2% formic acid), Mobile Phase B: ethanol; Flow rate: 20 mL/min; Gradient: 50% B to 50% B in 20 min; Wave Length: 220/254 nm; RT1(min): 8.115; (Mixture of Compounds 25A* and 25B*); RT2(min): 12.895 (Compound 25C*); RT3(min): 18.241 (Compound 25D*); Sample Solvent: methanol/dichloromethane=1:1; Injection Volume: 0.7 mL) to afford to a mixture of Compounds 25A* and 25B* (55 mg, 98% purity), Compound 25C* (11.2 mg, 99.8% purity) and Compound 25D* (10.6 mg, 99.9% purity); stereochemistry arbitrarily assigned.

Compound 25C*: LCMS: RT=0.61 min, m/z=371 [M+H]$^+$. $^1$H NMR (400 MHz, Methanol-d4) δ 9.80 (d, J=1.0 Hz, 1H), 8.87 (d, J=5.6 Hz, 1H), 7.53 (dd, J=5.7, 1.0 Hz, 1H), 7.38 (d, J=8.0 Hz, 1H), 7.10-7.02 (m, 2H), 4.73-4.66 (m, 1H), 4.11-3.86 (m, 3H), 2.18 (d, J=13.9 Hz, 1H), 2.12-1.97 (m, 2H), 1.58 (ddd, J=14.0, 10.0, 4.0 Hz, 1H), 1.35 (d, J=6.3 Hz, 3H).

Compound 25D*: LCMS: RT=0.62 min, m/z=371 [M+H]$^+$. $^1$H NMR (400 MHz, Methanol-d4) δ 9.80 (d, J=1.0 Hz, 1H), 8.87 (d, J=5.7 Hz, 1H), 7.53 (dd, J=5.7, 1.0 Hz, 1H), 7.38 (d, J=8.0 Hz, 1H), 7.10-7.02 (m, 2H), 4.73-4.66 (m, 1H), 4.11-3.86 (m, 3H), 2.18 (d, J=13.9 Hz, 1H), 2.12-1.97 (m, 2H), 1.76 (ddd, J=14.0, 10.0, 4.0 Hz, 1H), 1.26 (d, J=6.3 Hz, 3H).

Step 7: The mixture of Compounds 25A* and 25B* (55 mg) was purified by Prep-Chiral HPLC with the following conditions (Column: CHIRALPAK IE, 2*25 cm, 5 m Mobile Phase A: hexanes (0.2% formic acid), Mobile Phase B: ethanol; Flow rate: 20 mL/min; Gradient: 35% B to 35% B in 16.5 min; Wave Length: 254/220 nm; RT1(min): 1.179 (Compound 25A*); RT2(min): 4.19 (Compound 25B*); Sample Solvent: methanol; Injection Volume: 0.6 mL) to afford to Compound 25A* (14.7 mg, 98% purity) and Compound 25B* (15.5 mg, 99% purity); stereochemistry arbitrarily assigned.

Compound 25A*: LCMS: RT=0.91 min, m/z=371 [M+H]$^+$. $^1$H NMR (400 MHz, Methanol-d4) δ 9.69 (d, J=1.0 Hz, 1H), 8.85 (d, J=5.7 Hz, 1H), 7.51 (dd, J=5.7, 1.0 Hz, 1H), 7.38 (d, J=8.0 Hz, 1H), 7.09-7.02 (m, 2H), 4.63-4.52 (m, 1H), 4.13-4.05 (m, 1H), 3.73-3.62 (m, 2H), 2.30-2.22 (m, 1H), 2.18 (d, J=13.3 Hz, 1H), 1.72 (qd, J=12.3, 4.7 Hz, 1H), 1.44 (q, J=11.6 Hz, 1H), 1.27 (d, J=6.2 Hz, 3H).

Compound 25B*: LCMS: RT=0.91 min, m/z=371 [M+H]$^+$. $^1$H NMR (400 MHz, Methanol-d4) δ 9.72 (d, J=1.0 Hz, 1H), 8.68 (d, J=5.7 Hz, 1H), 7.54 (dd, J=5.7, 1.0 Hz, 1H), 7.38 (d, J=7.9 Hz, 1H), 7.09-7.02 (m, 2H), 4.63-4.53 (m, 1H), 4.13-4.04 (m, 1H), 3.73-3.62 (m, 2H), 2.30-2.22 (m, 1H), 2.21-2.13 (m, 1H), 1.72 (qd, J=12.3, 4.6 Hz, 1H), 1.44 (q, J=11.7 Hz, 1H), 1.24 (d, J=6.2 Hz, 3H).

Example 11. Synthesis of 3-chloro-2-(4-(((R)-5,5-dimethyltetrahydrofuran-3-yl)amino)pyrido[3,4-d]pyridazin-1-yl)-5-methylphenol (Compound 26*) and 3-chloro-2-(4-(((S)-5,5-dimethyltetrahydrofuran-3-yl)amino)pyrido[3,4-d]pyridazin-1-yl)-5-methylphenol (Compound 26B*)

Scheme 11A

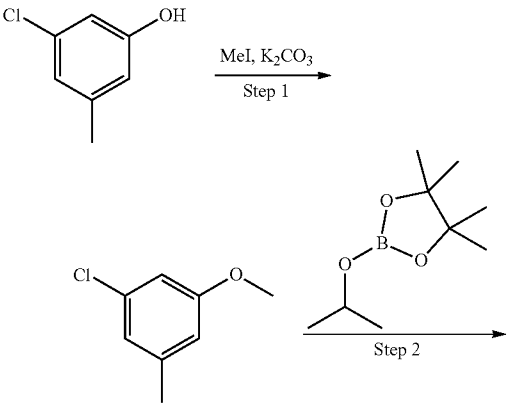

-continued

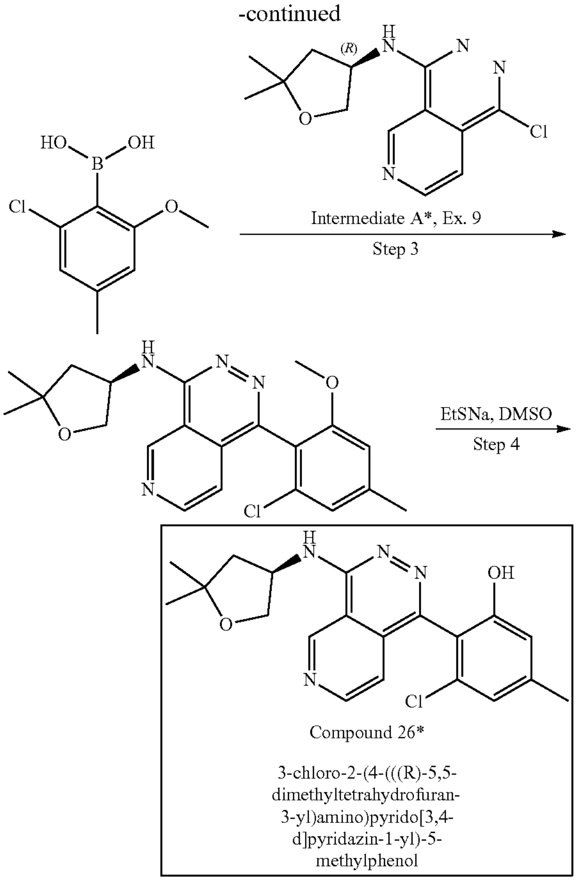

Compound 26*

3-chloro-2-(4-(((R)-5,5-dimethyltetrahydrofuran-3-yl)amino)pyrido[3,4-d]pyridazin-1-yl)-5-methylphenol Scheme 11B

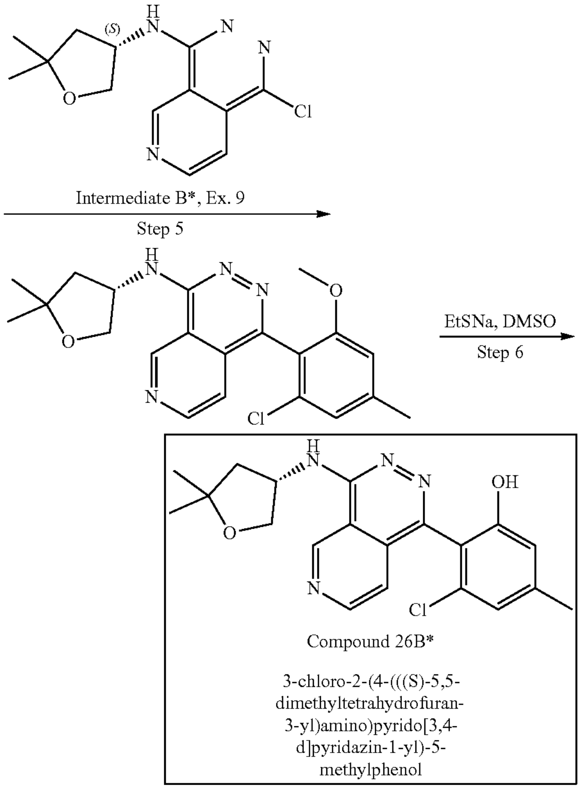

Compound 26B*

3-chloro-2-(4-(((S)-5,5-dimethyltetrahydrofuran-3-yl)amino)pyrido[3,4-d]pyridazin-1-yl)-5-methylphenol Example 11 follows Protocol A.

Step 1. Into a 40 mL vial were added chloro-M-cresol (3 g, 21.04 mmol, 1 equiv), acetonitrile (20 mL), $K_2CO_3$ (8.72 g, 63.12 mmol, 3 equiv) and methyl iodide (Mel) (8.96 g, 63.12 mmol, 3 equiv) at room temperature. The resulting mixture was stirred for 2 h at 80° C. The reaction was monitored by LCMS. The reaction was quenched with water (20 mL) at room temperature. The resulting mixture was extracted with ethyl acetate (EtOAc) (3x50 mL). The combined organic layers were washed with brine (1x20 mL) and dried over anhydrous $Na_2SO_4$. After filtration, the filtrate was concentrated under reduced pressure. The residue was purified by silica gel column chromatography, eluting with petroleum ether/ethyl acetate (18:1) to afford 1-chloro-3-methoxy-5-methylbenzene (3.1 g, 94% yield). LCMS: RT=1.04 min, m/z=157.0 $[M+H]^+$.

Step 2. In a 100-mL three-round bottom flask, to a solution of 1-chloro-3-methoxy-5-methylbenzene (3 g, 19.16 mmol, 1 equiv) in tetrahydrofuran (THF) (5 mL) was added t-butyllithium solution (1.6 M in hexane, 20 mL, 1.7 equiv) by dropwise at −78° C. under $N_2$ atmosphere. The reaction mixture was stirred at −78° C. for 1 h. Then a solution of triisopropyl borate (5.40 g, 28.73 mmol, 1.50 equiv) in THF (10 mL) was added by dropwise and the mixture was stirred at −20° C. for another 2 h. The reaction was monitored by LCMS. The reaction was quenched with sat. $NH_4Cl$ (10 mL), and then the mixture was extracted with ethyl acetate (EtOAc) (2x30 mL). The combined organic extracts were washed with brine (30 mL), dried over anhydrous $Na_2SO_4$, and concentrated under vacuum. The residue was purified by Prep-TLC (petroleum ether/ethyl acetate 3:1) to afford 2-chloro-6-methoxy-4-methylphenylboronic acid (780 mg, 20% yield). LCMS: RT=0.78 min, m/z=201.0 $[M+H]^+$.

Step 3. Into a 8 mL vial were added 2-chloro-6-methoxy-4-methylphenylboronic acid (287.60 mg, 1.40 mmol, 4 equiv), dioxane (1.5 mL), $H_2O$ (0.3 mL), Intermediate A* from Example 9 (100 mg, 0.36 mmol, 1 equiv), $Na_2CO_3$ (114.06 mg, 1.08 mmol, 3 equiv) and [1,1'-bis(diphenylphosphino)ferrocene]dichloropalladium(II), complex with dichloromethane ($Pd(dppf)_2Cl_2CH_2Cl_2$) (79.2 mg, 0.11 mmol, 0.3 equiv) at room temperature. The resulting mixture was stirred for 2 h at 80° C. under $N_2$ atmosphere. The reaction was monitored by LCMS. The reaction was quenched with water (5 mL) at room temperature. The resulting mixture was extracted with ethyl acetate (EtOAc) (3x10 mL). The combined organic layers were washed with brine (1x10 mL) and dried over anhydrous $Na_2SO_4$. After filtration, the filtrate was concentrated under reduced pressure. The residue was purified by reversed-phase flash chromatography with the following conditions: column, C18 silica gel; mobile phase, acetonitrile in Water, 10% to 50% gradient in 20 min; detector, UV 254 nm, to provide 1-(2-chloro-6-methoxy-4-methylphenyl)-N-[(3R)-5,5-dimethyloxolan-3-yl]pyrido[3,4-d]pyridazin-4-amine (80 mg, 56% yield). LCMS: RT=1.01 min, m/z=399.0 $[M+H]^+$. $^1H$ NMR (300 MHz, DMSO-$d_6$) δ 9.83 (s, 1H), 8.84 (d, J=5.5 Hz, 1H), 7.97 (d, J=5.8 Hz, 1H), 7.12-7.01 (m, 3H), 5.00-4.87 (m, 1H), 4.30-4.17 (m, 1H), 3.87-3.70 (m, 1H), 3.64 (s, 3H), 2.44 (s, 3H), 2.39-2.26 (m, 1H), 2.06-1.91 (m, 1H), 1.37 (s, 3H), 1.26 (s, 3H). Stereochemistry arbitrarily assigned.

Step 4. Into a 8 mL vial were added 1-(2-chloro-6-methoxy-4-methylphenyl)-N-[(3R)-5,5-dimethyloxolan-3-yl]pyrido[3,4-d]pyridazin-4-amine (80 mg, 0.20 mmol, 1 equiv), DMSO (1 mL) and (ethylsulfanyl)sodium (168.69 mg, 2.01 mmol, 10 equiv) at room temperature. The resulting mixture was stirred for 2 h at 120° C. The reaction was monitored by LCMS. The residue was purified by reversed-phase flash chromatography with the following conditions: column, C18 silica gel; mobile phase, acetonitrile in water, 10% to 40% gradient in 10 min; detector, UV 254/220 nm, to provide a crude product (70 mg, 90% purity), which was purified by Prep-HPLC with the following conditions (Column: Xselect CSH F-Phenyl OBD column, 19*250 mm, 5 μm; Mobile Phase A: Water (0.05% trifluoroacetic acid), Mobile Phase B: acetonitrile; Flow rate: 20 mL/min; Gradient: 20% B to 25% B in 8 min; Wave Length: 254 nm; RT1(min): 8 min; to provide Compound 26A* (25 mg, 25% yield). LCMS: $RT_1$=1.08 min, m/z=385.0 $[M+H]^+$. $^1$H NMR (400 MHz, DMSO-$d_6$) δ 10.15 (s, 1H), 10.02 (s, 1H), 9.03 (s, 1H), 7.29 (s, 1H), 6.98 (s, 1H), 6.84 (s, 1H), 4.87 (d, J=7.8 Hz, 1H), 4.26-4.17 (m, 1H), 3.91 (m, 2H), 2.35 (s, 3H), 2.10-1.98 (m, 1H), 1.38 (d, J=2.5 Hz, 3H), 1.26 (s, 3H).

Step 5. Into a 8 mL vial was added Intermediate B* from Example 9 (80.0 mg, 0.29 mmol, 1 equiv), dioxane (0.5 mL), $H_2O$ (0.1 mL), 2-chloro-6-methoxy-4-methylphenylboronic acid (173 mg, 0.86 mmol, 3 equiv), $Na_2CO_3$ (91.3 mg, 0.86 mmol, 3 equiv) and [1,1'-bis(diphenylphosphino) ferrocene]dichloropalladium(II), complex with dichloromethane ($Pd(dppf)_2Cl_2CH_2Cl_2$) (63 mg, 0.09 mmol, 0.3 equiv) at room temperature. The resulting mixture was stirred for 2 h at 60° C. under nitrogen atmosphere. The reaction was monitored by LCMS. The reaction was quenched with water (5 mL) at room temperature. The resulting mixture was extracted with ethyl acetate (EtOAc) (3×20 mL). The combined organic layers were washed with brine (15 mL) and dried over anhydrous $Na_2SO_4$. After filtration, the filtrate was concentrated under reduced pressure. The residue was purified by reversed-phase flash chromatography with the following conditions: column, C18 silica gel; mobile phase, acetonitrile in water, 15% to 40% gradient in 20 min; detector, UV 220/254 nm. This resulted in 1-(2-chloro-6-methoxy-4-methylphenyl)-N-[(3S)-5,5-dimethyloxolan-3-yl]pyrido[3,4-d]pyridazin-4-amine (40.4 mg, 26% yield). LCMS, ESI: RT=0.73 min, m/z=399.0 $[M+H]^+$; $^1$H NMR (300 MHz, DMSO-$d_6$) δ 9.84 (d, J 1.0 Hz, 1H), 8.84 (d, J 5.6 Hz, 1H), 8.00 (d, J 5.9 Hz, 1H), 7.14-7.03 (m, 3H), 4.93 (q, J 6.9 Hz, 1H), 4.32-4.13 (m, 1H), 3.87-3.72 (m, 1H), 3.64 (d, J=1.0 Hz, 3H), 2.44 (s, 3H), 2.39-2.21 (m, 1H), 2.08-1.86 (m, 1H), 1.36 (s, 3H), 1.26 (s, 3H). Stereochemistry was arbitrarily assigned.

Step 6. Into a 8 mL vial was added 1-(2-chloro-6-methoxy-4-methylphenyl)-N-[(3S)-5,5-dimethyloxolan-3-yl]pyrido [3,4-d]pyridazin-4-amine (80 mg, 0.20 mmol, 1 equiv), dimethyl formamide (DMF) (1 mL) and (ethylsulfanyl)sodium (168.69 mg, 2.01 mmol, 10 equiv) at room temperature. The resulting mixture was stirred for 2 h at 120° C. The reaction was monitored by LCMS. The resulting mixture was filtered, the filter cake was washed with DMF (4 mL). After filtration, the filtrate was concentrated under reduced pressure. The filtrate was purified by Prep-HPLC with the following conditions (2 #SHIMADZU (HPLC-01)): Column, XBridge Prep Phenyl OBD Column, 19*250 mm, 5 μm; mobile phase, water (10 mmol/L $NH_4HCO_3$) and acetonitrile (30% up to 40% in 10 min); Detector, UV 220/254 nm, to provide Compound 26B* (20 mg, 20% yield). LCMS, ESI: RT=0.85 min, m/z=385.0 $[M+H]^+$; H NMR (400 MHz, Methanol-$d_4$) δ 9.82 (s, 1H), 8.93 (s, 1H), 7.38 (d, J 5.4 Hz, 1H), 6.97 (s, 1H), 6.81 (s, 1H), 4.97 (d, J 6.2 Hz, 1H), 4.45-4.30 (m, 1H), 4.06-3.91 (m, 1H), 2.52-2.43 (m, 1H), 2.40 (s, 3H), 2.16-2.06 (m, 1H), 1.46 (d, J 2.4 Hz, 3H), 1.36 (s, 3H).

Example 12. Biological Activity of the Compounds of the Present Disclosure

The biological activity of the compounds of the present disclosure was determined utilizing the assay described herein.

Human Whole Blood—NLRP3

Heparin lithium coated tubes were used to collect blood from volunteers. Blood samples were distributed on 96 well plates using 90 μl per well. Priming was performed by adding 5 μl of LPS (O26:B6; Sigma L-2654) at a final concentration of 1 μg/ml for 4.5 hours in a humidified incubator with 37° C., 5% CO2. Thirty minutes prior to NLRP3 activation, 5 μl of a 20× compound solution or vehicle (2% DMSO) was added to each well and plates were incubated on a shaker (450 rpm) in a humidified incubator with 37° C., 5% CO2. Activation was then performed by adding 3.3 μl of a 31×ATP solution per well. At the end of the 30 minutes stimulation, the plates were centrifuged (800 g, 10 min, room temperature) and the plasma from each well was frozen at −80° C. IL-10 levels in the supernatant were analyzed using a mesoscale discovery assay (MSD K151TUK) according to the manufacturers' instructions. Human whole blood was drawn from healthy volunteers after obtaining written informed consent.

Brain Levels (Kp and Kpu,u)—NLRP3

The in vivo total brain to plasma ratio was assessed in CD1 mice after oral administration of the compound. Blood was collected at several timepoints up to 24 h, and transferred into plastic micro centrifuge tubes with EDTA-K2 as anticoagulant. Blood samples were centrifuged at 4000 g for 5 minutes at 4° C. to obtain plasma, then immediately frozen and stored at −75±15° C. prior to analysis. Animals were terminally anaesthetized with a rising concentration of CO2 gas at about 1 minute. At selected timepoints, whole brains were removed from the skull, rinsed in cold PBS to remove blood, dried with clean gauze, then frozen in liquid nitrogen and kept at −75±15° C. before analysis. At the time of analysis, brain samples were homogenized with PBS by tissue weight (g) to PBS volume (mL) ratio 1:3. Plasma and brain drug levels were quantified by LC/MS/MS on a AB Sciex Triple Quad 5500+ instrument, after separation on a HALO 160A ES-C18, 2.7 μm 2.1×50 mm column. Quantitation was performed using a calibration curve prepared in blank plasma or blank brain homogenate. The software WinNonlin (Phoenix™) was used for pharmacokinetic analysis from the concentrations versus time data, including the $AUC_{inf}$ and $AUC_{last}$. The Kp ratio (total brain concentration over total plasma concentration) was calculated as $(AUC_{tot,br})/(AUC_{tot,pl})$.

The unbound brain exposure was assessed as $Kp_{uu}$, which is the free brain/free plasma concentration ratio ($C_{u,br}/C_{u,pl}$). The $C_{u,br}/C_{u,pl}$ ratios were obtained from in vivo total brain to plasma ratios ($C_{tot,br}/C_{tot,pl}$) by using in vitro determined $F_{u,br}$ and $F_{u,pl}$.

Plasma protein binding and brain homogenate protein binding were measured by equilibrium dialysis in a HTDialysis plate. The dialysis membranes were soaked in ultrapure water for 60 minutes to separate strips, then in 20% ethanol for 20 minutes, finally in dialysis buffer for 20 minutes. The dialysis set up was assembled according to the manufacturer's instruction. Each cell received 150 μL of plasma or brain homogenate spiked with 1 mM of compound, and dialyzed against an equal volume of dialysis buffer (PBS). The dialysis plate was sealed and incubated in an incubator at 37° C. with 5% CO2 at 100 rpm for 6 hours. At the end of incubation, compound concentration was measured in both chambers by LC-MS/MS on a Triple Quad™ 5500 from AB Inc after separation on a XSelect Hss T3 2.5μ (2.1×30 mm) column. Free fraction (Fu) was calculated as (Peak Area Ratio buffer chamber/Peak Area Ratio plasma chamber).

$Kp_{uu}$ was calculated as $(AUC_{tot,br} \times F_{u,br})/(AUC_{tot,pl} \times F_{u,pl})$ Activity Data Table D assigns each compound a code for potency in the human whole blood (hWB) NLRP3 Assay: A or B. According to the code, A represents an $IC_{50}$ value ≤1.0 μM; B represents an $IC_{50}$ value >1.0 μM. The corresponding raw activity data is also included.

The below table also assigns each compound a code for kp and kpu,u values: A or B. According to the code, A represents a value of >0.3 and B represents a value of ≤0.3. The kp values were calculated by measuring whole brain drug levels over 24 h (AUC) in mice dosed at 20 mpk PO, and dividing by plasma AUC. The kpu,u was then calculated upon correcting this kp value with mouse plasma protein binding and mouse brain homogenates binding. A Kpu,u value >0.3 is brain penetrant, and Kpu,u value less than or equal to 0.3 is not brain penetrant. N.D.=not determined. The corresponding raw kp and kpu,u data is also included.

TABLE D

| Activity Data | | | | | | |
|---|---|---|---|---|---|---|
| Cmp. # | hWB $IC_{50}$ | hWB $IC_{50}$ | kp | kp | kpu, u | kpu, u |
| 1* | A | 1.0 | A | 0.90 | A | 0.31 |
| 1B* | B | 1.8 | N.D. | N.D | N.D. | N.D. |
| 2 | A | 0.16 | B | 0.24 | A | 2.2 |
| 3* | A | 0.19 | A | 0.58 | A | 2.2 |
| 3B* | B | 11 | N.D. | N.D. | N.D. | N.D. |
| 4* | A | 0.66 | A | 0.81 | A | 0.89 |
| 4B* | B | 1.7 | N.D. | N.D. | N.D. | N.D. |
| 5 | A | 0.22 | A | 0.44 | A | 0.94 |
| 5B | A | 0.21 | N.D. | N.D. | N.D. | N.D. |
| 6* | A | 0.43 | A | 0.66 | A | 2.3 |
| 6B* | B | 1.26 | N.D. | N.D. | N.D. | N.D. |
| 9* | A | 0.26 | A | 0.40 | A | 0.63 |
| 9B* | A | 0.061 | B | 0.24 | A | 0.52 |
| 10* | B | 1.4 | A | 0.35 | A | 0.51 |
| 10B* | B | 7.9 | N.D. | N.D. | N.D. | N.D. |
| 11* | B | 1.4 | A | 0.96 | A | 1.3 |
| 11B* | B | 10 | N.D. | N.D. | N.D. | N.D. |
| 12* | A | 0.82 | A | 0.33 | A | 1.3 |
| 12B* | B | 3.2 | N.D. | N.D. | N.D. | N.D. |
| 13* | A | 0.22 | A | 0.60 | A | 0.77 |
| 13B* | B | 9.8 | N.D. | N.D. | N.D. | N.D. |
| 14* | A | 0.51 | A | 0.64 | A | 0.33 |
| 14B* | B | 3.6 | N.D. | N.D. | N.D. | N.D. |
| 15* | B | 1.2 | A | 0.83 | A | 2.2 |
| 15B* | B | 18 | N.D. | N.D. | N.D. | N.D. |
| 16* | B | 1.8 | A | 0.48 | A | 0.59 |
| 16B* | B | 12 | N.D. | N.D. | N.D. | N.D. |
| 17* | A | 0.33 | A | 0.69 | A | 1.9 |
| 17B* | B | 2.4 | N.D. | N.D. | N.D. | N.D. |
| 18A* | B | 1.1 | A | 0.73 | A | 0.30 |
| 18* | A | 0.89 | A | 0.68 | A | 0.47 |
| 18C* | B | 1.2 | N.D. | N.D. | N.D. | N.D. |
| 18D* | B | 6.2 | N.D. | N.D. | N.D. | N.D. |
| 19* | B | 1.4 | A | 1.4 | A | 0.81 |
| 19B* | B | 1.2 | N.D. | N.D. | N.D. | N.D. |
| 20* | A | 0.89 | A | 0.61 | A | 0.46 |
| 20B* | B | 3.4 | N.D. | N.D. | N.D. | N.D. |
| 21* | A | 0.46 | A | 0.30 | A | 0.76 |
| 21B* | B | 2.3 | N.D. | N.D. | N.D. | N.D. |
| 22* | A | 0.96 | A | 1.1 | A | 0.34 |
| 22B* | B | 5.9 | N.D. | N.D. | N.D. | N.D. |
| 23* | A | 0.12 | B | 0.24 | A | 0.33 |
| 23B* | N.D. | N.D. | B | 0.28 | B | 0.09 |
| 24* | A | 0.33 | B | 0.05 | N.D. | N.D. |
| 24B* | N.D. | N.D. | N.D. | N.D. | N.D. | N.D. |
| 25A* | A | 0.58 | A | 1.1 | B | 0.1 |

TABLE D-continued

| Activity Data | | | | | | |
|---|---|---|---|---|---|---|
| Cmp. # | hWB $IC_{50}$ | hWB $IC_{50}$ | kp | kp | kpu, u | kpu, u |
| 25B* | A | 0.85 | N.D. | N.D. | N.D. | N.D. |
| 25C* | B | 1.4 | A | 0.65 | B | 0.099 |
| 25D* | B | 1.2 | A | 1.0 | B | 0.20 |
| 26* | A | 0.90 | B | 0.10 | B | 0.17 |
| 26B* | B | 1.3 | N.D. | N.D. | N.D. | N.D. |
| 7* Comparative Example 1 | A | 0.80 | B | 0.13 | B | 0.15 |
| 8 Comparative Example 2 | A | 0.20 | B | 0.18 | B | 0.11 |

Comparative Examples

The compounds described in the present disclosure are useful for the treatment of NLRP3 proteins-mediated diseases and/or disorders and are structurally related to compounds previously disclosed in U.S. patent application Ser. No. 17/528,928 as inhibitors of the same NLRP3 proteins. The brain levels of these active pharmaceutical ingredients, however, were unexpected, and hence not contemplated in the U.S. Ser. No. 17/528,928 application. Thus, the unanticipated ability of the instant compounds 1*, 2*, 3*, 4*, 5, and 6 to penetrate the brain blood barrier constitutes a novel invention.

Furthermore, as shown in the above Table D, it is not obvious that inhibitors of NLPR3 proteins described in U.S. application Ser. No. 17/528,928 exhibit this unpredicted activity. The selected NLPR3 inhibitors of the instant disclosure were found to exhibit more potent brain-penetrant properties in a head-to-head comparison with compounds of the U.S. Ser. No. 17/528,928 application similar in NLPR3 inhibitory activity in the blood as illustrated in Table D. By way of a clearer illustration in the above Table, Compounds 1*, 2, 3*, 4*, 5, and 6 of the present disclosure exhibit unexpected "A" brain levels compared to Compound 7* (Comparative Example 1, Compound 89 of U.S. Ser. No. 17/528,928) and Compound 8 (Comparative Example 2, Compound 96 of U.S. Ser. No. 17/528,928), each of which exhibit "B" brain levels and are not brain penetrant, thereby making the compounds of the instant application more available to treatment of NLPR3-mediated CNS diseases.

It has also been further discovered that the solubility of compounds of Formula (I) may be improved by replacing an $R^3$ halogen moiety, such as a chloro group, with an $C_1$-$C_6$ alkyl or $C_1$-$C_6$ alkoxy group (wherein alkyl or alk- is independently substituted with 0, 1, 2, or 3 halogen atoms) while still maintaining a Kpu,u of greater than 0.3. See, e.g., below Table E. Compare, for example, the solubility in phosphate buffered solution (PBS, pH 7.4) of Comparative Example 3 (Compound 105 of U.S. Ser. No. 17/528,928) having a chloro $R^3$ moiety, to Compounds 9*, 9B*, and 5: both Compound 9* and Compound 9B* result in a 7-fold increase in solubility moving from a chloro $R^3$ moiety to an —$OCHF_2R^3$ moiety; Compound 5 results in a 27-fold increase in solubility moving from a chloro $R^3$ moiety to an —$CH_3R^3$ moiety; and each of which maintains good brain penetrance. Incorporating a non-hydrogen group meta to the $R^3$ moiety of Compound 5, such as with Compound 21* (meta-fluoro moiety), Compound 26* (meta-chloro moiety), and Compound 24* (meta-$CH_3$ group) results in a further increase in solubility; compare Compound 21* (a 37-fold increase), Compound 26* (a 42-fold increase), and Compound 24* (a 43-fold increase) to Comparative Example 3. Compounds which are not brain penetrant but with improved properties, such as solubility may be useful in the treatment of systemic (non-CNS) NLPR3-mediated diseases.

TABLE E

| Compound | kp | kpu, u | Solubility (PBS, pH 7.4) uM |
|---|---|---|---|
| 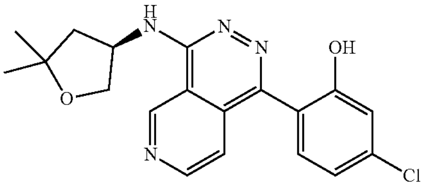 [SMILES: CC1(C)C[C@@H](Nc2nnc(-c3ccc(Cl)cc3O)c3ccncc23)CO1]<br>(R)-5-chloro-2-(4-((5,5-dimethyltetrahydrofuran-3-yl)amino)pyrido[3,4-d]pyridazin-1-yl)phenol<br>Comparative Example 3<br>(Compound 105 of USSN 17/528,928) | A (0.4) | A (0.43) | PBS (pH 7.4): 6.7 uM |
| 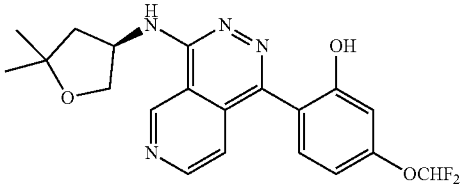 [SMILES: CC1(C)C[C@@H](Nc2nnc(-c3ccc(OC(F)F)cc3O)c3ccncc23)CO1]<br>Compound 9B* | B (0.24) | A (0.52) | PBS (pH 7.4): 45 uM (7-fold increase) |
| 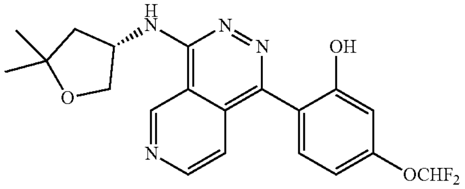 [SMILES: CC1(C)C[C@H](Nc2nnc(-c3ccc(OC(F)F)cc3O)c3ccncc23)CO1]<br>Compound 9* | A (0.40) | A (0.63) | PBS (pH 7.4): 45 uM (7-fold increase) |
| 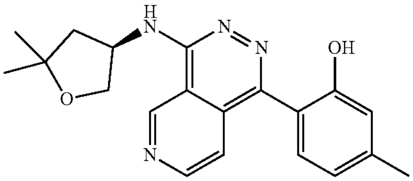<br>Compound 5 | A (0.44) | A (0.94) | PBS (pH 7.4): 180 uM (27-fold increase) |
| 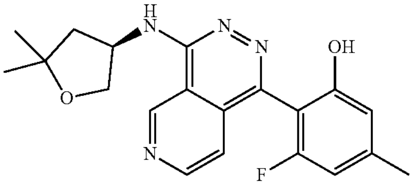<br>Compound 21* | B (0.30) | A (0.76) | PBS (pH 7.4): 250 uM (37-fold increase) |
| 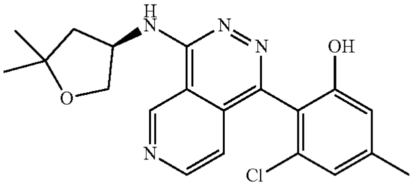<br>Compound 26* | B (0.10) | B (0.17) | PBS (pH 7.4): 280 uM (42-fold increase) |

TABLE E-continued

| Compound | kp | kpu, u | Solubility (PBS, pH 7.4) uM |
|---|---|---|---|
| 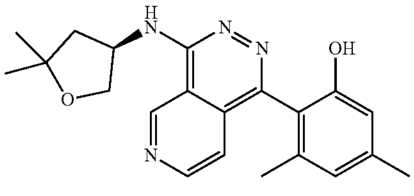 Compound 24* | B (0.05) | N.D. | PBS (pH 7.4): 290 uM (43-fold increase) |

EQUIVALENTS

The details of one or more embodiments of the disclosure are set forth in the accompanying description above. Although any methods and materials similar or equivalent to those described herein can be used in the practice or testing of the present disclosure, the desired methods and materials are herein described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

What is claimed:

1. A compound of Formula (IV-b1):

(IV-b1)

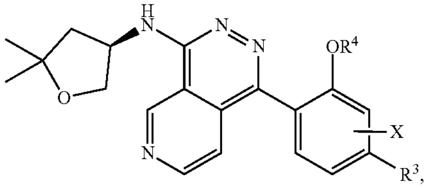

or a pharmaceutically acceptable salt or isotopically labeled compound thereof, wherein:

$R^3$ is $C_1$-$C_6$ alkoxy;

X is H or –F; and $R^4$ is H, wherein each instance of alk- is independently substituted with 0, 1, 2, or 3 halogen atoms.

2. The compound of claim 1, or a pharmaceutically acceptable salt or isotopically labeled compound thereof, wherein $R^3$ is —$OCHF_2$.

3. The compound of claim 1, or a pharmaceutically acceptable salt or isotopically labeled compound thereof, wherein X is H.

4. The compound of claim 1, or a pharmaceutically acceptable salt or isotopically labeled compound thereof, wherein X is —F.

5. The compound of claim 2, or a pharmaceutically acceptable salt or isotopically labeled compound thereof, wherein X is —F.

6. The compound of claim 1, wherein the compound is:

9B*

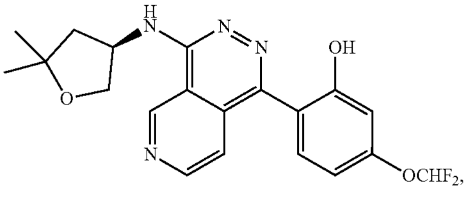

or a pharmaceutically acceptable salt or isotopically labeled compound thereof.

7. A pharmaceutical composition comprising the compound of claim 1, or a pharmaceutically acceptable salt or isotopically labeled compound thereof, and one or more pharmaceutically acceptable carriers.

8. A compound of Formula (IV-b1):

(IV-b1)

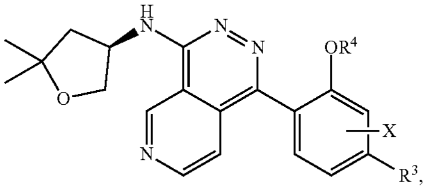

or a pharmaceutically acceptable salt thereof, wherein:

$R^3$ is $C_1$-$C_6$ alkoxy;

X is H or —F; and $R^4$ is H, wherein each instance of alk- is independently substituted with 0, 1, 2, or 3 halogen atoms.

9. The compound of claim 8, or a pharmaceutically acceptable salt thereof, wherein $R^3$ is —$OCHF_2$.

10. The compound of claim 8, or a pharmaceutically acceptable salt thereof, wherein X is H.

11. The compound of claim 8, or a pharmaceutically acceptable salt thereof, wherein X is —F.

12. The compound of claim 9, or a pharmaceutically acceptable salt thereof, wherein X is —F.

13. The compound of claim 8, wherein the compound is:

9B*

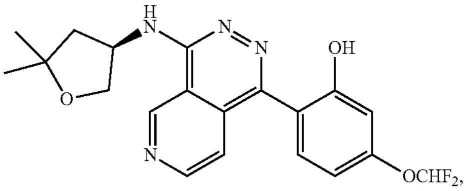

or a pharmaceutically acceptable salt thereof.

14. A pharmaceutical composition comprising the compound of claim 8, or a pharmaceutically acceptable salt thereof, and one or more pharmaceutically acceptable carriers.

15. The compound of claim 13, wherein the compound is:

9B*

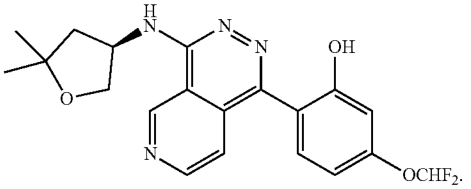

16. The compound of claim 13, wherein the compound is a pharmaceutically acceptable salt of:

9B*

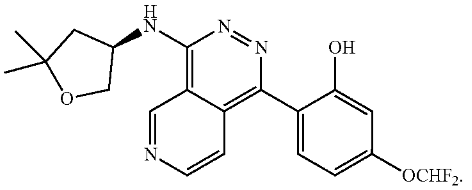

17. A pharmaceutical composition comprising the compound of claim 15, and one or more pharmaceutically acceptable carriers.

18. A pharmaceutical composition comprising the pharmaceutically acceptable salt of claim 16, and one or more pharmaceutically acceptable carriers.

* * * * *